US012648908B2

(12) United States Patent
Weng et al.

(10) Patent No.: US 12,648,908 B2
(45) Date of Patent: *Jun. 9, 2026

(54) CATIONIC LIPID, LIPOSOME CONTAINING CATIONIC LIPID, AND NUCLEIC-ACID PHARMACEUTICAL COMPOSITION CONTAINING LIPOSOME AND FORMULATION AND APPLICATION THEREOF

(71) Applicant: XIAMEN SINOPEG BIOTECH CO., LTD., Xiamen (CN)

(72) Inventors: Wengui Weng, Xiamen (CN); Chao Liu, Xiamen (CN); Ailan Wang, Xiamen (CN); Sheng Lin, Xiamen (CN)

(73) Assignee: XIAMEN SINOPEG BIOTECH CO., LTD., Xiamen (CN)

( * ) Notice: Subject to any disclaimer, the term of this patent is extended or adjusted under 35 U.S.C. 154(b) by 499 days.

This patent is subject to a terminal disclaimer.

(21) Appl. No.: 18/269,728

(22) PCT Filed: Apr. 1, 2022

(86) PCT No.: PCT/CN2022/084775

§ 371 (c)(1),
(2) Date: Jun. 26, 2023

(87) PCT Pub. No.: WO2022/213895

PCT Pub. Date: Oct. 13, 2022

(65) Prior Publication Data

US 2024/0342088 A1 Oct. 17, 2024

(30) Foreign Application Priority Data

Apr. 8, 2021 (CN) ......................... 202110379685.5
Jul. 23, 2021 (CN) ......................... 202110839008.4

(51) Int. Cl.

| | |
|---|---|
| ***C07C 219/06*** | (2006.01) |
| ***A61K 9/1272*** | (2025.01) |
| ***A61K 9/51*** | (2006.01) |
| ***A61K 45/06*** | (2006.01) |
| ***C07C 229/16*** | (2006.01) |
| ***C07C 229/26*** | (2006.01) |
| ***C07C 271/16*** | (2006.01) |
| ***C07C 271/18*** | (2006.01) |
| ***C07D 207/452*** | (2006.01) |
| ***C07D 233/60*** | (2006.01) |
| ***C12N 15/113*** | (2010.01) |

(52) U.S. Cl.

CPC .......... *A61K 9/1272* (2013.01); *A61K 9/5123* (2013.01); *A61K 45/06* (2013.01); *C07C 219/06* (2013.01); *C07C 229/16* (2013.01); *C07C 229/26* (2013.01); *C07C 271/16* (2013.01); *C07C 271/18* (2013.01); *C07D 207/452* (2013.01); *C07D 233/60* (2013.01); *C12N 15/113* (2013.01); *C12N 2310/14* (2013.01)

(58) Field of Classification Search

CPC ... C07C 219/06; C07C 229/16; C07C 229/26; C07C 271/16; A61K 9/1272; C07D 207/452

See application file for complete search history.

(56) References Cited

U.S. PATENT DOCUMENTS

| | | | | |
|---|---|---|---|---|
| 7,803,397 | B2 | 9/2010 | Heyes et al. | |
| 9,701,623 | B2 * | 7/2017 | Manoharan ............ | A61K 47/60 |
| 9,999,673 | B2 * | 6/2018 | Rajeev ................... | A61K 47/18 |
| 2005/0175682 | A1 | 8/2005 | Heyes et al. | |
| 2009/0239814 | A1 | 9/2009 | Manoharan et al. | |
| 2009/0247608 | A1 | 10/2009 | Manoharan et al. | |
| 2011/0091525 | A1 | 4/2011 | Heyes et al. | |
| 2012/0027803 | A1 | 2/2012 | Manoharan et al. | |
| 2012/0136042 | A1 | 5/2012 | Manoharan et al. | |
| 2013/0108685 | A1 | 5/2013 | Kuboyama et al. | |
| 2013/0178512 | A1 | 7/2013 | Manoharan et al. | |
| 2014/0045913 | A1 | 2/2014 | Kuboyama et al. | |

(Continued)

FOREIGN PATENT DOCUMENTS

| | | | |
|---|---|---|---|
| CN | 1882693 | A | 12/2006 |
| CN | 102006890 | A | 4/2011 |

(Continued)

OTHER PUBLICATIONS

Jun. 29, 2022 International Search Report issued in International Patent Application No. PCT/CN2022/084775.

(Continued)

*Primary Examiner* — Sikarl A Witherspoon
(74) *Attorney, Agent, or Firm* — Oliff PLC

(57) ABSTRACT

A novel cationic lipid has a structure as represented by general formula (1) and specifically relates to a nitrogen-branched cationic lipid, and a liposome containing the cationic lipid, and a nucleic-acid pharmaceutical composition containing the liposome, a preparation method and application thereof, wherein, the definition of each symbol in the formula (1) is as defined herein. The cationic liposome containing the cationic lipid as represented by formula (1) can improve the loading rate and transport efficiency of nucleic-acid drugs. The formulation of the cationic liposome nucleic-acid pharmaceutical composition has good cell compatibility and higher gene transfection capability, and can improve the treatment and/or prevention effects of nucleic-acid drugs.

35 Claims, No Drawings

(56) References Cited

U.S. PATENT DOCUMENTS

| | | | |
|---|---|---|---|
| 2014/0179761 | A1 | 6/2014 | Manoharan et al. |
| 2014/0255472 | A1 | 9/2014 | Geall et al. |
| 2015/0011615 | A1 | 1/2015 | Manoharan et al. |
| 2015/0119444 | A1 | 4/2015 | Manoharan et al. |
| 2015/0119445 | A1 | 4/2015 | Manoharan et al. |
| 2015/0203446 | A1 | 7/2015 | Manoharan et al. |
| 2015/0343062 | A1 | 12/2015 | Kuboyama et al. |
| 2015/0376115 | A1 | 12/2015 | Ansell et al. |
| 2016/0009637 | A1 | 1/2016 | Manoharan et al. |
| 2016/0051691 | A1 | 2/2016 | Manoharan et al. |
| 2016/0304487 | A1 | 10/2016 | Kuboyama et al. |
| 2017/0119904 | A1 | 5/2017 | Ansell et al. |
| 2017/0157268 | A1 | 6/2017 | Ansell et al. |
| 2017/0283367 | A1 | 10/2017 | Ansell et al. |
| 2018/0065920 | A1 | 3/2018 | Manoharan et al. |
| 2018/0326070 | A1 | 11/2018 | Manoharan et al. |
| 2019/0099493 | A1 | 4/2019 | Manoharan et al. |
| 2019/0184018 | A1 | 6/2019 | Manoharan et al. |
| 2019/0270697 | A1 | 9/2019 | Ansell et al. |
| 2019/0292130 | A1 | 9/2019 | Peer et al. |
| 2019/0314292 | A1 | 10/2019 | Benenato et al. |
| 2019/0314524 | A1 | 10/2019 | Ansell et al. |
| 2019/0380963 | A1 | 12/2019 | Chen et al. |
| 2020/0113830 | A1 | 4/2020 | Geall et al. |
| 2020/0121809 | A1 | 4/2020 | Hope et al. |
| 2020/0297853 | A1 | 9/2020 | Manoharan et al. |
| 2021/0107861 | A1 | 4/2021 | Ansell et al. |
| 2021/0154148 | A1 | 5/2021 | Benenato et al. |
| 2022/0008541 | A1 | 1/2022 | Manoharan et al. |
| 2022/0072155 | A1 | 3/2022 | Ansell et al. |
| 2022/0143189 | A1 | 5/2022 | Manoharan et al. |

FOREIGN PATENT DOCUMENTS

| | | | |
|---|---|---|---|
| CN | 102884041 | A | 1/2013 |
| CN | 103096875 | A | 5/2013 |
| CN | 103881084 | A | 6/2014 |
| CN | 103974719 | A | 8/2014 |
| CN | 104159615 | A | 11/2014 |
| CN | 104352440 | A | 2/2015 |
| CN | 104530413 | A | 4/2015 |
| CN | 104530415 | A | 4/2015 |
| CN | 104530417 | A | 4/2015 |
| CN | 106795096 | A | 5/2017 |
| CN | 108368028 | A | 8/2018 |
| CN | 110167922 | A | 8/2019 |
| CN | 110520409 | A | 11/2019 |
| CN | 113402405 | A | 9/2021 |
| EP | 4 186 888 | A1 | 5/2023 |
| JP | S59-70652 | A | 4/1984 |
| JP | 2020-514366 | A | 5/2020 |
| JP | 7167049 | B2 | 11/2022 |
| JP | 2023-021468 | A | 2/2023 |
| KR | 10-2019-0132405 | A | 11/2019 |
| WO | 98/45394 | A2 | 10/1998 |
| WO | 2016/050209 | A1 | 4/2016 |
| WO | 2017/100744 | A1 | 6/2017 |
| WO | 2017/177869 | A1 | 10/2017 |
| WO | 2018/081480 | A1 | 5/2018 |
| WO | 2018/170306 | A1 | 9/2018 |
| WO | 2018/232120 | A1 | 12/2018 |
| WO | 2020/061284 | A1 | 3/2020 |
| WO | 2020/072605 | A1 | 4/2020 |
| WO | 2021/026358 | A1 | 2/2021 |
| WO | 2021/055835 | A1 | 3/2021 |

OTHER PUBLICATIONS

Jul. 4, 2022 International Search Report issued in International Patent Application No. PCT/CN2022/085526.

Hua Zhang et al. "Highly Efficient Synthesis of Monodisperse Poly(Ethylene Glycols) and Derivatives Through Macrocyclization of Oligo(Ethylene Glycols)". Angewandte Chemie International Edition, 2015, vol. 54, pp. 3763-3767.

Alister C. French et al. "High-Purity Discrete Peg-Oligomer Crystals Allow Structural Insight". Angewandte Chemie, 2009, vol. 121, pp. 1274-1278.

Youngkyu Chang et al. "Amphiphilic Linear Peo-Dendritic Carbosilane Block Copolymers". Macromolecules, 2000, vol. 33, pp. 4496-4500.

Stephen P. Povoski et al. "Single Molecular Weight Discrete Peg Compounds: Emerging Roles in Molecular Diagnostics, Imaging and Therapeutics". Expert Reviews, 2013, vol. 13, No. 4, pp. 315-319.

Myung Sun Kim et al. "Synthesis and Characterization of Monodisperse Poly(Ethylene Glycol)-Conjugated Collagen Pentapeptides With Collagen Biosynthesis-Stimulating Activity". Bioorganic & Medicinal Chemistry Letters, 2015, vol. 25, pp. 38-42.

Saleh A. Ahmed et al. "Synthesis of Oligo(Ethylene Glycol) Toward 44-MER". Journal of Organic Chemistry, 2006, vol. 71, pp. 9884-9886.

Krzysztof Maranski et al. "Synthesis of Poly(Ethylene Oxide) Approaching Monodispersity". Angewandte Chemie, International Edition, 2014, vol. 53, pp. 6411-6413.

Oana M. Martin et al. "Synthesis and Ph-Dependent Self-Assembly of Semifluorinated Calix[4] Arenes". Tetrahedron, 2007, vol. 63, pp. 5539-5547.

Xi Wang et al. "Vesicle Aggregation by Multivalent Ligands: Relating Crosslinking Ability to Surface Affinity". Organic & Biomolecular Chemistry, 2007, vol. 5, pp. 2498-2505.

Jan. 5, 2022 Office Action issued in Chinese Patent Application No. 202110839008.7.

U.S. Appl. No. 18/284,762, filed Sep. 28, 2023 in the name of Wengui Weng et al.

U.S. Appl. No. 18/284,740, filed Sep. 28, 2023 in the name of Wengui Weng et al.

Jul. 25, 2022 International Search Report issued in International Patent Application No. PCT/CN2022/085528.

* cited by examiner

CATIONIC LIPID, LIPOSOME CONTAINING CATIONIC LIPID, AND NUCLEIC-ACID PHARMACEUTICAL COMPOSITION CONTAINING LIPOSOME AND FORMULATION AND APPLICATION THEREOF

CROSS-REFERENCE TO RELATED APPLICATIONS

This application is a U.S. National Phase Application of International Application No. PCT/CN2022/084775, filed Apr. 1, 2022 which claims priority to Chinese Application Nos. 202110379685.5, filed Apr. 8, 2021 and 202110839008.7, filed Jul. 23, 2021.

TECHNICAL FIELD

The present invention relates to the field of drug delivery, specifically to a cationic lipid as pharmaceutical carrier, in particular to a cationic lipid branched via nitrogen, liposomes containing the lipid, nucleic acid pharmaceutical compositions containing the liposome, formulations of the compositions and application thereof.

BACKGROUND OF THE INVENTION

Liposome is a microvesicle formed by encapsulating drugs in the lipid bilayer. Liposomal nanoparticle contains liposomes and nucleic acid drugs, which is similar in structure to biofilm, and is a biocompatible and non-toxic nanomaterial. Liposome can encapsulate water-soluble and liposoluble drugs, with advantages such as reducing drug dose, sustained release, targeted drug release and protecting encapsulated nucleic acids from degradation and clearance in serum. In addition, nanoliposome is also an excellent antigen carrier, which can not only encapsulate a series of antigens with different physicochemical properties and immune adjuvants, protect protein polypeptide antigens from degradation, but also promote the phagocytosis and presentation of antigen-presenting cells to antigen, thus enhancing the specific immune response of the body. Therefore, liposomal nanoparticles are widely used in the field of drug delivery.

Based on the aforementioned advantages, liposomal nanoparticle, as a new type of vaccine vector, has attracted wide attention. Liposomal nanoparticles are gradually used in the development of antiviral vaccines, antibacterial vaccines, antiparasitic vaccines, antitumor vaccines, and so on. Neutral liposomes and cationic liposomes with the surface carrying positive charges are the most commonly used nano-sized vaccine vectors. Cationic liposomes are not only excellent protein/peptide antigen carriers, but also new immunological adjuvants, which can directly activate antigen-presenting cells and enhance the immune response induced by vaccines. Therefore, cationic liposomes are widely used for encapsulating and transporting nucleic acid drugs in the field of vaccine.

The process of encapsulating and transporting nucleic acid drugs by cationic liposomes is as follows: (i) cationic liposome-nucleic acid drug complex forms via electrostatic interaction between positively charged cationic lipids and negatively charged nucleic acids; (ii) electrostatic interaction between the positively charged liposome and the negatively charged cell membrane promotes the adsorption of cationic liposome-nucleic acid drug complexes to the cell surface, followed by endocytosis and endosome formation; (iii) movement of negatively charged lipids from the outer leaflet to the inner leaflet of endosomal membrane is electrostatically promoted due to the presence of cationic lipids inside the cavity of endosome, and thus neutral ion pairs are formed, followed by the nucleic acid drugs detaching from cationic liposomes and entering the cytoplasm; (iv) nucleic acid drugs are transfected into cells and perform the corresponding functions within the cell. Cationic liposomes play an important role in the whole process of nucleic acid drugs being delivered into cells, and nucleic acid molecules expressing pathogens (e.g., bacteria and viruses), specific peptides or protein (antigen) fragments of tumor antigens in vivo and finally stimulating specific immune responses.

Cationic liposomes are usually composed of cationic lipids, neutral lipids, steroid lipids and PEGylated lipids under appropriate conditions. Cationic lipids and nucleic acids are electrostatically bound together, while co-lipids (neutral lipids and steroid lipids) play a role in preventing lipid oxidation, connecting ligands to the surface of liposomes, or reducing the aggregation of lipid particles. Cationic lipids, generally amphiphilic molecules, have a lipophilic region containing one or more hydrocarbon groups and a hydrophilic region containing at least one positively charged polar headgroup. Cationic lipids and nucleic acids or other giant molecules form a complex bearing overall positive charge, while the surface of cell membrane is overall negatively charged, which makes it easy for nucleic acids and other giant molecules to enter the cytoplasm through the protoplasmic membrane of cells, thus improving the transport efficiency of nucleic acid drugs.

Although cationic lipids have made the latest progress in drug delivery, there is still a need for improved cationic lipids that are suitable for regular therapeutic uses in this field.

SUMMARY OF THE INVENTION

The invention provides novel cationic lipids, cationic liposomes containing the lipids, nucleic acid pharmaceutical compositions containing the liposomes and formulations thereof.

The formulations of cationic liposome-nucleic acid pharmaceutical compositions could deliver nucleic acid drugs into cells, improve the transport efficiency of nucleic acid drugs, thereby improving the treatment effect of nucleic acid drugs.

The above-described purposes of this invention can be realized via embodiments below.

In one embodiment:

The cationic lipid is represented by the following general formula (1):

(1)

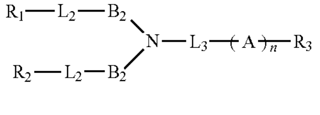

wherein, N is the nitrogen-atom branching center;

wherein, $L_1$ and $L_2$ are each independently a linking bond or a divalent linking group, said divalent linking group selected from the group consisting of $-OC(=O)-$, $-C(=O)O-$, $-OC(=O)O-$, $-C(=O)-$, $-O-$, $-O(CR_cR_c)_sO-$, $-S-$, $-C(=O)S-$, $-SC(=O)-$, $-NR_cC(=O)-$, $-C(=O)NR_c-$, $-NR_cC(=O)NR_c-$, $-OC(=O)NR_c-$, $-NR_cC(=O)O-$, —SC(=O)$NR_c$—, and —$NR_c$C(=O)S—; wherein, $R_c$ is, at each occurrence, independently a hydrogen atom or a $C_{1-12}$ alkyl group; wherein s is 2, 3 or 4;

wherein, $L_3$ is a linking bond selected from the group consisting of -$L_4$-, —Z-$L_4$-, -$L_4$-Z—, —Z-$L_4$-Z—, -$L_4$-Z-$L_5$-, —Z-$L_4$-Z-$L_5$-, and -$L_4$-Z-$L_5$-Z—; said $L_4$ and $L_5$ are carbon-chain linking groups, each independently represented by —$(CR_aR_b)_t$—$(CR_aR_b)_o$—$(CR_aR_b)_p$—; wherein, t, o, and p are each independently an integer from 0 to 12, said t, o, and p not being 0 simultaneously; $R_a$ and $R_b$ are, at each occurrence, independently a hydrogen atom or a $C_{1-6}$ alkyl group; said Z is, at each occurrence, independently selected from the group consisting of —C(=O)—, —OC(=O)—, —C(=O)O—, —OC(=O)O—, —O—, —S—, —C(=O)S—, —SC(=O)—, —$NR_c$, —C(=O)—, —C(=O)$NR_c$—, —$NR_c$C(=O)$NR_c$—, —OC(=O)$NR_c$—, —$NR_c$C(=O)O—, —SC(=O)$NR_c$—, —$NR_c$C(=O)S—, and

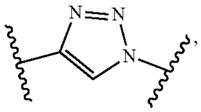 [SMILES: *c1cn(*)nn1], wherein $R_c$ is, at each occurrence, independently a hydrogen atom or a $C_{1-12}$ alkyl group;

$B_1$ and $B_2$ are each independently a linking bond or a $C_{1-30}$ alkylene group;

$R_1$ and $R_2$ are each independently a $C_{5-30}$ aliphatic group or

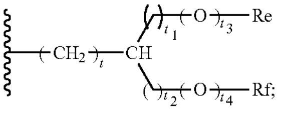;

wherein, t is an integer from 0 to 12; $t_1$ and $t_2$ are each independently an integer from 0 to 5; $t_3$ and $t_4$ are each independently 0 or 1, not being 0 simultaneously; $R_e$ and $R_f$ are each independently selected from the group consisting of a $C_{1-15}$ alkyl group, a $C_{2-15}$ alkenyl group, and a $C_{2-15}$ alkynyl group;

$R_3$ is selected from the group consisting of a hydrogen atom, —$R_d$, —$OR_d$, —$NR_dR_d$, —$SR_d$, —C(=O)$R_d$, —C(=O)$OR_d$, —OC(=O)$R_d$, —OC(=O)$OR_d$, and

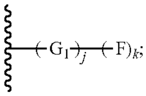;

wherein, $R_d$ is, at each occurrence, independently a $C_{1-12}$ alkyl group, wherein $G_1$ is a terminal branching group with the valence of k+1, wherein j is 0 or 1, and wherein F contains functional group $R_{01}$; when j is 0, $G_1$ is absent; when j is 1, $G_1$ protrudes F with the number of k, wherein k is an integer from 2 to 8;

A is selected from the group consisting of —$(CR_aR_b)_s$O—, —O$(CR_aR_b)_s$—, —$(CR_aR_b)_s$S—, —S$(CR_aR_b)_s$—, —$(CR_aR_b)_s$O$(CR_aR_b)_s$S—, —$(CR_aR_b)_s$S$(CR_aR_b)_s$O—, —$(CR_aR_b)_s$$NR_c$$(CR_aR_b)_s$S—, —$(CR_aR_b)_s$S$(CR_aR_b)_s$$NR_c$—, —$(CR_aR_b)_s$$NR_c$$(CR_aR_b)_s$O—, and —$(CR_aR_b)_s$O$(CR_aR_b)_s$$NR_c$—, wherein s is 2, 3 or 4, and wherein $R_a$ and $R_b$ are, at each occurrence, independently a hydrogen atom or a $C_{1-12}$ alkyl group;

when A is —$(CR_aR_b)_s$O— or —O$(CR_aR_b)_s$—, n is an integer from 2 to 6; when A is not either —$(CR_aR_b)_s$O— or —O$(CR_aR_b)_s$—, n is an integer from 1 to 6;

said alkyl group, alkylene group, alkoxy group, and aliphatic hydrocarbon group are each independently substituted or unsubstituted.

In another embodiment:

Provided herein is a cationic liposome containing cationic lipids represented by general formula (1).

In another embodiment:

Provided herein is a liposome-nucleic acid pharmaceutical composition containing cationic liposomes and drugs, said cationic liposomes containing cationic lipids represented by general formula (1) and nucleic acid drugs.

In another embodiment:

Provided herein is a formulation of liposome-nucleic acid pharmaceutical compositions, which contains the aforementioned liposome-nucleic acid pharmaceutical composition and pharmaceutically acceptable diluents or excipients.

Compared with the Prior Art, the Present Invention Brings the Following Beneficial Effects:

The novel cationic lipid of the present invention is branched via nitrogen, wherein the nitrogen center can be easily protonated under physiological pH to produce partial positive charge, and thus the lipid is capable of binding with negatively charged nucleic acids, improving the loading efficiency of nucleic acid drugs.

The surface of cationic liposome-nucleic acid pharmaceutical composition prepared with the novel cationic lipid in the present invention is positively charged, which promotes the adsorption to negatively charged cell surfaces through electrostatic interaction. The composition enters cells via endocytosis followed by endosome formation. The hydroxyl groups, amino groups, carboxyl groups, etc., at the terminal of the cationic lipid in the present invention can be easily protonated under acidic conditions. The cationic lipid in the present invention bears partial positive charge after being protonated in acidic endosomes, and electrostatically interacts with negatively charged lipids in endosomal membrane, resulting in the negatively charged lipids moving from the outside to the inner cavity of endosome and consequently forming neutral ion pairs consisting also the positively charged lipids. Eventually, drugs are delivered to the cytoplasm after detaching from cationic liposomes, thereby improving the transformation efficiency of nucleic acids.

The cationic liposome-nucleic acid pharmaceutical composition prepared with the novel cationic lipid in the present invention has high stability in serum, high gene complexation ability, high biocompatibility, and high gene transfection efficiency, which is conducive to improving the therapeutic effect of gene drugs, especially nucleic acid drugs.

The terminal of the novel cationic lipid in the present invention can also contain fluorescent groups or targeting groups; accordingly, the cationic liposome-nucleic acid pharmaceutical compositions containing the novel cationic lipid can also have fluorescence or targeting function, further improving the genetic therapeutic and/or diagnostic effects of nucleic acid drugs.

DETAILED DESCRIPTION OF THE INVENTION

Unless otherwise indicated, the related terms in the present invention are defined as follows.

In the present invention and unless otherwise specified, a structure with isomers may refer to any form of the isomers. For example, when cis- and trans-isomers are present, it can refer to either a cis-structure or a trans-structure; when E and Z isomers are present, it can refer to either an (E)-structure or a (Z)-structure; and when optical rotation properties are present, it can refer to either laevoisomer or dextroisomer.

In the present invention, a numerical interval can be marked either by a dash (e.g., 1-6) or by a wavy line (e.g., 1~6). In the present invention and unless otherwise specified, an integer interval represents the group of all integers between endpoints included. For example, the integer interval 1 to 6 represents the group composed of 1, 2, 3, 4, 5, and 6. The numerical interval in the present invention includes but is not limited to the integer interval, the non-integer interval, the percentage interval, and the fraction interval; unless otherwise specified, all of the foregoing numerical intervals include two endpoints.

In the present invention, "about" or "approximately" followed by a numerical value generally suggests a ±10% numerical range; in some cases, the numerical range can be increased to a greater one (e.g., ±15%) that is no more than ±20%. For example, when the molar percentage of steroid lipids among the total lipids in a solution containing solvent is about 40%, it can be considered that, generally, the molar percentage of steroid lipids is 30%-50%.

The terms "include", "contain", and similar expressions in the present invention shall be interpreted, unless otherwise specified, as "including but not limited to", "include but are not limited to", or "includes but is not limited to", etc., in the description and claims with openness and inclusiveness.

In the present invention, when two or more objects are "each independently preferably" selected from multiple levels of preferable options, the objects are not necessarily selected from preferable options of the same level. It is allowed that one is selected from a wider range of options while another one is selected from a narrower range of options. It is also allowed that one is selected from the maximum range of options while another is selected from any allowable options. It is also allowed that the objects are selected from preferable options of the same level. For example, "$R_1$ and $R_2$ are each independently preferably a linear alkyl group, more preferably a $C_{1-25}$ linear alkyl group, more preferably a $C_{1-17}$ linear alkyl group" includes but is not limited to one of the following situations, that $R_1$ is a $C_{1-25}$ linear alkyl group while $R_2$ is a $C_{1-17}$ linear alkyl group, that $R_1$ is a $C_{1-17}$ linear alkyl group while $R_2$ is a $C_{1-25}$ linear alkyl group, that $R_1$ and $R_2$ are both $C_{1-25}$ linear alkyl groups, and that $R_1$ and $R_2$ are both $C_{1-17}$ linear alkyl groups.

In the present invention and unless otherwise specified, for divalent linking groups e.g., hydrocarbylene group, alkylene group, arylene group, amide bond, and the like, either one of the two connection ends could be chosen to be connected to another group. For example, when an amide bond serves as a divalent linking group between C—$CH_2CH_2$— and —$CH_2$-D, both C—$CH_2CH_2$—C(=O)NH—$CH_2$-D and C—$CH_2CH_2$—NHC(=O)—$CH_2$-D are allowable.

In the present invention, when distinguishing the terminal groups from the substituents of a linking group becomes questionable, "∿∿" indicate the connection location between the linking group and the other group. For example, in structural formulas

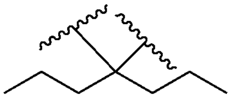

and

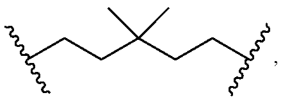

,

∿∿ are used to indicate the connection locations between the divalent linking groups and the other groups; the two structural formulas mentioned above represent —CH($CH_2CH_2CH_3$)$_2$— and —$CH_2CH_2CH(CH_3)_2$—$CH_2CH_2$—, respectively.

In the present invention, a number or a numerical interval written in the subscript of "C" can be used to indicate the number of carbon atoms of a group. For example, a $C_{1-12}$ group is a group having 1 to 12 carbon atoms; $C_{1-30}$ indicates "having 1 to 30 carbon atoms". "Substituted $C_{1-12}$ alkyl group" means a $C_{1-12}$ alkyl group with one or more hydrogen atoms being substituted. "$C_{1-12}$ substituted alkyl group" means an alkyl group with one or more hydrogen atoms being substituted has 1 to 12 carbon atoms remaining. For example, when a group can be selected from $C_{1-12}$ alkylene groups, it can be any alkylene group with the number of carbon atoms in the range indicated by the subscript, that is, the group can be selected from the group consisting of $C_1$, $C_2$, $C_3$, $C_4$, $C_5$, $C_6$, $C_7$, $C_8$, $C_9$, $C_{10}$, $C_{11}$, and $C_{12}$ alkylene groups. In the present invention and unless otherwise specified, a subscript being a numerical interval indicates that the subscript can be any integer within the interval which includes two endpoints.

In the present invention, heteroatoms are not particularly limited, including but not limited to O, S, N, P, Si, F, Cl, Br, I, B, etc.

In the present invention, the heteroatom used for substitution is referred to as "substituent atom", and the group used for substitution is referred to as "substituent group".

In the present invention, a "substituted" group indicates that at least one hydrogen atom of the group (any aforementioned group, unless otherwise specified, e.g., aliphatic groups, hydrocarbon groups, alkyl groups, or alkylene groups) is replaced by a substituent, said substituent including but not limited to halogen atom (F, Cl, Br, or I), oxo group (=O), hydroxyl group (—OH), hydrocarbyloxy group (—$OR_d$, wherein $R_d$ is a $C_{1-12}$ alkyl group), carboxyl group (—COOH), amine group (—$NR_cR_c$, wherein both $R_c$ are each independently a hydrogen atom or a $C_{1-12}$ alkyl group), $C_{1-12}$ alkyl group, and cycloalkyl group. In some embodiments, said substituent group is a $C_{1-12}$ alkyl group. In another embodiment, said substituent is a cycloalkyl group. In another embodiment, said substituent is a halo group, e.g., fluoro. In another embodiment, said substituent is an oxo group. In another embodiment, said substituent is a hydroxyl group. In another embodiment, said substituent is an alkoxy group. In another embodiment, said substituent is a carboxyl group. In another embodiment, said substituent is an amine group.

In the present invention, "atom spacing" refers to the distance measured in terms of the number of main-chain atoms, taking into account no pendant groups or side chains, which is usually the shortest atomic distance. Atom spacing can be used to represent the length of a linking group. For example, the atom spacing between A and B in A-CO—NH—B is 2, that in A-p-Ph-$CH_2$—B is 5 (wherein p-Ph is p-phenylene), and that in A-CH($CH_2CH_2CH_2CH_3$)—B is 1.

The "main-chain atoms" accounting for the atom spacing can be only non-hydrogen atoms. As for divalent linking groups containing ring structures, the atom spacing involves particular ring segments, and the smallest number of atoms calculated should be adopted. For example, the atom spacing of p-phenylene, namely 1,4-phenylene, is 4, the atom spacing of m-phenylene is 3, and the atom spacing of o-phenylene is 2. For another example, the atom spacing of $—CH_2—$, $—CH(CH_3)—$, $—C(CH_3)_2—$, $—CH(CH_2Ph)_2$-, and $—C(CH_2OX)—$ are all 1.

In the present invention, "carbon chain linker" or "carbon chain linking group" refers to the linking group whose main-chain atoms are all carbon, allowing heteroatoms or groups containing heteroatoms in the side chains which substitute for hydrogen atoms connected to main-chain carbon atoms. When a "main-chain atom" is a heteroatom, it can also be called "main-chain heteroatom". For example, A-S—$CH_2$—B, A-O—$CH_2$—B, and

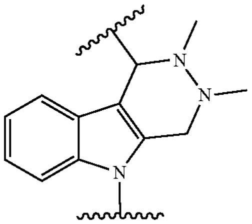 [SMILES: *C1c2c(n(*)c3ccccc23)CN(C)N1C]

(wherein the atom spacing is 4) are considered to contain main-chain heteroatoms. Carbon chain linkers include hydrocarbylene groups and those whose pendant groups contain heteroatoms; said carbon chain linkers whose pendant groups contain heteroatoms include but are not limited to oxo group (═O), thioxo group (═S), imino group (═N—R, wherein R is hydrogen or an organic group, and wherein the nitrogen is connected to the main-chain carbon through a carbon-nitrogen double bond), oxa-hydrocarbon group that forms ether bond, thia-hydrocarbon group that forms thioether bond, and aza-hydrocarbon group in the form of tertiary amino group, etc. The main chain of the "carbon chain linker" is entirely composed of carbon atoms, and the pendant groups of the carbon chain are allowed to contain heteroatoms, that is, the main chain is constructed by connecting methylene groups or substituted methylene groups. Said substituted methylene groups can have one monovalent substituent, two monovalent substituents, or one divalent substituent (e.g., a divalent oxygen (═O), a methyleneoxy group ($—CH_2O—$) that forms a three-membered ring

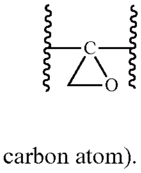

with the main-chain carbon atom). Said substituted methylene groups can have one hydrogen atom being substituted (e.g., $—CH(CH_3)—$), two hydrogen atoms being respectively substituted (e.g., $—(CH_3)C(OCH_3)—$), or two hydrogen atoms being simultaneously substituted (e.g., carbonyl groups, thiocarbonyl groups, —C(═NH)—, and $—C(═N^+H_2)—$), or contain a cyclic pendant group (e.g.,

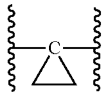

wherein the atom spacing is 1).

In the present invention, secondary amino bonds and hydrazine bonds indicate that both sides of "—NH—" are terminated by hydrocarbylene groups, e.g., $—CH_2—NH—CH_2—$; whereas —C(═O)—NH— is described as an amide bond, instead of containing a secondary amino bond.

In the present invention, a compound or a group can be substituted and heteroatom-containing at the same time, e.g., when a hydrogen atom in a compound or a group is replaced by a nitrobenzene, and when $—CH_2—CH_2—CH_2—$ is replaced by $—CH_2—S—CH(CH_3)—$.

In the present invention, "linking bond" without any atom is only for connection, that is, when a group is denoted as a linking bond, it is regarded as non-existent.

In the present invention, "each independently at each occurrence", "at each occurrence, independently", and similar expressions not only means that different objects of description can each independently be any option from their own given definitions, but also means that the same object at different positions can each independently be any option from its definition; said object including but not limited to the groups mentioned above. For example, in $—Z-L_4-Z—$, provided that "Z is, at each occurrence, independently selected from the group consisting of —C(═O)—, —OC(═O)—, —C(═O)O—, —OC(═O)O—, —O—, —S—, —C(═O)S—, —SC(═O)—, $—NR_cC(═O)—$, $—C(═O)NR_c—$, $—NR_cC(═O)NR_c—$, $—OC(═O)NR_c—$, $—NR_cC(═O)O—$, $—SC(═O)NR_c—$, $—NR_cC(═O)S—$, and

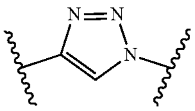

wherein $R_c$ is, at each occurrence, independently a hydrogen atom or a $C_{1-12}$ alkyl group", two Z groups in "$—Z-L_4-Z—$" can be the same or different, and two $R_c$ groups in "$—NR_cC(═O)NR_c—$" can be the same or different, each independently a hydrogen atom or a $C_{1-12}$ alkyl group.

In the present invention, "group" contains at least one atom, referring to the radical remaining of a compound losing one or more atoms. With respect to a compound, the remaining group formed by removal of other groups is also denoted as "residue". The valence of groups is not particularly limited, said groups include monovalent group, divalent group, trivalent group, tetravalent group, . . . , hectovalent group, etc. Wherein, groups with valence being equal to or greater than two are collectively defined as linking groups. A linking group can also contain only one atom, such as oxo group and thio group.

In the present invention, "hydrocarbons" refer to a class of compounds that contain only carbon atoms and hydrogen atoms.

In the present invention, hydrocarbons are classified into aliphatic hydrocarbons and aromatic hydrocarbons (also referred to as arenes, aromatics, or aryl hydrocarbons) in terms of the type of hydrocarbon group. Hydrocarbons containing neither phenyl rings nor hydrocarbyl-substituted phenyl rings are defined as aliphatic hydrocarbons. Hydrocarbons containing at least one phenyl ring or hydrocarbyl-substituted phenyl ring are defined as aromatic hydrocarbons. An aromatic hydrocarbon can contain one or more aliphatic hydrocarbyl groups, such as toluene, diphenylmethane, 2,3-dihydroindene, etc.

In the present invention, hydrocarbons are classified into saturated hydrocarbons and unsaturated hydrocarbons in terms of saturation or unsaturation. All aromatic hydrocarbons are unsaturated hydrocarbons. Saturated aliphatic hydrocarbons are also termed alkanes. The degree of unsaturation of unsaturated aliphatic hydrocarbons is not particularly limited. For example, unsaturated aliphatic hydrocarbons include but are not limited to alkenes containing carbon-carbon double bonds, alkynes containing carbon-carbon triple bonds, dienes containing two carbon-carbon double bonds, and the like. When the aliphatic moieties of aromatic hydrocarbons are saturated, said aromatic hydrocarbons are also termed aralkanes, such as toluene.

In the present invention, the structures of hydrocarbons are not particularly limited, including linear (straight-chain) structures without pendant groups, branched structures with pendant groups, ring-containing structures, dendritic structures, comb structures, hyperbranched structures, etc. Unless otherwise specified, preferable structures include linear structures without pendant groups, branched structures with pendant groups, and ring-containing structures, corresponding to linear hydrocarbons (acyclic unbranched hydrocarbons), branched hydrocarbons and cyclic hydrocarbons (cyclohydrocarbons), respectively. Wherein, hydrocarbons that contain no rings are termed open-chain hydrocarbons (acyclic hydrocarbons), including but not limited to linear structures without pendant groups, and branched structures with pendant groups. Open-chain hydrocarbons belong to aliphatic hydrocarbons. Therefore, linear hydrocarbons are also referred to as linear aliphatic hydrocarbons, and branched hydrocarbons are also referred to as branched aliphatic hydrocarbons.

In the present invention, hydrocarbons with any carbon atom replaced by heteroatom are generally referred to as heterosubstituted hydrocarbons (heterohydrocarbons).

In the present invention, aliphatic-derived heterohydrocarbons refer to heterohydrocarbons that derived from aliphatic hydrocarbons, including aliphatic-derived heterocyclic hydrocarbons (aliphatic-derived heterocyclohydrocarbons or heterosubstituted aliphatic cyclohydrocarbons) and aliphatic-derived open-chain heterosubstituted hydrocarbons (heterosubstituted aliphatic open-chain hydrocarbons). Saturated aliphatic-derived heterohydrocarbons are also termed heteroalkanes.

In the present invention, "hydrocarbon group" refers to the residue of a hydrocarbon molecule with at least one hydrogen atom being removed. According to the number of removed hydrogen, hydrocarbon groups can be classified into monovalent hydrocarbon groups (with one hydrogen atom being removed; also termed as hydrocarbyl groups), divalent hydrocarbon groups (with two hydrogen atoms being removed; also termed as hydrocarbylene groups), trivalent hydrocarbon groups (with three hydrogen atoms being removed), and the like. Accordingly, a hydrocarbon group of valence n is that with n hydrogen atoms being removed, compared with the original molecule. Unless otherwise specified, hydrocarbon groups in the present invention refer to monovalent hydrocarbon groups. In the present invention, the sources of hydrocarbon groups are not particularly limited; e.g., they can be derived from aliphatic hydrocarbons or aromatic hydrocarbons, from saturated hydrocarbons or unsaturated hydrocarbons, from linear hydrocarbons, branched hydrocarbons or cyclic hydrocarbons, or from hydrocarbons or heterohydrocarbons, etc. According to the degree of saturation, hydrocarbon groups can be derived from alkanes, alkenes, alkynes, dienes, etc. With respect to cyclic hydrocarbons, hydrocarbon groups can be derived from alicyclic hydrocarbons or aromatic hydrocarbons, or from monocyclic hydrocarbons or polycyclic hydrocarbons. With respect to heterocyclic hydrocarbons, hydrocarbon groups can be derived from aliphatic-derived heterocyclic hydrocarbons or aromatic-derived heterocyclic hydrocarbons.

In the present invention, "aliphatic group" refers to the residue of an aliphatic hydrocarbon molecule with at least one hydrogen atom being removed. Unless otherwise specified, aliphatic groups refer to monovalent hydrocarbon groups. Aliphatic group includes saturated aliphatic groups and unsaturated aliphatic groups.

In the present invention, "alkyl group" refers to hydrocarbon groups derived from alkanes, unless otherwise specified, with any hydrogen atom removed; said alkyl group can be linear or branched, substituted or unsubstituted. Specific examples include that a propyl group refers to either a 1-propyl group or an isopropyl group, and that a propylene group can refer to a 1,3-propylene group, a 1,2-propylene group, or an isopropylidene group.

In the present invention, "unsaturated hydrocarbon group" refers to the hydrocarbon group derived from an unsaturated hydrocarbon losing one or more hydrogen atoms. The hydrocarbon groups formed by removing hydrogen atoms bonded to unsaturated carbon atoms of unsaturated hydrocarbons, can include alkenyl groups, alkynyl groups, dienyl groups, and the like, e.g., propenyl group and propynyl group. According to the type of unsaturated bond, the hydrocarbon groups formed by removing hydrogen atoms bonded to saturated carbon atoms of unsaturated hydrocarbons, include alkenyl-hydrocarbyl groups, alkynyl-hydrocarbyl groups, dienyl-hydrocarbyl groups, and the like, such as allyl group and propargyl group.

In the present invention, "alkenyl group" refers to a substituted or unsubstituted alkenyl group with linear structure or branched structure, containing two or more carbon atoms (e.g., 2, 3, 4, 5, . . . , 20 or more carbon atoms) and at least one carbon-carbon double bond. "$C_{2-15}$ alkenyl group" refers to a substituted or unsubstituted alkenyl group with linear structure or branched structure, containing 2 to 15 carbon atoms and at least one carbon-carbon double bond, that is, an alkenyl group can contain one, two, three, four, or more carbon-carbon double bonds. Unless otherwise specified, alkenyl groups include substituted and unsubstituted alkenyl groups in the present invention.

In the present invention, "alkynyl group" refers to an optionally substituted hydrocarbon with linear structure or branched structure, containing two or more carbon atoms (such as 2, 3, 4, 5, . . . , 20, or more carbon atoms) and at least one carbon-carbon triple bond. "$C_{2-15}$ alkynyl group" refers to a substituted or unsubstituted alkynyl groups with linear structure or branched structure, containing 2 to 15 carbon atoms and at least one carbon-carbon triple bond, that is, an alkynyl group can contain one, two, three, four, or more carbon-carbon triple bonds. Unless otherwise specified, alkynyl groups include substituted and unsubstituted alkynyl groups in the present invention.

In the present invention, "molecular weight" is synonymous with relative molecular mass, referring to the mass of a given molecule. The "average molecular weight" of a compound represented by a general formula refers to the molecular mass of the compound in macroscopic matter, and unless otherwise specified, also refers to the "number average molecular weight" ($M_n$). The number average molecular weight can be used to describe the molecular weight of blocks or substances being polydisperse or monodisperse. The measuring unit of "molecular weight" and "average molecular weight" is dalton (Da), unless otherwise specified. The molecular weight of polyethylene glycol chain can also be measured in "degree of polymerization" which is, specifically, the number of repeat units (oxyethylene units, i.e., EO units) in the compound molecule. Accordingly, the average and the number average of the number of repeat units can be measured in "average degree of polymerization", preferably in "number average degree of polymerization".

In the present invention, the term "about" before a percentage refers to a range of 0.5%.

In the present invention, the terms "stable" (or "can remain stable") and "degradable" (or "can be degraded") are a pair of opposing concepts.

In the present invention, the term "be degradable or can be degraded" means that a group or a compound can be cleaved into two or more residues via breakage of chemical bonds. If a linking group remains whole, regardless of structural change via chemical reactions, then it still falls into the scope of "stable groups". The conditions to be "degradable" are not particularly limited, which can be either physiological condition in vivo, or simulated physiological environment in vitro, or other conditions, preferably physiological conditions in vivo or simulated physiological environment in vitro. Said physiological conditions are not particularly limited, including but not limited to physiological environments of serum, heart, liver, spleen, lung, kidney, bone, muscle, fat, brain, lymph node, small intestine, gonads, etc., and said physiological environments could be intracellular or in the extracellular matrix, and could be in normal tissues or in pathologic tissues (e.g., tumor, inflamed tissue). Said simulated physiological environment in vitro is not particularly limited, including but not limited to physiological saline, buffer, culture medium, and the like. The rate of degradation is not particularly limited, e.g., rapid degradation via enzymolysis, or slow degradation via physiological hydrolysis, etc. Said physiological conditions in vivo include physiological conditions during treatment, such as ultraviolet radiation, thermal therapy, etc. The conditions to be "degradable" include but are not limited to light illumination, heat, low temperature, enzymatic condition, oxidation-reduction (redox) condition, acidic condition, basic condition, physiological condition, simulated physiological environment in vitro, etc., preferably light illumination, heat, enzymatic condition, oxidation-reduction condition, acidic condition, basic condition, etc. Said "degradable" means that the degradation can occur under the stimulation of any above condition. Said light illumination condition includes but is not limited to visible light, ultraviolet light, infrared light, near-infrared light, mid-infrared light, etc. Said heat condition means a temperature higher than normal physiological temperature, and normally means a temperature higher than 37° C. and also normally below 45° C., preferably below 42° C. Said low temperature refers to the temperature below human physiological temperature, preferably below 25° C., more preferably <10° C., with specific examples such as refrigerated temperature, freezing temperature, liquid nitrogen therapeutic temperature, 2~10° C., 4~8° C., 4° C., 0° C., −20±5° C., etc. Said enzymatic condition is not particularly limited, and all enzymes that can be physiologically generated are incorporated, e.g., peptidases, proteases, and lyases. Said oxidation-reduction condition is not particularly limited, e.g., redox transformation or hydrogenation transformation between a mercapto group and a disulfide bond. Said acidic condition and basic condition mainly refer to the pH conditions of internal body parts such as normal tissues, pathologic tissues, and organs or tissues in the treatment period; for example, stomach is under acidic condition, and tumor location is under acidic condition as well. Said "degradable" means that the degradation can be realized through metabolism (e.g., physiological effect, enzymatic reactions, oxidation-reduction, etc.), microenvironment stimulation in specific areas of the body (e.g., acidic condition and basic condition), or clinical therapeutic stimulation (e.g., light illumination, heat, low temperature), etc. What should be noted is that some conditions in organic chemistry, such as bond cleavage under strong acid, strong base, and high temperature (e.g., above 100° C.), which are extreme with respect to living organism, are not included in the scope of degradable conditions in the present invention. For example, although the ether bond can be cleaved under strong acid conditions (e.g., hydrobromic acid), it is classified as a stable linking group in the present invention.

In the present invention, as long as a linking group can keep existing as a whole linking group (i.e., a linking group which can be stably connected to the adjacent groups in covalent manner), it would be defined as "stable", wherein chemical changes without breaking the wholeness of the linking group are allowed. Said chemical changes are not particularly limited, including but not limited to isomerization, oxidation, reduction, ionization, protonation, deprotonation, substitution, etc. The conditions to be "stable" are not particularly limited, including but not limited to light illumination, heat, low temperature, enzymatic condition, oxidation-reduction, neutral condition, acidic condition, basic condition, physiological condition, simulated physiological environment in vitro, etc., preferably light illumination, heat, enzymatic condition, oxidation-reduction, acidic condition, basic condition, etc. A group or compound being "stable" indicates that the components can remain stably connected in the metabolic cycle in vivo and the molecular weight will not be reduced due to chain cleavage as long as the group or compound maintains integrity, without particular stimulation (e.g., pH condition in specific areas, and light illumination, heat, and low temperature in treatment).

In the present invention, "stable" is not an absolute concept with respect to a particular linking group. For example, an amide bond is much more stable than an ester bond under acidic or basic conditions. Accordingly, "stable" linking groups in the present invention include amide bonds. However, a peptide bond which is an amide-type of bond formed via dehydration condensation of two amino acids that respectively provide an α-carboxyl group and an α-amino group as reactive groups, could also be broken under specific enzymatic conditions, and therefore it can also be classified as a "degradable" linking group. Similarly, carbamate group (urethane group), thiocarbamate group (thiourethane group), and the like, could be either a "stable" linking group or a "degradable" linking group. More generally, urethane groups, thiourethane groups, and the like, tend to degrade slowly, while amide bond other than peptide bond can remain stable in the metabolic cycle in vivo. For another example, common ester bonds will degrade under acidic or basic conditions, while the ester bonds in some special structures will degrade under UV exposure. For another example, even though some chemical bonds can degrade under specific enzymatic conditions, they can still be regard as stable if the circulation in clinical use (e.g., point-of-site administration) does not or basically do not go through the enzymatic conditions.

In order to define more clearly the degradability of compound in the present invention, a criterion for reference is provided, which is, a specific percentage (e.g., 90%) threshold of chemical bonds remaining intact within a limited time interval. Take 90% for example, the percentage usually takes the pharmacokinetic curve as a reference, based on the dose percentage that meets the clinical evaluation criteria. Regarding the intravenous pegylated drugs, for example, when the plasma concentration (calculated by effective drug ingredients, including pegylated drugs and non-pegylated components after degration) is lower than 15% of the initial concentration (or other proportions that are more consistent with the clinical evaluation criteria), the remaining 85% is taken as the base value; if the proportion of a linking group without cleaved chemical bonds exceeds 90%, then the linking group is regarded as a stable group in the present invention; on the contrary, if said 90% is not met, then the linking group belongs to degradable groups. The hydrolytic stabilization and enzymatic degradation reported in the published literature are also included in the present invention. For example, the hydrolysis rate in the process of hydrolytic stabilization reported in the published literature is also included herein, preferably referring to the hydrolysis rate less than 1-2% (generally 2%; mass or molar percentage) per day under physiological conditions. The hydrolysis rate of typical chemical bonds can be found in most standard chemical handbooks In the present invention, "hydroxyl protecting group" includes all the groups that can be used as common hydroxyl protecting groups. Hydroxy protecting group is preferably alkanoyl (e.g., acetyl, butyryl), aromatic alkanoyl (e.g., benzoyl), benzyl, triphenylmethyl, trimethylsilyl, t-butyldimethylsilyl, allyl, acetal, or ketal. Removal of acetyl groups is generally carried out under basic conditions, most commonly by the ammonolysis with $NH_3$/MeOH or by the methanolysis catalyzed by methanol anion. The benzyl group can be easily removed via palladium-catalyzed hydrogenolysis in neutral solution at room temperature, or via reduction reaction by sodium metal in ethanol or liquid ammonia. The triphenylmethyl group is generally removed via catalytic hydrogenolysis. The trimethylsilyl groups are generally removed using reagents containing fluoride ions (e.g., tetrabutylammonium fluoride/anhydrous THF, etc.). The t-butyldimethylsilyl ether is relatively stable, which can withstand ester hydrolysis conditions with alcoholic potassium hydroxide and mild reduction conditions (e.g., $Zn/CH_3OH$ and the like), so that it can be removed by fluoride ions (e.g., $Bu_4N^+F^-$) in THE solution or by aqueous acetic acid at room temperature.

In the present invention, "carboxyl protecting group" refers to the protecting group which can be transformed into a carboxyl group via the hydrolysis of itself or the deprotection reaction of a protected carboxyl group. Carboxyl protecting group is preferably selected from the group consisting of an alkyl group (e.g., a methyl group, an ethyl group, and a butyl group) and an aralkyl group (e.g., a benzyl group), and more preferably selected from the group consisting of a butyl group (tBu), a methyl group (Me), and an ethyl group (Et). In the present invention, "protected carboxyl group" refers to the group protected by an appropriate carboxyl protecting group, preferably selected from the group consisting of a methoxycarbonyl group, an ethoxycarbonyl group, a t-butyloxycarbonyl group, and a benzyloxycarbonyl group. Said carboxyl protecting groups can be removed through hydrolysis catalyzed by acids or alkalis, or through pyrolysis reactions occasionally; for example, the t-butyl groups can be removed under mild acidic conditions, and the benzyl group can be removed by hydrogenolysis. The reagent used for removal of carboxyl protecting groups is selected from the group consisting of TFA, $H_2O$, LiOH, NaOH, KOH, MeOH, EtOH, and combinations thereof, preferably selected from the group consisting of the combination of TFA and $H_2O$, the combination of LiOH and MeOH, and the combination of LiOH and EtOH. A protected carboxyl group can undergo deprotection and then produce the corresponding free acid; said deprotection is conducted in the presence of an alkali, and said alkali forms pharmaceutically acceptable salt with said free acid produced via said deprotection.

In the present invention, "amino protecting group" includes all the groups which are used as amino protecting groups generally, such as an aryl $C_{1-6}$ alkyl group, a $C_{1-6}$ alkoxy $C_{1-6}$ alkyl group, a $C_{1-6}$ alkoxycarbonyl group, an aryloxycarbonyl group, a $C_{1-6}$ alkylsulfonyl group, an arylsulfonyl, a silyl group, etc. Amino protecting groups are preferably selected from the group consisting of a t-butoxycarbonyl group (Boc), a p-methoxybenzyloxycarbonyl group (Moz), and a 9-fluorenylmethoxycarbonyl group (Fmoc). The reagent used for removal of amino protecting groups is selected from the group consisting of TFA, $H_2O$, LiOH, NaOH, KOH, MeOH, EtOH, and combinations thereof, preferably selected from the group consisting of the combination of TFA and $H_2O$, the combination of LiOH and MeOH, and the combination of LiOH and EtOH. The reagent used for removal of the protecting group of Boc can be TFA or HCl/EA, preferably TFA. The reagent used for removal of the protecting group of Fmoc can be the solution of 20% piperidine in N,N-dimethylformamide (DMF).

In the present invention, "activation of carboxyl group" refers to the activation of carboxyl groups with carboxyl activating reagent, wherein the activated carboxyl group can promote condensation reactions, for example, by inhibiting the generation of racemic impurities, and by accelerating the reaction rate through catalysis, etc. "Carboxyl activating group" refers to the residue of carboxyl activating reagent. Said carboxyl activating reagent is selected from the group consisting of N-hydroxysuccinimide (NHS), 1-ethyl-3-(3-dimethylaminopropyl)carbodiimide (EDCI), N-hydroxy-5-norbornene-2,3-dicarboximide (HONb), N,N'-dicyclohexylcarbodiimide (DCC), and any combination thereof, preferably selected from the group consisting of combination of NHS/EDCI, NHS/DCC, and HONb/DCC, more preferably the combination of NHS/EDCI.

In the present invention, "cation" refers to the corresponding structure bearing a positive charge, either permanently, or non-permanently but in response to certain conditions such as pH. Therefore, the cations include permanent cations and cationisable compounds, groups, or atoms. Permanent cations refer to the corresponding structures (compounds, groups, or atoms) that bear positive charges under conditions of any pH value or hydrogen ion activity of their environment; typically, the presence of a quaternary nitrogen atom is accompanied by a positive charge. When a compound carries multiple such positive charges, it can be termed permanent cation. Cationisable substance refers to a compound, group, or atom that is positively charged at a lower pH and uncharged at a higher pH of its environment. Moreover, in non-aqueous environments where pH cannot be determined, a cationic compound, group, or atom is positively charged at high hydrogen ion concentration and uncharged at low concentration or activity of hydrogen ions, which depends on the individual properties of the cationisable or polycationisable compound, especially the pKa of the cationisable groups or atoms which are charged or uncharged at the corresponding pH or hydrogen ion concentration. In the diluted aqueous environment, the Henderson-Hasselbalch equation can be used to estimate the fraction of positively charged cationisable compounds, groups or atoms, which is well-known to those skilled in the art. For example, in some embodiments, if a compound or moiety is cationisable, it is preferred that it is positively charged at a pH value of about 1 to 9, preferably 4 to 9, 5 to 8 or even 6 to 8, more preferably of a pH value of or below 9, of or below 8, of or below 7, most preferably at physiological pH values, e.g., about 7.3 to 7.4, i.e. under physiological conditions, particularly under physiological salt conditions of the cell in vivo. In other embodiments, it is preferred that the cationisable compound or moiety is predominantly neutral at physiological pH values, e.g., about 7.0-7.4, but becomes positively charged at lower pH values. In some embodiments, the preferred range of pKa for the cationisable compound or moiety is about 5 to about 7.

In the present invention, "cationic liposome" refers to the liposome which is positively charged or ionizable. Except for the molecules represented by the general formula (1), cationic liposomes include but are not limited to N,N-dioleyl-N,N-dimethylammonium chloride (DODAC), N,N-distearyl-N,N-dimethylammonium bromide (DDAB), 1,2-dioleoyl-3-trimethylammonium-propane (DOTAP), N-[1-(2,3-dioleoyloxy)propyl]-N,N,N-trimethylammonium chloride (DOTMA) 1,2-dioleyloxy-N,N-dimethylaminopropane (DODMA), 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-DMA), 2,2-dilinoleyl-4-(2-dimethylaminoethyl)-[1,3]-dioxolane (DLin-KC2-DMA), and mixtures thereof.

In the present invention, "PEG-lipid" (i.e., PEGylated lipid) refers to the molecules containing both lipid and PEG moieties. Except for the molecules represented by the general formula (2), PEG-lipids include but are not limited to 1,2-dimyristoyl-sn-glycerol methoxypolyethylene glycol (PEG-DMG), 1,2-distearoyl-sn-glycero-3-phosphoethanolamine-N-[amino(polyethylene glycol)](PEG-DSPE), PEG-cholesterol, PEG-diacylglycamide (PEG-DAG), PEG-dialkyloxypropyl (PEG-DAA), specifically including PEG500-dipalmitoylphosphatidylcholine, PEG2000-dipalmitoylphosphatidylcholine, PEG500-distearylphosphatidylethanolamine PEG2000-distearylphosphatidylethanolamine, PEG500-1,2-dioleoylphosphatidylethanolamine, PEG2000-1,2-dioleoylphosphatidylethanolamine, and PEG2000-2,3-distearoylglycerol, etc.

In the present invention, "neutral lipid" refers to any lipid substance which is uncharged or exists in the form of neutral zwitterion at the chosen pH, preferably phospholipid. Neutral lipids include but are not limited to 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanola mine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), dioleoylphosphatidylserine (DOPS), dipalmitoylphosphatidylglycerol (DPPG), palmitoyloleoylphosphatidylethanolamine (POPE), distearoylphosphatidylethanolamine (DSPE), dipalmitoylphosphatidylethanolamine (DPPE), dimyristoylphosphoethanolamine (DMPE), 1-stearoyl-2-oleoyl-phosphatidyethanolamine (SOPE), 1-stearoyl-2-oleoyl-phosphatidylcholine (SOPC), sphingomyelin, phosphatidylcholine, phosphatidylethanolamine, phosphatidylserine, phosphatidylinositol, phosphatidic acid, palmitoyloleoylphosphatidylcholine, lysophosphatidylcholine, lysophosphatidylethanolamine (LPE), and combinations thereof. The neutral lipid can be synthetic or natural.

In the present invention, "steroid lipid" is selected from the group consisting of cholesterol, coprostanol, sitosterol, ergosterol, campesterol, stigmasterol, brassicasterol tomatidine, ursolic acid, α-tocopherol, and mixtures thereof.

In the present invention, "amino acid residue" is an amino acid from which, formally, a hydrogen atom has been removed from an amino group and/or from which, formally, a hydroxy group has been removed from a carboxy group and/or from which, formally, a hydrogen atom has been removed from a sulfydryl group and/or with a protected amino group and/or with a protected carboxyl group and/or with a protected sulfydryl group. Imprecisely, amino acid residue can be described as amino acid. The source of the amino acid in the present invention, unless otherwise specified, is not particularly limited; that is, said amino acid can be either natural or unnatural, or a mixture thereof. The configuration of the amino acid in the present invention is not particularly limited, which could be L-type or D-type, or a mixture thereof.

In the present invention, "functional group source" refers to the structure or molecule having reaction activity or potential reaction activity, photosensitivity or potential photosensitivity, targeting property or potential targeting property. Said "potential" indicates that the structure or molecule can convert to a reactive group through chemical process including but not limited to functional modification (grafting, substitution, etc.), deprotection, salt complexation and decomplexation, ionization, protonation, deprotonation, leaving group transformation, etc., or generate luminescence or targeting property through external stimuli of light illumination, heat, enzymes, specific binding molecules, or microenvironment in vivo, etc. The luminescence is not particularly limited, including but not limited to visible light, fluorescence, phosphorescence, etc.

In the present invention, "variant form" refers to a structure that can be transformed into the target reactive group after any process of chemical change selected from the group consisting of oxidation, reduction, hydration, dehydration, electronic rearrangement, structural rearrangement, salt complexation and decomplexation, ionization, protonation, deprotonation, substitution, deprotection, leaving group transformation, etc.

In the present invention, "variant form of reactive group" refers to a reactive group that remains reactive after at least one process of chemical change selected from oxidation, reduction, hydration, dehydration, electronic rearrangement, structural rearrangement, salt complexation and decomplexation, ionization, protonation, deprotonation, substitution, deprotection, leaving group transformation, etc., or a non-reactive form of protected reactive group.

In the present invention, "micro-modification" refers to a process of chemical modification that can be completed through simple chemical reactions. Said simple chemical reactions mainly include deprotection, salt complexation and decomplexation, ionization, protonation, deprotonation, leaving group transformation, etc. Accordingly, "variant form with micro-modification" refers to a structure that can be transformed into the target reactive group after simple chemical reactions selected from deprotection, salt complexation and decomplexation, ionization, protonation, deprotonation, leaving group transformation, etc., said leaving group transformation including the transformation from the form of ester to the form of acyl chloride.

In the present invention, "adjuvant" or "adjuvant component" is typically a (e.g., pharmacological or immunological) agent or composition that may modify (e.g., enhance) the efficacy of other agents (e.g., drugs or vaccines). Conventionally the term refers in the context of the invention to a compound or composition that serves as a carrier or auxiliary substance for immunogens and/or other pharmaceutically active compounds. It is to be interpreted in a broad sense and refers to a broad spectrum of substances that are able to increase the immunogenicity of antigens incorporated into or co-administered with an adjuvant in question. In the context of the present invention an adjuvant will preferably enhance the specific immunogenic effect of the active agents of the present invention. Typically, "adjuvant" or "adjuvant component" has the same meaning and can be used mutually. Adjuvants may be divided, e.g., into immuno potentiators, antigenic delivery systems or even combinations thereof.

In the present invention, "N/P ratio" refers to molar ratio of nitrogen atoms in cationic lipids to phosphate in nucleic acids.

In the present invention, "nucleic acid" refers to DNA, RNA or their modified form, including purine or pyrimidine bases in DNA (adenine "A", cytosine "C", guanine "G", thymine "T"), and purine or pyrimidine bases in RNA (adenine "A", cytosine "C", guanine "G", uracil "U").

In the present invention, "RNA" refers to ribonucleic acid that may be naturally or non-naturally occurring. For example, an RNA may include modified and/or non-naturally occurring components such as one or more nucleobases, nucleosides, nucleotides, and linkers.

An RNA may include a cap structure, a chain terminating nucleoside, a stem loop, a polyA sequence, and/or a polyadenylation signal. An RNA may have a nucleotide sequence encoding a polypeptide of interest. For example, an RNA may be a messenger RNA (mRNA). Translation of an mRNA encoding a particular polypeptide, for example, in vivo translation of an mRNA inside a mammalian cell, may produce the encoded polypeptide. RNAs may be selected from the non-limiting group consisting of small interfering RNA (siRNA), asymmetrical interfering RNA (aiRNA), microRNA (miRNA), Dicer-substrate RNA (dsRNA), small hairpin RNA (shRNA), mRNA (messenger RNA), single-guiderna RNA (sgRNA), cas9 mRNA, and mixtures thereof.

In the present invention, antisense oligonucleotide and small interfering RNA (siRNA) can inhibit the expression of target gene and target protein in vitro or in vivo.

In the present invention, FLuc mRNA can express luciferase protein which emits bioluminescence in the presence of fluorescein substrate, so FLuc is commonly used in mammalian cell culture to measure gene expression and cell activity.

In the present invention, "inhibiting expression of a target gene" refers to the ability of nucleic acids to silence, reduce or inhibit the expression of a target gene. To examine the extent of gene silencing, a test sample (e.g., a sample of cells in culture expressing the target gene) is contacted with nucleic acids that inhibit the expression of the target gene. The expression of the target gene in the test sample or test animal is compared to expression of the target gene in a control sample (e.g., a sample of cells in culture expressing the target gene) which is not contacted with or administered the nucleic acids. The expression of the target gene in the control sample may be assigned a value of 100%. In particular embodiments, inhibition of expression of a target gene is achieved when the level of target gene expression in the test sample or the test mammal relative to the level of target gene expression in the control sample or the control mammal is about 95%, 90%, 85%, 80%, 75%, 70%, 65%, 60%, 55%, 50%, 45%, 40%, 35%, 30%, 25%, 20%, 15%, 10%, 5%, or 0%.

In the present invention, suitable assays for determining the level of target gene expression include but are not limited to dot blots, northern blots, in situ hybridization, ELISA, immunoprecipitation, enzyme function, and phenotypic assays.

In the present invention, "transfection" refers to the introduction of a species (e.g., an RNA) into a cell. Transfection may occur, for example, in vitro, ex vivo, or in vivo.

In the present invention, "antigen" typically refers to a substance that can be recognized by the immune system, preferably recognized by the adaptive immune system, and trigger an antigen-specific immune response, for example, forming antibodies and/or antigen-specific T cells as a part of the adaptive immune response. Typically, the antigen may be or may contain a peptide or a protein that can be presented to T cells by MHC. In the present invention, the antigen may be a translation product of the provided nucleic acid molecule (preferably mRNA as defined herein). In this context, fragments, variants, and derivatives of peptides and proteins containing at least one epitope are also defined as antigens.

In the present invention, "delivery" refers to delivering an entity to the target, for example, delivering drugs and/or therapeutic agents and/or prophylactic agents to subjects, said subjects are tissues and/or cells of human and/or other animals.

In the present invention, "pharmaceutically acceptable carrier" refers to a diluent, adjuvant, excipient, or vehicle administered together with the therapeutic agent, which is, within the scope of reasonable medical judgement, suitable for contacting with tissues of human and/or other animals without causing excessive toxicity, irritation, allergic reaction, or other problems or complications corresponding to reasonable benefit/risk ratio. Pharmaceutically acceptable carriers that can be used in the pharmaceutical composition in the present invention include but are not limited to sterile liquids, such as water and oil, including those from petroleum, animal, vegetable, or synthesis, e.g., peanut oil, soybean oil, mineral oil, sesame oil, etc. When said pharmaceutical composition is administered intravenously, water is an exemplary carrier. Physiological saline, glucose, and aqueous glycerol solution can also be used as liquid carriers, especially as injection. Suitable pharmaceutical excipients include starch, glucose, lactose, sucrose, gelatin, maltose, chalk, silica gel, sodium stearate, glyceryl monostearate, talc, sodium chloride, defatted milk powder, glycerol, propylene glycol, water, ethanol, etc. Said composition can also contain a small amount of humectant, emulsifier, or pH buffer as needed. Oral preparations can contain standard carriers, such as pharmaceutical grade mannitol, lactose, starch, magnesium stearate, sodium saccharin, cellulose, magnesium carbonate, etc. Specifically, excipients include but are not limited to anti-adherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. More specifically, excipients include but are not limited to butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E (α-tocopherol), vitamin C, and xylitol.

In the present invention, pharmaceutical compositions can act systematically or locally act. For this purpose, they can be administered by appropriate routes such as injection (e.g., intravenous, intraarterial, subcutaneous, intraperitoneal, or intramuscular injection, including instillation) and transdermal delivery, and can also be administered by oral, buccal, transnasal, transmucosal, or topical routes, or in the form of ophthalmic preparation, or by inhalation.

Regarding these routes of administration, the pharmaceutical compositions of the present invention can be administered in suitable dosage forms. Said dosage forms include but are not limited to, tablets, capsules, lozenges, hard sugar agents, powders, sprays, creams, ointments, suppositories, gels, pastes, lotions, aqueous suspensions, injectable solutions, elixirs, and syrups.

In the present invention, vaccines are preventive or therapeutic materials that provide at least one antigen or antigenic function. Antigen or antigenic function can stimulate the body's adaptive immune system to provide an adaptive immune response.

In the present invention, treatment refers to the management and care of patients to resist diseases, obstacles, or symptoms, which is intended to delay the development of diseases, obstacles, or symptoms, reduce or alleviate symptoms and complications, and/or cure or eliminate diseases, obstacles, or symptoms. The patients to be treated are preferably mammals, especially humans.

1.1. The Cationic Lipid, Wherein its Structure is Represented by the Following General Formula (1):

(1)

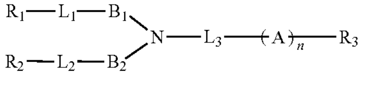

wherein, N is a nitrogen-atom branching center;

wherein, $L_1$ and $L_2$ are each independently a linking bond or a divalent linking group, said divalent linking group is selected from the group consisting of —OC(═O)—, —C(═O)O—, —OC(═O)O—, —C(═O)—, —O—, —O($CR_cR_c$)$_s$O—, —S—, —C(═O)S—, —SC(═O)—, —$NR_c$C(═O)—, —C(═O)$NR_c$—, —$NR_c$C(═O)$NR_c$—, —OC(═O)$NR_c$—, —$NR_c$C(═O)O—, —SC(═O)$NR_c$—, and —$NR_c$C(═O)S—; wherein, $R_c$ is, at each occurrence, independently a hydrogen atom or a $C_{1-12}$ alkyl group; wherein s is 2, 3 or 4;

wherein, $L_3$ is a linking bond, -$L_4$-, —Z-$L_4$-, -$L_4$-Z—, —Z-$L_4$-Z—, -$L_4$-Z-$L_5$-, —Z-$L_4$-Z-$L_5$-, or -$L_4$-Z-$L_5$-Z—; said $L_4$ and $L_5$ are carbon-chain linking groups, each independently represented by —$(CR_aR_b)_t$—$(CR_aR_b)_o$—$(CR_aR_b)_p$—; wherein, t, o, and p are each independently an integer from 0 to 12, said t, o, and p not being 0 simultaneously; $R_a$ and $R_b$ are, at each occurrence, independently a hydrogen atom or a $C_{1-6}$ alkyl group; said Z is, at each occurrence, independently selected from the group consisting of —C(═O)—, —OC(═O)—, —C(═O)O—, —OC(═O)O—, —O—, —S—, —C(═O)S—, —SC(═O)—, —$NR_c$C(═O)—, —C(═O)$NR_c$—, —$NR_c$C(═O)$NR_c$—, —OC(═O)$NR_c$—, —$NR_c$C(═O)O—, —SC(═O)$NR_c$—, —$NR_c$C(═O)S—, and

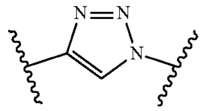, wherein $R_c$ is, at each occurrence, independently a hydrogen atom or a $C_{1-12}$ alkyl group;

$B_1$ and $B_2$ are each independently a linking bond or a $C_{1-30}$ alkylene group;

$R_1$ and $R_2$ are each independently a $C_{5-30}$ aliphatic group or

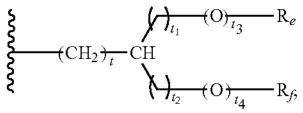

wherein, t is an integer from 0 to 12; $t_1$ and $t_2$ are each independently an integer from 0 to 5; $t_3$ and $t_4$ are each independently 0 or 1, not being 0 simultaneously; $R_e$ and $R_f$ are each independently selected from the group consisting of a $C_{1-15}$ alkyl group, a $C_{2-15}$ alkenyl group, and a $C_{2-15}$ alkynyl group;

$R_3$ is selected from the group consisting of a hydrogen atom, —$R_d$, —$OR_d$, —$NR_dR_d$, —$SR_d$, —C(═O)$R_d$, —C(═O)$OR_d$, —OC(═O)$R_d$, —OC(═O)$OR_d$, and

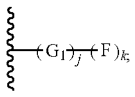

wherein, $R_d$ is, at each occurrence, independently a $C_{1-12}$ alkyl group, wherein $G_1$ is a terminal branching group with the valence of k+1, wherein j is 0 or 1, and wherein F contains functional group $R_{01}$; when j is 0, $G_1$ is absent; when j is 1, $G_1$ protrudes F with the number of k, wherein k is an integer from 2 to 8;

A is selected from the group consisting of $-(CR_aR_b)_sO-$, $-O(CR_aR_b)_s-$, $-(CR_aR_b)_sS-$, $-S(CR_aR_b)_s-$, $-(CR_aR_b)_sO(CR_aR_b)_sS-$, $-(CR_aR_b)_sS(CR_aR_b)_sO-$, $-(CR_aR_b)_sNR_c(CR_aR_b)_sS-$, $-(CR_aR_b)_sS(CR_aR_b)_sNR_c-$, $-(CR_aR_b)_sNR_c(CR_aR_b)_sO-$, and $-(CR_aR_b)_sO(CR_aR_b)_sNR_c-$, wherein s is 2, 3 or 4, and wherein $R_a$ and $R_b$ are, at each occurrence, independently a hydrogen atom or a $C_{1-6}$ alkyl group;

when A is $-(CR_aR_b)_sO-$ or $-O(CR_aR_b)_s-$, n is an integer from 2 to 6; when A is not either $-(CR_aR_b)_sO-$ or $-O(CR_aR_b)_s-$, n is an integer from 1 to 6;

said alkyl group, alkylene group, alkoxy group, and aliphatic hydrocarbon group are each independently substituted or unsubstituted.

1.1.1. $L_1$, $L_2$, $L_3$, $L_4$, $L_5$, $L_7$, $L_8$, Z, $Z_1$, $Z_2$

The structures of $L_1$, $L_2$, $L_3$, $L_4$, $L_5$, $L_7$, $L_8$, Z, $Z_1$, and $Z_2$ are not particularly limited, which include but are not limited to linear structures, branched structures, or ring-containing structures.

In the present invention, the numbers of non-hydrogen atoms of $L_1$, $L_2$, $L_3$, $L_4$, $L_5$, $L_7$, $L_8$, Z, $Z_1$, and $Z_2$ are not particularly limited, each independently preferably from 1 to 50, more preferably from 1 to 20, and more preferably from 1 to 10. Said non-hydrogen atom is carbon atom or heteroatom. Said heteroatom includes but is not limited to O, S, N, P, Si, B, etc. When the number of non-hydrogen atoms is 1, it can be a carbon atom or a heteroatom. When the number of non-hydrogen atoms is larger than 1, the species of non-hydrogen atoms are not particularly limited, and can be a single species or a combination of two or more species, said non-hydrogen atoms are any combination selected from carbon atoms and carbon atoms, carbon atoms and heteroatoms, and heteroatoms and heteroatoms.

In the present invention, two identical or different reactive groups may form a divalent linking group after reaction. The reaction conditions are related to the types of resulting covalent linking groups, and the prior art can be introduced herein. For example, an amino group can react with an active ester, an active formate, a sulfonate ester, an aldehyde, an α,β-unsaturated compound, a carboxylic acid, an epoxide, an isocyanate, or an isothiocyanate to obtain a divalent linking group such as an amide bond, an urethane bond, an amino bond, an imide bond (which can be further reduced to a secondary amino group), an amino bond, an amide bond, a hydroxyalkylamino bond, an urea bonds (a carbamide bond or an ureido bond), and a thiourea bond, respectively; a mercapto group can react with an active ester, an active formate, a sulfonate group, a mercapto group, a maleimido group, an aldehyde group, an α,β-unsaturated bond, a carboxyl group, an iodoacetamide group, and an anhydride group to obtain a divalent linking group such as a thioester bond, a thiocarbonate bond, a thioether bond, a disulfide bond, a thioether bond, a thiohemiacetal linkage, a thioether bond, a thioester bond, a thioether bond, and an imide linkage, respectively; an unsaturated bond can react with a mercapto group to obtain a thioether group; a carboxyl group or an acyl halide can react with a mercapto group and an amino group to obtain a thioester bond and an amide bond, respectively; a hydroxyl group can react with a carboxyl group, an isocyanate, an epoxide, or a chlorocarbonyloxy group to obtain a divalent linking group such as an ester bond, a carbamate bond, a ether bond, and a carbonate group, respectively; a carbonyl group or an aldehyde group can react with an amino group, a hydrazines and a hydrazides to obtain a divalent linking group such as an imine bond, a hydrazone bond, and an acylhydrazone bond, respectively; reactive groups including an azido group, an alkynyl group, an alkenyl group, a mercapto group, an azido group, a dienyl group, a maleimido group, a 1,2,4-triazoline-3,5-dione group, a dithioester group, a hydroxylamine, a hydrazide, an acrylate, an allyloxy group, an isocyanate, a tetrazole, and the like, can undergo click reactions to form various linking groups including but not limited to a triazole linkage, an isoxazole linkage, a thioether bond, and the like.

The stability of divalent linking groups $L_1$, $L_2$, $L_3$, $L_4$, $L_5$, $L_7$, $L_8$, Z, $Z_1$, and $Z_2$ are not particularly limited; any one of said divalent linking groups, or a joint divalent linking group consisting of any one of said divalent linking groups and its adjacent hetero-atom groups, is independently a stable linking group STAG or a degradable linking group DEGG.

1.1.1.1. $L_1$, $L_2$

In the present invention, $L_1$ and $L_2$ are each independently a linking bond or a divalent linking group, said divalent linking group selected from the group consisting of $-OC(=O)-$, $-C(=O)O-$, $-OC(=O)O-$, $-C(=O)-$, $-O-$, $-O(CR_cR_c)_sO-$, $-S-$, $-C(=O)S-$, $-SC(=O)-$, $-NR_cC(=O)-$, $-C(=O)NR_c-$, $-NR_cC(=O)NR_c-$, $-OC(=O)NR_c-$, $-NR_cC(=O)O-$, $-SC(=O)NR_c-$, and $-NR_cC(=O)S-$; wherein, $R_c$ is, at each occurrence, independently a hydrogen atom or a $C_{1-12}$ alkyl group; wherein s is 2, 3 or 4.

In one specific embodiment of the present invention, $L_1$ and $L_2$ are each independently selected from the group consisting of a linking bond, $-OC(=O)-$, $-C(=O)O-$, $-OC(=O)O-$, $-C(=O)-$, $-O-$, $-O(CH_2)_sO-$, $-S-$, $-SC(=O)-$, $-NHC(=O)-$, $-C(=O)NH-$, $-NHC(=O)NH-$, $-OC(=O)NH-$, $-NHC(=O)O-$, $-SC(=O)NH-$, and $-NHC(=O)S-$.

In one specific embodiment of the present invention, preferably one of $L_1$ and $L_2$ is a linking bond, and the other is selected from the group consisting of $-OC(=O)-$, $-C(=O)O-$, $-OC(=O)O-$, $-C(=O)-$, $-O-$, $-O(CH_2)_sO-$, $-S-$, $-C(=O)S-$, $-SC(=O)-$, $-NHC(=O)-$, $-C(=O)NH-$, $-NHC(=O)NH-$, $-OC(=O)NH-$, $-NHC(=O)O-$, $-SC(=O)NH-$, and $-NHC(=O)S-$.

In one specific embodiment of the present invention, preferably $L_1$ and $L_2$ are each independently selected from the group consisting of $-OC(=O)-$, $-C(=O)O-$, $-OC(=O)O-$, $-C(=O)-$, $-O-$, $-O(CH_2)_sO-$, $-S-$, $-C(=O)S-$, $-SC(=O)-$, $-NHC(=O)-$, $-C(=O)NH-$, $-NHC(=O)NH-$, $-OC(=O)NH-$, $-NHC(=O)O-$, $-SC(=O)NH-$, and $-NHC(=O)S-$.

In one specific embodiment of the present invention, preferably $L_1$ and $L_2$ are each independently selected from the group consisting of $-OC(=O)-$, $-C(=O)O-$, and $-OC(=O)O-$.

In one specific embodiment of the present invention, preferably one of $L_1$ and $L_2$ is selected from the group consisting of $-OC(=O)-$, $-C(=O)O-$, and $-OC(=O)O-$, and the other is selected from the group consisting of $-C(=O)O-$, $-OC(=O)O-$, and $-C(=O)-$.

In one specific embodiment of the present invention, preferably one of $L_1$ and $L_2$ is selected from the group consisting of $-OC(=O)-$, $-C(=O)O-$, and $-OC(=O)O-$, and the other is $-C(=O)-$.

In one specific embodiment of the present invention, preferably $L_1$ and $L_2$ are both $-OC(=O)-$, or both $-C(=O)O-$, or both $-OC(=O)O-$; more preferably $L_1$ and $L_2$ are both $-C(=O)O-$ or both $-OC(=O)O-$. In one embodiment, $R_c$ is preferably a hydrogen atom; or, $R_c$ is preferably a $C_{1-12}$ alkyl group, more preferably a $C_{1-8}$ alkyl group, more preferably a methyl group, an ethyl group, a propyl group, a butyl group, a butyl group, a pentyl group, or a hexyl group.

1.1.1.2. $L_7$, $L_8$

In the present invention, $L_7$ and $L_8$ are each independently a linking bond or a divalent linking group, said divalent linking group are selected from the group consisting of —OC(═O)—, —C(═O)O—, —OC(═O)O—, —C(═O)—, —O—, —S—, —C(═O)S—, —SC(═O)—, —NR$_c$C(═O)—, —C(═O)NR$_c$—, —NR$_c$C(═O)NR$_c$—, —OC(═O)NR$_c$—, —NR$_c$C(═O)O—, —SC(═O)NR$_c$—, and —NR$_c$C(═S)S—, wherein $R_c$ is, at each occurrence, independently a hydrogen atom or a $C_{1-12}$ alkyl group.

In one embodiment, $R_c$ is preferably a hydrogen atom; or, $R_c$ is preferably a $C_{1-12}$ alkyl group, more preferably $C_{1-8}$ alkyl group, more preferably a methyl group, an ethyl group, a propyl group, a butyl group, a butyl group, a pentyl group, or a hexyl group.

1.1.1.3. $L_3$

In the present invention, $L_3$ is a linking bond selected from the group consisting of -$L_4$-, —Z-$L_4$-, -$L_4$-Z—, —Z-$L_4$-Z—, -$L_4$-Z-$L_5$-, —Z-$L_4$-Z-$L_5$-, and -$L_4$-Z-$L_5$-Z—; said $L_4$ and $L_5$ are carbon-chain linking groups, each independently represented by —$(CR_aR_b)_t$—$(CR_aR_b)_o$—$(CR_aR_b)_p$—; wherein, t, o, and p are each independently an integer from 0 to 12, not being 0 simultaneously; $R_a$ and $R_b$ are, at each occurrence, independently a hydrogen atom or a $C_{1-6}$ alkyl group; said Z is, at each occurrence, independently selected from the group consisting of —C(═O)—, —OC(═O)—, —C(═O)O—, —OC(═O)O—, —O—, —S—, —C(═O)S—, —SC(═O)—, —NR$_c$C(═O)—, —C(═O)NR$_c$—, —NR$_c$C(═O)NR$_c$—, —OC(═O)NR$_c$—, —NR$_c$C(═O)O—, —SC(═O)NR$_c$—, —NR$_c$C(═O)S—, and

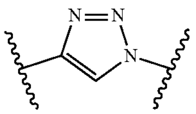

, wherein $R_c$ is, at each occurrence, independently a hydrogen atom or a $C_{1-12}$ alkyl group.

In one embodiment, said $R_c$ is preferably a hydrogen atom.

In one embodiment, $L_3$ is selected from the group consisting of a linking bond, —(CH$_2$)—, —(CH$_2$)$_t$Z—, —Z(CH$_2$)$_t$—, —(CH$_2$)$_t$Z(CH$_2$)$_t$—, and —Z(CH$_2$)$_t$Z—, wherein t is an integer from 0 to 12, and Z is selected from the group consisting of —C(═O)—, —OC(═O)—, —C(═O)O—, —OC(═O)O—, —O—, —S—, —C(═O)S—, —SC(═O)—, —NR$_c$C(═O)—, —C(═O)NR$_c$—, —NR$_c$C(ONR$_c$)NR$_c$—, —OC(═O)NR$_c$—, —NR$_c$C(═O)O—, —SC(═O)NR$_c$—, —NR$_c$C(═O)S—, and

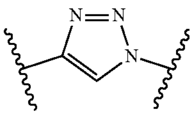

.

Preferably, $L_3$ is selected from the group consisting of a linking bond, —(CH$_2$)—, —(CH$_2$)$_t$O—, —(CH$_2$)$_t$C(═O)—, —(CH$_2$)C(═O)O—, —(CH$_2$)OC(═O)—, —(CH$_2$)C(═O)NH—, —(CH$_2$)$_t$NHC(═O)—, —(CH$_2$)$_t$OC(═O)O—, —(CH$_2$)$_t$NHC(═O)O—, —(CH$_2$)$_t$OC(═O)NH—, —(CH$_2$)$_t$NHC(═O)NH—, —O(CH$_2$)$_t$—, —C(═O)(CH$_2$)$_t$—, —C(═O)O(CH$_2$)—, —OC(═O)(CH$_2$)$_t$—, —C(═O)NH(CH$_2$)$_t$—, —NHC(═O)(CH$_2$)$_t$—, —OC(═O)O(CH$_2$)$_t$—, —NHC(═O)O(CH$_2$)—, —OC(═O)NH(CH$_2$)$_t$—, —NHC(═O)NH(CH$_2$)$_t$—, —(CH$_2$)O(CH$_2$)$_t$—, —(CH$_2$)C(═O)(CH$_2$)$_t$—, —(CH$_2$)C(═O)O(CH$_2$)$_t$—, —(CH$_2$)$_t$OC(═O)(CH$_2$)—, —(CH$_2$)C(═O)NH(CH$_2$)$_t$—, —(CH$_2$)$_t$NHC(═O)(CH$_2$)—, —(CH$_2$)OC(═O)O(CH$_2$)$_t$—, —(CH$_2$)$_t$NHC(═O)O(CH$_2$)—, —(CH$_2$)$_t$OC(═O)NH(CH$_2$)—, —(CH$_2$)$_t$NHC(═O)NH(CH$_2$)—, —O(CH$_2$)$_t$O—, —C(═O)(CH$_2$)$_t$C(═O)—, —C(═O)O(CH$_2$)C(═O)O—, —OC(═O)(CH$_2$)$_t$OC(═O)—, —C(═O)O(CH$_2$)OC(═O)—, —OC(═O)(CH$_2$)$_t$C(═O)O—, —OC(═O)O(CH$_2$)$_t$OC(═O)O—, —C(═O)NH(CH$_2$)C(═O)NH—, —NHC(═O)(CH$_2$)$_t$NHC(═O)—, —NHC(═O)(CH$_2$)$_t$C(═O)NH—, —C(═O)NH(CH$_2$)$_t$NHC(═O)—, —NHC(═O)O(CH$_2$)$_t$NHC(═O)O—, —OC(═O)NH(CH$_2$)OC(═O)NH—, —NHC(═O)O(CH$_2$)$_t$OC(═O)NH—, —OC(═O)NH(CH$_2$)$_t$NHC(═O)O—, —NHC(═O)NH(CH$_2$)$_t$NHC(═O)NH—, —C(═O)(CH$_2$)$_t$O—, —C(═O)(CH$_2$)$_t$C(═O)O—, —C(═O)(CH$_2$)$_t$OC(═O)—, —C(═O)(CH$_2$)OC(═O)O—, —C(═O)(CH$_2$)$_t$NHC(═O)O—, —C(═O)(CH$_2$)$_t$OC(═O)NH—, and —C(═O)(CH$_2$)$_t$NHC(═O)NH—.

1.1.2. Description of Stable and Degradable Groups

In the present invention, a stable linking group denoted as STAG, or a degradable linking group denoted as DEGG, can be part of any above-mentioned divalent linking group including $L_3$, $L_4$, $L_5$, $L_7$, $L_8$, Z, $Z_1$, and $Z_2$, or any joint divalent linking group consisting of said above-mentioned divalent linking group and its adjacent hetero-atom groups.

1.1.2.1. Stable Divalent Linking Groups: STAG

The conditions for stable divalent linking groups, STAG, to be stable are not particularly limited, including but not limited to light illumination, heat, low temperature, enzymatic condition, oxidation-reduction, acidic condition, basic condition, physiological condition, simulated physiological environment in vitro, etc., preferably light illumination, heat, enzymatic condition, oxidation-reduction, acidic condition, basic condition, etc.

The type of STAG is not particularly limited, including but not limited to the stable divalent linking group consisting of any one, two or more groups selected from the group consisting of an alkylene group, a divalent heteroalkyl group, a carbon-carbon double bond, a carbon-carbon triple bond, a divalent dienyl group, a divalent cycloalkyl group, a divalent cycloalkenyl group, a divalent cycloalkenylhydrocarbyl group, a divalent cycloalkynyl group, an arylene group, an aliphatic-derived heterocyclic group, a heterophenylene group (with one or more hetero ring atoms), an aroheterocyclic group, a hetero-fused heterocyclic group, a substituted alkylene group, a substituted heteroalkylene group (or a substituted divalent heteroalkyl group), a substituted double bond, a substituted triple bond, a substituted divalent dienyl group, a substituted divalent cycloalkyl group, a substituted divalent cycloalkenyl group, a substituted divalent cycloalkenylhydrocarbyl group, a substituted divalent cycloalkynylhydrocarbyl group, a substituted arylene group, a substituted aliphatic-derived heterocyclic group, a substituted heterophenylene group, a substituted aroheterocyclic group, a substituted hetero-fused heterocyclic group, ether bond, a thioether bond, urea bond, a thiourea bond, a carbamate bond, a thiocarbamate bond, —P(═O)—, a divalent silyl group without active hydrogen atoms, a boron-containing divalent linking group, a secondary amino group, a tertiary amino group, a carbonyl group, a thiocarbonyl group, an amido group, a thioamido group, a sulphonamido group, an enamine group, a triazole linkage, a 4,5-dihydroisoxazole linkage, and the skeleton of an amino acid and its derivatives.

Specifically, a stable divalent linking group STAG includes but is not limited to the structures listed or disclosed in references of CN104530413A, CN104530415A, and CN104530417A. Taking CN104530417A as an example, the corresponding paragraphs are [0627]~[0704]. The manner in which two or more stable divalent linking groups combine into a STAG is not particularly limited, including but not limited to those listed or disclosed in the paragraph [0704] of CN104530417A.

1.1.2.2. Degradable Divalent Linking Group: DEGG

The conditions to be "degradable" are not particularly limited, including but not limited to light illumination, heat, enzymatic condition, oxidation-reduction, acidic condition, basic condition, physiological condition, simulated physiological environment in vitro, etc., preferably light illumination, heat, enzymatic condition, oxidation-reduction, acidic condition, basic condition, etc.

The divalent linking group formed by the combination of a degradable divalent linking group DEGG and a stable divalent linking group STAG is a degradable linking group. Degradable divalent linking groups containing aryl rings can also be formed by the combination of aryl rings and degradable divalent linking groups.

The type of DEGG is not particularly limited, including but not limited to the degradable divalent linking group containing any one, two or more groups selected from the group consisting of a disulfide bond, a vinylether bond, an ester group, a thioester group, a thiocarboxylate group (e.g., a thioate bond, a monothioester bond), a dithioester group, a carbonate group, a thiocarbonate group, a dithiocarbonate group, a trithiocarbonate group, a carbamate group, a thiocarbamate group, a dithiocarbamate group, an acetal group, a cycloacetal acetal group, a mercaptal group, an azaacetal group, an azacycloacetal group, an azathiaacetal group, a dithioacetal group, a hemiacetal group, a thiohemiacetal group, an azahemiacetal group, a ketal group, a thioketal group, an azaketal group, an azacycloketal group, an azathiaketal group, an imine bond (e.g., —CH═N—), a hydrazone bond, an acylhydrazone bond, an oxime bond (e.g., —C(alkyl)=N—O—, an iminoxy bond, an iminooxy bond, an oxyimino bond, an oximino bond, e.g., —O—N═CH—), a thiooxime bond (e.g., —C(alkyl)=N—S—), a semicarbazone bond, a thiosemicarbazone bond, a hydrazino bond, an acylhydrazino bond, a thiocarbonylhydrazino group (—C(═S)—NH—NH—), an azocarbonylhydrazino group (e.g., —N═N—C(═O)—NH—NH—), an azo-thiocarbonyl-hydrazino group (e.g., —N═N—C(═S)—NH—NH—), a hydrazino formate group, a hydrazino thioformate group, a carbohydrazide group, a thiocarbohydrazide group, an azo group, an isourea group, an isothiourea group, an allophanate group, a thioallophanate group, a guanidino group, an amidino group, an aminoguanidino group, an aminoamidino group, an iminocarbonyl-oxy group (e.g., —C(═NH)—O—), an iminocarbonyl-thioxy group (e.g., —C(═NH)—S—), a sulfonate group, a sulfinate group, a sulfonylhydrazino group, a sulfonylureido group, a maleimide group, an orthoester maleimide group, a phosphate group, a phosphirate group, a phosphinate group, a phosphonate group, a phosphosilicate group, a silicate group, an amide group, thioamide group, a sulfonamide bond, a polyamide group, a phosphamide group, a phosphoramidite group, a pyrophosphamide group, a cyclophosphamide group, an ifosfamide group, a thiophosphamide group, an aconityl group, a peptide fragment, the skeleton of a nucleotide and derivatives thereof, and the skeleton of a deoxynucleotide and derivatives thereof.

Herein, said carbamate group, thiocarbamate group, amide group, phosphamide group, and the like, can exist as either a stable linking group or a degradable linking group, depending on the characteristics of the environment in which they are used.

Specifically, a degradable divalent linking group STAG includes but is not limited to the structures listed or disclosed in references of CN104530413A, CN104530415A, and CN104530417A. Taking CN104530417A as an example, the corresponding paragraphs are [0705]~[0725].

1.1.3. $B_1$, $B_2$, $B_3$, $B_4$

In the present invention, $B_1$ and $B_2$ are each independently a linking bond or a $C_{1-30}$ alkylene group.

In one embodiment, $B_1$ and $B_2$ are, preferably, each independently a linking bond or a $C_{1-20}$ alkylene group; more preferably, one of $B_1$ and $B_2$ is a linking bond, and the other is a $C_{1-20}$ alkylene group which is specifically selected from the group consisting of a methylene group, an ethylene group, a propylene group, a butylene group, a pentylene group, a hexylene group, a heptylene group, an octylene group, a nonylene group, a decylene group, an undecylene group, a dodecylene group, a tridecylene group, a tetradecylene group, a pentadecylene group, a hexadecylene group, a heptadecylene group, an octadecylene group, a nonadecylene group, and an eicosylene group.

In the present invention, $B_3$ and $B_4$ are each independently a linking bond or a $C_{1-12}$ alkylene group.

1.1.4. $R_1$, $R_2$

In the present invention, $R_1$ and $R_2$ are each independently a $C_{5-30}$ aliphatic group or

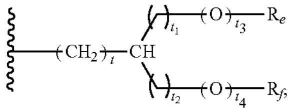

wherein, t is an integer from 0 to 12, $t_1$ and $t_2$ are each independently an integer from 0 to 5, $t_3$ and $t_4$ are each independently 0 or 1, not being 0 simultaneously; $R_c$ and $R_f$ are each independently selected from the group consisting of a $C_{1-15}$ alkyl group, a $C_{2-15}$ alkenyl group, and a $C_{2-15}$ alkynyl group.

In one specific embodiment of the present invention, $R_1$ and $R_2$ are, preferably, each independently a $C_{5-30}$ aliphatic group, more preferably a $C_{10-30}$ aliphatic group, most preferably a $C_{10-20}$ aliphatic group.

In one specific embodiment of the present invention, $R_1$ and $R_2$ are, preferably, each independently a linear alkyl group, a branched alkyl group, a linear alkenyl group, a branched alkenyl group, a linear alkynyl group, or a branched alkynyl group, preferably a linear alkyl group; more preferably, each independently a $C_{1-25}$ linear alkyl group; more preferably, each independently a $C_{1-17}$ linear alkyl group; most preferably, each independently a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a heneicosyl group, a docosyl group, a tricosyl group, a lignoceroylv group, a (Z)-tridec-8-enyl group, a (Z)-tetradec-9-enyl group, a (Z)-pentadec-8-enyl group, a (Z)-hexadec-9-enyl group, a (Z)-heptadec-5-enyl group, a (Z)-heptadec-8-enyl group, an (E)-heptadec-8-enyl group, a (Z)-heptadec-10-enyl group, an (8Z,11Z)-heptadec-8,11-dienyl group, a (Z)-octodec-6-enyl group, a (Z)-octodec-9-enyl group, an (E)-octodec-9-enyl group, a (Z)-octodec-11-enyl group, a (9Z,12Z)-octodec-9,12-dienyl group, a (9Z,12Z, 15Z)-octodec-9,12,15-trienyl group, an (8Z,11Z, 14Z)-octodec-8,11,14-trienyl group, a (Z)-eicos-11-enyl group, an (11Z,14Z)-eicos-11,14-dienyl group, a (Z)-nonadec-10-enyl group, a (10Z,13Z)-nonadec-10,13-dienyl group, a 2,6,10-trimethylundec-1,5,9-trienyl group, a 3,7,11-trimethyldodec-2,6,10-trienyl group, or a 3,7,11,15-tetramethylhexadec-2-enyltridecyl group.

In one specific embodiment of the present invention, $R_1$ and $R_2$ are, preferably, each independently represented as

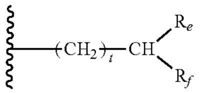

or

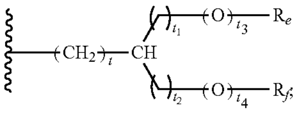

wherein, $R_e$ and $R_f$ are each independently selected from the group consisting of a 1-15 alkyl group, a $C_{2-15}$ alkenyl group, and a $C_{2-15}$ alkynyl group, more preferably selected from the group consisting of a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a vinyl group, a propenyl group, an allyl group, a butenyl group, an allyl carbinyl group, a pentenyl group, a neopentyl group, a hexenyl group, a neohexenyl group, a heptenyl group, a neoheptenyl group, an octenyl group, a neooctenyl group, a nonenyl group, a neononenyl group, a decenoyl group, a neodecenoyl group, an ethynyl group, a propynyl group, a propargyl group, a butynyl group, a butynediyl group, a pentynyl group, a neopentyl group, a hexynyl group, a neohexyl group, a heptynyl group, a neoheptyl group, an octynyl group, a neooctyl group, a nonynyl group, a neononyl group, a decynylgroup, and a neodecyl group, more preferably selected from the group consisting of a methyl group, an ethyl group, a propyl group, a butyl group, a pentyl group, a hexyl group, a heptyl group, an octyl group, a nonyl group, and a decyl group. Further preferably, $R_1$ and $R_2$ are each independently selected from the group consisting of the following structures:

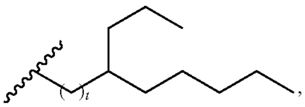
,
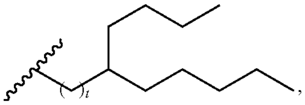
,
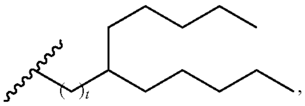
,
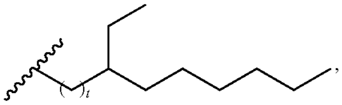
,

-continued

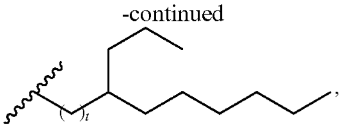
,
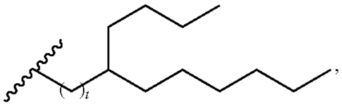
,
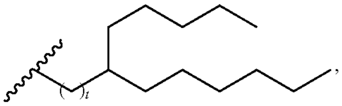
,
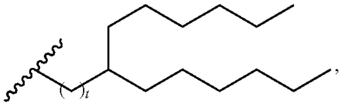
,
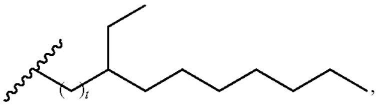
,
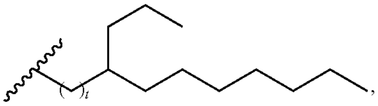
,
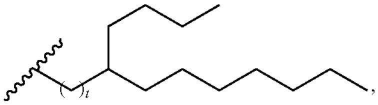
,
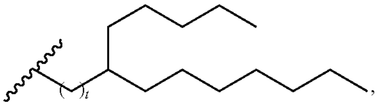
,
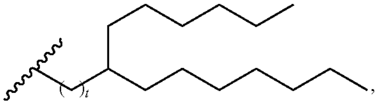
,
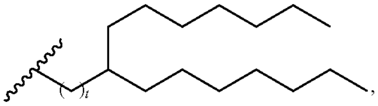
,
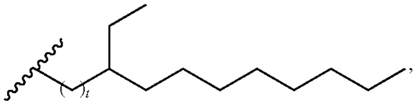
,
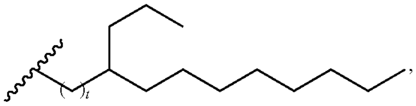
,
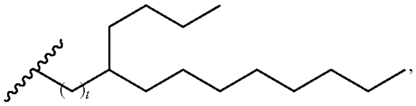
,
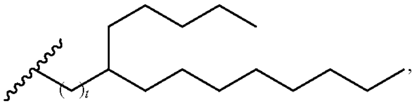
,
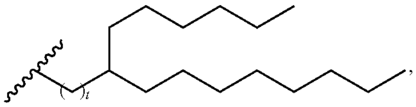
,
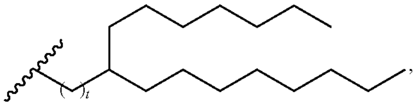
, -continued
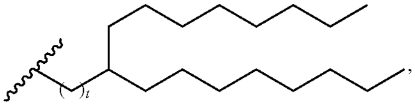
,
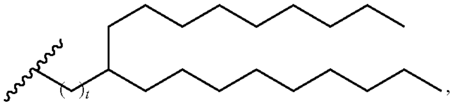
,
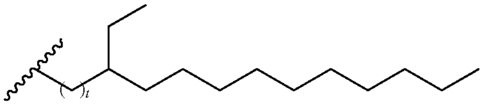
,
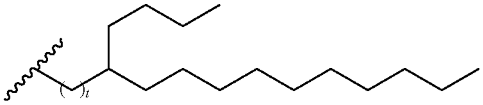
,
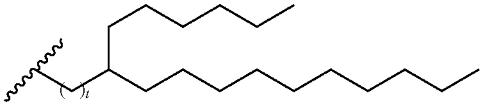
,
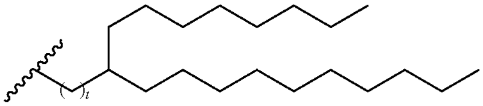
,
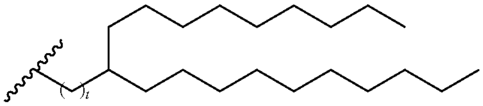
,
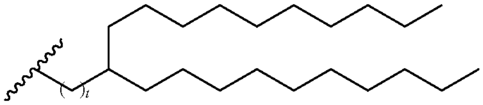
,
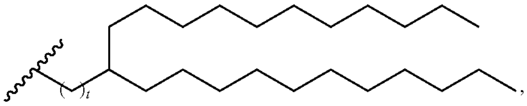
,
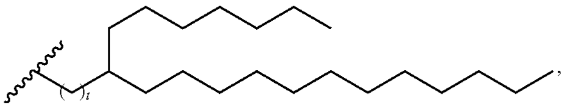
,
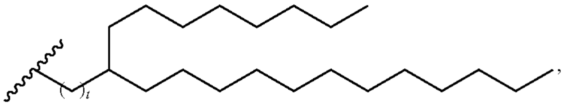
,
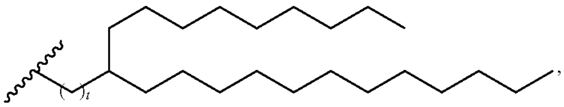
,
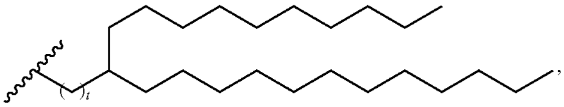
,
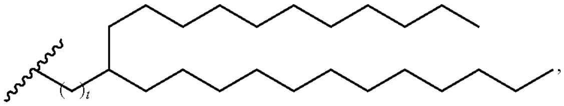
,
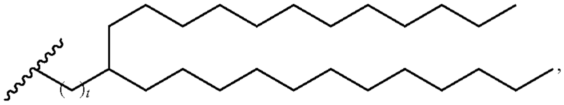
,
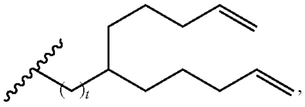
,
-continued
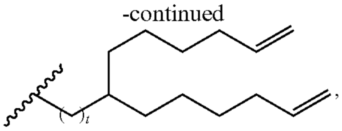
,
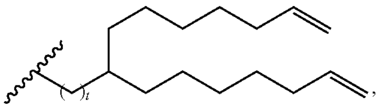
,
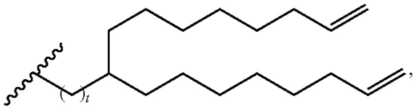
,
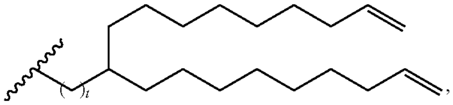
,
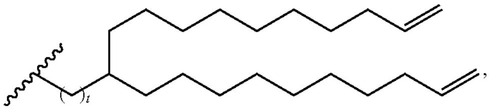
,
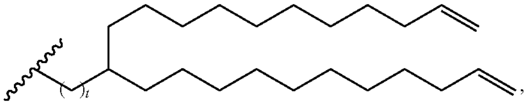
,
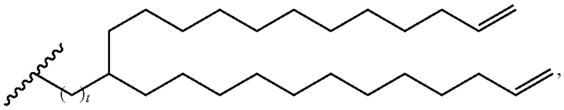
,
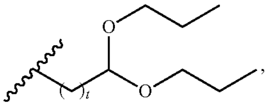
,
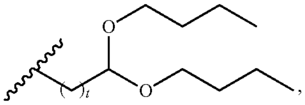
,
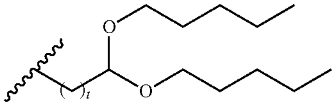
,
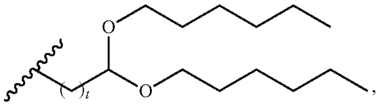
,
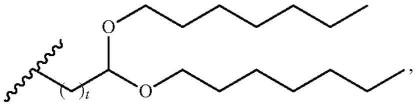
,
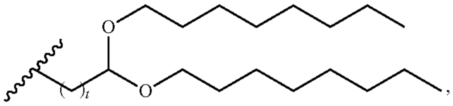
,
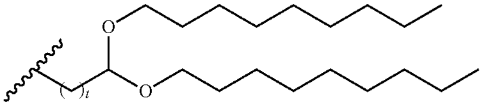
,
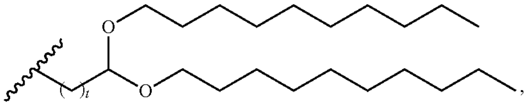
,
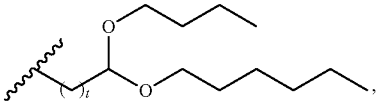
, -continued

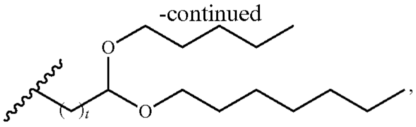

,

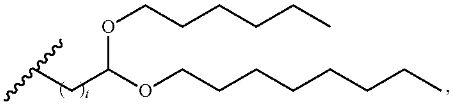

,

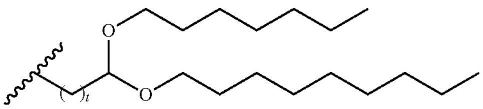

,

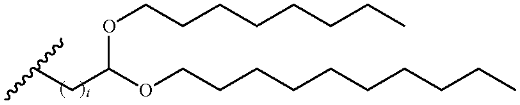

,

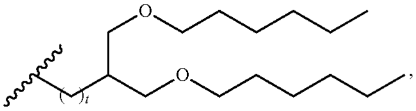

,

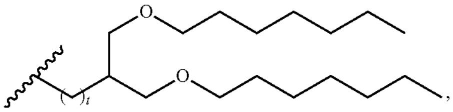

, and

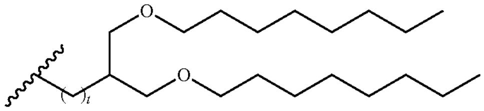

, wherein, t is an integer from 0 to 12; preferably, t is 0 or an integer from 1 to 12; more preferably, t is 0, 1, 2, 3, or 4.

1.1.5. $R_3$, R

In the present invention, $R_3$ is selected from the consisting of a hydrogen atom, —$R_d$, —$OR_d$, —$NR_dR_d$, —$SR_d$, —C(═O)$R_d$, —C(═O)$OR_d$, —OC(═O)$R_d$, —OC(═O)$OR_d$, and

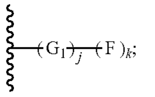

;

wherein, $R_d$ is, at each occurrence, independently a $C_{1-12}$ alkyl group, wherein $G_1$ is a terminal branching group with the valence of k+1, wherein j is 0 or 1, and wherein F contains functional group $R_{01}$; when j is 0, $G_1$ is absent; when j is 1, $G_1$ protrudes F with the number of k, wherein k is an integer from 2 to 8.

In the present invention, R is selected from the group consisting of a hydrogen atom, an alkyl group, an alkoxy group, —C(═O)$R_d$, —C(═O)$OR_d$, —OC(═O)$R_d$, —OC(═O)$OR_d$, and

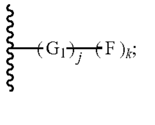

;

wherein, $R_d$ is, at each occurrence, independently a $C_{1-12}$ alkyl group, wherein $G_1$ is a terminal branching group with the valence of k+1, wherein j is 0 or 1, and wherein F contains functional group $R_{01}$; when j is 0, $G_1$ is absent; when j is 1, $G_1$ protrudes F with the number of k, wherein k is an integer from 2 to 8.

1.1.5.1. $R_d$

In the present invention, $R_d$ is, at each occurrence, independently a $C_{1-12}$ alkyl group.

In one specific embodiment of the present invention, $R_d$ is preferably a $C_{1-8}$ alkyl group, specifically a methyl group, an ethyl group, a propyl group, a butyl group, a pentyl group, a hexyl group, a heptyl group, or an octyl group.

1.1.5.2. $G_1$

In the present invention, j is 0 or 1; when j is 0, $G_1$ is absent; when j is 1, $G_1$ exists as a terminal branching group with the valence of k+1 and protrudes F with the number of k, wherein F contains the functional group, wherein k is an integer from 2 to 8, preferably 2, 3 or 4.

In one specific embodiment of the present invention, $G_1$ is preferably a branching group being trivalent or more, preferably trivalent or tetravalent; preferably, $G_1$ is a trivalent branching group; more preferably, $G_1$ is a trivalent branching group selected from the residues of glycerol or amino acids.

In the present invention, with respect to terminal bifunctionalization which is also referred to as end-bifunctionalization, $G_1$ is preferably derived from small molecule compounds which contain two unprotected or protected hydroxyl groups (e.g., triethanolamine p-toluenesulfonate, glycerol monomercaptoacetate, 2-chloro-3',4'-dihydroxyacetophenone and hydroxyl-protected forms thereof), two unprotected or protected mercapto groups (e.g., dimercaptopropanol and its mercapto-protected form), two primary amino groups, two secondary amino groups, two protected primary amino groups, or two protected secondary amino groups, wherein said small molecule compounds include alcohols, thiols, primary amines, secondary amines, sulfonates, and halides, etc. $G_1$ can also be derived from the group consisting of alcohols containing two primary amino groups (e.g., 1,3-diamino-2-propanol), aldehydes containing an epoxy group, alcohols containing an epoxy group (e.g.,

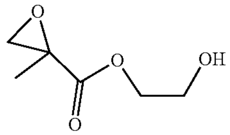

), sulfonates containing an epoxy group, halides containing an epoxy group, and compounds containing an epoxy group and another different type of reactive group. $G_1$ can also be derived from the product obtained by Michael addition reaction of a primary amine with two molecules of acrylic acid ester. $G_1$ can also be derived from the process in which the lipoic acid is used for end-capping and then the disulfide bond undergoes reduction and ring-opening reactions, and eventually two terminal mercapto groups are obtained.

In the present invention, with respect to terminal trifunctionalization, $G_1$ is preferably derived from tetrafunctionalized small molecules (htetraSM) which contain three hydroxyl groups and one different kind of reactive group. Said htetraSM molecules include but are not limited to N-tris(hydroxymethyl)methyl-2-aminoethanesulfonic acid, 3-[tris(hydroxymethyl)methylamino]-1-propanesulfonic acid, methyl 6-O-tosyl-α-D-glucopyranoside, 2-(bromomethyl)-2-(hydroxymethyl)-1,3-propanediol, tris(hydroxymethyl)aminomethane, 2-amino-1,3,4-octadecanetriol, 3-aminopropylsilanetriol, 4-(2-amino-1-hydroxylethyl)-1,2-benzenediol, 4-[1-hydroxy-2-(propan-2-ylamino)ethyl]benzene-1,2-diol, 3,4-dihydroxy-alpha- (methylaminomethyl)benzyl alcohol, 2,5-anhydro-1-azido-1-deoxy-D-glucitol, 2,3,4-trihydroxybutanal (L-erythrose, D-erythrose, L-(+)-threose and D-(+)-threose), 2,3,4-trihydroxybenzaldehyde, 3,4,5-trihydroxybenzaldehyde, N-[tris(hydroxymethyl)methyl]glycine, 2,3,4-trihydroxybutyric acid (including but not limited to erythorbic acid and threonic acid), 2,4,6-trihydroxybenzoic acid, shikimic acid, 3,4,5-trihydroxybenzoic acid, 2,3,4-trihydroxybenzoic acid, arjunolic acid, 1,4,7-tris(tert-butoxycarbonyl)-1,4,7,10-tetraazacyclododecane, tri-(t-butoxycarbonyl)spermine, the like, and hydroxyl-protected forms of above-said htetraSM molecules. The htetraSM molecules can also be citric acid, laricic acid, N-(2-hydroxyethyl)ethylenediamine-triacetic acid, pentaerythritol triacrylate, 4-amino-4-(2-carboxyehtyl)-heptanedioic acid, di-tert-butyl 4-amino-4-(3-(tert-butoxy)-3-oxopropyl)heptanedioate, or the like. The resulting compound formed via the reaction based on an alkenyl, trichlorosilane, and allylmagnesium chloride, along with the formation of a tetravalent silicon-atom branching center, referring to the literature "Macromolecules, Vol. 33, No. 12, 2000", is also included. Trifunctionalized small molecules, such as 1,4,7-tris(t-butoxycarbonylmethyl)-1,4,7,10-azacyclotetradecane (NOTA), are also included and require an excess amount in the reaction.

1.1.5.3. F Containing Functional Group $R_{01}$

In one specific embodiment of the present invention, F is preferably $—(Z_2)_q—(Z_1)_{q1}—R_{01}$, wherein q and q1 are each independently 0 or 1; $Z_1$ and $Z_2$ are each independently a divalent linking group, more preferably $-L_4-$, $—Z-L_4-Z—$, $-L_4-Z-L_5-$, $—Z-L_4-Z-L_5$, or $-L_4-Z-L_5-Z—$; $R_{01}$ is a functional group capable of interreacting with bio-related substances.

In one specific embodiment of the present invention, $R_{01}$ is preferably a functional group, a variant form of functional group, a therapeutic targeting functional group, or a fluorescent functional group, wherein said variant forms include precursors of functional groups, active forms with functional groups as precursors, substituted active forms, protected forms, and unprotected forms; wherein, said precursors of functional groups refer to structures which can transform into the functional group through at least one process of oxidation, reduction, hydration, dehydration, electronic rearrangement, structural rearrangement, salt complexation and decomplexation, ionization, protonation, and deprotonation; wherein, the variant forms of functional groups refer to those remain reactive after at least one process of chemical change selected from oxidation, reduction, hydration, dehydration, electronic rearrangement, structural rearrangement, salt complexation and decomplexation, ionization, protonation, deprotonation, substitution, and deprotection, or non-reactive forms after protection; said $R_{01}$ is more preferably a functional group selected from the group consisting of functional groups in the following classes A~H and variant forms thereof, or selected from the group consisting of functional groups in the following classes I~J:

Class A: active ester groups, and analogs thereof; wherein, active ester groups include a succinimidyl ester group, a p-nitrophenyl ester group, an o-nitrophenyl ester group, a benzotriazole ester group, a 1,3,5-trichlorophenyl ester group, a 1,3,5-trifluorophenyl ester group, a pentafluorophenyl ester group, a iminazole ester group, wherein analogs of active ester groups include a 2-thioxo-3-thiazolidine-formate group, a 2-thioxo-thiazolidine-3-carboxylate group, a 2-thioxo-pyrrolidine-carboxylate group, a 2-thioxo-pyrrolidine-formate group, a 2-thioxo-benzothiazole-formate group, and a 1-oxo-3-thioxoisoindoline-formate group;

Class B: a sulfonate group, a sulfinate group, a sulfonyl group, a sulfoxide group, a 1,3-disulfonyl-2-propylcarbonylphenyl group, and a (2-sulfonylmethyl)acryl group; Class C: a hydroxylamino group, a mercapto group, a primary, a secondary amino group, a halogen atom, a haloacetylamino group, a tetramethylpiperidinyloxy group, a dioxapiperidinyloxy group, an ammonia salt group, a hydrazino group, a disulfide group, an ester group, a thioester group (with a —S—C(=O)— bond), a thiocarboxylate group (e.g., a thioate group with a —O—(C=S)— bond), a carbonate group, a thiocarbonate ester group, a dithiocarbonate ester group, a trithiocarbonate ester group, a xanthate group, a perthiocarbonate group, a tetrasulfide group, an O-carbonylamidoxyl group, an acylamino (i.e., amido or amide) group, an imide group, an acylhydrazino group, a sulfonylhydrazino group, a hydrazone group, an imino group, an enoamino group, an alkynylamino group, a urethane group, a thiourethane group, a dithiourethane group, and a protected amino group;

Class D: a carboxyl group, a sulfonic acid group, a sulfenic acid group, a hydroxamic acid group, a thiohydroxamic acid group, a xanthogenic acid group, an acylhalide group (i.e., a haloacyl group), a chlorosulfonyl group, an aldehyde group, a glyoxal group, an acetal group, a hemiacetal group, a hydrated aldehyde group, a keto group, a ketal group, a hemiketal group, a hydrated ketone group, an orthoacid group, an orthoester group, a cyanato group, a thiocyanate group, an isocyanato group, an ester group, an oxycarbonyl halide group, an oxazolinyl group, an isoxazolinyl group, a thioformyl group, a thione group (i.e., a thioketone group), a thioacetal group, a thione hydrate group, a thioketal group, a thioester group (with a —S—C(=O)— bond), a thiocarboxylate group (e.g., a thioate group with a —O—(C=S)— bond), a dithiocarboxylate group, a thiohemiacetal group (a hemithioacetal group), a monothiohydrate group, a dithiohydrate group, a thiolhydrate group, a thiocarbonyl monothiocarboxylic acid group, a thiohydroxyl monothiocarboxylic acid group, a dithiocarboxylic acid group, a ureido group, a thioureido group, a guanidino group and its protonated form thereof, an amidino group and its protonated form thereof, an anhydride group, a squaric acid group, a squarate group, a semisquaric acid group, a semi-squarate group, an N-carbamoyl-3-imidazole group, an N-carbamoyl-3-methylimidazolium iodide group, an imidic acid group, an imidic ester group, a nitrone group, an oxime group, and a pseudourea group;

Class E: a maleimido group, an acrylate group, an N-acrylamide group, a methacrylate group, an N-methacrylamide group, a protected maleimido group, a maleamic acid group, a 1,2,4-triazoline-3,5-dione group, a linear azo group, a cyclic azo group, a cycloalkenyl group; wherein, the cycloalkenyl group include a cyclooctenyl group, a norbornenyl group, 7-oxabicyclo[2.2.1]hept-5-en-2-yl, a dicycloheptadienyl group, a 7-oxa-dicycloheptadienyl group;

Class F: an epoxy group, an ethenyl group, a propenyl group, an alkenyl-hydrocarbyl group, an alkynyl group, and an alkynyl-hydrocarbyl group.

Class G,

Class Ga: a cycloalkynyl group, a heterosubstituted cycloalkynyl group, a linear conjugated dienyl group, a cyclic conjugated dienyl group, a heterosubstituted cyclic conjugated dienyl group with hetero ring-atoms, and a 1,2,4,5-tetrazinyl group;

Class Gb: an azide group, a nitrile oxide group, a cyano group, an isocyano group, an aldoxime group, a diazo group, a diazonium group, an azoxy group, a nitrilimine group, an N-aldimine oxide group, a tetrazole group, a 4-acetyl-2-methoxy-5-nitrophenoxy group and its diazo form, and other functional groups which can undergo 1,3-dipolar cycloaddition reactions;

Class H: a hydroxyl group, a protected hydroxyl group, a siloxy group, a protected dihydroxyl group, a trihydroxysilyl group, a protected trihydroxysilyl group; wherein, the hydroxyl group includes an alcoholic hydroxyl group, a phenolic hydroxyl group, an enolic hydroxyl group, and a hemiacetal hydroxyl group;

Class I: targeting groups, and pharmaceutically acceptable salts thereof;

Class J: fluorescent groups, such as a fluorescein group, a rhodamine group, an anthracenyl group, a pyrenyl group, a coumarin group, a fluorescent yellow 3G group, a carbazole group, an imidazole group, an indole group, a galleinmonohydrate group and any functional derivative residue thereof.

Further, $R_{01}$ is preferably selected from the group consisting of functional groups in classes A~J, variant forms of classes A~H, and functional derivatives of classes I~J, said variant form being a precursor of functional group, an active form with functional group as precursor, a substituted active form, a protected form, or an unprotected form:

Class A:

A1

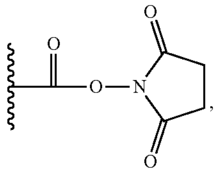

A2

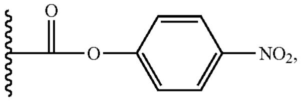

A3

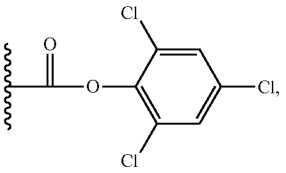

A4

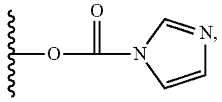

A5

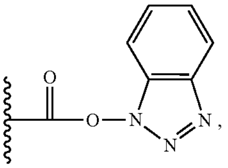

-continued

A6

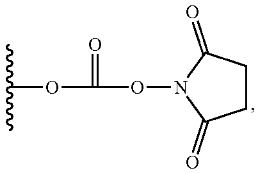

A7

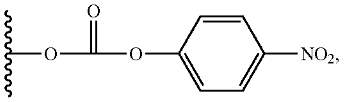

A8

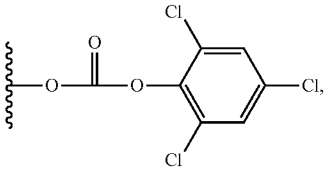

A9

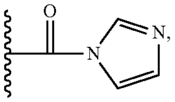

A10

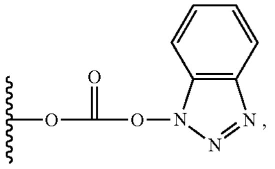

A11

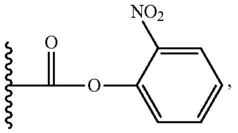

A12

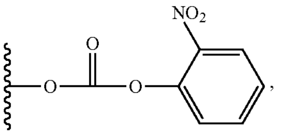

A13

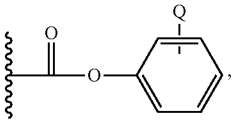

A14

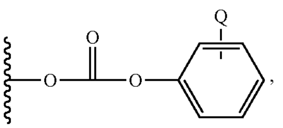

A15

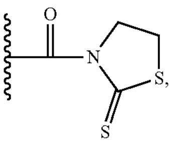

-continued
A16
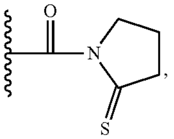
A17
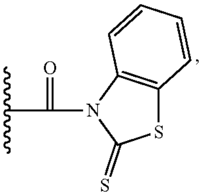
A18
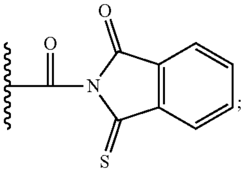
Class B:
B1
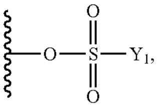
B2
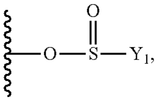
B3
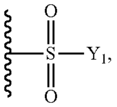
B4
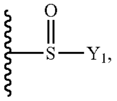
B5
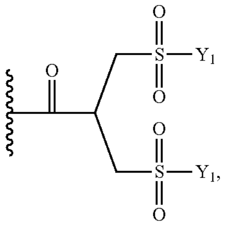
B6
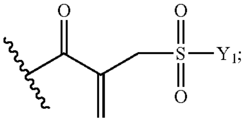
Class C:
C1
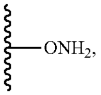
-continued
C2
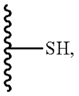
C3
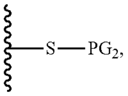
C4
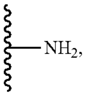
C5
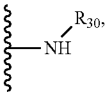
C6
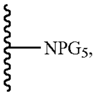
C7
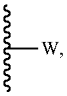
C8
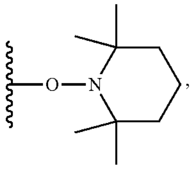
C9
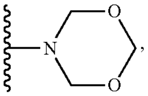
C10
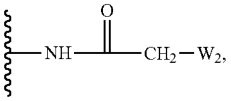
C11
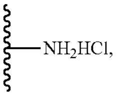
C12
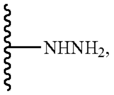
C13
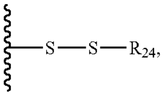
C14
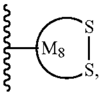
C15
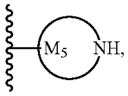

-continued
C16
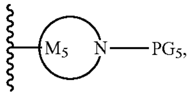
C17
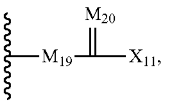
C18
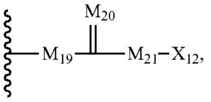
C19
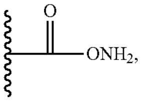
C20
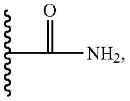
C21
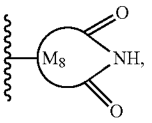
C22
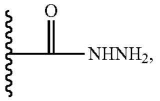
C23
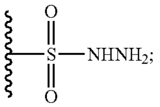
Class D:
D1
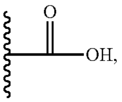
D2
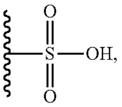
D3
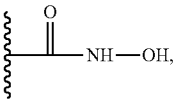
D4
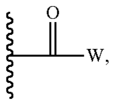
D5
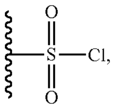
-continued
D6
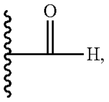
D7
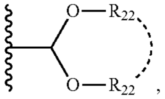
D8
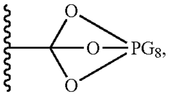
D9
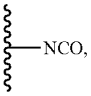
D10
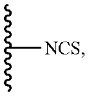
D11
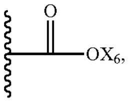
D12
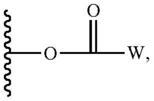
D13
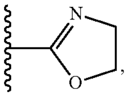
D14
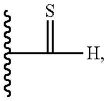
D15
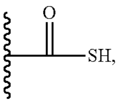
D16
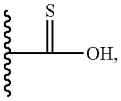
D17
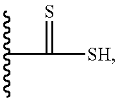
D18
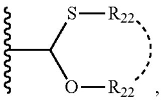
D19
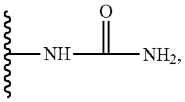

-continued
D20
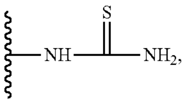
D21
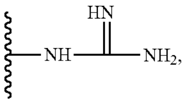
D22
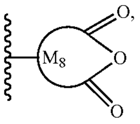
D23
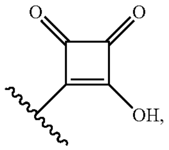
D24
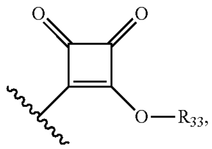
D25
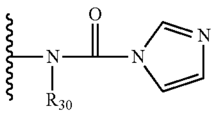
or
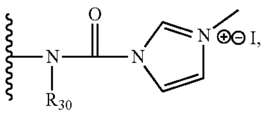
D26
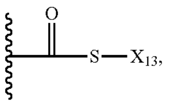
D27
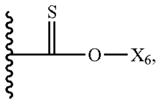
D28
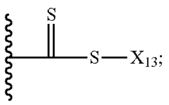
Class E:
E1
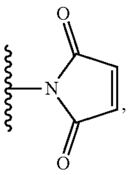
E2
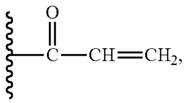
-continued
E3
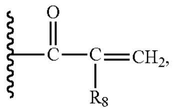
E4
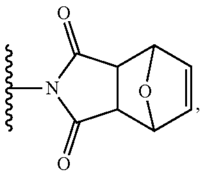
E5
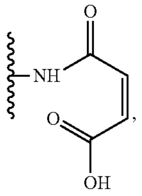
E6
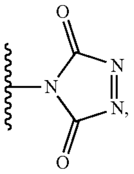
E7
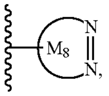
E8
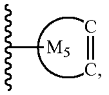
E9
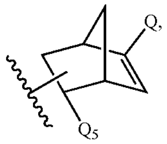
E10
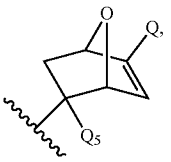
E11
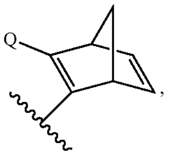
E12
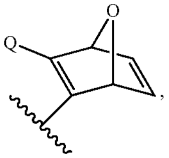

-continued
E13
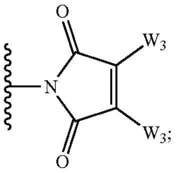
Class F:
F1
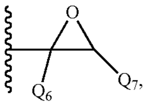
F2
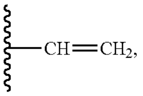
F3
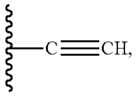
F4
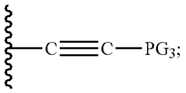
Class G:
Class Ga:
G1
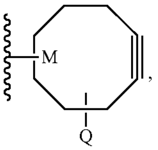
G2
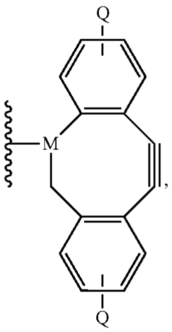
G3
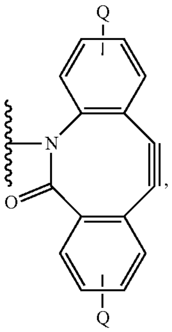
-continued
G4
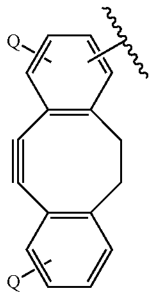
G5
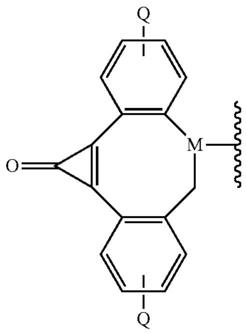
G6
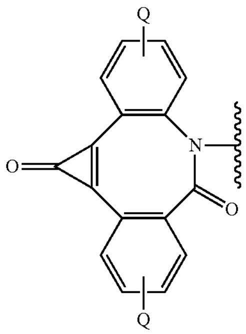
G7
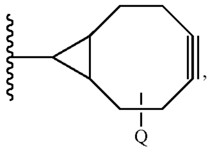
G8
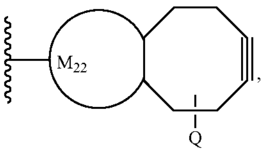
G9
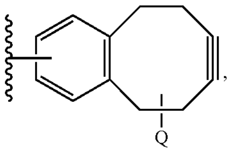
G10
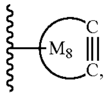

-continued
G11
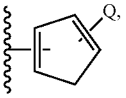
G12
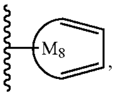
G13
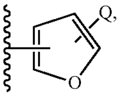
G14
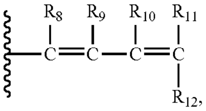
G15
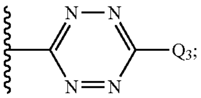
Class Gb:
G21
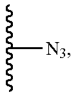
G22
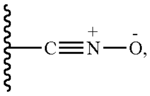
G23
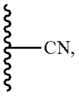
G24
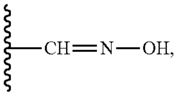
G25
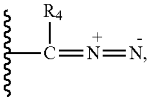
G26
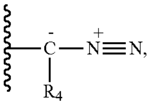
G27
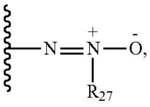
G28
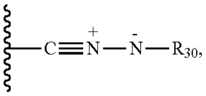
G29
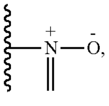
-continued
G30
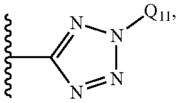
G31
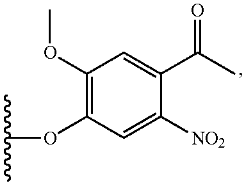
G32
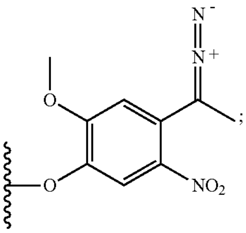
Class H:
H1
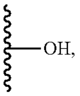
H2
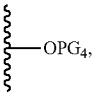
H3
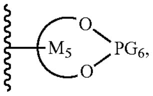
H4
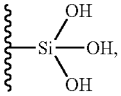
H5
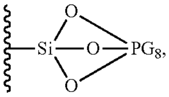
H6
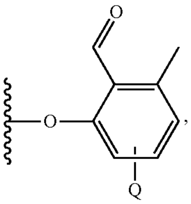
H7
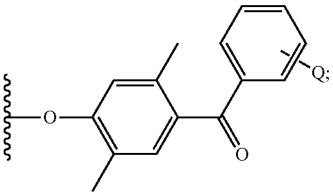

-continued
Class I:
I1
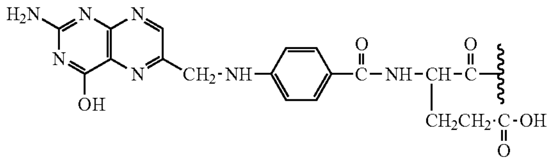
or
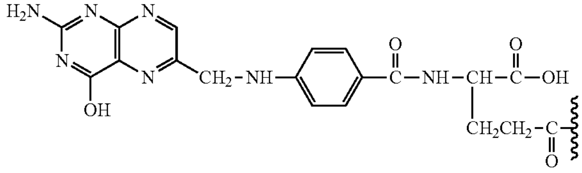
I2
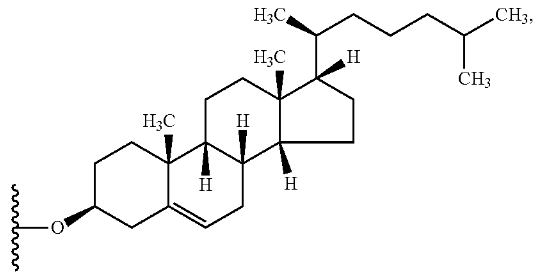
I3
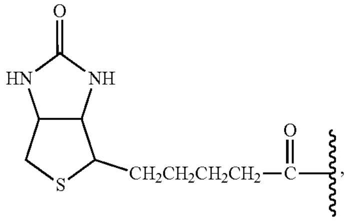
Or group J:
J1
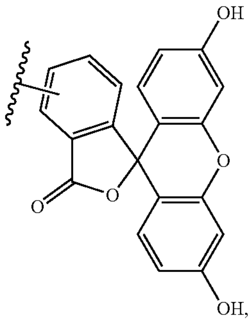
J2
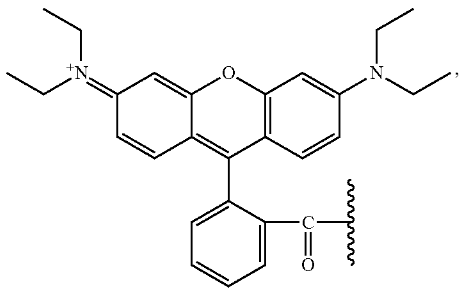
-continued
J3
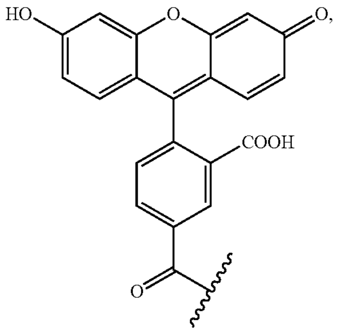
J4
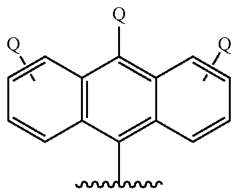
or
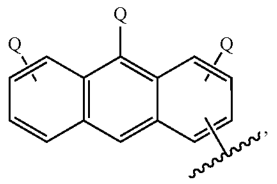
J5
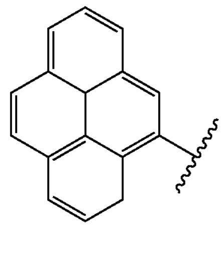
or
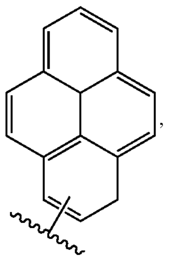
J6
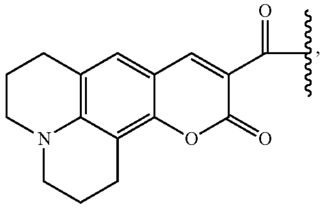
J7
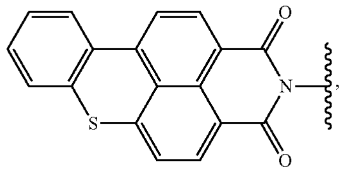
J8
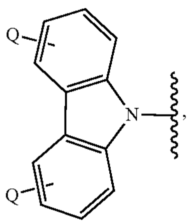
J9
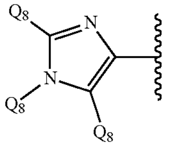
or
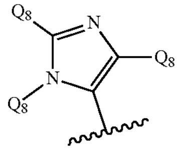
or -continued

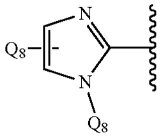 or 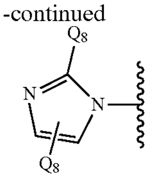

J10

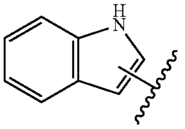 or 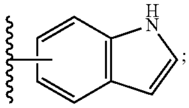;

wherein, $M_5$ is a ring-atom (ring-forming atom) selected from the group consisting of a carbon atom, a nitrogen atom, a phosphorus atom, and a silicon atom. The number of ring-atoms of a cyclic structure containing $M_5$ is from 3 to 50, preferably from 3 to 32, more preferably from 3 to 18, and more preferably from 5 to 18; said cyclic structure is derived from the group consisting of cyclohexane, furanose ring, pyranose ring, benzene, tetrahydrofuran, pyrrolidine, thiazolidine, cyclohexene, tetrahydropyran, piperidine, 1,4-dioxane, pyridine, pyridazine, pyrimidine, pyrazine, 1,3,5-triazine, 1,4,7-triazacyclononane, cyclotripeptide, indene, indane, indole, isoindole, purine, naphthalene, dihydroanthracene, xanthene, thioxanthene, dihydrophenanthrene, 10,11-dihydro-5H-dibenzo[a,d] cycloheptane, dibenzocycloheptene, 5-dibenzosuberenone, quinoline, isoquinoline, fluorene, carbazole, iminodibenzyl, acenaphthene (or 1,2-dihydroacena-phthylene), dibenzocyclooctyne, aza-dibenzocyclooctyne, and substituted forms and heterosubstituted forms thereof;

wherein, $Y_1$ is a leaving group connected to a sulfonyl group, a sulfinyl group, an oxysulfonyl group (a sulfonate group), or an oxysulfinyl group (a sulfinate group), which is selected from the group consisting of a methyl group, an ethyl group, an n-propyl group, an isopropyl group, a butyl group, a pentyl group, a hexyl group, a heptyl group, an octyl group, a nonyl group, a decyl group, a vinyl group, a phenyl group, a benzyl group, a p-methylphenyl group, a 4-(trifluoromethoxy) phenyl group, a trifluoromethyl group, and a 2,2,2-trifluoroethyl group;

wherein, W is F, Cl, Br, or I;

wherein, $W_2$ is F, Cl, Br, or I;

wherein, $W_3$ is a leaving group, selected from the group consisting of F, Cl, Br, I, and PhS;

wherein,

, 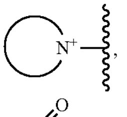, , , , ,

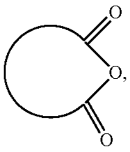, 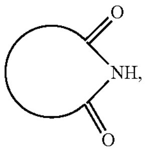, and 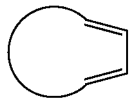

are cyclic structures (or ring structures) of which the skeletons contain a nitrogen atom, a nitrogen-onium ion, a carbon-carbon double bond, an azo bond, a carbon-carbon triple bond, a disulfide bond, an anhydride group, an imide group, and a dienylene linkage, respectively, said cyclic structures selected from the group consisting of carbon rings, heterorings, benzoheterorings, substituted carbon rings, substituted heterorings, and substituted benzoheterorings;

wherein, M is a carbon atom, a nitrogen atom, a phosphorus atom, or a silicon atom of the ring skeleton;

wherein, $M_8$ is a carbon atom, a nitrogen atom, a phosphorus atom, or a silicon atom of the ring skeleton; the number of ring-atoms of the cyclic structure where $M_8$ is located is from 4 to 50, preferably from 4 to 32, and more preferably from 5 to 32;

wherein, $M_{22}$ is a carbon atom, a nitrogen atom, a phosphorus atom, or a silicon atom of an alicyclic ring or an aliphatic-derived heterocycle; the number of ring-atoms of the cyclic structure where $M_{22}$ is located is 4, 5, 6, 7, or 8;

wherein, $R_{22}$ is a terminal group or a divalent linking group, which is connected to an oxygen atom or a sulfur atom, which is, a hydrogen atom, or any atom or group selected from $R_{21}$ or $R_{33}$;

wherein, $R_{21}$ is a divalent linking group and participates in forming a ring; $R_{21}$ is a $C_{1-20}$ hydrocarbylene group, a divalent $C_{1-20}$ heterohydrocarbyl group, a substituted $C_{1-20}$ hydrocarbylene group, a substituted divalent $C_{1-20}$ heterohydrocarbyl group, or the combination of any two or three thereof; $R_{21}$ is preferably a methylene group, an ethylene group, a propylene group, a butylene group, a pentylene group, a hexylene group, a heptylene group, an octylene group, a nonylene group, a decylene group, a 1,2-phenylene group, a benzylene group, a $C_{1-20}$ oxa-alkylene group, a $C_{1-20}$ thia-alkylene group, a $C_{1-20}$ aza-alkylene group, an aza-arylhydrocarbylene group, or any substituted form thereof, or the combination of any two or more of an identical form or different forms or substituted forms thereof, wherein, $R_{33}$ is a terminal group connected to an oxygen atom or a sulfur atom, which is selected from the group consisting of a $C_{1-20}$ hydrocarbyl group, a $C_{1-20}$ heterohydrocarbyl group, a substituted $C_{1-20}$ hydrocarbyl group, and a $C_{1-20}$ substituted heterohydrocarbyl group, preferably selected from the group consisting of a methyl group, an ethyl group, an n-propyl group, an isopropyl group, a butyl group, a pentyl group, a hexyl group, a heptyl group, an octyl group, a nonyl group, a decyl group, a benzyl group, an allyl group, and substituted forms thereof;

wherein, $R_4$ is a hydrogen atom, a substituent atom, or a substituent group, which is bonded to the carbon atom of a structure with the formula of $-(R_4)C{=}N^+{=}N^-$ or $-(R_4)C^--N^+{\equiv}N$;

$R_4$ is preferably an atom or a group selected from the group consisting of a hydrogen atom, a methyl group, an ethyl group, an n-propyl group, an isopropyl group, a butyl group, a pentyl group, a hexyl group, a heptyl group, an octyl group, a nonyl group, a decyl group, an allyl group, a propenyl group, an ethenyl group, a phenyl group, a methylphenyl group, a butylphenyl group, and a benzyl group;

wherein, $R_8$, $R_9$, $R_{10}$, $R_{11}$, and $R_{12}$ are each independently a hydrogen atom, an substituent atom, or a substituent group, being connected to the double bond ($-C{=}C-$), and $R_8$, $R_9$, $R_{10}$, $R_{11}$, and $R_{12}$ can be the same or different in one molecule; $R_8$, $R_9$, $R_{10}$, $R_{11}$, and $R_{12}$ are each independently selected from the group consisting of a hydrogen atom, a fluorine atom, and a methyl group; with respect to functional groups of the class E3, $R_8$ is preferably a methyl group;

wherein, $R_{24}$ is a terminal group connected to a disulfide bond, selected from the group consisting of a $C_{1-20}$ alkyl group, an aryl group, and a heterosubstituted phenyl group;

wherein, $R_{27}$ is a substituent connected to an azo group, selected from the group consisting of a phenyl group, a substituted phenyl group, and a heterosubstituted phenyl group;

wherein, $R_{30}$ is a hydrocarbyl group, selected from the group consisting of a $C_{1-20}$ alkyl group, a benzyl group, and a benzyl group in which the benzene ring is substituted with $C_{1-20}$ hydrocarbyl groups;

wherein, $M_{19}$, $M_{20}$, and $M_{21}$ are each independently an oxygen atom or a sulfur atom, and in one molecule they can be the same or different;

wherein, $X_6$ is a terminal group connected to the oxygen atom of an ester group, and can be a hydroxyl protecting group or a group $LG_4$; $LG_4$ is selected from the group consisting of a $C_{1-20}$ alkyl group, an aryl group, an aralkyl group, a $C_{1-20}$ heteroalkyl group, a heteroaryl group, a heteroarylalkyl group, a $C_{1-20}$ alkylcarbonyl group, an arylcarbonyl group, an arylalkylcarbonyl group, a $C_{1-20}$ heteroalkylcarbonyl group, a heteroarylcarbonyl group, a heteroarylalkylcarbonyl group, a $C_{1-20}$ alkoxycarbonyl group, an aryloxycarbonyl group, an arylalkoxycarbonyl group, a $C_{1-20}$ (alkylthio)carbonyl group, an (arylthio)carbonyl group, an (arylalkylthio)carbonyl group, a $C_{1-20}$ alkylaminocarbonyl group, an arylaminocarbonyl group, an arylalkylaminocarbonyl group, a $C_{1-20}$ heteroalkoxycarbonyl group, a heteroaryloxycarbonyl group, a heteroarylalkoxycarbonyl group, a $C_{1-20}$ hetero(alkylthio)carbonyl group, a hetero(arylthio)carbonyl group, a hetero(arylalkylthio)carbonyl group, a $C_{1-20}$ heteroalkylaminocarbonyl group, a heteroarylaminocarbonyl group, a heteroarylalkylaminocarbonyl group, a $C_{1-20}$ (alkyl)thiocarbonyl group, an (aryl)thiocarbonyl group, an (arylalkyl)thiocarbonyl group, a $C_{1-20}$ hetero(alkyl)thiocarbonyl group, a hetero(aryl)thiocarbonyl group, a hetero(arylalkyl)thiocarbonyl group, a $C_{1-20}$ alkoxy-thiocarbonyl group, an aryloxy-thiocarbonyl group, an arylalkoxy-thiocarbonyl group, a $C_{1-20}$ (alkylthio)thiocarbonyl group, an (arylthio)thiocarbonyl group, an (arylalkylthio)thiocarbonyl group, a $C_{1-20}$ alkylaminothiocarbonyl group, an arylaminothiocarbonyl group, an arylalkylaminothiocarbonyl group, a $C_{1-20}$ heteroalkyloxy-thiocarbonyl group, a heteroaryloxy-thiocarbonyl group, a heteroarylalkoxy-thiocarbonyl group, a $C_{1-20}$ hetero(alkylthio)thiocarbonyl group, a hetero(arylthio)thiocarbonyl group, a hetero(arylalkylthio)thiocarbonyl group, a $C_{1-20}$ heteroalkylaminothiocarbonyl group, a heteroarylaminothiocarbonyl group, a heteroarylalkylaminothiocarbonyl group, and substituted forms thereof, wherein, the substituent atom or substituent group is a fluorine atom, an alkoxy group, or a nitro group;

wherein, $X_{11}$ is a terminal group connected to a carbonyl group or a thiocarbonyl group, selected from $C_{1-20}$ alkyl groups;

wherein, $X_{12}$ is a terminal group connected to a carbonate group or a thiocarbonate group, selected from $C_{1-20}$ hydrocarbyl groups;

wherein, $X_5$ is a terminal group connected to a thioxy group, selected from a mercapto protecting group and a group $LG_2$;

wherein, $LG_2$ is selected from the group consisting of a methyl group, an ethyl group, an n-propyl group, an isopropyl group, a t-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, an allyl group, a trityl group, a phenyl group, a benzyl group, a methylbenzyl group, a nitrobenzyl group, a t-butylthio group, a benzylthio group, a 2-pyridylthio group, an acetyl group, a benzoyl group, a methoxycarbonyl group, an ethoxycarbonyl group, a t-butoxycarbonyl group, a phenoxycarbonyl group, a benzyloxycarbonyl group, a (methylthio)carbonyl group, an (ethylthio)carbonyl group, a (t-butylthio)carbonyl group, a (phenylthio)carbonyl group, a (benzylthio)carbonyl group, a 2-pyridylcarbonyl group, a methylaminocarbonyl group, an ethylaminocarbonyl group, a t-butylaminocarbonyl group, a benzylaminocarbonyl group, an ethyl-thiocarbonyl group, a phenyl-methyl-thiocarbonyl group, a methoxy-thiocarbonyl group, an ethoxy-thiocarbonyl group, a t-butyloxy-thiocarbonyl group, a phenoxy-thiocarbonyl group, a benzyloxy-thiocarbonyl group, a (methylthio)thiocarbonyl group, an (ethylthio)thiocarbonyl group, a (t-butylthio)thiocarbonyl group, a (phenylthio)thiocarbonyl group, a (benzylthio)thiocarbonyl group, a methylaminothiocarbonyl group, an ethylaminothiocarbonyl group, a t-butylaminothiocarbonyl group, a benzylaminothiocarbonyl group, a $C_{1-10}$ halohydrocarbyl group, a trifluoroacetyl group, a nitrophenyl group, and substituted forms thereof, wherein, the substituent atom or substituent group is a fluorine atom, an alkoxy group, or a nitro group;

wherein, Q is an atom or a substituent that can promote the inductive effect and the conjugate effect of electrons of unsaturated bonds; when Q is connected to the ring, the number of Q can be one or greater than one; when the number of Q is greater than one, they can have the same structure or be a combination of two or more different structures; when Q is a substituent group, it can be a linear structure, a branched structure bearing pendant groups, or a ring-containing structure;

wherein, $Q_3$ is a hydrogen atom or a substituent that can promote the inductive effect and the conjugate effect of electrons of unsaturated bonds, which can be any atom or group selected from the group consisting of a hydrogen atom, a fluorine atom, a chlorine atom, a bromine atom, an iodine atom, a methyl group, an ethyl group, an n-propyl group, an isopropyl group, a butyl group, a pentyl group, a hexyl group, a heptyl group, an octyl group, a nonyl group, a decyl group, an ethenyl group, a propenyl group, an allyl group, a propynyl group, a propargyl group, a cyclopropyl group, a cyclopropenyl group, a phenyl group, a benzyl group, a butylphenyl group, a p-methylphenyl group, a p-nitrophenyl group, an o-nitrophenyl group, a p-methoxyphenyl group, an azaphenyl group, a methoxy group, an ethoxy group, a phenoxy group, a benzyloxy group, a methylthio group, an ethylthio group, a phenylthio group, a benzylthio group, a trifluoromethyl group, a 2,2,2-trifluoroethyl group, and substituted forms thereof;

wherein, $Q_5$ is a hydrogen atom, a methyl group, an ethyl group, or a propyl group; when $Q_5$ is connected to the ring, the number of Q can be one or greater than one; when the number of Q is greater than one, they can have the same structure, or be a combination of two or more different structures;

wherein, $Q_6$ is a hydrogen atom or a methyl group; $Q_7$ is a hydrogen atom, a methyl group, a phenyl group, or a substituted phenyl group; in one molecule, $Q_6$ and $Q_7$ can be identical or different from each other;

wherein, $Q_8$ is a substituent atom or substituent group of an imidazole group, which is selected from the group consisting of a hydrogen atom, a methyl group, an ethyl group, a propyl group, a butyl group, and a phenyl group; the number of $Q_8$ can be one or greater than one; when the number of $Q_8$ is greater than one, they can have the same structure, or be a combination of two or more different structures;

wherein, $Q_{11}$ is a substituent group connected to a nitrogen atom of tetrazole group, and is selected from the group consisting of a phenyl group, a substituted phenyl group, and an azaphenyl group;

wherein, $PG_2$ is a mercapto protecting group, and the protected mercapto group is represented as $SPG_2$ which is preferably selected from the group consisting of a sulfide (or a thioether), a disulfide, a silyl thioether, and a thiocarboxylate;

wherein, $PG_3$ is an alkynyl protecting group, preferably a silyl group;

wherein, $PG_4$ is a hydroxyl protecting group, and the protected hydroxyl group is represented as $OPG_4$ which is preferably selected from the group consisting of an ether, a silyl ether, an ester, a carbonate, and a sulfonate;

wherein, $PG_5$ is an amino protecting group, and the protected amino group is represented as $NPG_5$ which is preferably selected from the group consisting of a carbamate, an amide, an imide, an N-alkyl amine, an N-aryl amine, an imine, an enamine, an imidazole, a pyrrole, and an indole;

wherein, $PG_6$ is a dihydroxyl protecting group, and forms a five- or six-membered cyclic acetal structure with two oxygen atoms; $PG_6$ is a methylene group or a substituted methylene group; wherein, the substituent of $PG_6$ is a hydrocarbyl substituent or a heteroatom-containing substituent, selected from the group consisting of a methylene group, a 1-methylmethylene group, a 1,1-dimethylmethylene group, a 1,1-cyclopentylene group, a 1,1-cyclohexylene group, a 1-phenylmethylene group, and a 3,4-dimethylphenylmethylene group;

wherein, $PG_8$ is a protecting group of orthocarbonic acid or orthosilicic acid.

1.1.5.4. Specific Examples of $R_3$

In one specific embodiment of the present invention, $R_3$ preferably contains a hydrogen atom, an alkyl group, an alkoxy group, an alcoholic hydroxyl group, a protected alcoholic hydroxyl group, a thiol group, a protected thiol group, a carboxyl group, a protected carboxyl group, an amino group, a protected amino group, an aldehyde group, a protected aldehyde group, an ester group, a carbonate group, a urethane group, a succinimidyl group, a maleimido group, a protected maleimido group, a dimethylamino group, an alkenyl group, an alkenoate group, an azido group, an alkynyl group, a folate group, a rhodamine group, or a biotinyl group, and more preferably contains H, $CH_3$, $—(CH_2)OH$, $—(CH_2)_tSH$, $—OCH_3$, $—OCH_2CH_3$, $—(CH_2)_t NH_2$, $—(CH_2)C({=}O)OH$, $—C({=}O)(CH_2)_tC({=}O)OH$, $—C({=}O)CH_3$, $—(CH_2)_tN_3$, $—C({=}O)CH_2CH_3$, $—C({=}O)OCH_3$, $—OC({=}O)OCH_3$, $—C({=}O)OCH_2CH_3$, $—OC({=}O)OCH_2CH_3$, $—(CH_2)_tN(CH_3)_2$, $—(CH_2)CHO$,

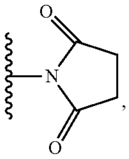,
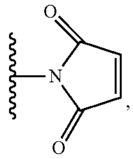,
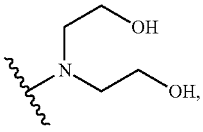
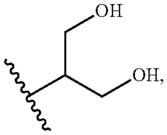
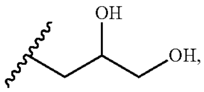 or
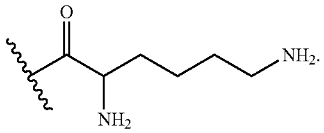.

1.1.5.5. The Atom Spacing Between $R_3$ and the Nitrogen-Atom Branching Center

The length of carbon chain and the atom spacing between two groups have great influence on the properties of compounds.

In one specific embodiment of the present invention, the atom spacing between $R_3$ and the nitrogen-atom branching center is greater than or equal to 6, preferably from 6 to 50, more preferably from 6 to 35, more preferably from 6 to 25, most preferably from 6 to 15.

Specific examples: in Example-1, the group between $R_3$ (a hydrogen atom) and the nitrogen-atom branching center is $—CH_2CH_2OCH_2CH_2O—$, so the atom spacing between $R_3$ and the nitrogen-atom branching center is 6; in Example-2 and Example-4, the group between $R_3$ (—OH) and the nitrogen-atom branching center is $—CH_2CH_2OCH_2CH_2OCH_2CH_2—$, so the atom spacing between $R_3$ and the nitrogen-atom branching center is 8; in Example-8, the group between $R_3$ (a hydrogen atom) and the nitrogen-atom branching center is $—CH_2CH_2NHC({=}O)CH_2CH_2OCH_2CH_2O—$, so the atom spacing between $R_3$ and the nitrogen-atom branching center is 10.

1.1.6. A

In the present invention, A is selected from the group consisting of $—(CR_aR_b)_sO—$, $—O(CR_aR_b)_s—$, $—(CR_aR_b)_sS—$, $—S(CR_aR_b)_s—$, $—(CR_aR_b)_sO(CR_aR_b)_sS—$, $—(CR_aR_b)_sS(CR_aR_b)_sO—$, $—(CR_aR_b)_sNR_c(CR_aR_b)_sS—$, $—(CR_aR_b)_sS(CR_aR_b)_sNR_c—$, $—(CR_aR_b)_sNR_c(CR_aR_b)_sO—$, and $—(CR_aR_b)_sO(CR_aR_b)_sNR_c—$, wherein, s is 2, 3 or 4, and $R_a$ and $R_b$ are, at each occurrence, independently a hydrogen atom or a $C_{1-6}$ alkyl group.

In one specific embodiment of the present invention, A is preferably $—CH_2CH_2O—$, $—OCH_2CH_2—$, $—CH(CH_3)CH_2O—$, $—OCH(CH_3)CH_2—$, $—CH_2CH_2S—$, $—SCH_2CH_2—$, $—CH_2CH_2NHCH_2CH_2O—$, $—CH_2CH_2OCH_2CH_2NH—$, $—CH_2CH_2SCH_2CH_2O—$, or $—CH_2CH_2OCH_2CH_2S—$, more preferably $—CH_2CH_2O—$, $—OCH_2CH_2—$, $—CH_2CH_2SCH_2CH_2O—$, or $—CH_2CH_2OCH_2CH_2S—$, most preferably $—CH_2CH_2O—$ or $—OCH_2CH_2—$.

1.1.7. Examples of Specific General Formulas

In one specific embodiment of the present invention, when the A is $—CH_2CH_2O—$, $—OCH_2CH_2—$, $—CH(CH_3)CH_2O—$, $—OCH(CH_3)CH_2—$, $—CH_2CH_2S—$, —$SCH_2CH_2$—, —$CH_2CH_2NHCH_2CH_2O$—, —$CH_2CH_2OCH_2CH_2NH$—, —$CH_2CH_2SCH_2CH_2O$—, or —$CH_2CH_2OCH_2CH_2S$— in the general formula (1), the structure of cationic lipid in the present invention is preferably the structure of any formula selected from the group consisting of the following formulas:

(1-1)

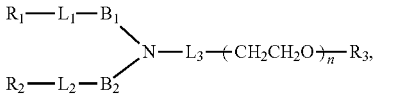

(1-2)

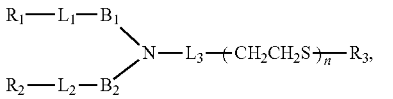

(1-3)

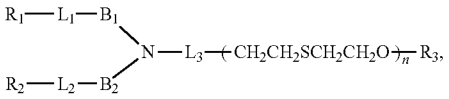

(1-4)

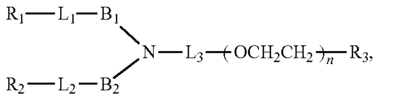

(1-5)

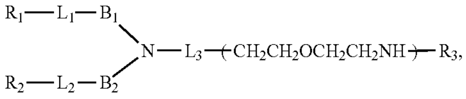

(1-6)

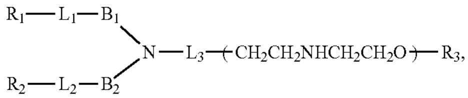

and (1-7)

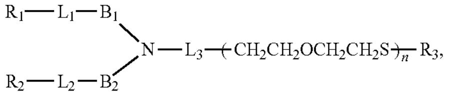

wherein, the definitions of $L_1$, $L_2$, $L_3$, $B_1$, $B_2$, $R_1$, $R_2$, $R_3$, and n are the same as those in the general formula (1).

In one specific embodiment of the present invention, when the $L_1$ and $L_2$ in the general formula (1) are each independently selected from the group consisting of a linking bond, —OC(═O)—, —C(═O)O—, —OC(═O)O—, —C(═O)—, —O—, —$O(CH_2)_sO$—, —S—, —C(═O)S—, —SC(═O)—, —NHC(═O)—, —C(═O)NH—, —NHC(═O)NH—, —OC(═O)NH—, —NHC(═O)O—, —SC(═O)NH—, and —NHC(═O)S—, the structure of cationic lipid in the present invention is preferably the structure of any formula selected from the group consisting of the following formulas:

(2-3)

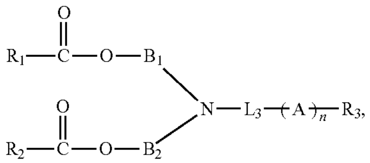

-continued (2-4)

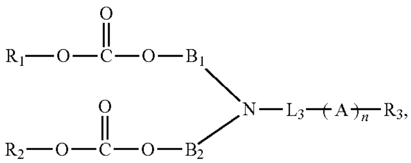

(2-12)

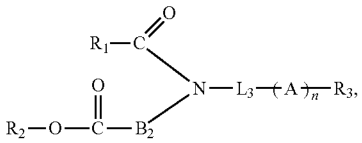

(2-13)

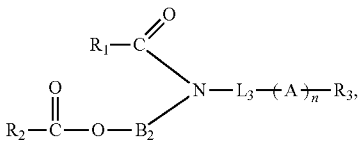

(2-14)

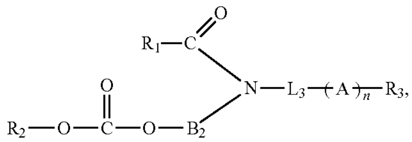

(2-23)

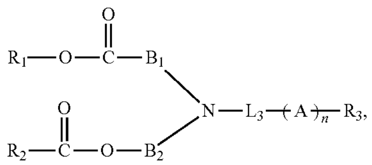

(2-24)

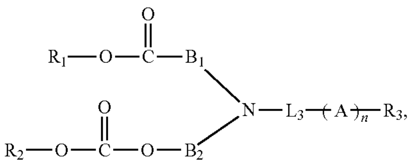

and (2-41)

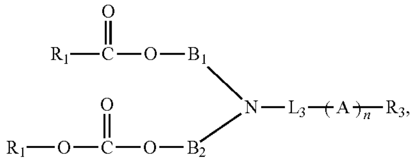

wherein, the definitions of $L_3$, $B_1$, $B_2$, $R_1$, $R_2$, $R_3$, A, and n are the same as those in the general formula (1); said A is preferably selected from the group consisting of —$CH_2CH_2O$—, —$OCH_2CH_2$—, —$CH_2CH_2S$—, —$SCH_2CH_2$—, —$CH_2CH_2NHCH_2CH_2O$—, —$CH_2CH_2OCH_2CH_2NH$—, —$CH_2CH_2SCH_2CH_2O$—, and —$CH_2CH_2OCH_2CH_2S$—, more preferably —$CH_2CH_2O$— or —$OCH_2CH_2$—.

1.1.8. Examples of Specific Structures

In some specific embodiments of the present invention, cationic lipids with the following structures are finally obtained, which include but are not limited to the following structures:

P-1
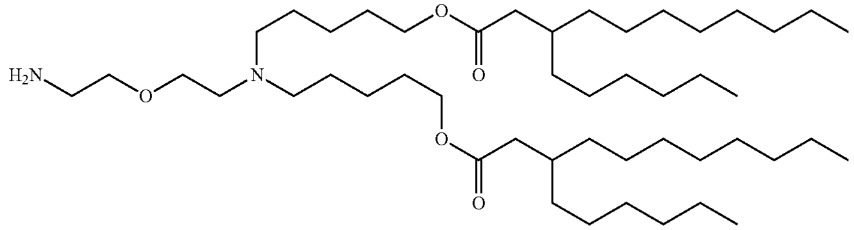
,
P-3
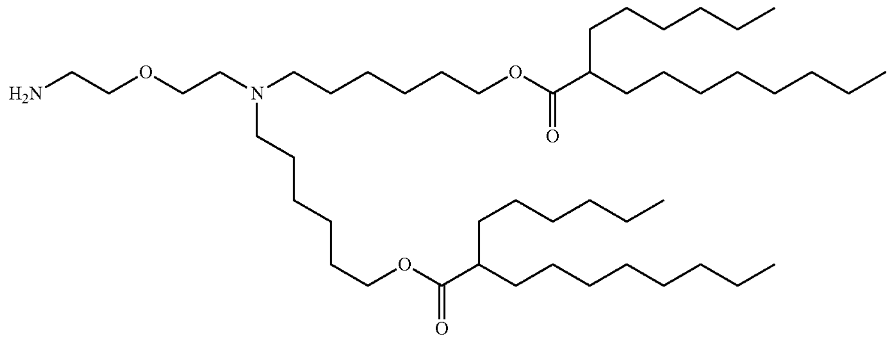
,
P-4
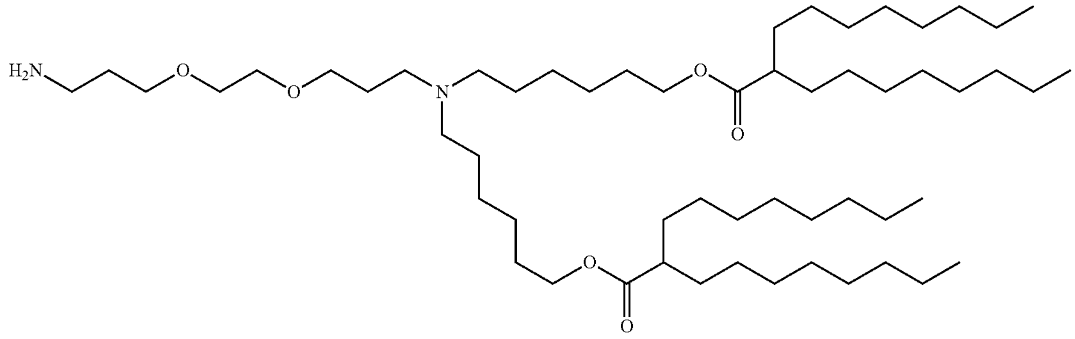
,
P-7
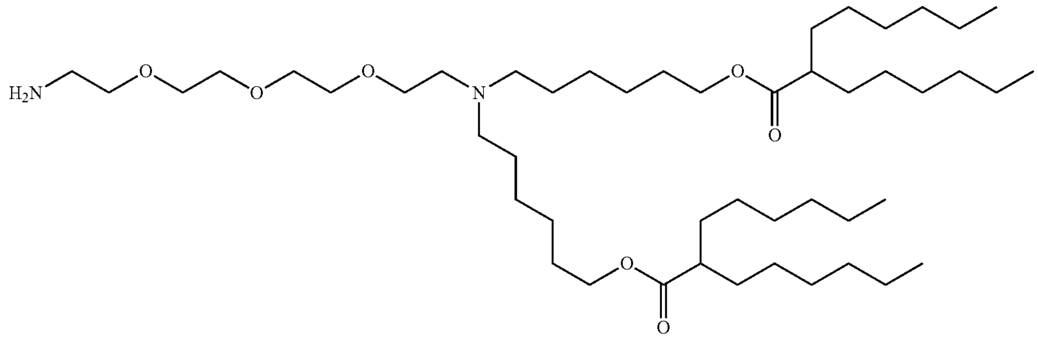
,
P-9
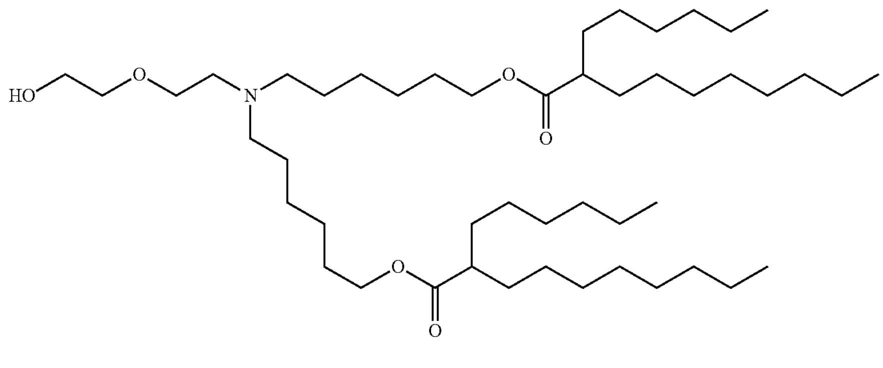
, -continued
P-10
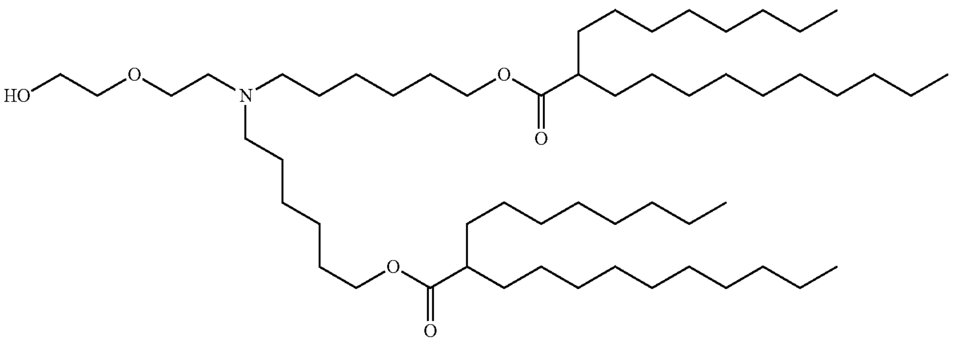
,
P-15
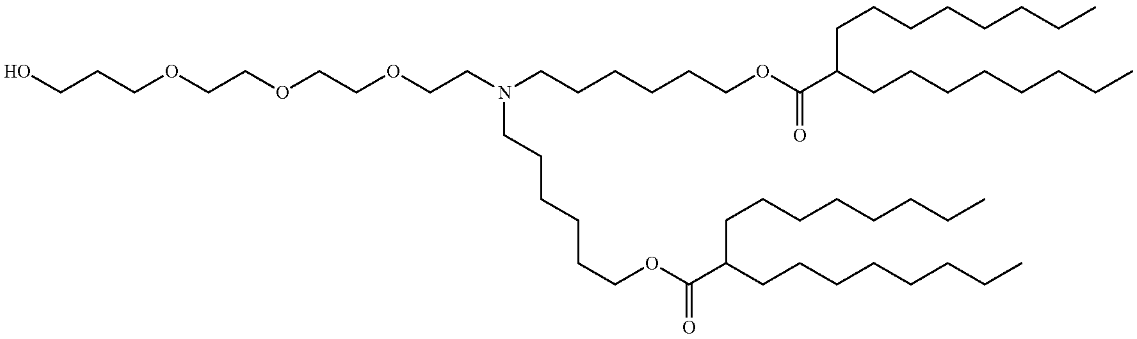
,
P-16
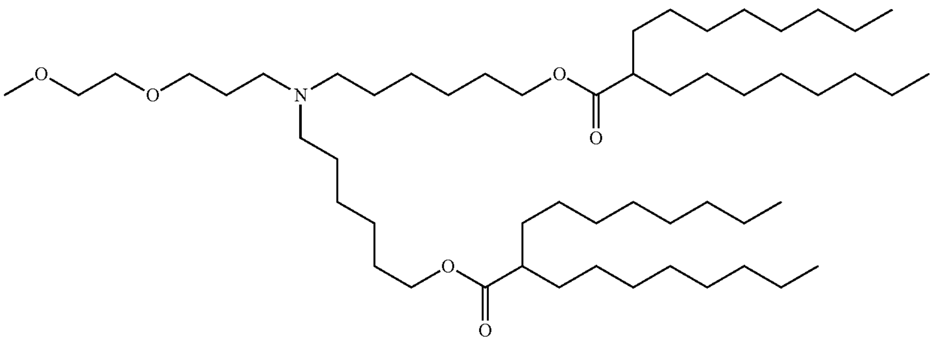
,
P-18
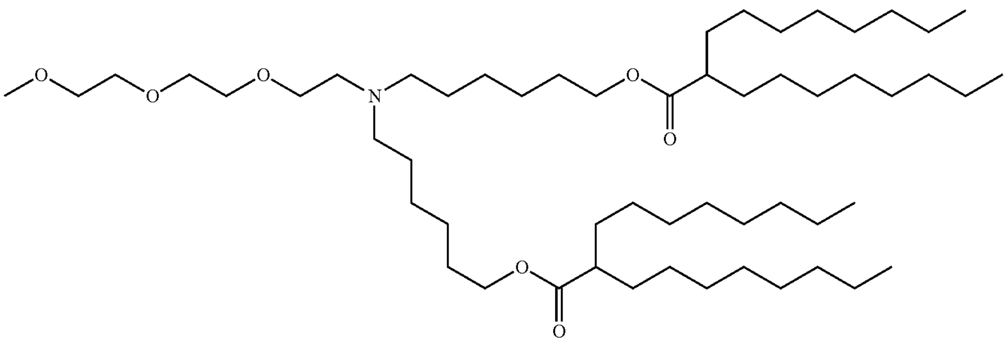
, -continued
P-20
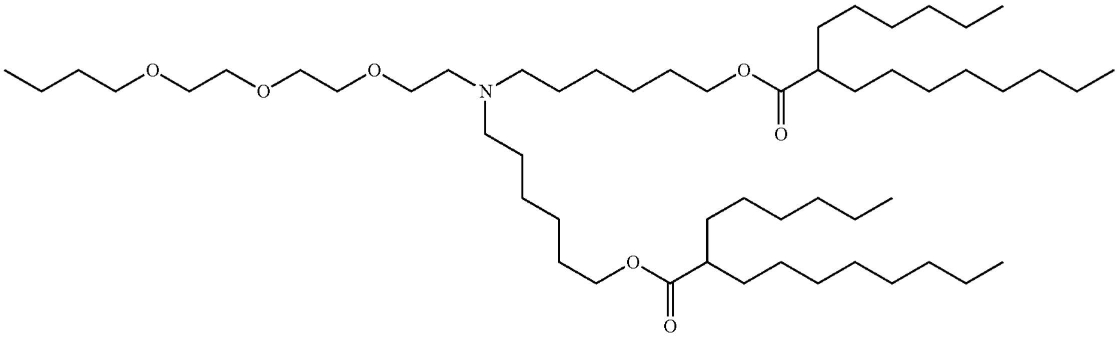
,
P-21
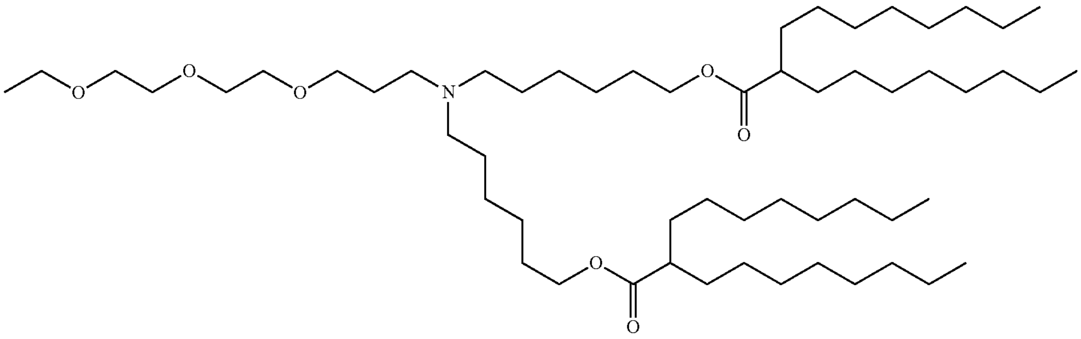
,
P-22
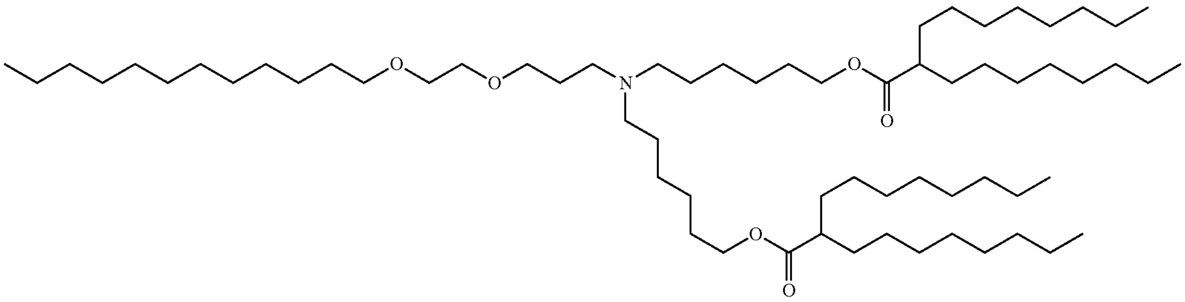
,
P-23
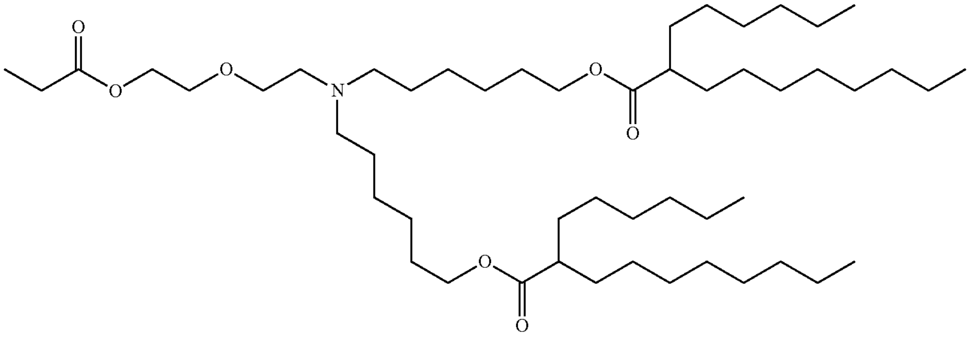
, -continued
P-24
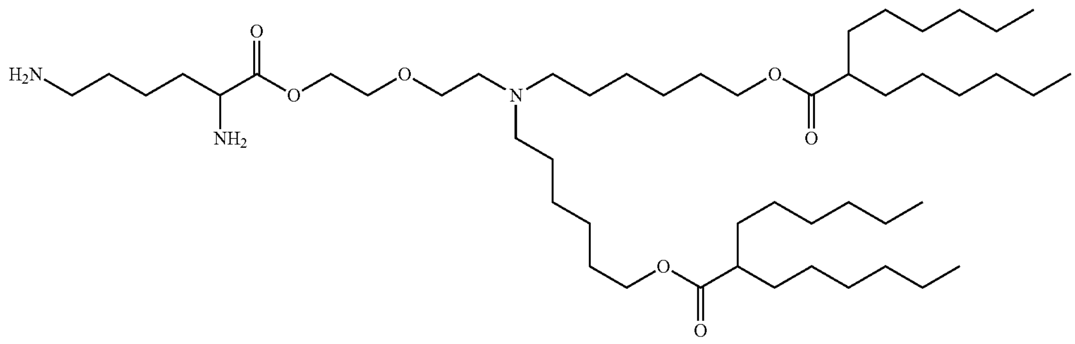
,
P-25
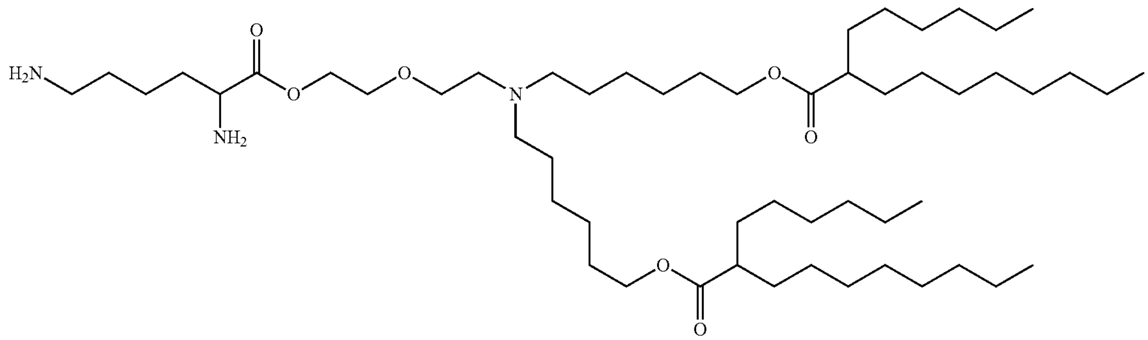
,
P-26
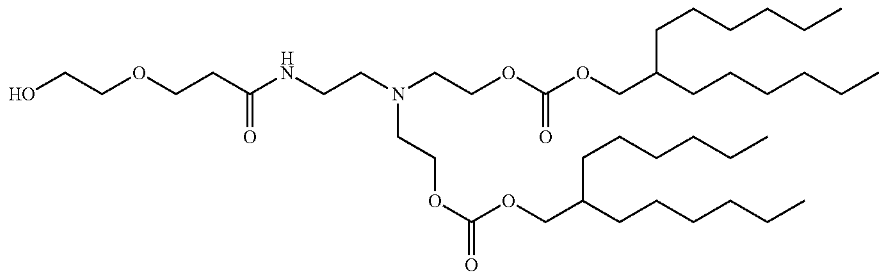
,
P-27
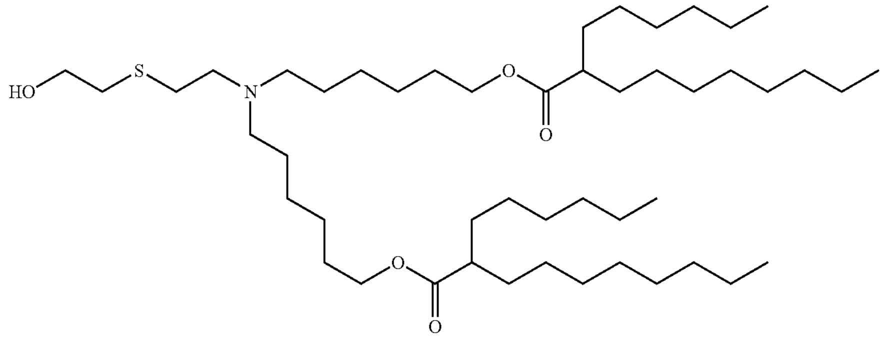
, -continued
P-28
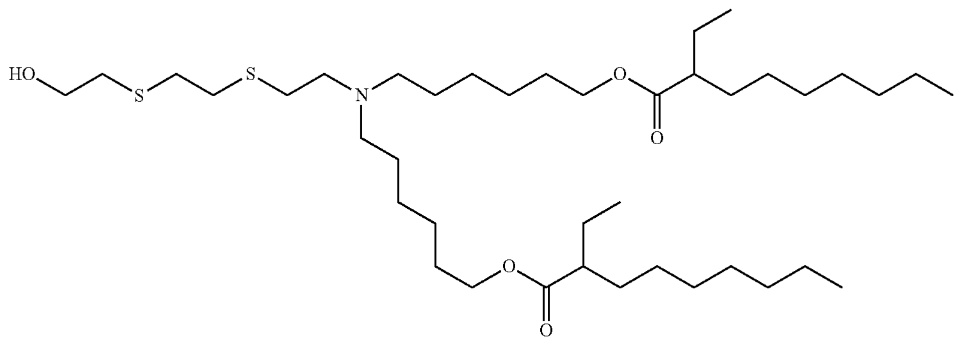
,
P-29
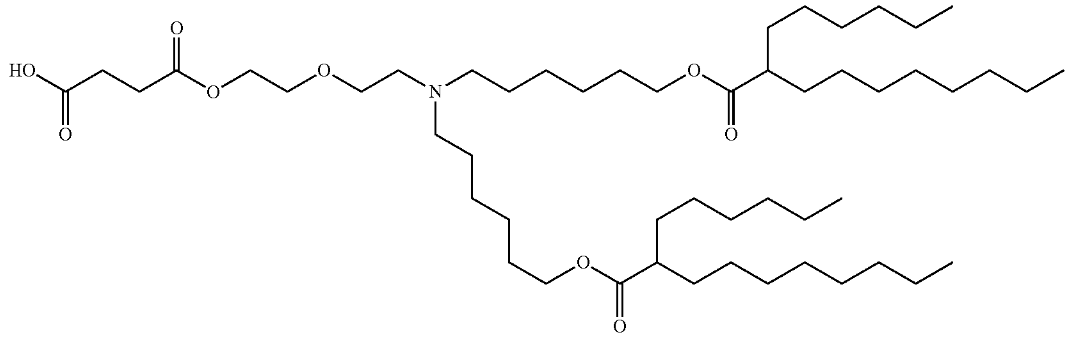
,
P-30
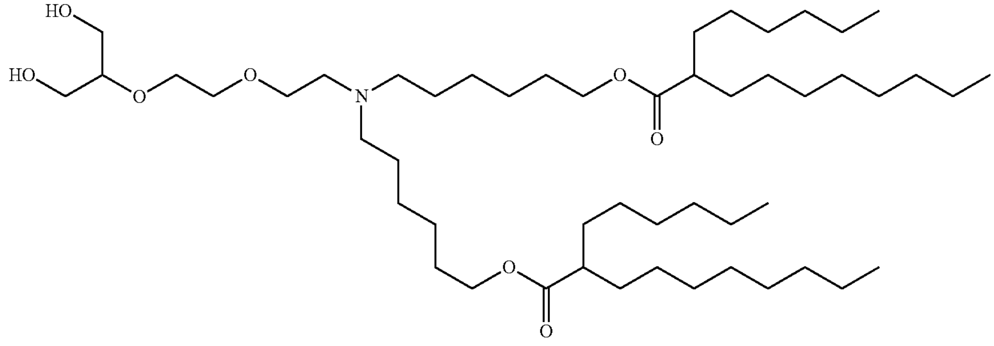
,
P-31
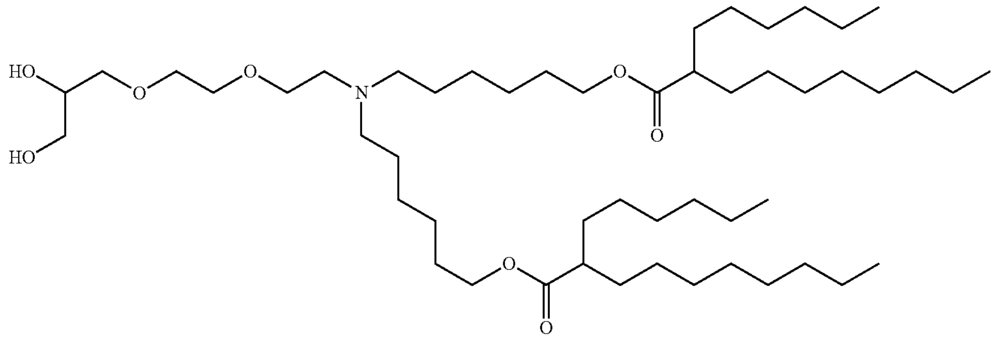
, -continued
P-32
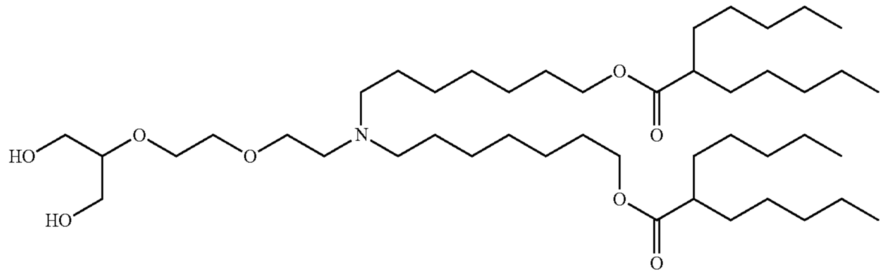
,
P-35
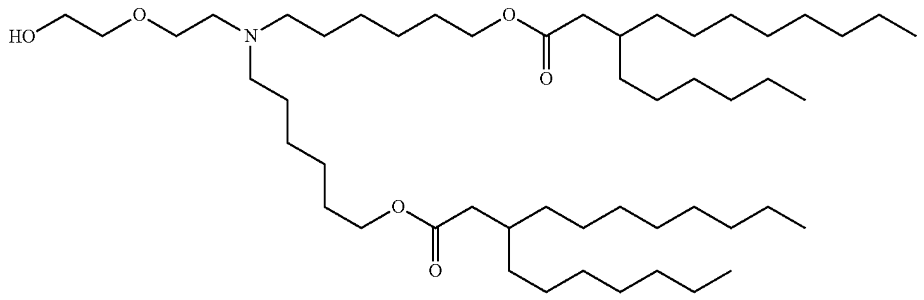
,
P-40
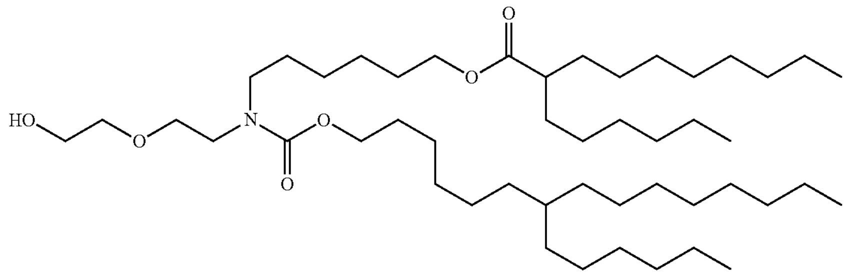
,
P-41
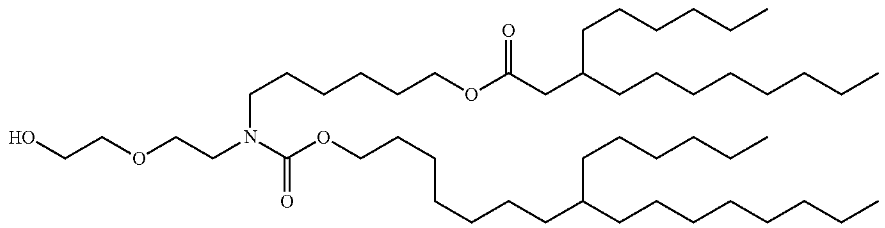
,
P-42
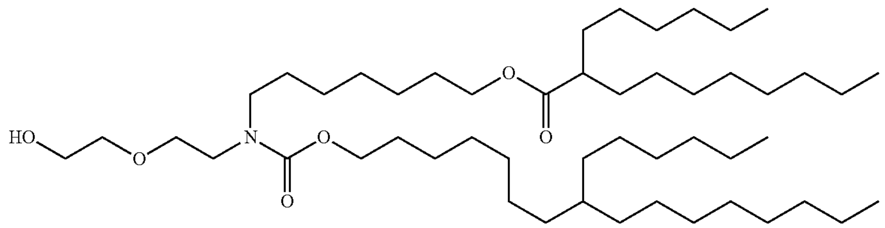
, -continued
P-43
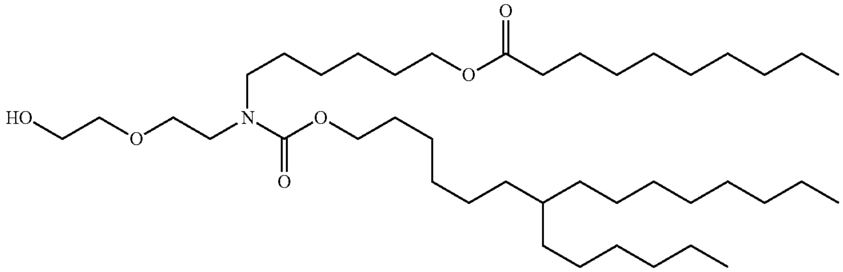
,
P-48
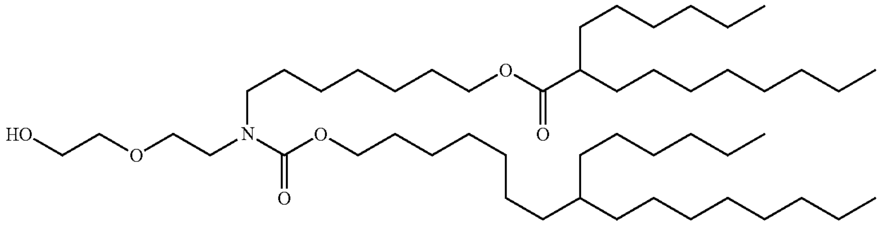
,
P-49
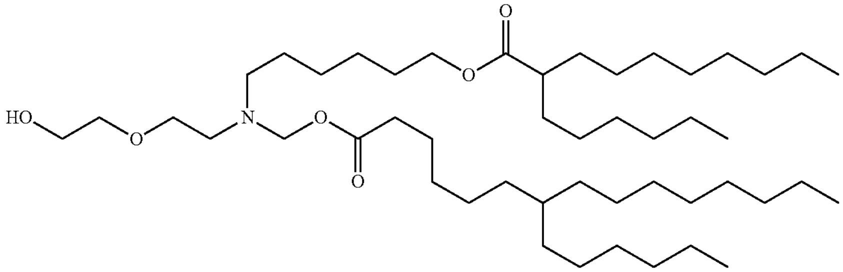
,
P-50
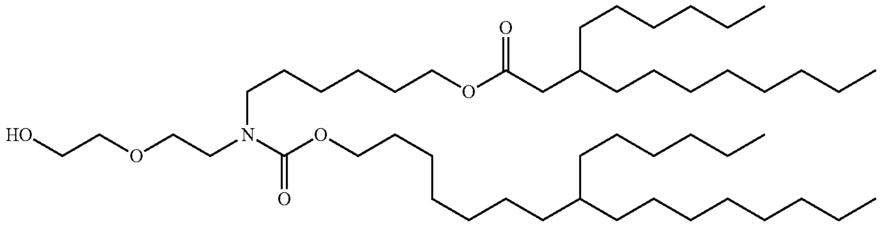
,
P-51
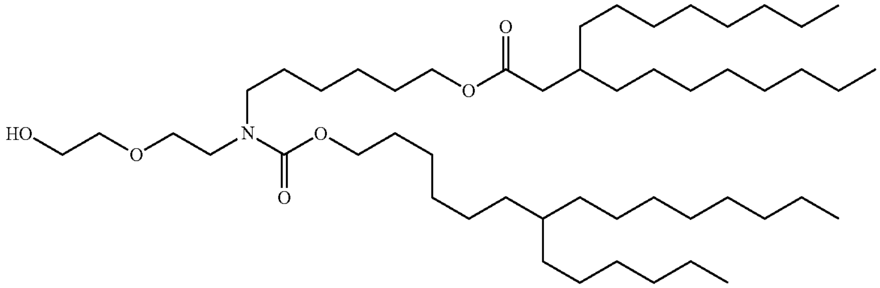
,
P-52
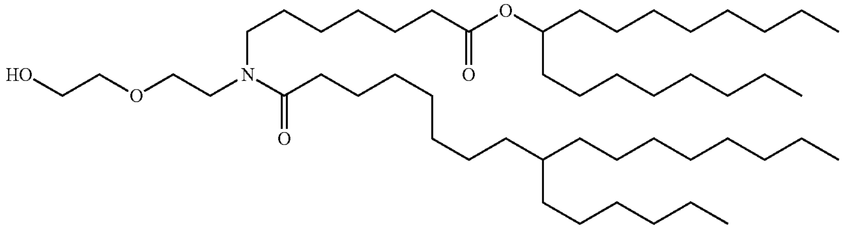
, -continued
P-53
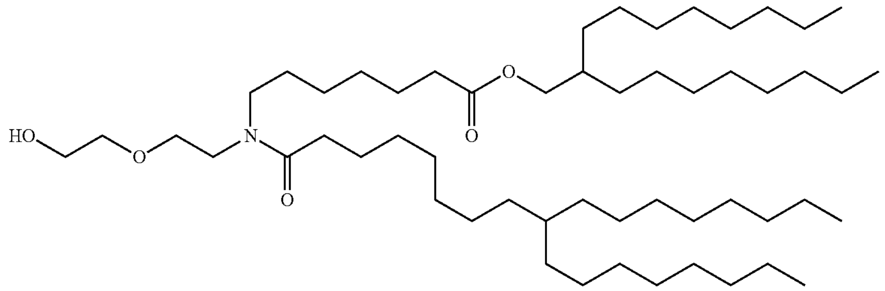
,
P-54
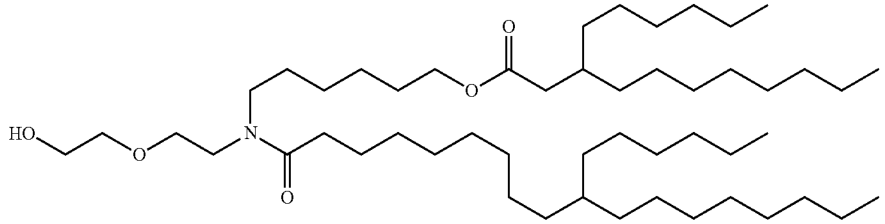
,
P-55
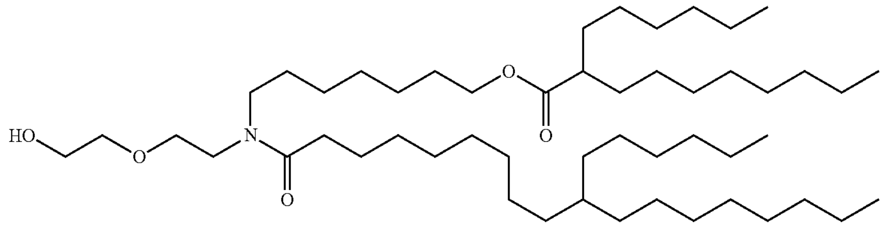
,
P-56
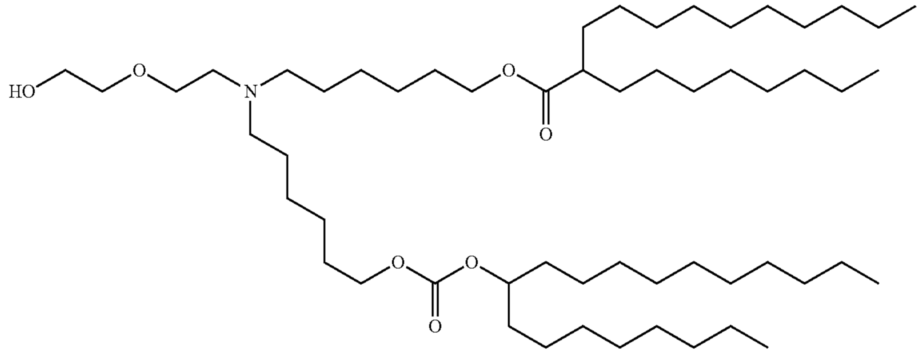
,
P-57
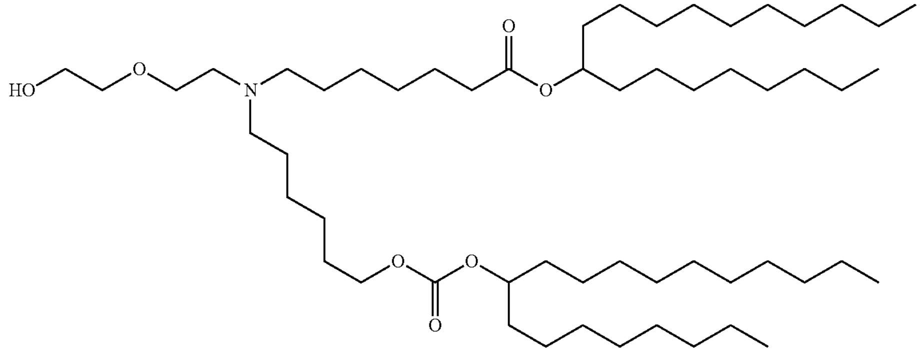
, -continued
P-58
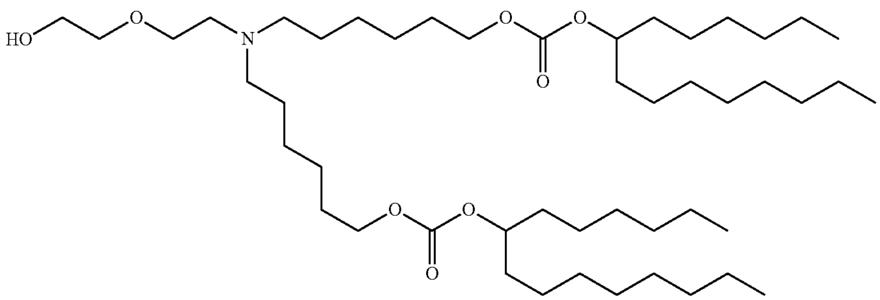
,
P-59
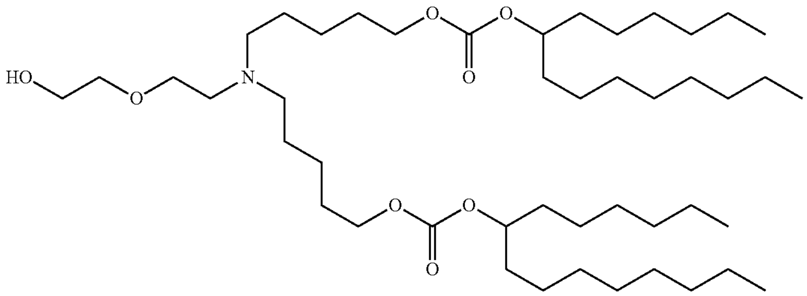
,
P-60
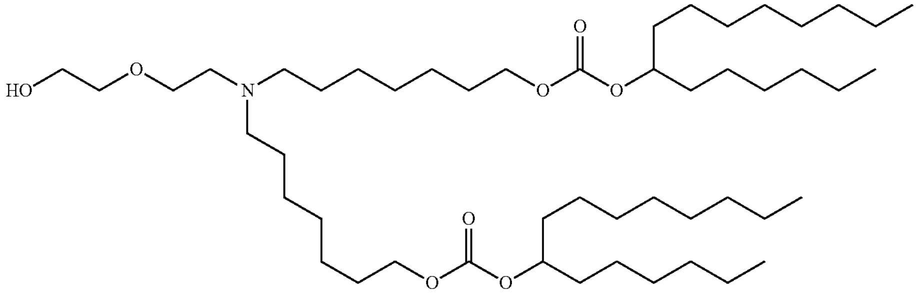
,
P-61
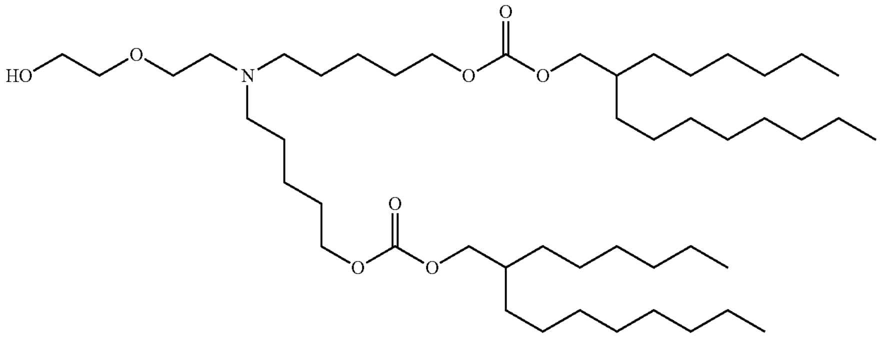
,
P-62
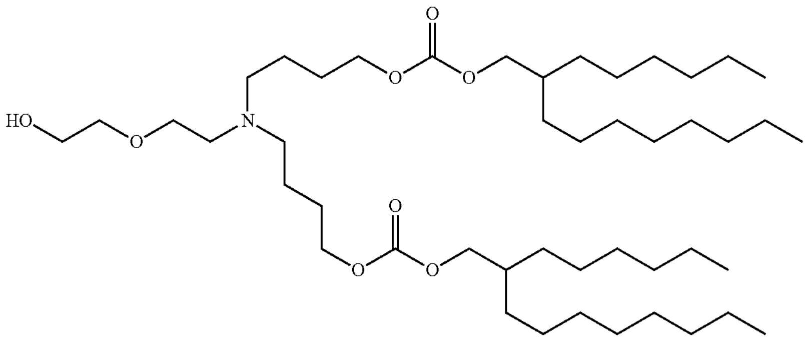
, -continued
P-63
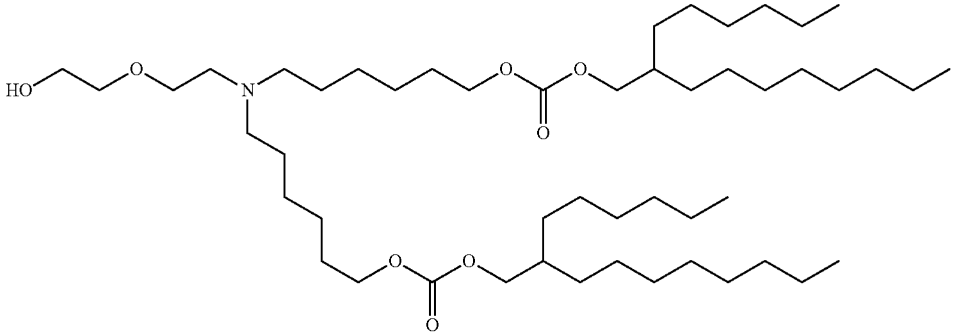
,
P-65
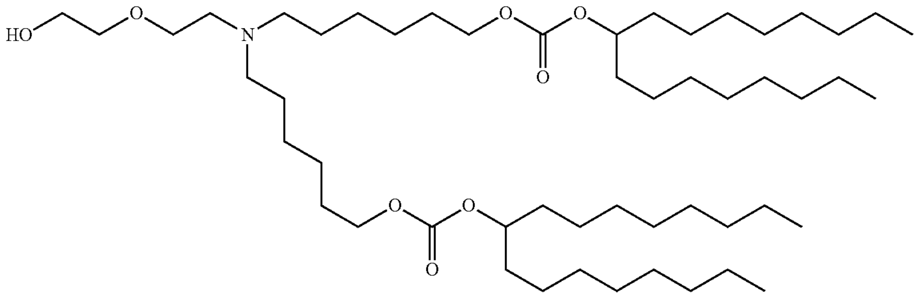
,
P-66
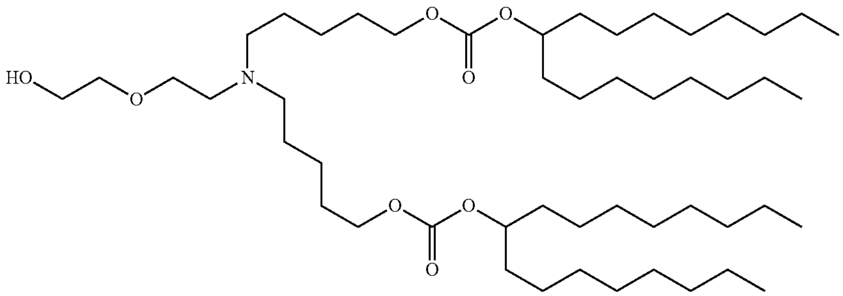
,
P-67
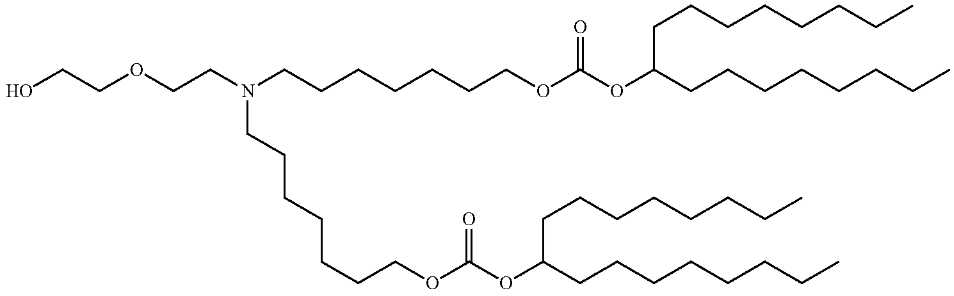
,
P-68
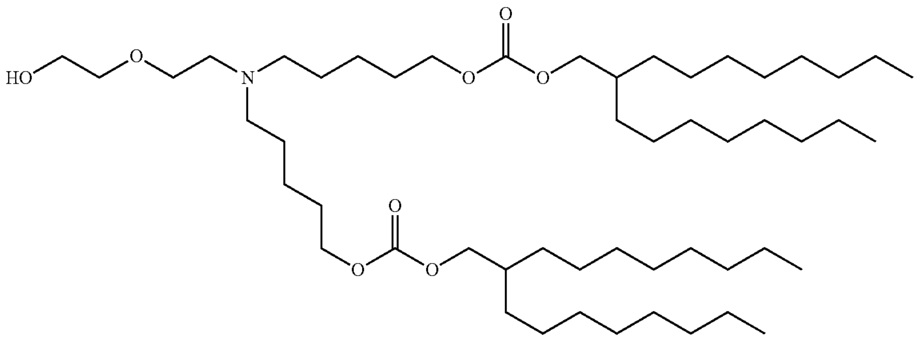
, -continued
P-69
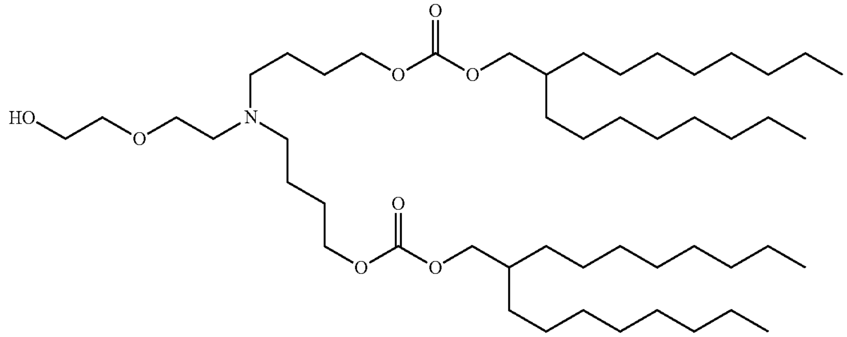
,
P-70
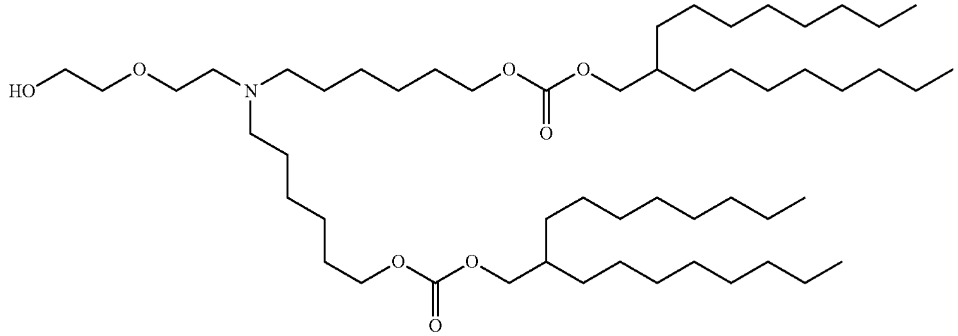
,
P-83
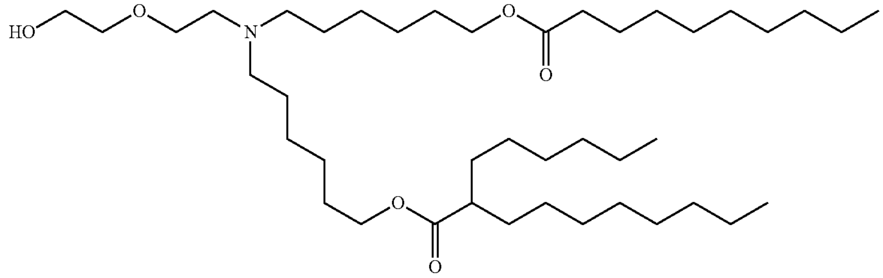
,
P-85
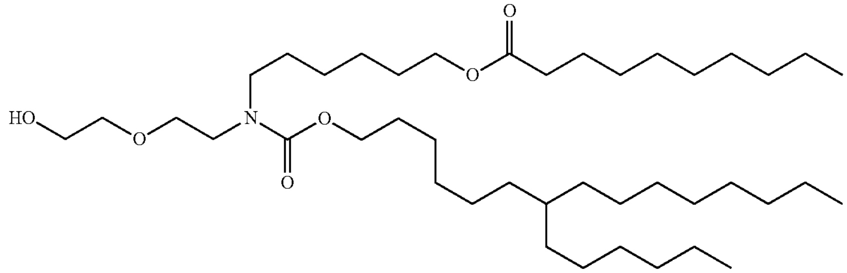
,
P-86
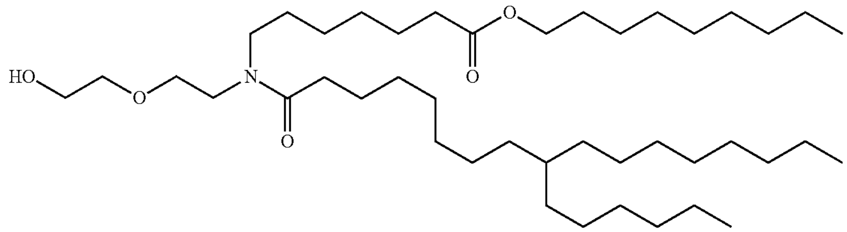
, -continued
P-87
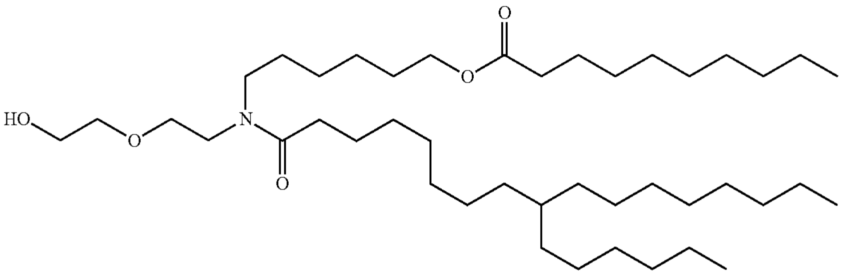
,
P-88
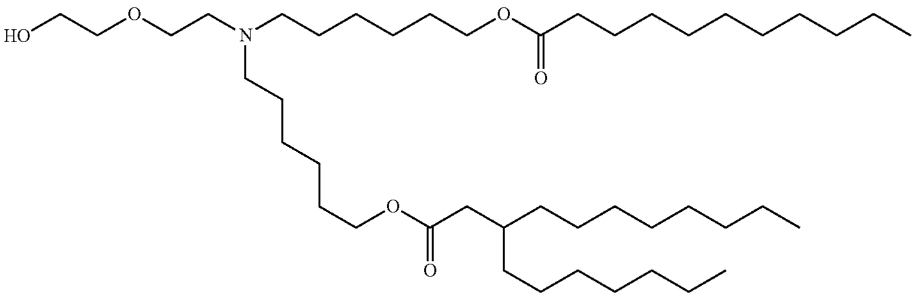
,
P-90
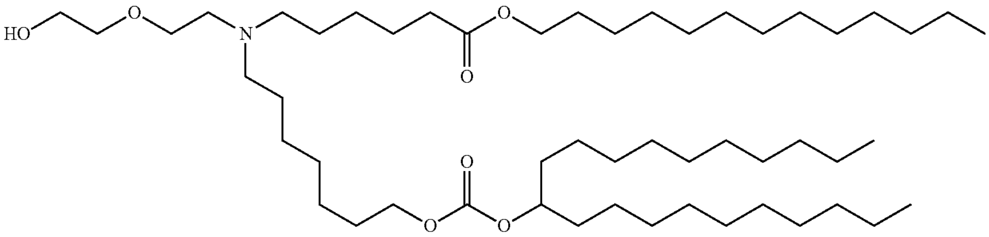
,
P-91
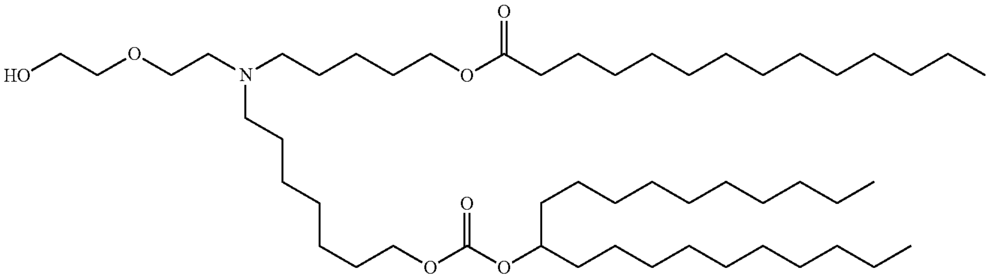
,
P-92
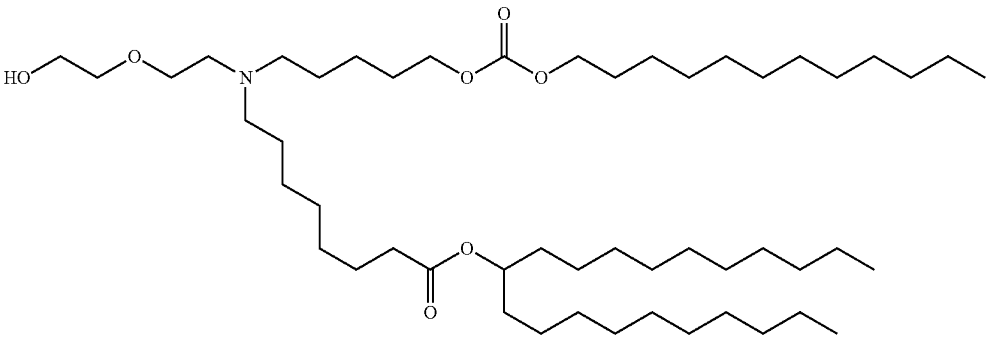
, -continued
P-93
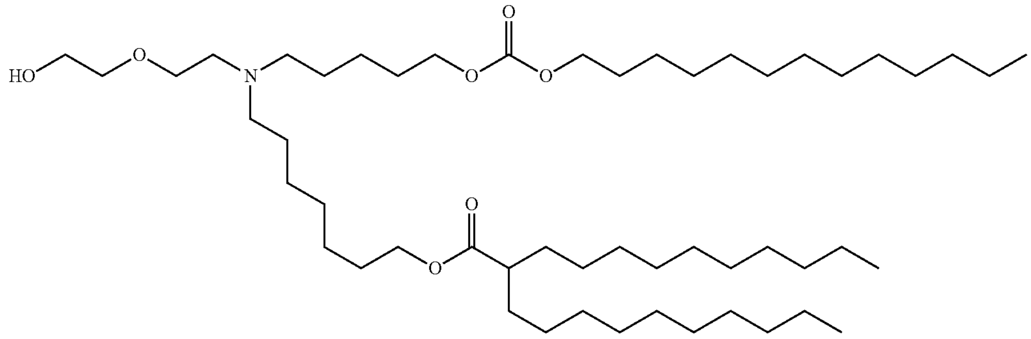
,
P-94
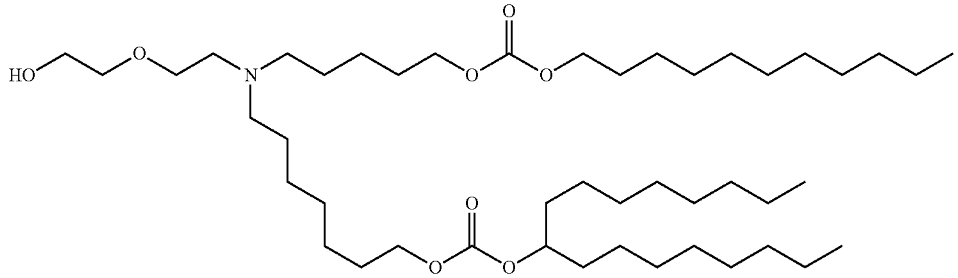
,
P-95
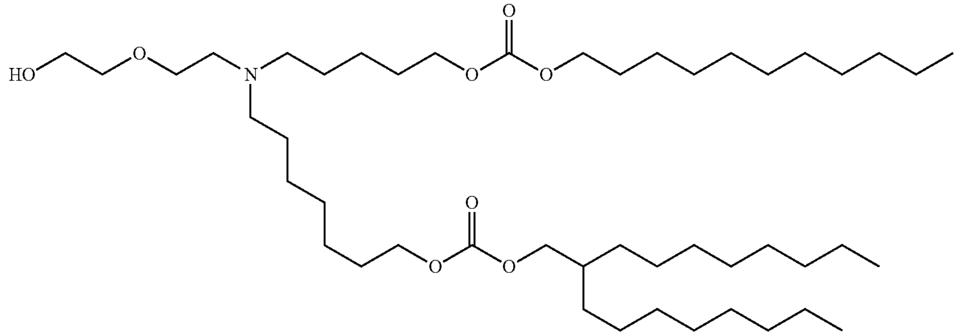
,
P-102
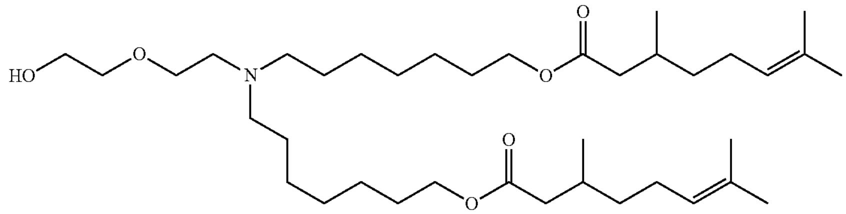
,
P-105
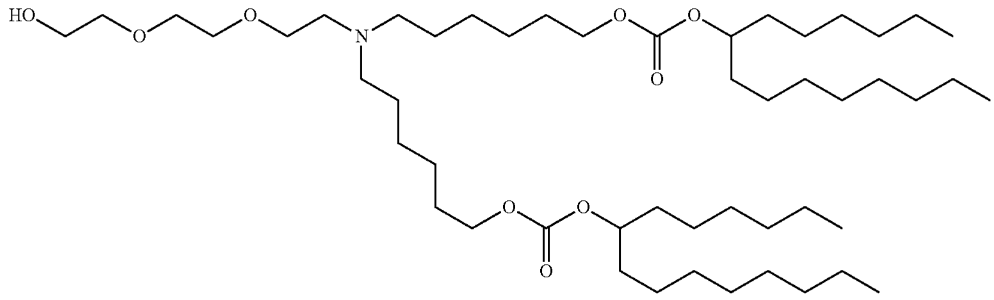
, -continued
P-106
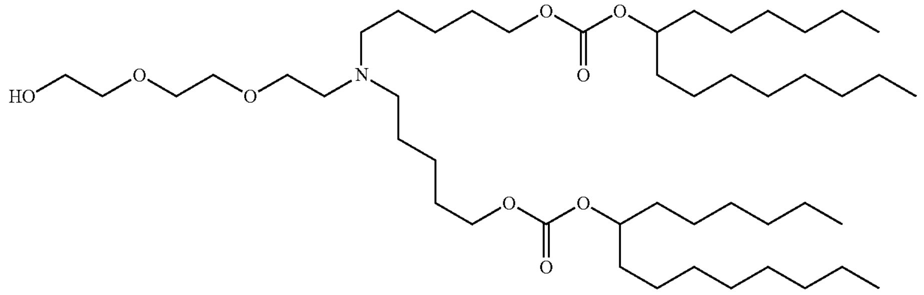
,
P-107
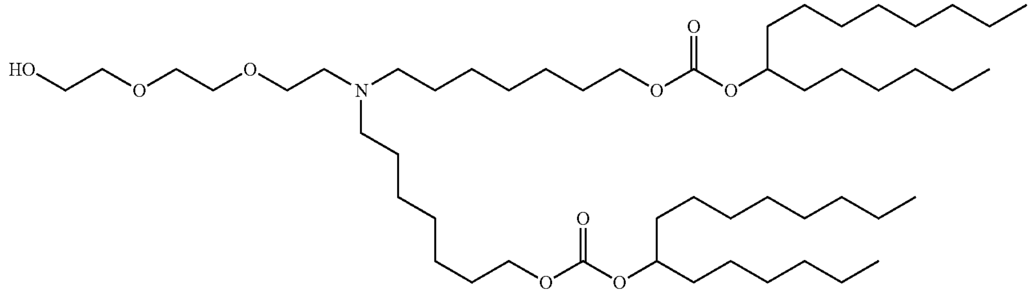
,
P-108
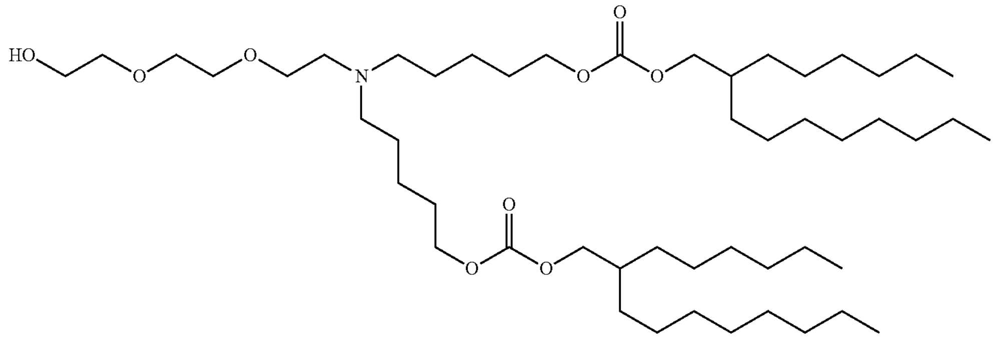
,
P-109
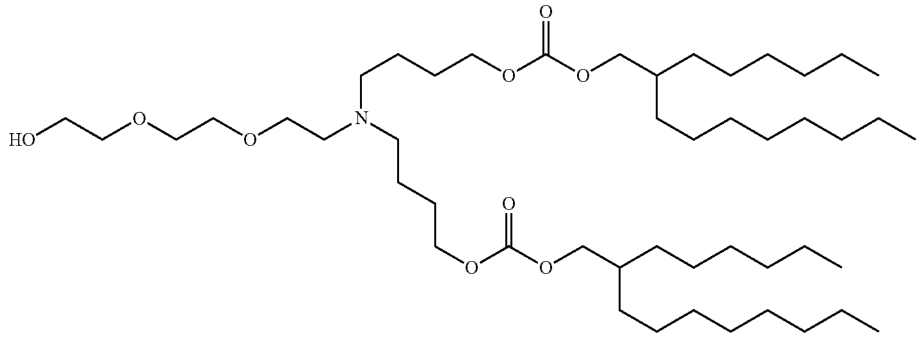
,
P-110
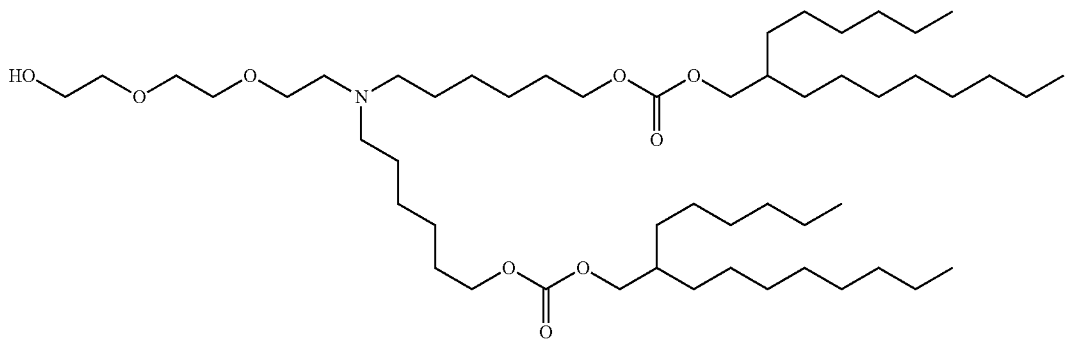
, -continued
P-111
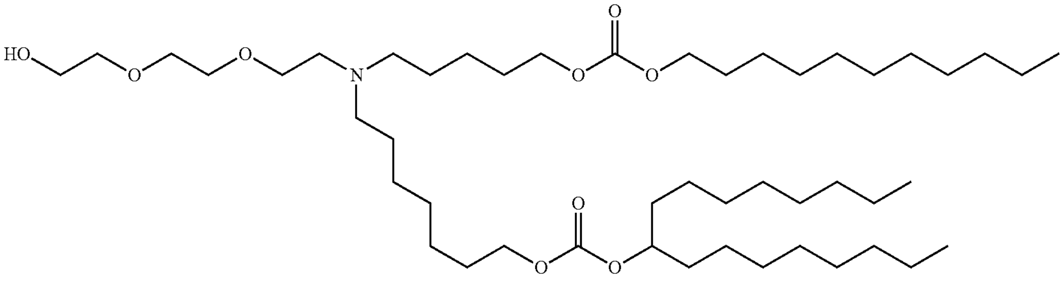
,
P-112
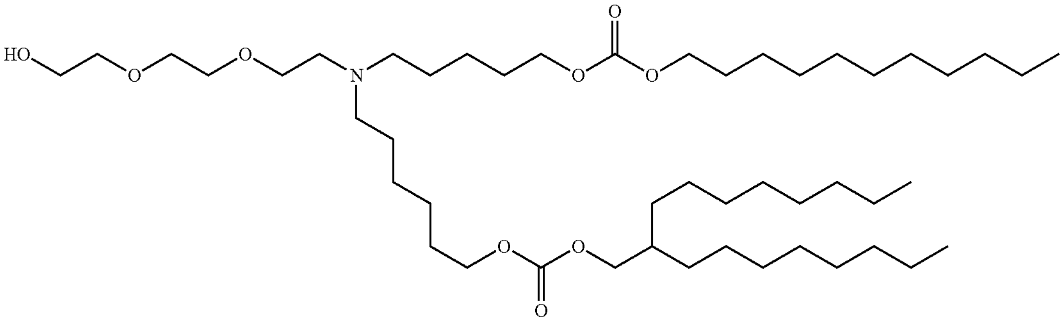
,
P-113
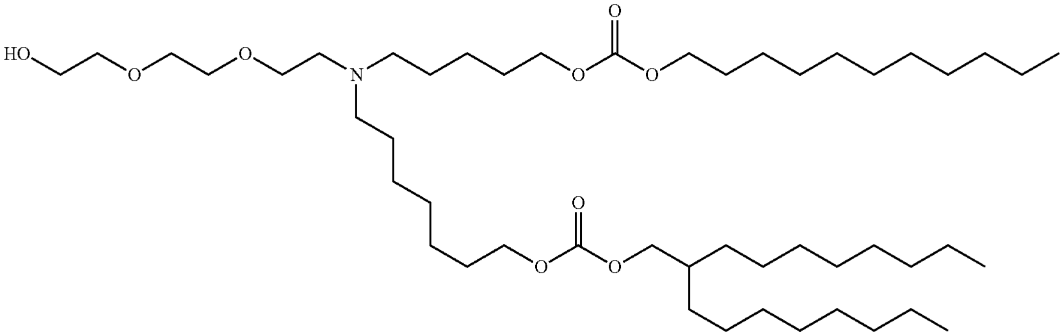
,
P-114
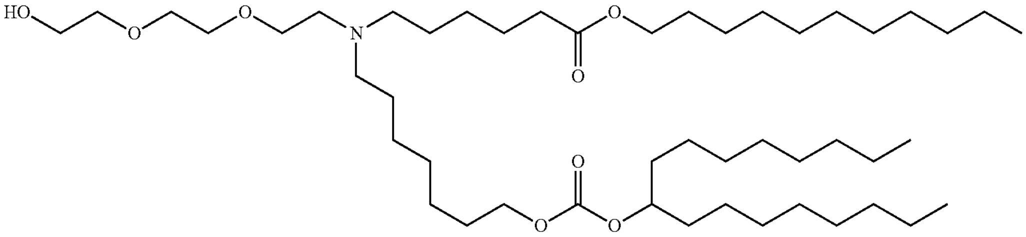
,
P-115
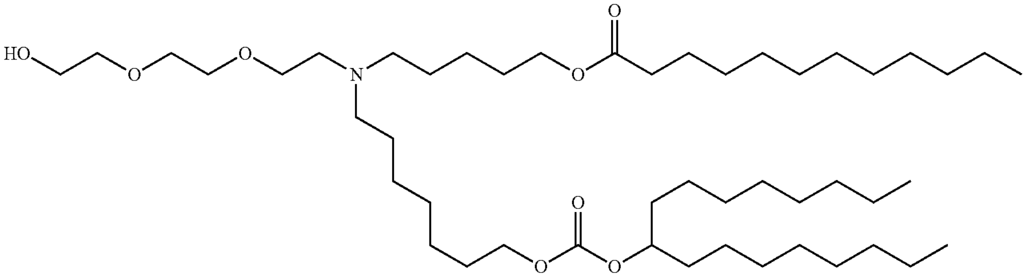
, -continued
P-116
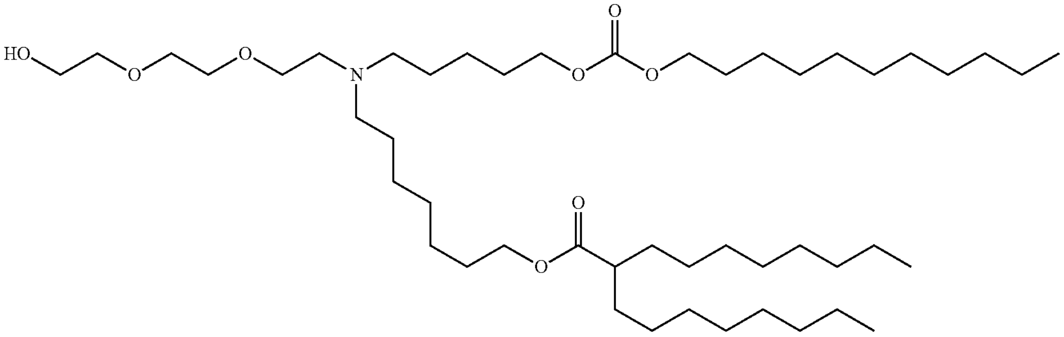
,
P-117
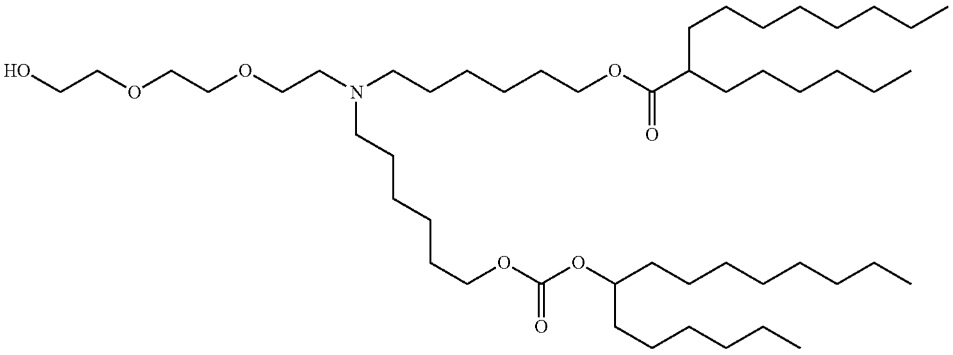
,
P-118
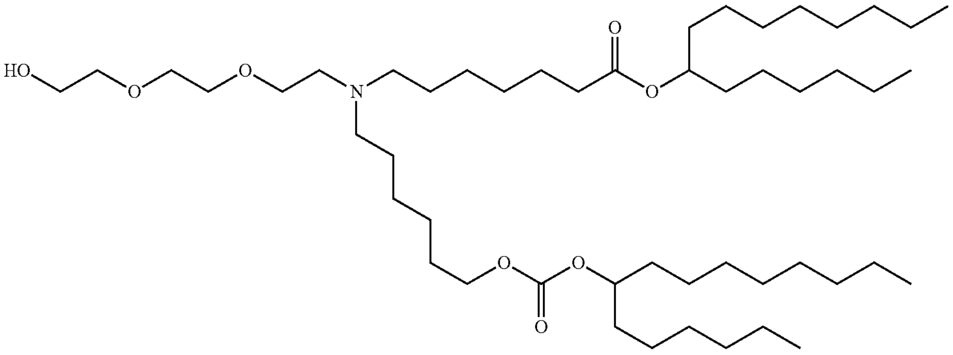
,
P-119
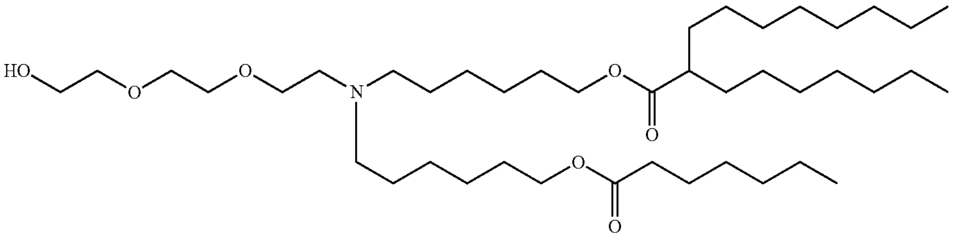
,
P-126
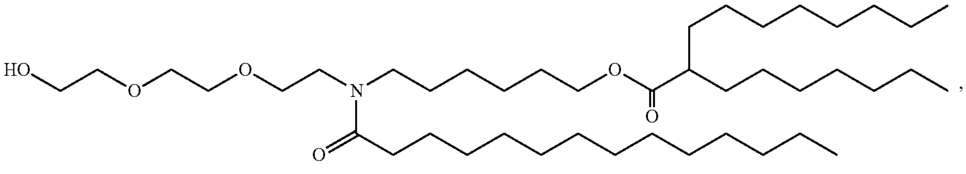
, -continued
P-130
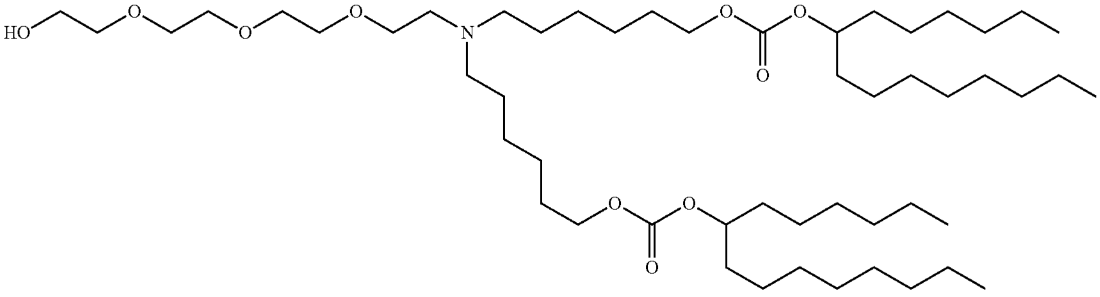
,
P-131
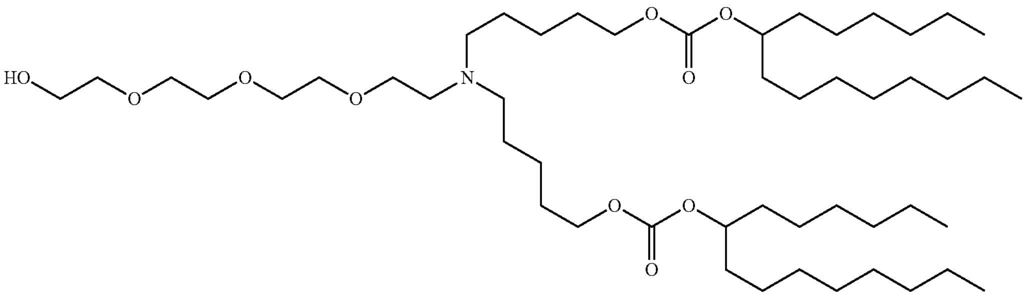
,
P-132
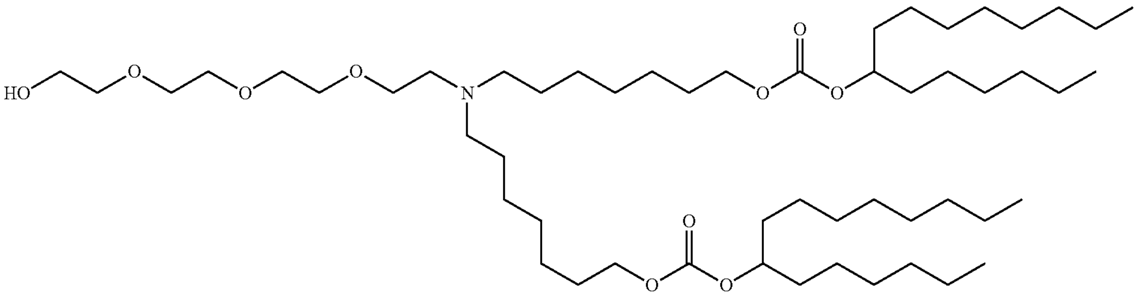
,
P-133
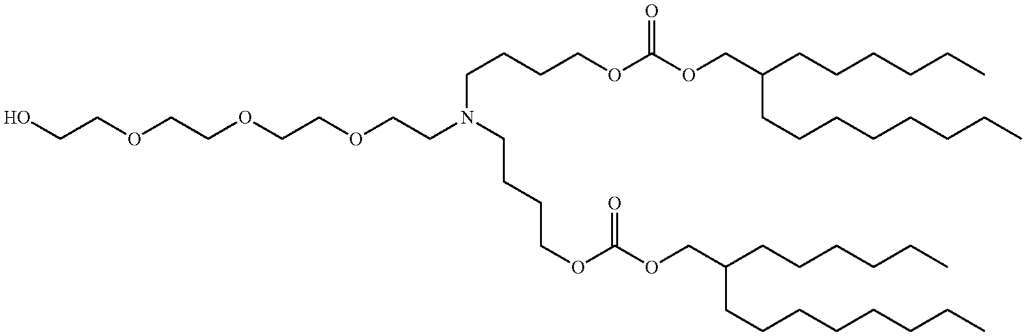
,
P-134
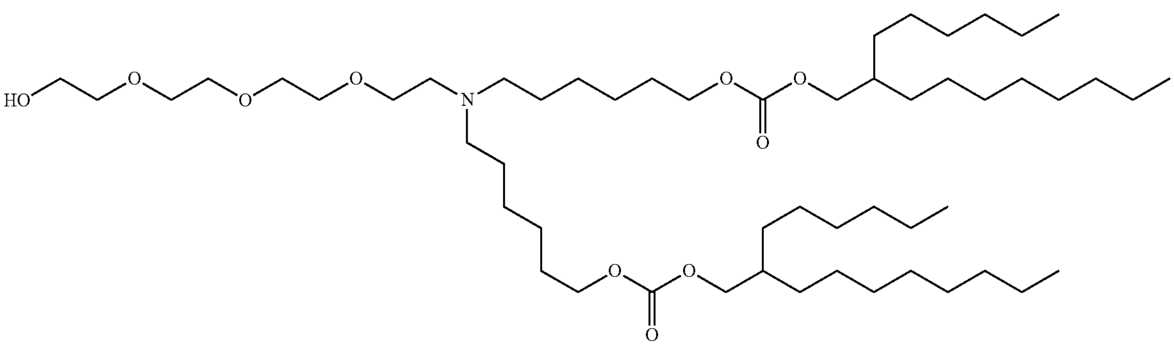
, -continued
P-135
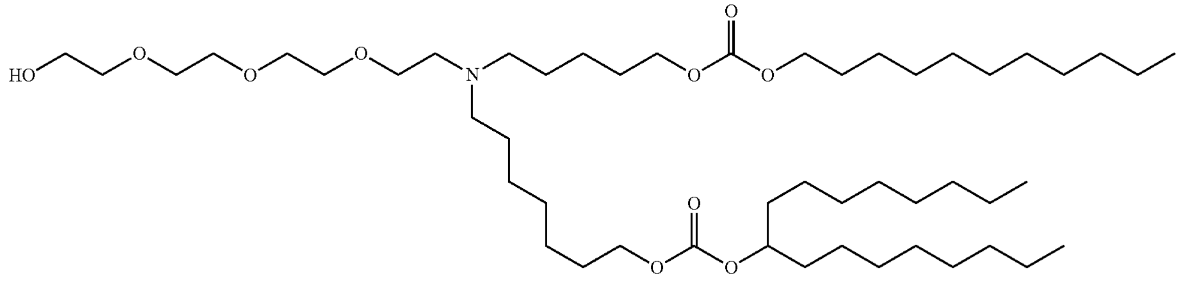
,
P-136
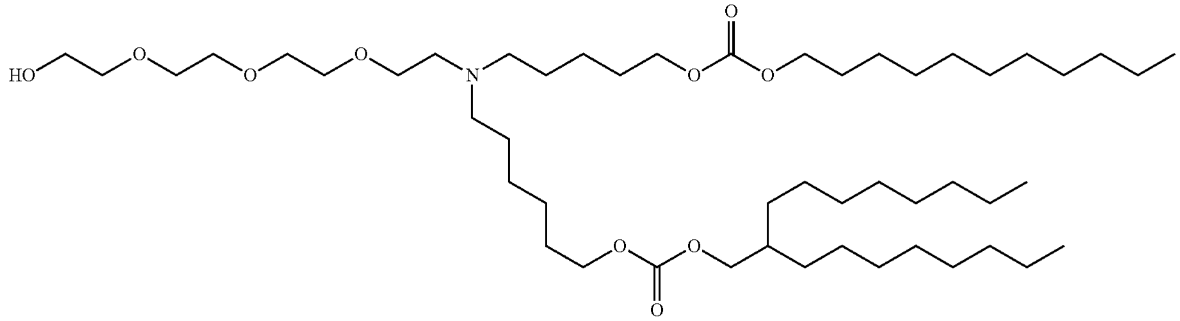
,
P-137
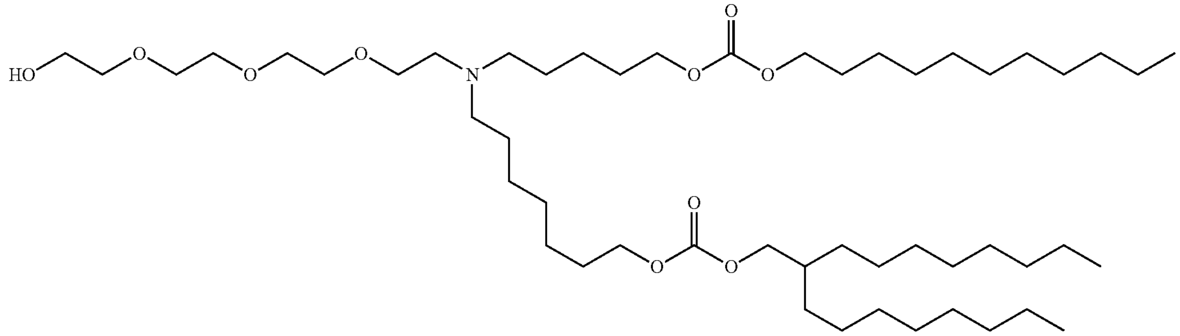
,
P-138
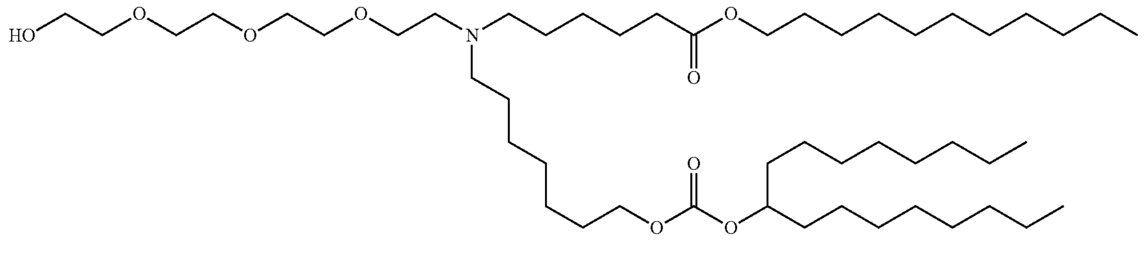
,
P-139
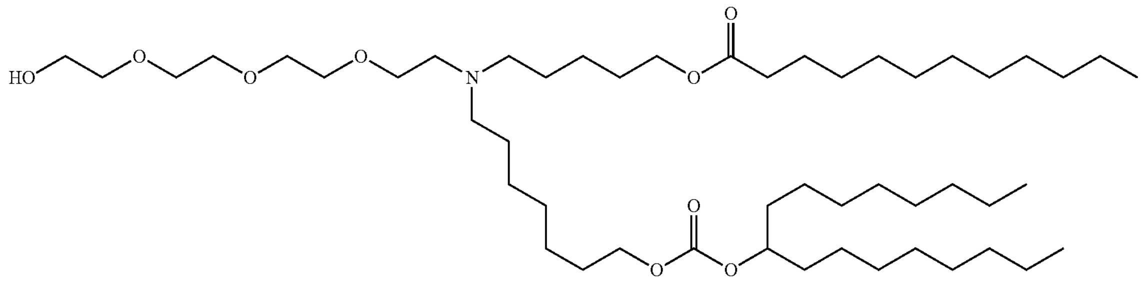
, -continued
P-140
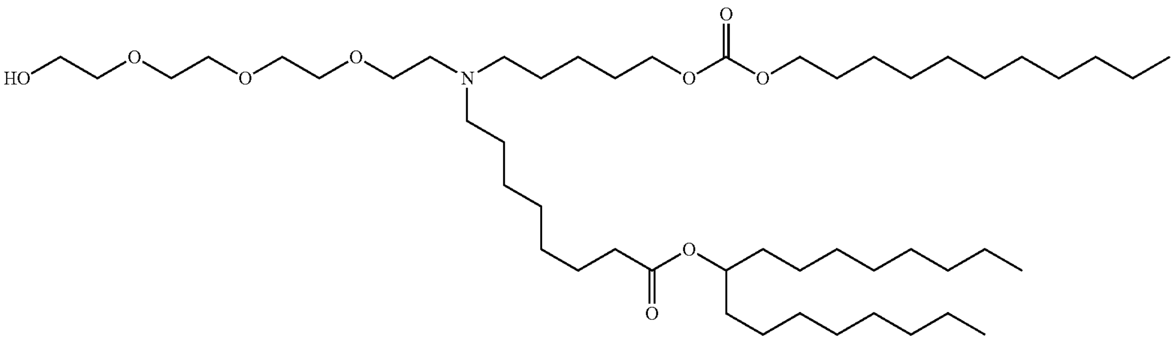
,
P-141
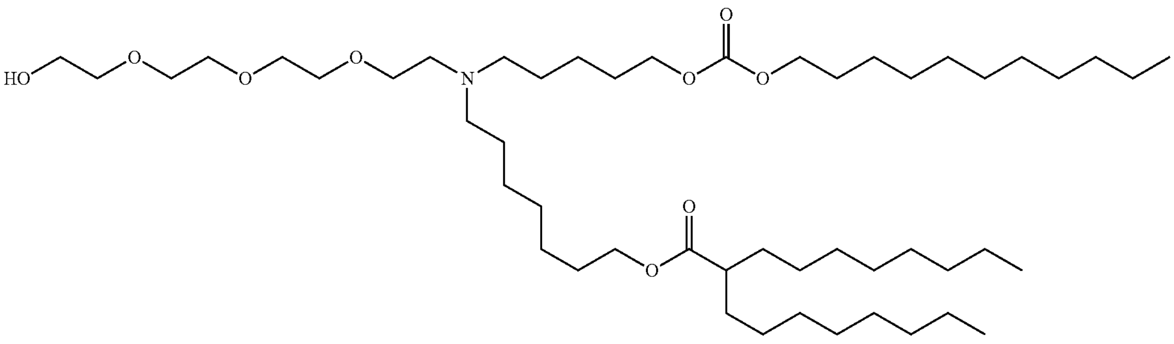
,
P-142
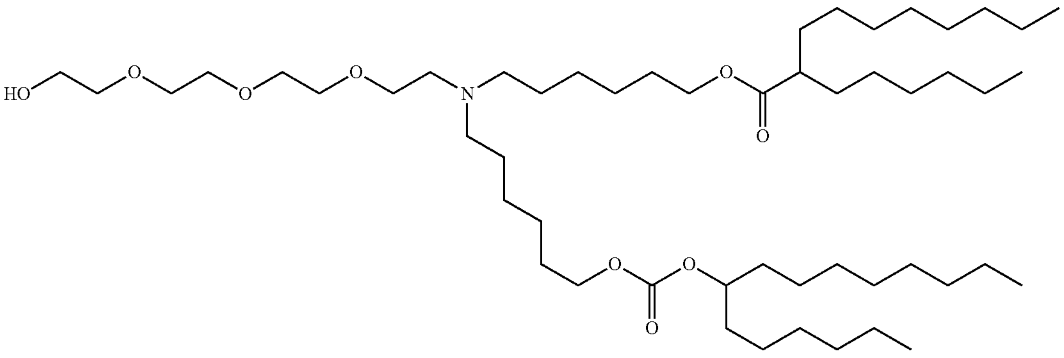
,
P-143
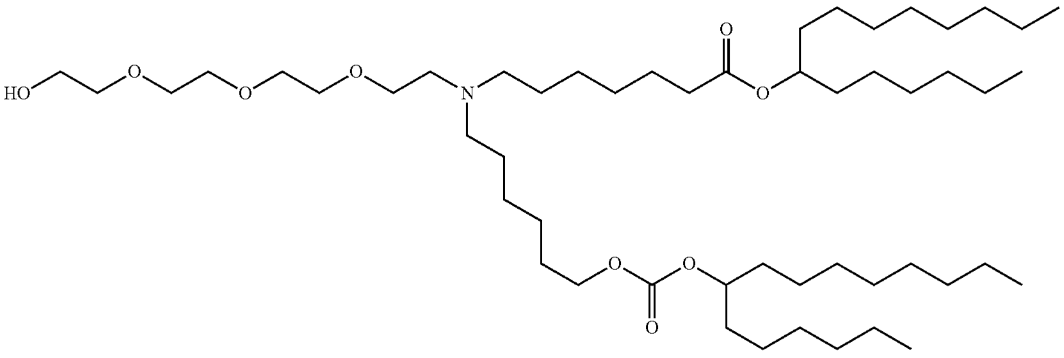
, -continued
P-144
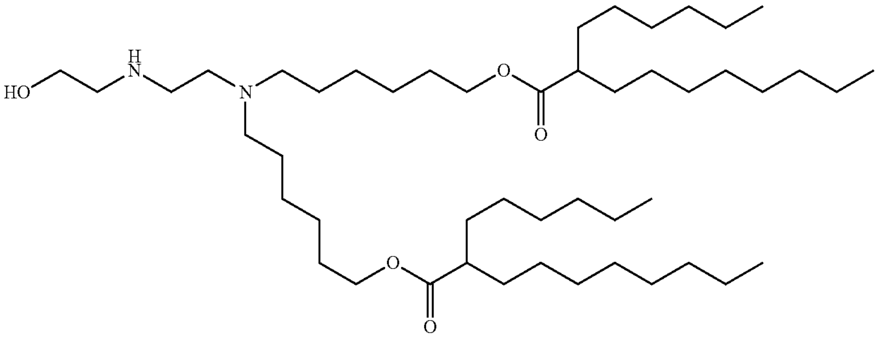
,
P-145
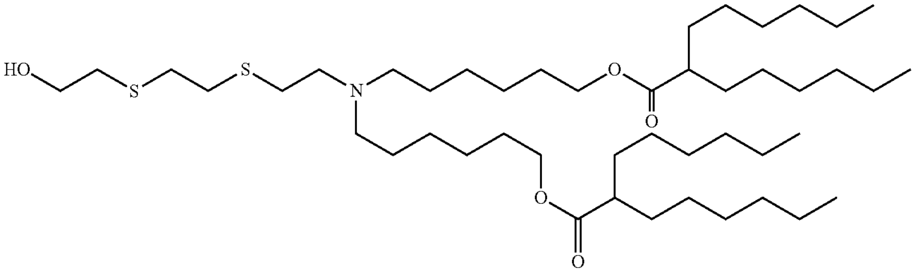
,
P-146
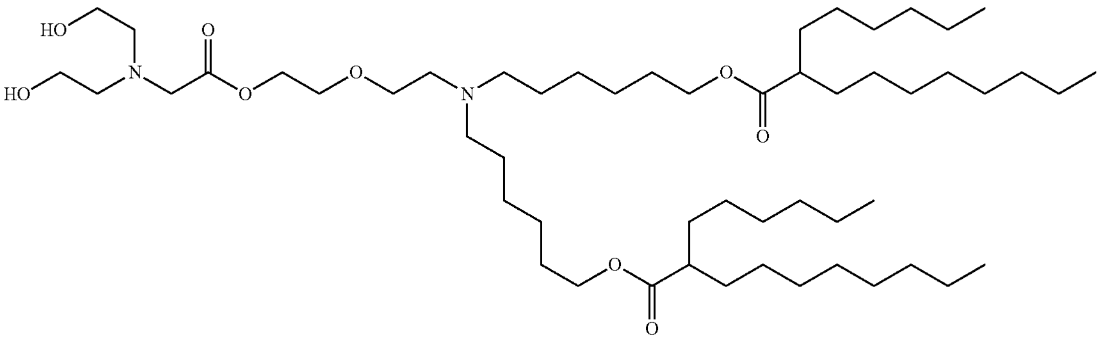
,
P-147
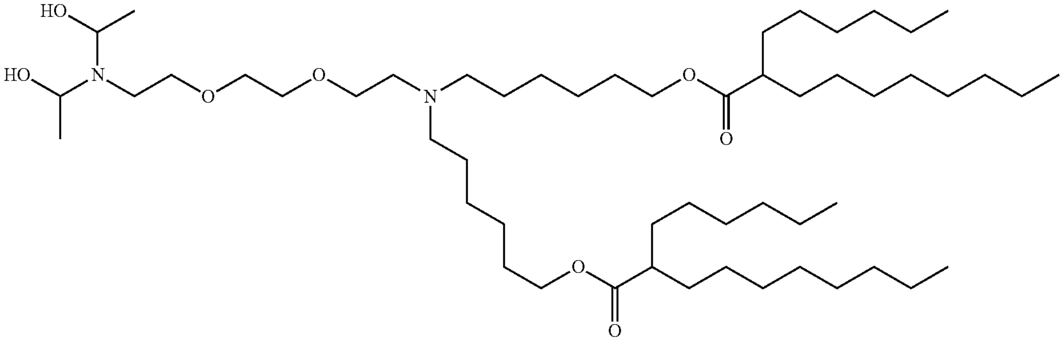
, -continued
P-149
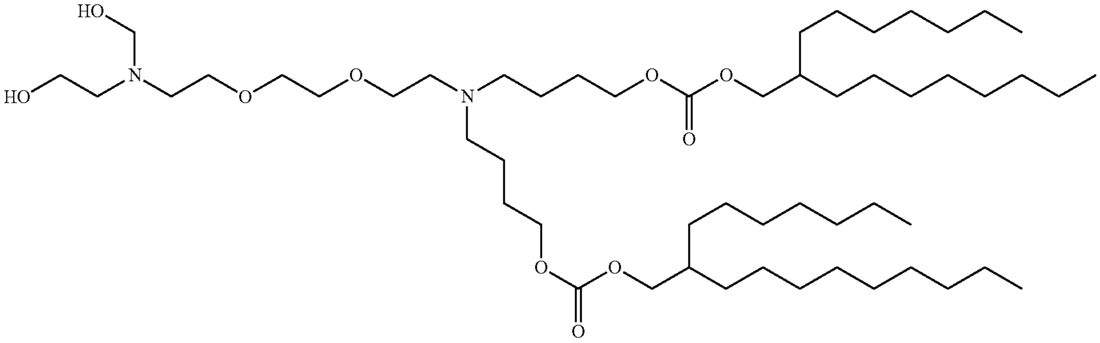
,
P-152
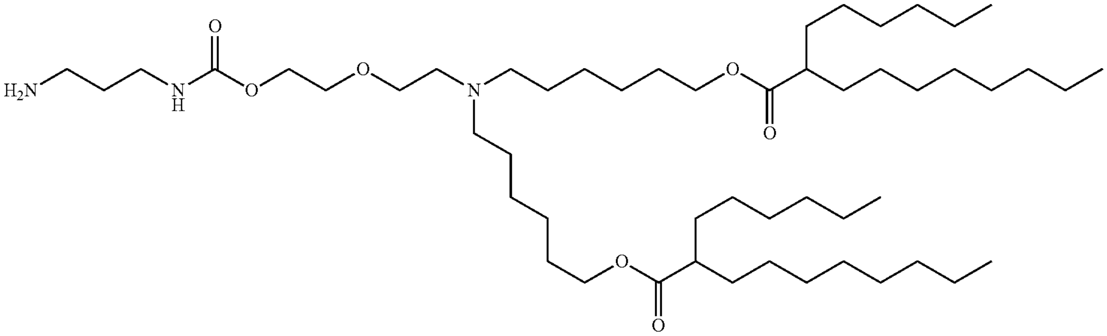
,
P-155
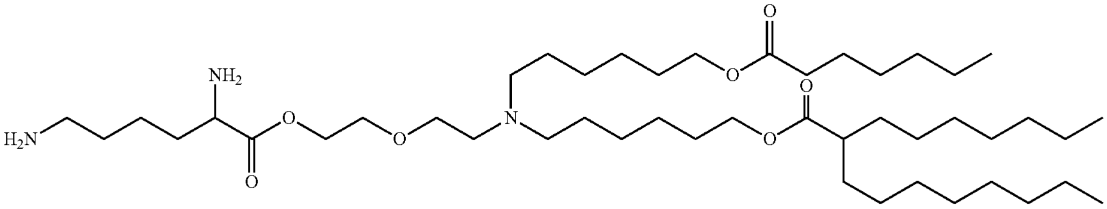
,
P-157
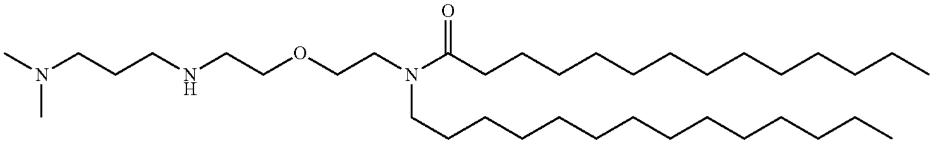
,
P-158
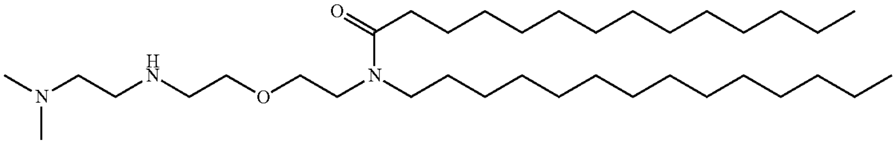
,
P-159
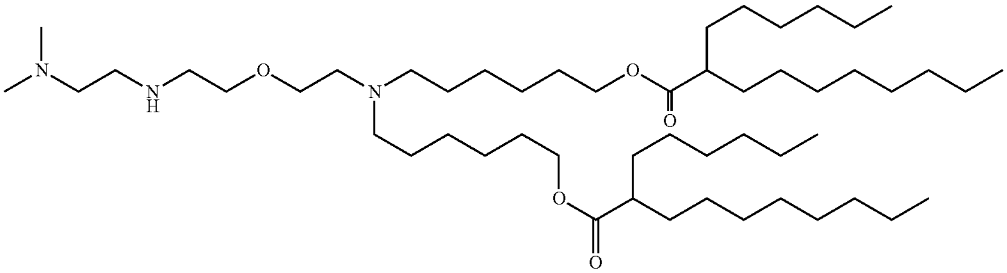
, -continued
P-162
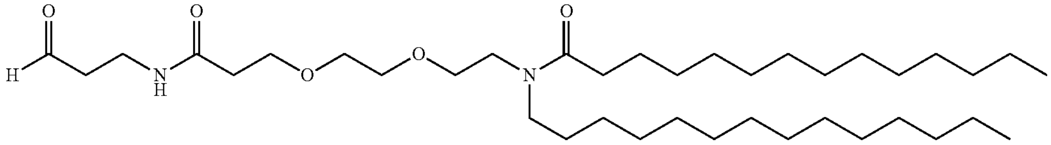
,
P-163
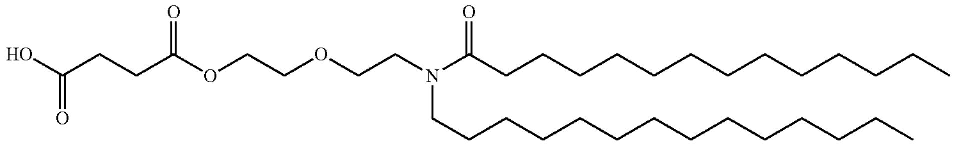
,
P-164
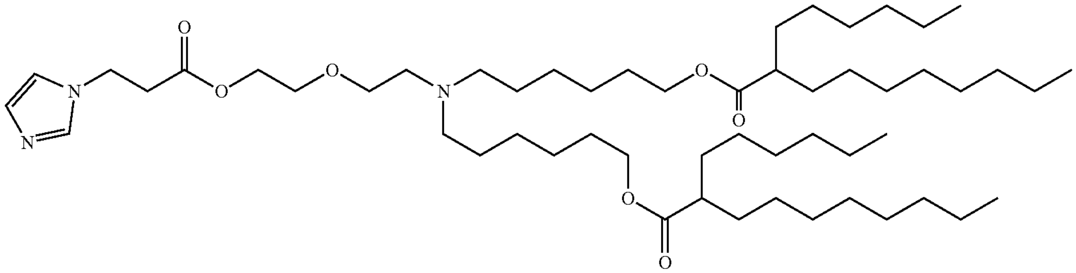
,
P-165
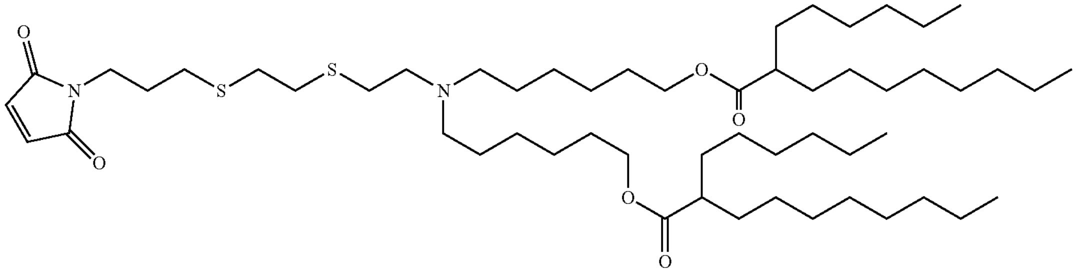
,
P-166
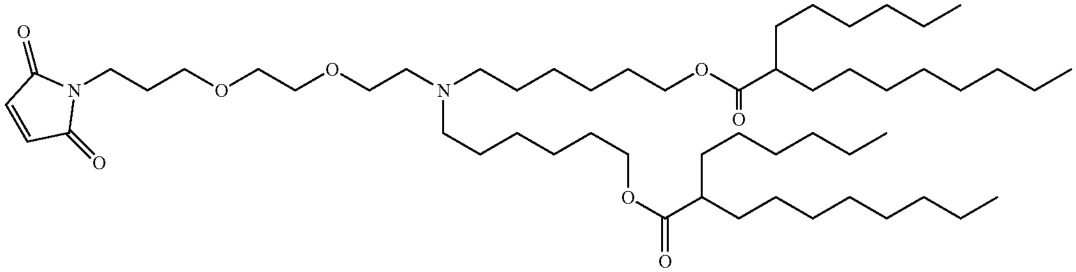
,
P-168
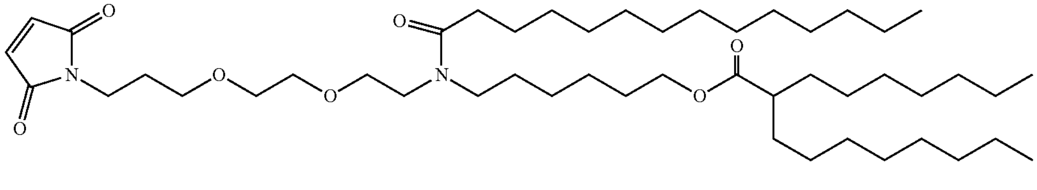
, -continued
P-169
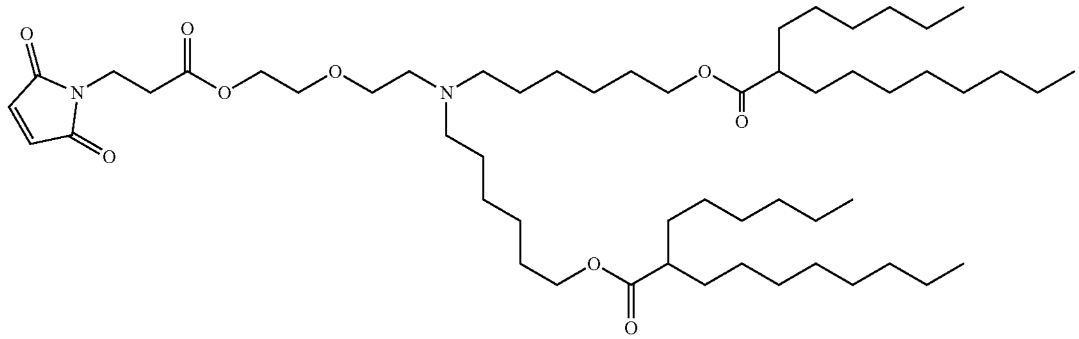
,
P-170
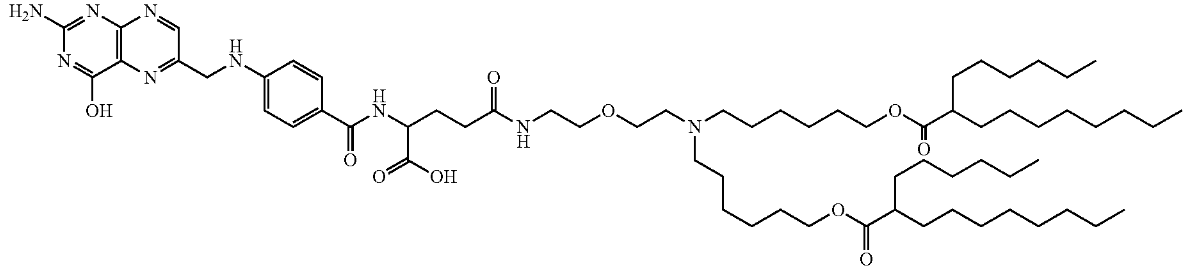
,
P-171
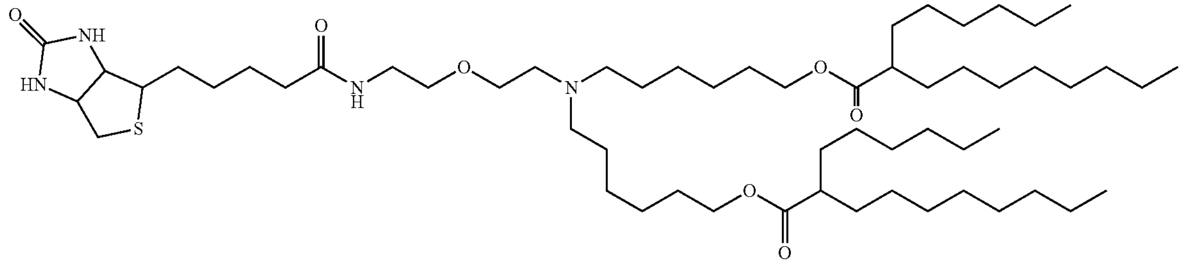
,
P-172
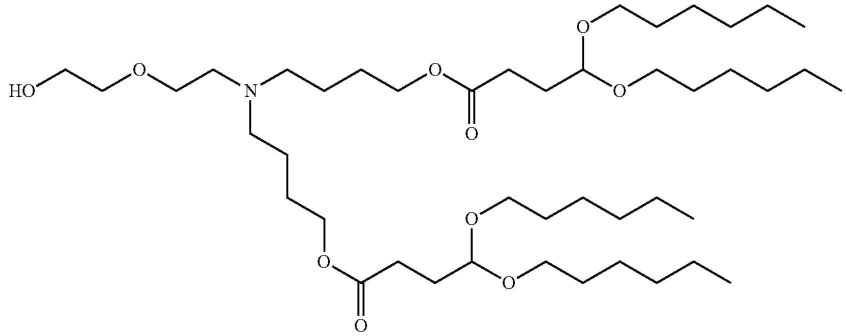
,
P-173
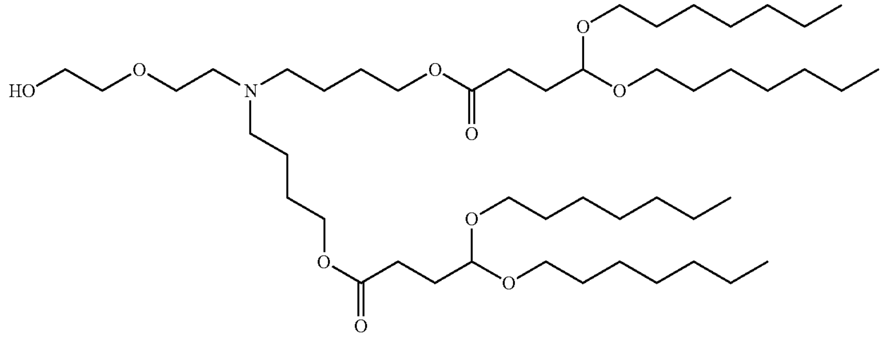
, -continued

P-174

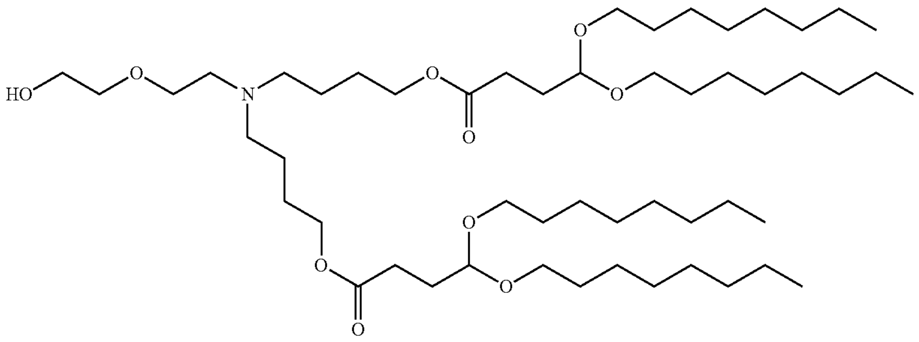

,

P-175

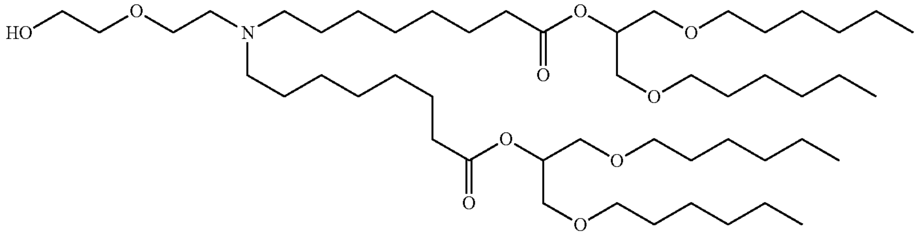

,

P-176

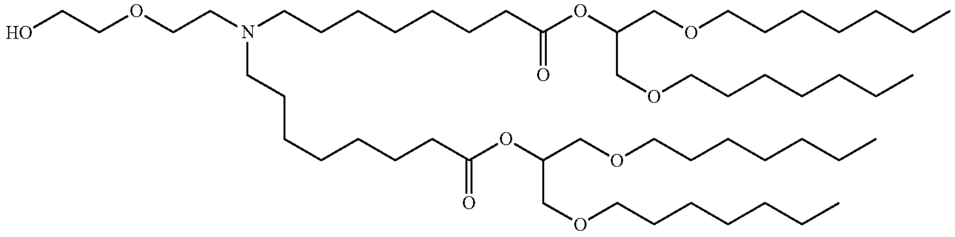

,

P-177

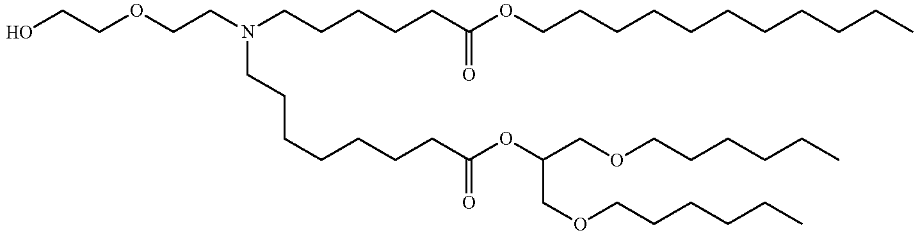

, and

P-178

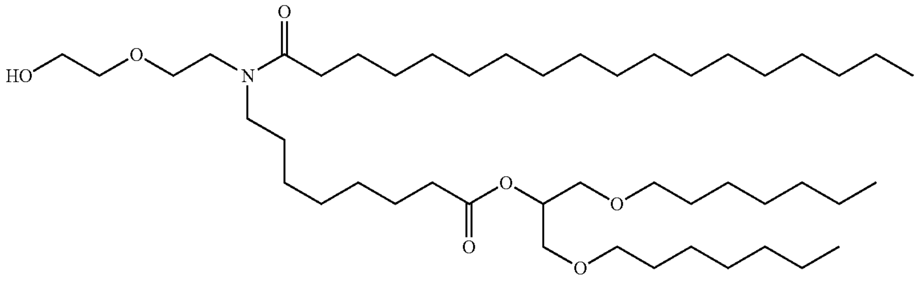

.

2. Preparation of Cationic Lipids

In the present invention, any of the above-mentioned cationic lipids can be prepared by methods including but not limited to the following:

2.1. Method-1:

Step 1: activating the carboxyl terminus of acid A-1 (or A-1') containing an unprotected carboxyl group, using carboxyl activating agents, from which the ester A-2 (or A-2') containing an activated carboxyl terminus is obtained; wherein, $B_1$' and $B_2$' are each independently a linking bond or an alkylene group having one less methylene group than $B_1$ or $B_2$; wherein, $R_1$' and $R_2$' are each independently $R_1$ or $R_2$, or an aliphatic group having one less methylene group than $R_1$ or $R_2$; wherein, $R_7$ is a carboxyl-activating group, and when either $B_1$' or $L_1$ is not a linking bond, $R_1$' is $R_1$, and when both $B_1$' and $L_1$ are linking bonds, $R_1$' is an aliphatic group having one less methylene group than $R_1$, and when either $B_2$' or $L_2$ is not a linking bond, $R_2$' is $R_2$, and when both $B_2$' and $L_2$ are linking bonds, $R_2$' is an aliphatic group having one less methylene group than $R_2$;

Step 2: carrying out the condensation reaction of the ester A-2 (or A-2') containing an activated carboxyl terminus with the primary amine derivative A-3 (or A-3') containing a nitrogen-source terminal group to obtain the amide intermediate A-4 (or A-4');

Step 3: using reduction reagent to reduce the amide intermediate A-4 (or A-4') to the secondary amine intermediate A-5 (or A-5');

Step 4: carrying out the coupling reaction of the secondary amine intermediate A-5 (or A-5') with the dual-end functionalized small molecule A-6 to obtain the cationic lipid derivative A-7 (or A-7'); wherein, the two terminal functional groups of A-6 can be the same or different; wherein, the $R_3$' end of A-6 contains the functional group $R_{01}$ or a variant form with micro-modification of $R_{01}$; said variant form with micro-modification refers to the group which can be transformed into $R_{01}$ through any process of chemical reaction selected from deprotonation, salt complexation and decomplexation, ionization, protonation, deprotonation, and changing leaving groups; wherein, the $F_1$ in A-6 contains active functional groups which can react with the amino group of the secondary amine intermediate A-5 (or A-5') to obtain the nitrogen-atom branching center and the divalent linking group $L_3$;

when $R_3$' is $R_3$, the structure of A-7 (or A-7') is represented by the general formula (1);

when $R_3$' is not $R_3$, A-8 (or A-8') represented by the general formula (1) is obtained via terminal micro-modification of A-7 (or A-7'); said terminal micro-modification is selected from the group consisting of deprotection, salt complexation and decomplexation, ionization, protonation, deprotonation, and changing leaving groups.

Step 1:

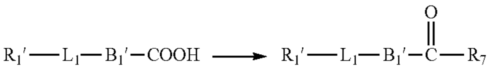
A-1 A-2 or

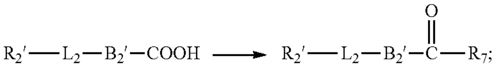
A-1' A-2';

Step 2:

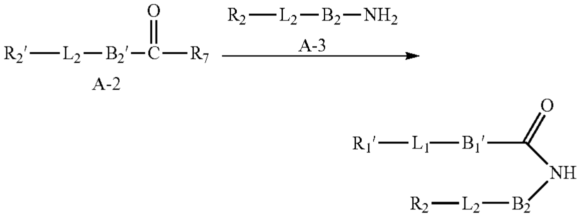

A-2 A-4 or

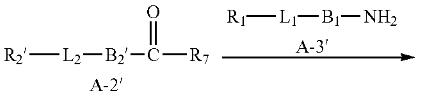

A-2'

-continued

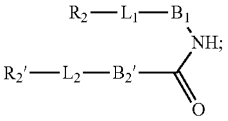
A-4

Step 3:

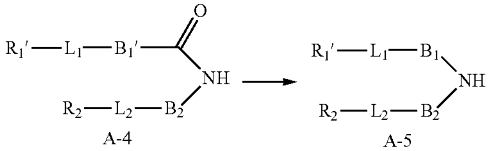
A-4 A-5 or

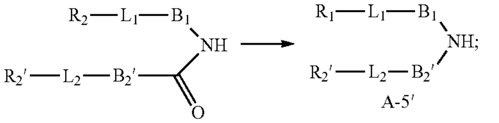
A-4' A-5'

Step 4:

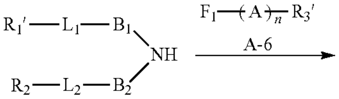

A-5

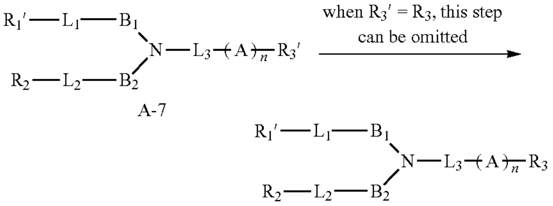

A-7 A-8 or

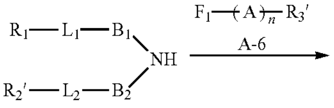

A-5'

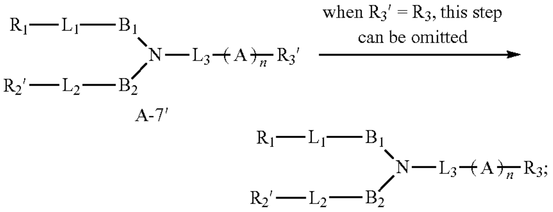

A-7' A-8' wherein, $L_3$, $L_1$, $L_2$, $B_1$, $B_2$, $R_3$, $R_1$, $R_2$, and n are the same as those in the general formula (1), and are not described again here.

In one specific embodiment of the present invention and with respect to the aforementioned Method-1, said A-1 is preferably $R_1$'—COOH or $R_2$'—COOH, said A-3 is preferably $R_1$—$NH_2$ or $R_2$—$NH_2$, said carboxyl activating agent is preferably selected from the group consisting of N-hydroxysuccinimide (NHS), 1-ethyl-3-(3-dimethylaminopropyl)carbodiimide (EDCI), N-hydroxy-5-norbornene-2,3-dicarboximide (HONb), and N,N'-Dicyclohexylcarbodiimide (DCC), and said cationic lipid is preferably produced by the following routes:

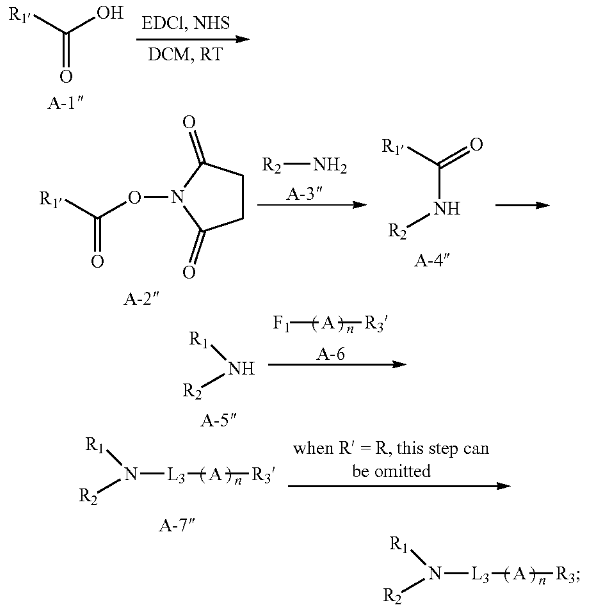

A-1″ A-2″ A-4″ A-5″ A-7″ A-8″

2.2 Method-2:

Step 1: carrying out the coupling reaction of the primary amine derivative B-2 (or B-2') containing a nitrogen-source terminal group, with the dual-end functionalized small molecule B-1, from which the secondary amine derivative B-3 (or B-3') is obtained; wherein, the two terminal functional groups of B-1 can be the same or different; the $R_3$' end of B-1 contains the functional group $R_{01}$ or a variant form with micro-modification of $R_{01}$; said variant form with micro-modification refers to the group which can be transformed into $R_{01}$ through any process of chemical reaction selected from deprotonation, salt complexation and decomplexation, ionization, protonation, deprotonation, and changing leaving groups; the $F_1$ contains active functional groups, which can react with the amino group of the primary amine B-2 (or B-2') to obtain the secondary amine derivative B-3 (or B-3') containing the divalent linking group $L_3$;

Step 2: carrying out the alkylation reaction of the secondary amine derivative B-3 (or B-3') with B-4 (or B-4') which contains the functional group $F_N$, from which the cationic lipid derivative B-5 (or B-5') is obtained; said $F_N$ is a functional group which can react with amino groups or secondary amino groups, preferably —OMs, —OTs, —CHO, —F, —Cl, or —Br;

when $R_3$' is $R_3$, the structure of B-5 (or B-5') is represented by the general formula (1);

when $R_3$' is not $R_3$, B-6 (or B-6') represented by the general formula (1) is obtained via terminal micro-modification of B-5 (or B-5'); said terminal micro-modification is selected from the group consisting of deprotection, salt complexation and decomplexation, ionization, protonation, deprotonation, and changing leaving group.

Step 1:

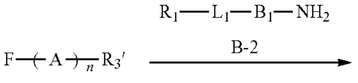

B-1

-continued

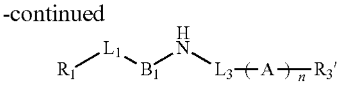
B-1 or

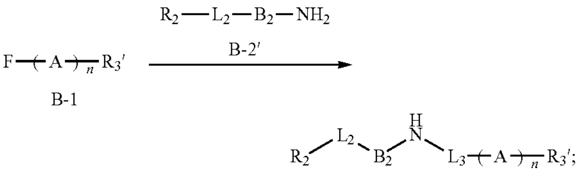

B-1 B-3′;

Step 2:

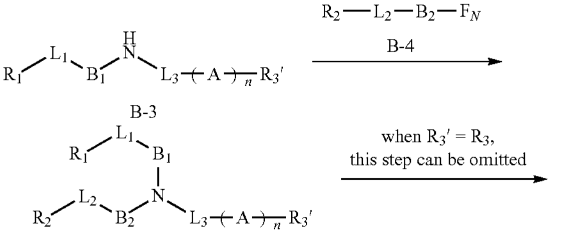

B-3 B-5 B-6 or

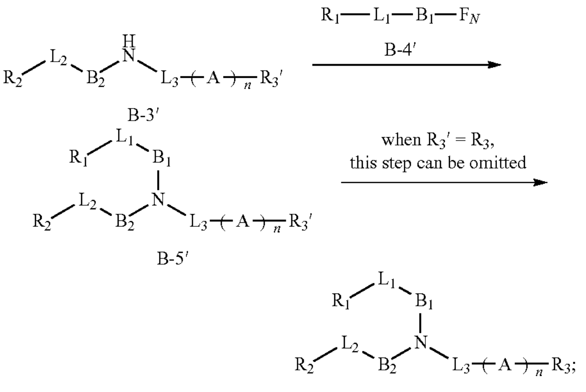

B-3′ B-5′ B-6′ wherein, $L_3$, $L_1$, $L_2$, $B_1$, $B_2$, $R_3$, $R_1$, $R_2$, and n are the same as those in the general formula (1), and are not described again here.

In one specific embodiment of the present invention and with respect to the aforementioned Method-2, said B-3 (or B-3') is $R_1$—$NH_2$ or $R_2$—$NH_2$, said B-4 or B-4' is $R_2$-$L_2$-$B_2$—Br or $R_1$-$L_1$-$B_1$—Br, and said $F_1$ contains the —OMs group.

2.3. Method-3:

Step 1: carrying out the reaction of the small molecule C-1 with the small molecule C-2 to obtain the small-molecule intermediate C-3 which contains the divalent linking group $L_1$, the functional group $F_N$ at one terminal, and the aliphatic group $R_1$ at the other terminal; wherein, $F_3$ and $F_4$ are each independently a functional group, which can react with each other and form the divalent linking group $L_1$; wherein, C-2 contains a hetero-functional group pair consisting of $F_3$ and $F_N$; said $F_N$ is a functional group which can react with amino groups or secondary amino groups, preferably —OMs, —OTs, —CHO, —F, —Cl, or —Br;

Step 2: carrying out the alkylation reaction of two small-molecule intermediates C-3 with the primary amine derivative C-4 which contains a nitrogen-source terminal group, from which the cationic lipid C-5 is obtained; wherein, the $R_3$' end contains the functional group $R_{01}$ or a variant form with micro-modification of $R_{01}$; said variant form with micro-modification refers to the group which can be transformed into $R_{01}$ through any process of chemical reaction selected from deprotonation, salt complexation and decomplexation, ionization, protonation, deprotonation, and changing leaving groups;

when $R_3$' is $R_3$, the structure of C-5 is represented by the general formula (1);

when $R_3$' is not $R_3$, C-6 represented by the general formula (1) is obtained via terminal micro-modification of C-5; said terminal micro-modification is selected from deprotection, salt complexation and decomplexation, ionization, protonation, deprotonation, and changing leaving groups;

wherein, $L_3$, $L_1$, $L_2$, $B_1$, $B_2$, $R_3$, $R_1$, $R_2$, and n are the same as those in the general formula (1), and are not described again here.

Step 1:

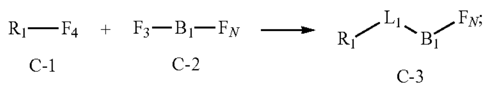

C-1 C-2 C-3

Step 2:

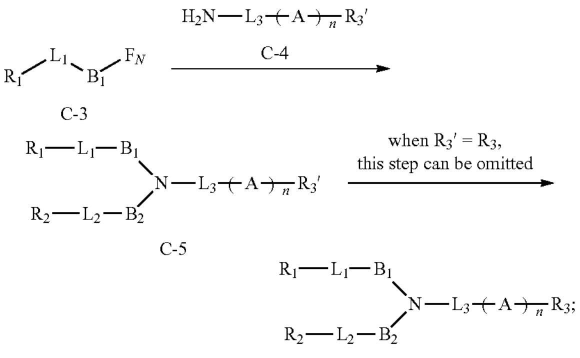

C-4 C-3 C-5 C-6

2.4 Method-4:

Step 1: carrying out the reaction of the small molecule D-1 with the small molecule D-2 to obtain the small molecule intermediate D-3 which contains the divalent linking group $L_1$, a hydroxyl group at one terminal, and the aliphatic group $R_1$ at the other terminal; wherein, $F_3$ and $F_4$ are each independently a functional group, which can react with each other and form the divalent linking group $L_1$; wherein, D-2 contains a hetero-functional group pair consisting of $F_3$ and a hydroxyl group;

Step 2: oxidizing the hydroxyl group of the small-molecule intermediate D-3 to an aldehyde group, from which the small-molecule intermediate D-4 containing an aldehyde group is obtained; wherein, $B_1$' is an alkylene group with one less methylene group than $B_1$;

Step 3: carrying out the addition reaction of two small-molecule intermediates D-4 containing an aldehyde group with the primary amine derivative D-5 containing a nitrogen-source terminal group, from which the cationic lipid D-6 is obtained; wherein, the $R_3$' end contains the functional group $R_{01}$ or a variant form with micro-modification of $R_{01}$; said variant form with micro-modification refers to the group which can be transformed into $R_{01}$ through any process of chemical reaction selected from deprotonation, salt complexation and decomplexation, ionization, protonation, deprotonation, and changing leaving groups;

when $R_3$' is $R_3$, the structure of D-6 is represented by the general formula (1);

when $R_3$' is not $R_3$, D-7 represented by the general formula (1) is obtained via terminal micro-modification of D-6; said terminal micro-modification is selected from deprotection, salt complexation and decomplexation, ionization, protonation, deprotonation, and changing leaving groups; wherein, $R_1$ is the same as $R_2$, $B_1$ is the same as $B_2$, and $L_1$ is the same as $L_2$.

Step 1:

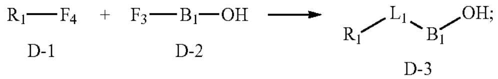

D-1 D-2 D-3

Step 2:

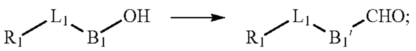

D-3 D-4

Step 3:

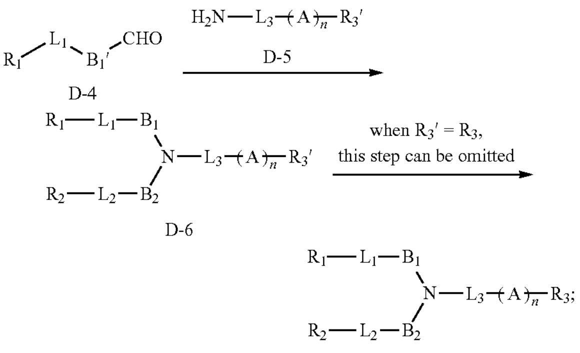

D-5 D-4 D-6 D-7 wherein, $L_3$, $L_1$, $L_2$, $B_1$, $B_2$, $R_3$, $R_1$, $R_2$, and n are the same as those in the general formula (1), and are not described again here.

$R_1$', $R_1$, $R_2$', and $R_2$ in foregoing Method-1 to Method-4 can be etherified residues of aliphatic hydrocarbon derivatives, which are represented as

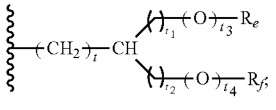

wherein, t is an integer from 0 to 12, $t_1$ and $t_2$ are each independently an integer from 0 to 5, and $t_3$ and $t_4$ are each independently 0 or 1 and not simultaneously 0; wherein, $R_e$ and $R_f$ are each independently selected from the group consisting of a $C_{1-15}$ alkyl group, a $C_{2-15}$ alkenyl group, and a $C_{2-15}$ alkynyl group; the compound containing the etherified residues can be purchased from commercial sources or synthesized; for example,

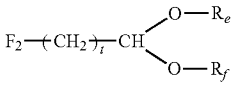

can be purchased or synthesized, wherein the synthesis can utilize the addition reaction between alcohol and aldehyde, e.g., the addition reaction between one molecule of $$F_2-(CH_2)_t-CHO$$

and two molecules of $R_c$—OH when $R_c$ is the same as $R_f$; for another example,

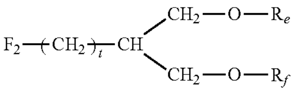

can also be purchased or synthesized, wherein the synthesis can utilize the reaction between

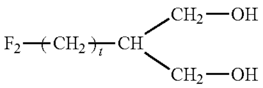

and relevant alkylating agent, said alkylating agent being preferably halide; e.g.,

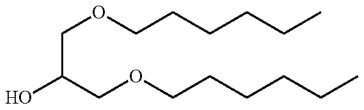 [SMILES: CCCCCCOCC(O)COCCCCCC]

can be obtained after deprotection of a product obtained via the reaction between one molecule of glycerol containing TBS-protected hydroxyl groups and two molecules of hexyl bromides.

2.5. Description of Relevant Materials and/or Steps in the Preparation Process 2.5.1. Carboxyl Activating Agent, Condensing Agent, Oxidizing Agent, and Reducing Agent In the present invention, "activation of carboxyl groups" refers to the activation treatment for carboxyl groups using carboxyl activating agents, wherein the activated carboxyl groups can promote condensation reactions by, e.g., inhibiting the generation of racemic impurities, accelerating the reaction rate through catalysis, etc. An "activating group of carboxyl groups" refers to the residue of a carboxyl activating agent. Said carboxyl activating agent is selected from the group consisting of N-hydroxysuccinimide (NHS), 1-ethyl-3-(3-dimethylaminopropyl)carbodiimide (EDCI), N-hydroxy-5-norbornene-2,3-dicarboximide (HONb), N,N'-dicyclohexylcarbodiimide (DCC), and combinations thereof, preferably the combination of NHS/EDCI, NHS/DCC, or HONb/DCC, and most preferably the combination of NHS/EDCI.

In the present invention, the condensing agent is not particularly limited, preferably N,N'-dicyclohexylcarbodiimide (DCC), 1-ethyl-(3-dimethylaminopropyl)carbodiimide hydrochloride (EDC-HCl), 2-(7-azobenzotriazole-N,N,N,N'-tetramethyluronium hexafluorophosphate (HATU), or 2-(1H-benzotriazol-1-yl)-1,1,3,3-tetramethyluronium hexafluorophosphate (HBTU), and most preferably DDC. Generally, the molar equivalent of the condensing agent is 1 to 20 folds of that of the carboxylic acid, preferably 5 to 10 folds, and suitable catalysts such as 4-dimethylaminopyridine (DMAP) can be added to the reaction.

In the present invention, the oxidizing agent is not particularly limited as long as it is a compound or a combination of multiple compounds capable of increasing the valence of the substrate, preferably phenyliodine(III) bis(trifluoroacetate), 1,4-benzoquinone, benzyl trimethyl ammonium tribromide, pyridinium dichromate, ozone, oxygen, hydrofluoric acid, sodium hypochlorite, cobaltic acetate, cobalt acetate, manganous acetate, palladium(II) acetate, cupric acetate, monoperoxyphthalic acid, iodine, N-iodosuccinimide, iodoxybenzene, 2-iodylbenzoic acid, dimethyldioxirane, dimethyl sulfoxide-oxalyl chloride, DDQ, dichlorotris(triphenylphosphine)ruthenium, manganese dioxide, (diacetoxyiodo)benzene, periodic acid, sodium periodate, sodium periodate-osmium tetraoxide, potassium permanganate, sodium perborate, perbenzoic acid, dibenzoyl peroxide, nickel peroxide, hydrogen peroxide, cumyl hydroperoxide, 1-butyl hydroperoxide, peracetic acid, m-chloroperbenzoic acid, N-chlorosuccinimide, pyridinium chlorochromate, palladium chloride-cupric chloride, urea hydrogen peroxide adduct, triphenylcarbenium tetrafluoroborate, tributyltin oxide, cobalt trifluoride, vanadium oxytrifluoride, chromium trioxide, manganese triacetate, TEMPO, diammonium cerium nitrate, bromine, pyridine N-oxide, silver oxide, O-ethylperoxycarbonic acid, manganese acetyllacetonate, vanadyl acetylacetonate, aluminium isopropoxide, peroxymonosulfate, dichloroiodobenzene, the like, or any combination thereof, and more preferably oxygen, sodium hypochlorite, hydrogen peroxide, dichloroiodobenzene, peroxymonosulfate, the like, or any combination thereof, the molar equivalent of the oxidizing agent is 1 to 50 folds of that of the hydroxyl group of the intermediate compound, preferably 1 to 20 folds, and more preferably 5 to 10 folds.

In the present invention, the reducing agent is not particularly limited as long as it can reduce the Schiff base formed by the reaction of an amine with an aldehyde or ketone to an amino group, preferably sodium borohydride, sodium cyanoborohydride, lithium aluminum hydride, borane, diborane, diisobutylaluminum hydride, diisopinocampheylborane, lithium borohydride, zinc borohydride, borane-pyridine, borane-methyl sulfide, borane-tetrahydrofuran, the like, or any combination thereof, and more preferably sodium cyanoborohydride; the molar equivalent of the reducing agent is 1 to 50 folds of that of the amino group to be modified, preferably 1 to 20 folds, and more preferably 5 to 10 folds.

In the present invention, the reaction temperature is 0 to 200° C., preferably 0 to 100° C., and more preferably 0 to 25° C.; the reaction time is preferably 10 min to 48 h, and more preferably 30 min to 24 h. The obtained product can be purified by a purification means such as extraction, recrystallization, adsorption treatment, precipitation, reverse precipitation, membrane dialysis, and supercritical extraction.

In the present invention, the reaction solvent can be absent or an aprotic solvent including toluene, benzene, xylene, acetonitrile, ethyl acetate, diethyl ether, tert-butyl methyl ether, tetrahydrofuran, chloroform, dichloromethane, dimethylsulfoxide, dimethylformamide, and dimethylacetamide; said aprotic solvent is preferably tetrahydrofuran, dichloromethane, dimethylsulfoxide, or dimethylformamide.

In the present invention, the bases used in reactions are generally organic bases, such as trimethylamine, pyridine, 4-dimethylaminopyridine, imidazole, and N,N-diisopropylethylamine, and more preferably trimethylamine and pyridine. The molar equivalent of the base is 1 to 50 folds of that of carboxylic acids, preferably 1 to 10 folds, and more preferably 2 to 3 folds.

2.5.2. "Protection" and "Deprotection" of Relevant Groups Involved in the Reaction Process In the present invention, the reaction process also involves the "protection" and "deprotection" processes of relevant groups. In order to prevent a functional group from affecting the reaction, the functional group is usually protected. In addition, when there are two or more functional groups and only the target functional group needs to react, the other functional groups should therefore be protected. The protecting group not only protects the functional group stably, but also needs to be removed easily as needed. Therefore, in organic synthesis, it is important to remove only the protecting group bonded to the specified functional group under appropriate conditions.

In the present invention, "carboxyl protecting group" refers to the protecting group which can be transformed into a carboxyl group via the hydrolysis of itself or the deprotection reaction of a protected carboxyl group. Carboxyl protecting group is preferably selected from the group consisting of an alkyl group (e.g., a methyl group, an ethyl group, and a butyl group) and an aralkyl group (e.g., a benzyl group), more preferably selected from the group consisting of a butyl group (tBu), a methyl group (Me), and an ethyl group (Et). In the present invention, "protected carboxyl group" refers to the group protected by an appropriate carboxyl protecting group, preferably selected from the group consisting of a methoxycarbonyl group, an ethoxycarbonyl group, a t-butyloxycarbonyl group, and a benzyloxycarbonyl group. Said carboxyl protecting groups can be removed through hydrolysis catalyzed by acids or alkalis, or through pyrolysis reactions occasionally; for example, t-butyl groups can be removed under mild acidic conditions, and benzyl groups can be removed by hydrogenolysis. The reagent used for removal of carboxyl protecting groups is selected from the group consisting of TFA, $H_2O$, LiOH, NaOH, KOH, MeOH, EtOH, and combinations thereof, preferably the combination of TFA and $H_2O$, the combination of LiOH and MeOH or the combination of LiOH and EtOH. A protected carboxyl group can undergo deprotection and then produce the corresponding free acid; said deprotection is conducted in the presence of an alkali, and said alkali forms pharmaceutically acceptable salt with said free acid produced via said deprotection.

In the present invention, "amino protecting group" includes all the groups which are used as amino protecting groups generally, such as a $C_{1-6}$ alkoxycarbonyl group, an aryloxycarbonyl group, a $C_{1-6}$ alkylsulfonyl group, an arylsulfonyl, a silyl group, etc. An amino protecting group is preferably a t-butoxycarbonyl group (Boc), a p-methoxybenzyloxycarbonyl group (Moz), or a 9-fluorenylmethoxycarbonyl group (Fmoc). The reagent used for removal of amino protecting groups is selected from the group consisting of TFA, $H_2O$, LiOH, NaOH, KOH, MeOH, EtOH, and combinations thereof, preferably the combination of TFA and $H_2O$, the combination of LiOH and MeOH, or the combination of LiOH and EtOH. The reagent used for removal of protection group Boc is TFA or HC/EA, preferably TFA. The reagent used for removal of protecting group Fmoc is the solution of 20% piperidine in N,N-dimethylformamide (DMF). Said amino groups protected by amino protecting groups are not particularly limited, such as those from primary amines, secondary amines, hydrazines, and amides. Amino groups in the present invention are not particularly limited, including but not limited to primary amino groups, secondary amino groups, tertiary amino groups, and quaternary ammonium ions.

In the present invention, said hydroxyl groups protected by hydroxyl protecting groups are not particularly limited, e.g., alcoholic hydroxyl groups, phenolic hydroxyl groups, and the like.

In the present invention, the deprotection of hydroxyl groups is related to the types of hydroxyl protecting groups. Said types of hydroxyl protecting groups are not particularly limited; for example, benzyl, silyl ether, acetal, ketal, or tert-butyl groups can be used to protect terminal hydroxyl groups, and the corresponding deprotection methods include the follows:

A: Removal of Benzyl Groups

The removal of benzyl groups can be achieved via hydrogenation using a hydrogenative reduction catalyst and a hydrogen donor. As used herein, the water content should be less than 1% in order to facilitate the reaction.

The hydrogenative reduction catalyst is not particularly limited, preferably palladium or nickel. The catalyst carrier is not particularly limited, preferably alumina or carbon, and more preferably carbon. The amount of palladium is 1 to 100 wt % of that of compounds containing protected hydroxyl groups, preferably 1 to 20 wt %.

The reaction solvent is not particularly limited, as long as it allows the reagents and the products to be dissolved. Preferable solvents include methanol, ethanol, ethyl acetate, tetrahydrofuran, and acetic acid, wherein methanol is more preferable. The hydrogen donor is not particularly limited, preferably hydrogen gas, cyclohexene, 2-propanol, ammonium formate, or the like. The reaction temperature is preferably 25 to 40° C. The reaction time is not particularly limited, which is negatively correlated with the amount of catalyst used and preferably 1 to 5 hours.

B: Deprotection of Acetals or Ketals

The compounds used for protecting hydroxyl groups in the forms of acetals or ketals are preferably ethyl vinyl ether, tetrahydropyran, acetone, 2,2-dimethoxypropane, benzaldehyde, or the like, while the deprotection of such acetals or ketals should be carried out under an acidic condition and the pH of the solution is preferably 0 to 4. The acid is not particularly limited, but is preferably acetic acid, phosphoric acid, sulfuric acid, hydrochloric acid, or nitric acid, and more preferably hydrochloric acid. The reaction solvent is not particularly limited as long as it allows the reagents and the products to be dissolved, preferably water. The reaction temperature is preferably 0 to 30° C.

C: Deprotection of Silyl Ethers

The hydroxyl groups protected in the forms of silyl ethers include groups of trimethylsilyl ether, triethylsilyl ether, tert-butyldimethylsilyl ether, tert-butyldiphenylsilyl ether, and the like. The deprotection of such silyl ethers uses compounds containing fluoride ions, wherein said compound is preferably tetrabutylammonium fluoride, tetraethylammonium fluoride, hydrofluoric acid, or potassium fluoride, and more preferably tetrabutylammonium fluoride or potassium fluoride. The amount of the fluorine-containing compound is 5 to 20 and preferably 8 to 15 molar equivalents per molar equivalent of the initiator. When the amount of the fluorine-containing compound used is less than 5 molar equivalents per molar equivalent of protected hydroxyl groups, the deprotonation might not be complete. When the amount of deprotection reagent used exceeds 20 molar equivalents per molar equivalent of the initiator, the excess reagent tends to cause difficulty in the purification process and result in side reactions in subsequent steps. The reaction solvent is not particularly limited as long as it can dissolve the reagents and the products, preferably an aprotic solvent, and more preferably tetrahydrofuran or dichloromethane. The reaction temperature is preferably 0 to 30° C.; when it is lower than 0° C., the reaction rate is relatively slow, and the protective group cannot be completely removed.

D: Removal of t-Butyl Groups

The removal of tert-butyl groups is carried out under an acidic condition, and the pH of the solution is preferably 0 to 4. The acid is not particularly limited, but is preferably acetic acid, phosphoric acid, sulfuric acid, hydrochloric acid, or nitric acid and more preferably hydrochloric acid. The reaction solvent is not particularly limited as long as it can dissolve the reagents and the products, preferably water. The reaction temperature is preferably 0 to 30° C.

With respect to the methods for end-functionalization, it is preferred that q is 0, $q_1$ is 1, and $Z_1$ is a 1,2-methylene group. When q is not 0 and a linking group (e.g., amino acid group, succinyl group, etc.) is present between A and $R_{01}$, the prior art capable of generating $Z_2$ or $Z_1$ can be used, including but not limited to alkylation, condensation, click reactions, etc., and be carried out referring to the following linear functionalization methods.

2.5.3. Alkylation Reaction

In the present invention, the alkylation reactions are preferably those based on hydroxyl groups, mercapto groups, or amino groups, corresponding to the formation of ether bonds, thioether bonds, and secondary or tertiary amino groups, respectively. Specific examples are as follows:

2.5.3.1. Alkylation Reaction of Substrate Alcohols with Sulfonates or Halides

The amine intermediate can be obtained via the nucleophilic substitution of the substrate alcohol with a sulfonate or halide under a basic condition. Wherein, the amount of the sulfonate or halide is 1 to 50 and preferably 1 to 5 molar equivalents per molar equivalent of the substrate alcohol. When the amount of the sulfonate or halide is less than 1 molar equivalent per molar equivalent of the substrate alcohol, the substitution may not be complete, causing difficulty in the purification process. When the amount of the sulfonate or halide exceeds 50 molar equivalents per molar equivalent of the substrate alcohol, the excess sulfonate or halide tends to cause difficulty in the purification process and result in side reactions in the subsequent steps.

The resulting product is a mixture of ether intermediate and excess sulfonate or halide, and can be purified by a purification means such as anion exchange resin, osmosis treatment, ultrafiltration treatment, and the like. Wherein, the anion exchange resin is not particularly limited as long as the target product can undergo ion-exchange and adsorb on the resin, preferably the ion exchange resin of a tertiary amine or quaternary ammonia salt based on dextran, agarose, polyacrylate, polystyrene, poly(diphenylethylene), or the like. The solvents used for osmosis treatment and ultrafiltration treatment are not limited, generally water or an organic solvent. Said organic solvent is not particularly limited as long as the product can be dissolved therein, preferably dichloromethane, chloroform, or the like.

The reaction solvent is not limited, preferably an aprotic solvent such as toluene, benzene, xylene, acetonitrile, ethyl acetate, tetrahydrofuran, chloroform, dichloromethane, dimethylsulfoxide, dimethylformamide, and dimethylacetamide, and more preferably dimethylformamide, dichloromethane, dimethylsulfoxide, or tetrahydrofuran.

The base can be an organic base such as triethylamine, pyridine, 4-dimethylaminopyridine, imidazole, and diisopropylethylamine, or an inorganic base such as sodium carbonate, sodium hydroxide, sodium bicarbonate, sodium acetate, potassium carbonate, and potassium hydroxide, preferably an organic base, and more preferably triethylamine or pyridine. The amount of the base is 1 to 50 and preferably 1 to 10 and more preferably 3 to 5 molar equivalents per molar equivalent of the sulfonate or halide.

2.5.3.2. Alkylation Reaction of Substrate Amines with Sulfonates or Halides

The amine intermediate can be obtained via the nucleophilic substitution of the substrate amine with a sulfonate or halide under a basic condition. Wherein, the amount of the sulfonate or halide is 1 to 50 and preferably 1 to 5 molar equivalents per molar equivalent of the substrate amine. When the amount of the sulfonate or halide is less than 1 molar equivalent per molar equivalent of the substrate amine, the substitution may not be complete, causing difficulty in the purification process. When the amount of the sulfonate or halide exceeds 50 molar equivalents per molar equivalent of the substrate amine, the excess sulfonate or halide tends to cause difficulty in the purification process and result in side reactions in the subsequent steps.

The resulting product is a mixture of amine intermediate and excess sulfonate or halide, and can be purified by a purification means such as anion exchange resin, osmosis treatment, ultrafiltration treatment, and the like. Wherein, the anion exchange resin is not particularly limited as long as the target product can undergo ion-exchange and adsorb on the resin, preferably the ion exchange resin of a tertiary amine or quaternary ammonia salt based on dextran, agarose, polyacrylate, polystyrene, poly(diphenylethylene), or the like. The solvents used for osmosis treatment and ultrafiltration treatment are not limited, generally water or an organic solvent. Said organic solvent is not particularly limited as long as the product can be dissolved therein, preferably dichloromethane, chloroform, or the like.

The reaction solvent is not limited, preferably an aprotic solvent such as toluene, benzene, xylene, acetonitrile, ethyl acetate, tetrahydrofuran, chloroform, dichloromethane, dimethylsulfoxide, dimethylformamide, and dimethylacetamide, and more preferably dimethylformamide, dichloromethane, dimethylsulfoxide, or tetrahydrofuran.

The base can be an organic base such as triethylamine, pyridine, 4-dimethylaminopyridine, imidazole, and diisopropylethylamine, or an inorganic base such as sodium carbonate, sodium hydroxide, sodium bicarbonate, sodium acetate, potassium carbonate, and potassium hydroxide, preferably an organic base, and more preferably triethylamine or pyridine. The amount of the base is 1 to 50 and preferably 1 to 10 and more preferably 3 to 5 molar equivalents per molar equivalent of the sulfonate or halide.

2.5.3.3. Alkylation Reaction of Substrate Amines with Aldehyde Derivatives

The substrate amine reacts with an aldehyde derivative to obtain an imine intermediate, which is followed by obtaining an intermediate by reduction reagents. Wherein, the amount of the aldehyde derivative is 1 to 20 and preferably 1 to 2 and more preferably 1 to 1.5 molar equivalents per molar equivalent of the substrate amine. When the amount of aldehyde exceeds 20 molar equivalents per molar equivalent of the substrate amine, the excess reagent tends to cause difficulty in the purification process and result in side reactions in the subsequent steps. When the amount of aldehyde is less than 1 molar equivalent per molar equivalent of the substrate amine, the substitution may not be complete, causing the purification process to be difficult. Wherein, the resulting product can be obtained after purification by means such as cation exchange resin, osmosis treatment, ultrafiltration treatment, and the like. Said cation exchange resin is not particularly limited as long as it can undergo ion-exchange with quaternary ammonium cations and realize the isolation. The solvents used for osmosis treatment and ultrafiltration treatment are not limited, generally water or an organic solvent. Said organic solvent is not particularly limited as long as the product can be dissolved therein, preferably dichloromethane, chloroform, or the like.

The reaction solvent is not limited, preferably an organic solvent such as methanol, ethanol, water, toluene, benzene, xylene, acetonitrile, ethyl acetate, tetrahydrofuran, chloroform, dichloromethane, dimethylsulfoxide, dimethylformamide, dimethylacetamide, and the like, and more preferably water or methanol.

The reduction reagent is not particularly limited as long as the imine can be reduced to an amine, preferably sodium borohydride, lithium aluminum hydride, sodium cyanoborohydride, Zn/AcOH, or the like, and more preferably sodium cyanoborohydride. The molar amount of the reduction reagent is generally 0.5 to 50 folds and preferably 1 to 10 folds of that of aldehyde derivatives.

2.5.3. The Linear End-Functionalization

The method for linear end-functionalization (i.e., linear functionalization of the terminal group) is not particularly limited, but related to the type of the final functional group or its protected form. The method mainly includes the functionalization of the terminal hydroxyl group and the conversion of a reactive group into the target functional group or its protected form.

The method for functionalization of the terminal hydroxyl group is described herein, which is by converting the terminal hydroxyl group of A into a group from classes A~J via end-functionalization. A specific preparation method is described in paragraphs [0960] to [1205] of the document CN104530417A. The general formula of the reaction is as follows:

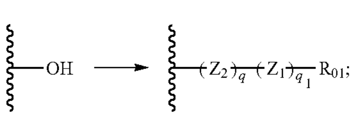

wherein, the definitions of q, $Z_2$, $q_1$, $Z_1$, and $R_{01}$ are the same as above defined.

Conversion of reactive groups into the target functional groups or protected forms thereof, can be achieved by any of the following approaches:

Approach 1: direct modification. The target functional group or its protected form can be obtained via direct modification of a reactive group. Said direct modification includes, for example, the conversion of a carboxyl group to an acyl halide group, a hydrazide group, an ester group, a thioester group, or a dithioester group, the conversion of a hydroxyl group, a mercapto group, an alkynyl group, an amino group, a carboxyl group, or the like to the corresponding protected form, and the modification of a hydroxyl group, an amino group, or the like with an anhydride.

Approach 2: coupling reaction between two reactive groups. Said coupling reaction uses a heterofunctional reagent which contains both a reactive group and the target functional group or its protected form as the material, said reactive group is capable of reacting with the terminal group of A to introduce the target functional group or its protected form. The modes and methods for the reaction between two reactive groups are not particularly limited, wherein the reaction conditions are related to the types of divalent linking groups formed via the reaction. The available prior art such as alkylation reaction, addition reaction of alkenes, addition reaction of alkynes, combination of Schiff-base reaction and reduction reaction, condensation reaction, and the like, can be used herein. Wherein, the alkylation reaction is preferably based on a mercapto group or an amino group, corresponding to the formation of a thioether bond, and a secondary or tertiary amino group, respectively. Wherein, the condensation reaction includes but is not limited to those forming an ester bond, a thioester bond, an amide bond, an imine bond (—C═N—), a hydrazone bond, a carbamate bond, or the like. The target functional group or its protected form can also be introduced via click reactions using materials such as a heterofunctional reagent containing both the target functional group or its protected form and a reactive group selected from the group consisting of an azido group, an alkynyl group, an alkenyl group, a trithioester group, a mercapto group, a dienyl group, a furyl group, a 1,2,4,5-tetrazinyl group, a cyanate group, and the like. The reaction between two reactive groups is accompanied by the formation of new bonds. Typical representatives of the newly formed divalent linking groups include amide bond, urethane bond, ester bond, secondary amino bond, thioether bond, triazole group, and the like.

Approach 3: combination of direct modification and coupling reaction; wherein, the target functional group or its protected form can be obtained via said combination.

In the present invention, materials in every preparation method can be synthesized or purchased.

The intermediates and end-products prepared in the present invention can be purified by the purification method including but not limited to extraction, recrystallization, adsorption treatment, precipitation, reverse precipitation, membrane dialysis, supercritical extraction, and the like. The characterization of the structure and the molecular weight of end-products can use methods including but not limited to NMR, electrophoresis, UV-visible spectrophotometer, FTIR, AFM, GPC, HPLC, MALDI-TOF, circular dichroism spectroscopy, and the like.

3.1. The Cationic Liposome

In the present invention, provided herein is a cationic liposome containing any foregoing cationic lipid whose structure is represented by the general formula (1).

In one embodiment, the cationic liposome contains not only the cationic lipid whose structure is represented by the general formula (1), but also one or more lipids selected from the group consisting of neutral lipids, steroid lipids, and PEGylated lipids, preferably contains neutral lipids, steroid lipids, and PEGylated lipids simultaneously. Said neutral lipid is preferably phospholipid.

In one specific embodiment of the present invention, neutral lipids in the cationic liposomes preferably include but are not limited to 1,2-dilinoleoyl-sn-glycero-3-phosphocholines (DLPC), 1,2-dimyristoleoyl-sn-glycero-3-phosphocholines (DMPC), 1,2-dioleoyl-sn-glycero-3-phosphocholines (DOPC), 1,2-dipalmitoyl-sn-glycero-3-phosphocholines (DPPC), 1,2-distearoyl-sn-glycero-3-phosphatidylcholines (DSPC), 1,2-diundecanoyl-snglycero-3-phosphatidylcholines (DUPC), 1-plamitoyl-2-oleoyl-sn-glycero-3-phosphocholines (POPC), 1,2-di-O-octadecenyl-sn-glycero-3-phosphatidylcholines (18:0 Diether PC), 1-oleoyl-2-cholesterylhemisuccinyl-sn-glycero-3-phosphocholines (OChemsPC), 1-O-hexadecyl-sn-glycero-3-phosphatidylcholines (C16 Lyso PC), 1,2-dilinolenoyl-sn-glycero-3-phosphatidylcholines, 1,2-diarachidonoyl-sn-glycero-3-phosphatidylcholines, 1,2-didecosahexaenoyl-sn-glycero-3-phosphocholines, 1,2-dioleoyl-sn-glycero-3-phosphoethanolamines (DOPE), 1,2-diphytanyl-sn-glycero-3-phosphoethanolamines (ME 16.0 PE), 1,2-distearoyl-sn-glycero-3-phosphoethanolamines, 1,2-dilinoleoyl-sn-glycero-3-phosphoethanolamines, 1,2-dilinolenoyl-sn-glycero-3-phosphoethanolamines, 1,2-diarachidonoyl-sn-glycero-3-phosphoethanolamines, 1,2-didecosahexaenoyl-sn-glycero-3-phosphoethanolamines, 1,2-dioleoyl-sn-glycero-3-phospho-rac-(1-glycerol) sodium salts (DOPG), dioleoyl phosphatidylserines (DOPS), dipalmitoylphosphatidylglycerols (DPPG), palmitoyloleoyl phosphatidylethanolamines (POPE), distearoyl phosphatidylethanolamines (DSPE), dipalmitoyl phosphatidylethanolamines (DPPE), dimyristoleoyl phosphoethanolamines (DMPE), 1-stearoyl-2-oleoyl-stearoylethanolamines (SOPE), 1-stearoyl-2-oleoyl-phosphatidylcholines (SOPC), sphingomyelins, phosphatidylcholines, phosphatidylethnolamines, phosphatidylserines, phosphatidylinositols, phosphatidic acids, palmitoyloleoyl phosphatidylcholines, lysophosphatidylcholines, lysophosphatidylethanolamines (LPE), and combinations thereof.

In one specific embodiment of the present invention, steroid lipids in the cationic liposomes are preferably cholesterols, coprostanols, sitosterols, ergosterols, campesterols, stigmasterols, brassicasterol tomatidines, ursolic acids, α-tocopherols, or any mixture thereof.

In one specific embodiment of the present invention, PEG-lipids in the cationic liposomes are preferably 1,2-dimyristoyl-sn-glycerol methoxypolyethylene glycol (PEG-DMG), 1,2-distearoyl-sn-glycero-3-phosphoethanolamine-N-[amino(polyethylene glycol)](PEG-DSPE), PEG-cholesterol, PEG-diacylglycamide (PEG-DAG), PEG-dialkyloxypropyl (PEG-DAA), PEG500-dipalmitoylphosphatidylcholine, PEG2000-dipalmitoylphosphatidylcholine, PEG500-stearylphosphatidylethanolamine PEG2000-distearylphosphatidylethanolamine, PEG500-1,2-dioleoylphosphatidylethanolamine, PEG2000-1,2-dioleoylphosphatidylethanolamine, or PEG2000-2,3-distearoylglycerol.

In one specific embodiment of the present invention, PEGylated lipids in the cationic liposomes are preferably represented by the general formula (2):

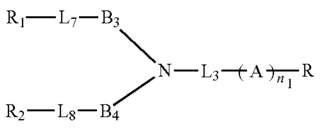

(2)

or pharmaceutically acceptable salts, tautomers, and stereoisomers thereof;

wherein, $L_7$ and $L_8$ are each independently a linking bond or a divalent linking group, said divalent linking group selected from the group consisting of —OC(═O)—, —C(═O)O—, —OC(═O)O—, —C(═O)—, —O—, —S—, —C(═O)S—, —SC(═O)—, —$NR_c$C(═O)—, —C(═O)$NR_c$—, —$NR_c$C(═O)$NR_c$—, —OC(═O)$NR_c$—, —$NR_c$C(═O)O—, —SC(═O)$NR_c$—, and —$NR_c$C(═O)S—; wherein, $R_c$ is, at each occurrence, independently a hydrogen atom or a $C_{1-12}$ alkyl group;

$L_3$ is selected from the group consisting of a linking bond, -$L_4$-, —Z-$L_4$-, -$L_4$-Z—, —Z-$L_4$-Z—, -$L_4$-Z-$L_5$-, —Z-$L_4$-Z-$L_5$-, and -$L_4$-Z-$L_5$-Z—; said $L_4$ and $L_5$ are carbon-chain linking groups and each independently represented by —$(CR_aR_b)_t$—$(CR_aR_b)_o$—$(CR_aR_b)_p$—, wherein t, o, and p are each independently an integer from 0 to 12, not being 0 simultaneously, and wherein $R_a$ and $R_b$ are, at each occurrence, independently a hydrogen atom or a $C_{1-6}$ alkyl group; said Z is, at each occurrence, independently selected from the group consisting of —C(═O)—, —OC(═O)—, —C(═O)O—, —OC(═O)O—, —O—, —S—, —C(═O)S—, —SC(═O)—, —$NR_c$C(═O)—, —C(═O)$NR_c$—, —$NR_c$C(═O)$NR_c$—, —OC(═O)$NR_c$—, —$NR_c$C(═O)O—, —SC(═O)$NR_c$—, —$NR_c$C(═O)S—, and

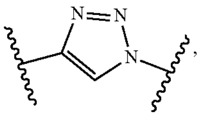 [SMILES: *c1cn(*)nn1]

wherein $R_c$ is, at each occurrence, independently a hydrogen atom or a $C_{1-12}$ alkyl group;

$B_3$ and $B_4$ are each independently a linking bond or a $C_{1-12}$ alkylene group;

$R_1$ and $R_2$ are each independently a $C_{1-30}$ aliphatic group;

R is selected from the group consisting of a hydrogen atom, an alkyl group, an alkoxy group, —C(═O)$R_d$, —C(═O)O$R_d$, —OC(═O)$R_d$, —OC(═O)O$R_d$, and

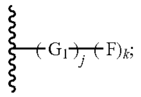

wherein, $R_d$ is a $C_{1-12}$ alkyl group, $G_1$ is a terminal branching group with the valence of k+1, j is 0 or 1, and F contains functional groups; when j is 0, $G_1$ is absent; when j is 1, $G_1$ protrudes F with the number of k; wherein, k is an integer from 2 to 8;

A is —$(CR_aR_b)_s$O— or —O$(CR_aR_b)_s$—, wherein, s is 2, 3 or 4, and $R_a$ and $R_b$ are each independently a hydrogen atom or a $C_{1-6}$ alkyl group;

$n_1$ is an integer from 20 to 250;

said alkyl group, alkylene group, alkoxy group, and aliphatic group are each independently substituted or unsubstituted.

In one specific embodiment of the present invention, PEGylated lipids in the cationic liposomes are selected from the following structures:

PL-1
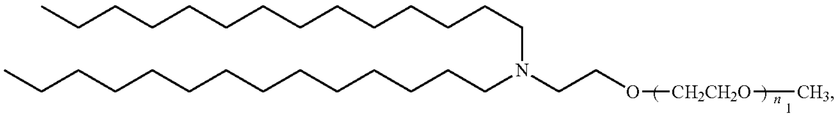
PL-2
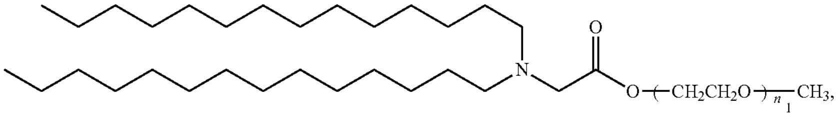
PL-3
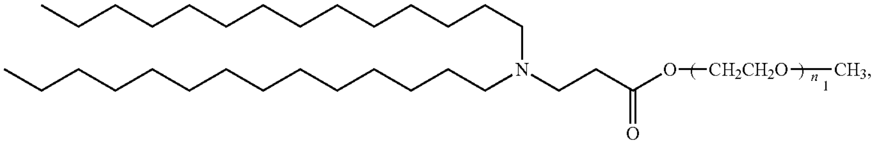
PL-4
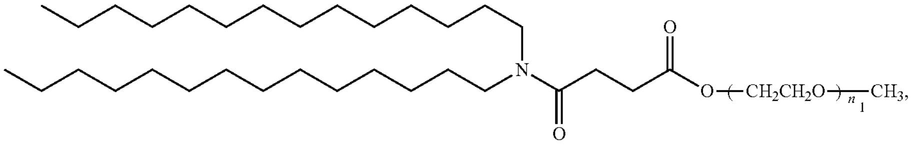
PL-5
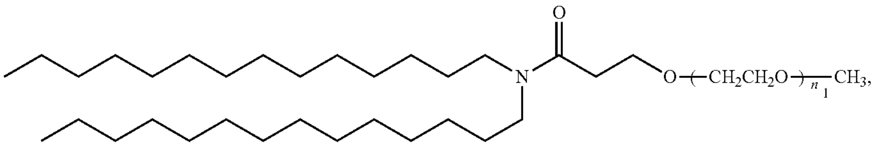
PL-6
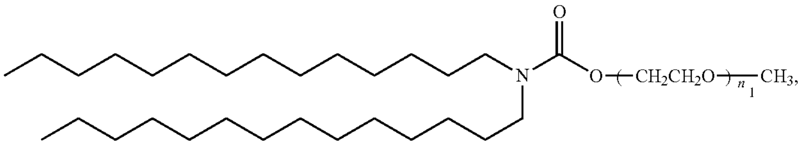
PL-7
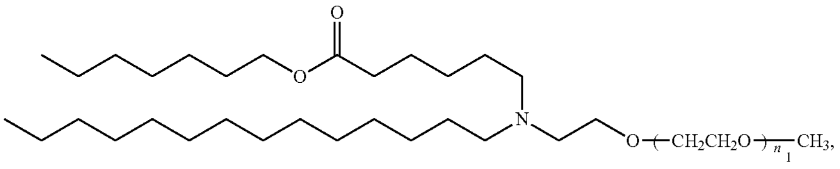
PL-8
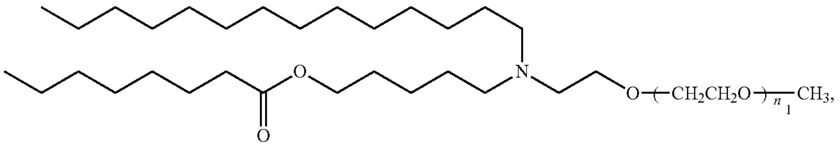
PL-9
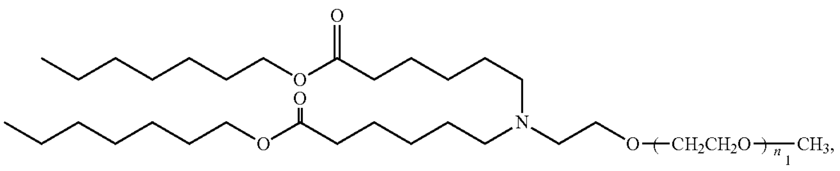
PL-10
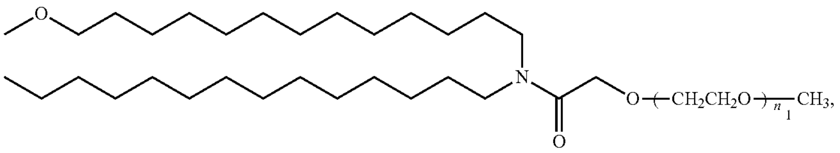

-continued
PL-11
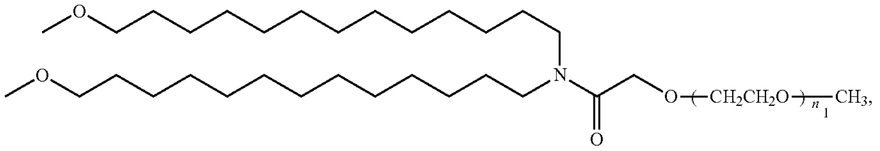
PL-12
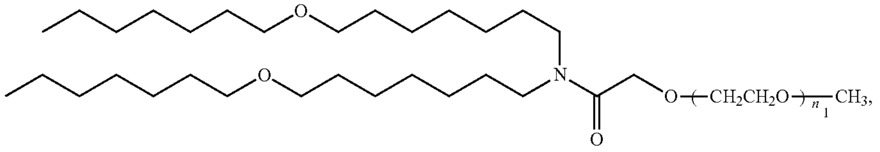
PL-13
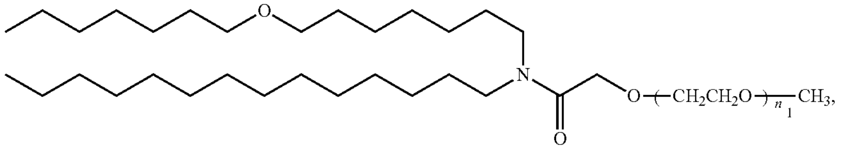
PL-14
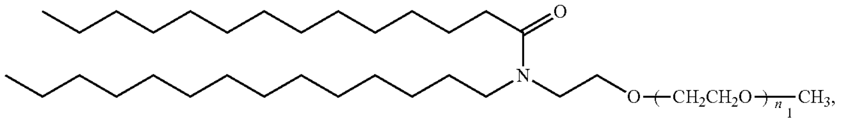
PL-15
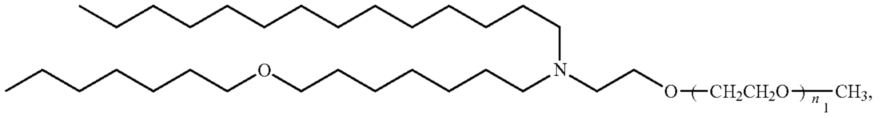
PL-16
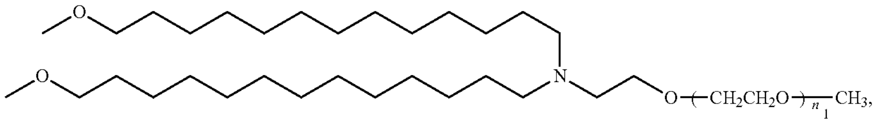
PL-17
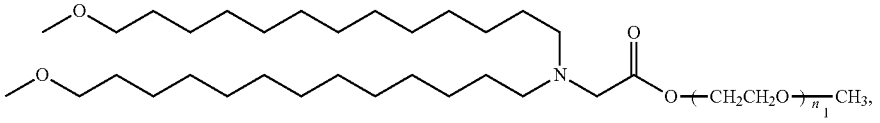
PL-18
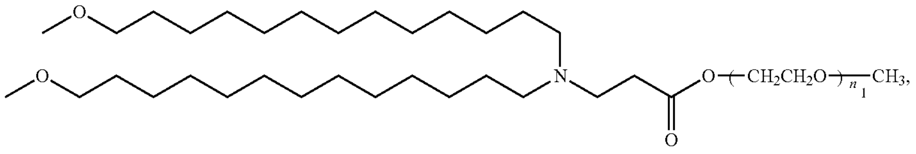
PL-19
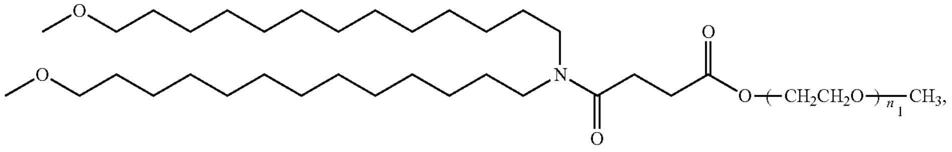
PL-20
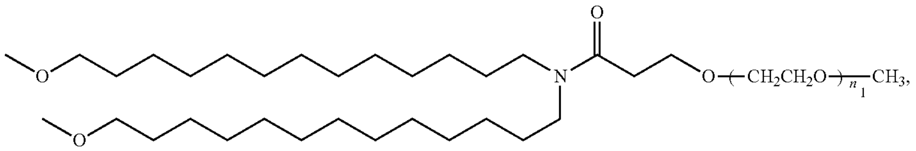

-continued

PL-21

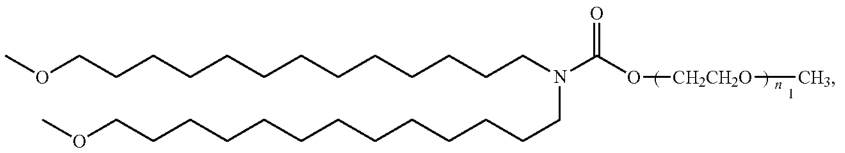

PL-22

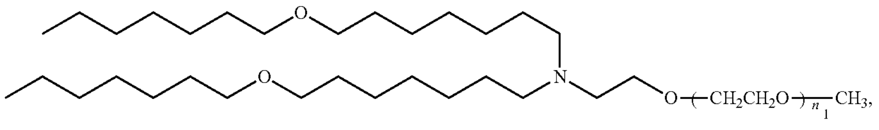

PL-23

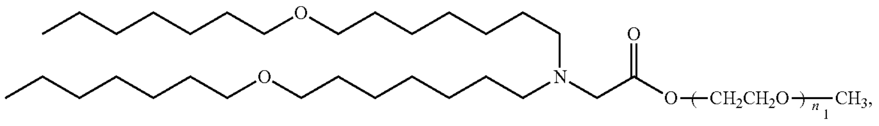

PL-24

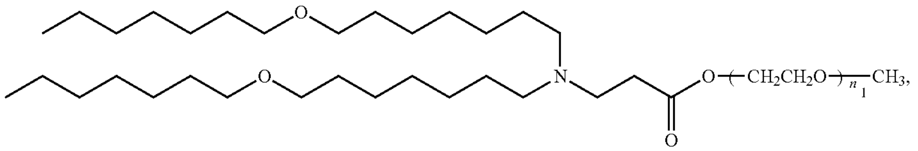

PL-25

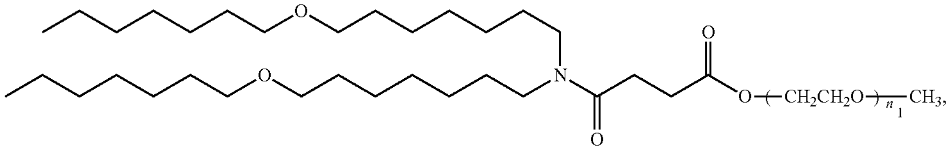

and

PL-26

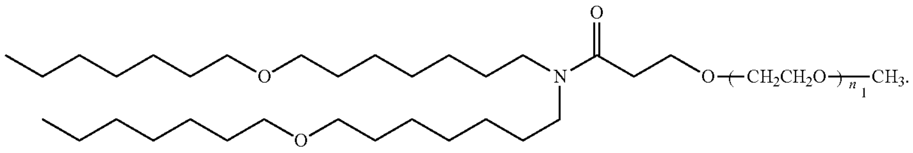

In one specific embodiment of the present invention, it is preferred that any foregoing cationic liposome contains 20-80%0 the cationic lipids represented by the general formula (1), 5-15% neutral lipids, 25-55% steroid lipids, and 0.5-10% PEGylated lipids, said percentage is the molar percentage of each type of lipid relative to the total lipids in a solution containing a solvent.

In one specific embodiment of the present invention, it is preferred that, in any foregoing cationic liposome, the molar percentage of cationic lipids relative to the total lipids in a solution containing a solvent is 30% to 65%, preferably about 35%, 40%, 45%, 46%, 47%, 48%, 49%, 50%, or 55%.

In one specific embodiment of the present invention, it is preferred that, in any foregoing cationic liposome, the molar percentage of neutral lipids relative to the total lipids in a solution containing a solvent is 7.5% to 13%, preferably about 8%, 9%, 10%, 11%, or 12%.

In one specific embodiment of the present invention, it is preferred that, in any foregoing cationic liposome, the molar percentage of steroid lipids relative to the total lipids in a solution containing a solvent is 35% to 50%, preferably about 40%, 41%, 42%, 43%, 44%, 45%, 46%, 47%, 48%, 49%, or 50%.

In one specific embodiment of the present invention, it is preferred that, in any foregoing cationic liposome, the molar percentage of PEGylated lipids relative to the total lipids in a solution containing a solvent is 0.5% to 5%, preferably 1% to 3%, and more preferably about 1.5%, 1.6%, 1.7%, 1.8%, or 1.9%.

3.2. Preparation of Cationic Liposomes

In the present invention, cationic liposomes can be prepared by methods including but not limited to thin-film dispersion method, ultrasonic dispersion method, reverse-phase evaporation method, freeze-drying method, freeze-thaw method, double emulsion method, injection method, and combinations thereof, preferably by thin-film dispersion method, ultrasonic dispersion method, reverse-phase evaporation method, or a combination thereof.

Among the preparation methods for cationic liposomes in the present invention, said thin-film dispersion method could include the following steps:

Step (1): weigh cationic lipids, steroid lipids, neutral lipids, and PEGylated lipids, fully dissolve them in organic solvents, shake them well, remove the organic solvents by vacuum rotary evaporation to obtain an oil film, and furtherly dry with a vacuum pump to remove the organic solvents;

Step (2): add phosphate buffer with dissolved cryoprotectant, and use water-bath ultrasonication to obtain a translucent emulsion;

Step (3): add the emulsion to a high-pressure homogenizer for overpressure, and then add the overpressurized homogenized emulsion to the liposome extruder for film-passing to obtain cationic liposomes;

Step (4): optionally, dry the said cationic liposomes in a freeze dryer to obtain a cationic liposome powder;

wherein, said organic solvent is preferably dichloromethane, chloroform, methanol, or a combination thereof, more preferably chloroform, methanol, or the combination thereof; wherein, the rotational speed of vacuum rotary evaporation is preferably 30 to 300 rpm, more preferably 50 to 200 rpm, and most preferably 100 to 170 rpm; and wherein, the temperature of vacuum rotary evaporation is preferably 10 to 200° C., more preferably 20 to 200° C., and most preferably 40 to 80° C.;

the time of said drying with a vacuum pump is preferably 1 to 72 h, more preferably 5 to 48 h, and most preferably 15 to 36 h;

the mass concentration of said cryoprotectant dissolved in phosphate buffer is preferably 0.1 to 80%, preferably 1 to 50%, and more preferably 5 to 20%;

the frequency of said water-bath ultrasonication is preferably 10 to 300 kHz, more preferably 30 to 200 kHz, and most preferably 60 to 150 kHz;

the time of said water-bath ultrasonication is preferably 0.1 to 5 h, more preferably 0.2 to 2 h, and most preferably 0.25 to 1 h;

the pressure of said high-pressure homogenizer is preferably 50 to 240 MPa, more preferably 80 to 200 MPa, and most preferably 100 to 150 MPa;

the times of said overpressure of high-pressure homogenizer is preferably any integer from 1 to 50, more preferably any integer from 3 to 20, and most preferably any integer from 5 to 10;

the pressure of said liposome extruder is preferably 50 to 300 MPa, more preferably 80 to 250 MPa, and most preferably 120 to 200 MPa;

the times of said film-passing of liposome extruder is preferably any integer from 1 to 50, more preferably any integer from 3 to 30, and most preferably any integer from 5 to 20;

the time of said drying in a freeze dryer is preferably 1 to 120 h, more preferably 5 to 72 h, and most preferably 10 to 36 h.

In the preparation methods for cationic liposomes in the present invention, the ratio of cationic liposome to phosphate buffer with dissolved cryoprotectant could be 1 mg:(0.1~100) mL, preferably 1 mg:(0.3~50) mL, and more preferably 1 mg:(0.5~5) mL.

4.1. Cationic Liposome-Nucleic Acid Pharmaceutical Composition

In one embodiment, cationic liposome-nucleic acid pharmaceutical composition contains any foregoing cationic liposome and nucleic acid drugs, wherein the cationic liposome contains any foregoing cationic lipid whose structure is represented by the general formula (1).

In one specific embodiment of the present invention and with respect to the cationic liposome-nucleic acid pharmaceutical composition, said nucleic acid drug is selected from the group consisting of RNA, DNA, antisense nucleic acid, plasmid, mRNA (messenger RNA), interfering nucleic acid, aptamer, miRNA inhibitor (antagomir), microRNA (miRNA), ribozyme, and small interfering RNA (siRNA), preferably selected from the group consisting of RNA, miRNA, and siRNA.

In one specific embodiment of the present invention, the cationic liposome-nucleic acid pharmaceutical composition is preferably used as a drug selected from the group consisting of drugs for treating any disease from cancer, malignant tumor, liver diseases, hepatitis, diabetes, gout, rheumatism, rheumatoid, senile dementia, and cardiovascular diseases, antiallergic drugs, anti-infectious agents, antibiotic agents, antiviral agents, antifungal agents, vaccines, central nervous system depressants, central nervous system stimulants, psychotropic drugs, respiratory drugs, peripheral nervous system drugs, drugs acting at synaptic junctions or neuroeffector junctions, smooth muscle active drugs, histaminergic agents, antihistaminergic agents, drugs for the blood and hematopoietic system, gastrointestinal drugs, steroid agents, cytostatic agents, anthelmintics, antimalarials, antiprotozoal agents, antimicrobial agents, anti-inflammatory agents, immunosuppressants, drugs for Alzheimer's, imaging agents, antidotes, antispasmodics, muscle relaxants, appetite suppressants, migraine drugs, inotropes, antimalarials, antiemetic agents, bronchodilators, antithrombotic drugs, antihypertensive drugs, antiarrhythmic drugs, antioxidants, antiasthmatics, diuretics, lipid modulators, antiandrogens, antiparasitics, anticoagulants, antineoplastics, hypoglycemic drugs, nutrition agents, additives, growth supplements, anti-enteritis agents, antibodies, diagnostic reagents, contrast agents, hypnotics, sedatives, psychostimulants, tranquilizers, antiparkinsonian drugs, analgesics, antianxiety drugs, drugs for muscle infection, and drugs for auditory diseases; more preferably used as a drug for treating hemophilia, cystic fibrosis, familial hypercholesterolemia, breast cancer, ovarian cancer, liver cancer, lung cancer, colon cancer, esophageal cancer, gastric cancer, colorectal cancer, nasopharyngeal cancer, brain tumor, cervical cancer, blood cancer, bone cancer, AIDS, or virus infection.

In the present invention, it is further preferred that said drugs include but are not limited to doxorubicin, mitoxantrone, camptothecin, cisplatin, bleomycin, cyclophosphamide, streptozotocin, actinomycin D, vincristine, vinblastine, cytosine arabinoside, anthracycline, nitrogen mustard, tioteppa, chlorambucil, rachelmycin, melphalan, carmustine, romustine, busulfan, dibromannitol, mitomycin C, cis-diammineplatinum(II) dichloride, methotrexate, 6-mercaptopurine, 6-thioguanine, cytosine arabinoside, 5-fluorouracil dacarbazine, dibucaine, chlorpromazine, propranolol, demorol, labetalol, clonidine, hydralazine, imipramine, amitriptyline, doxepin, phenytoin, diphenhydramine, chlorpheniramine, promethazine, gentamicin, ciprofloxacin, cefoxitin, miconazole, terconazole, econazole, isoconazole, butoconazole, clotrimazole, itraconazole, nystatin, naftifine, amphotericin B, antiparasitic agents, hormones, hormone antagonists, immunomodulators, neurotransmitter antagonists, glaucoma drugs, vitamins, tranquilizers, imaging agents, taxol, cytochalasin B, gramicidin D, ethidium bromide, emetine, mitomycin, etoposide, teniposide, colchicine, daunorubicin, quinizarin, mithramycin, 1-dihydrotestosterone, glucocorticoid, procaine, tetracaine, lidocaine, puromycin, and maytansinoid.

In one specific embodiment of the present invention, the N/P ratio of said cationic liposomes to said nucleic acids is preferably (0.1-100):1, more preferably (0.2~30):1, and most preferably (0.5-20):1.

In one specific embodiment of the present invention, the working solution of formulation of cationic liposome-nucleic acid pharmaceutical composition is preferably deionized water, ultrapure water, phosphate buffer, or physiological saline, more preferably phosphate buffer or physiological saline, and most preferably physiological saline; the ratio of cationic liposomes to working solution is preferably (0.05~20) g:100 mL, more preferably (0.1~10) g:100 mL, and most preferably (0.2~5) g:100 mL.

5. Formulation of Cationic Liposome-Nucleic Acid Pharmaceutical Composition

In the present invention, formulation of cationic liposome-nucleic acid pharmaceutical composition contains any foregoing cationic liposome-nucleic acid pharmaceutical composition and pharmaceutically acceptable diluents or excipients, said diluent or excipient being preferably deionized water, ultrapure water, phosphate buffer, or physiological saline, more preferably phosphate buffer or physiological saline, and most preferably physiological saline.

In the present invention, the formulation of cationic liposome-nucleic acid pharmaceutical composition could include the following steps:

Step (1): equilibrate said cationic liposomes in the diluent or excipient;

Step (2): add nucleic acid drugs to the mixture of the equilibrated cationic liposomes and the diluent or excipient, for complexation;

wherein, the equilibration time is 0.1 to 12 h, preferably 0.2 to 6 h, and more preferably 0.5 to 3 h; wherein, the complexation time is 0.1 to 12 h, preferably 0.2 to 5 h, and more preferably 0.5 to 2 h.

The following specific examples are further descriptions of the preparation methods of cationic lipids, cationic liposomes, and cationic liposome-nucleic acid pharmaceutical compositions, and the biological activity assays for cationic liposome-nucleic acid pharmaceutical compositions; said specific examples are disclosed to further illustrate the invention, but should not be regarded as a limitation of the scope of present invention. Wherein, in the embodiments of preparing cationic lipids, the structures of end products are characterized by NMR, and the molecular weight is confirmed by MALDI-TOF.

Example-1: Cationic Lipid (E1-1)

E1-1

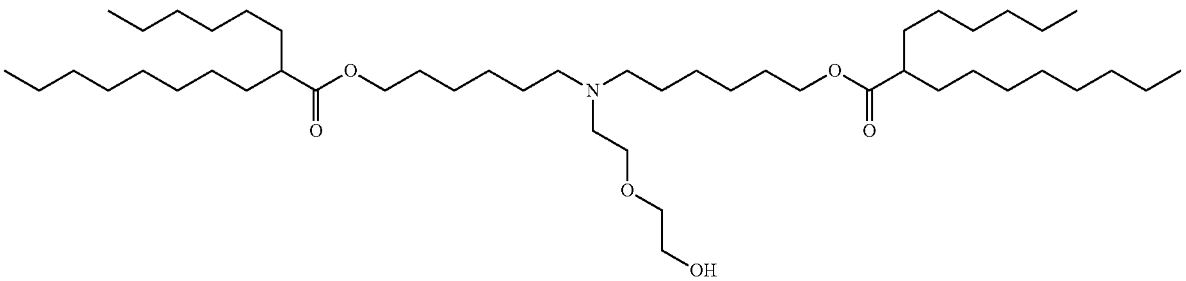

E1-1 corresponds to the general formula (1), wherein, $L_1$ and $L_2$ are both —C(=O)O—, $L_3$ is a linking bond, $B_1$ and $B_2$ are both hexylene groups, $R_1$ and $R_2$ are both

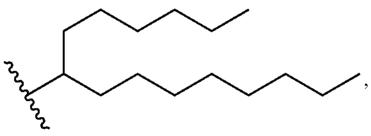,

A is $—(CR_aR_b)_sO—$, $R_a$ and $R_b$ are both hydrogen atoms, s is 2, n is 2, and $R_3$ is a hydrogen atom. The molecular weight is approximately 782 Da.

The preparation process is as follows:

Step a: Into a flask under nitrogen protection, 2-hexyldecanoic acid (S1-1, 100.00 g, 390.6 mmol) was dissolved in anhydrous DCM (1 L). After the temperature of the solution was cooled to 0-10° C., 1,6-hexanediol (S1-2, 92.19 g, 781.3 mmol) and 4-dimethylaminopyridine (DMAP, 57.18 g, 468.7 mmol) were added into the solution carefully, and then 1-ethyl-(3-dimethylaminopropyl) carbodiimide hydrochloride (EDCI, 82.56 g, 430.0 mmol) was added in batches, after which the reaction solution was returned to room temperature, and the reaction was continued. After reaction for 16 h, S1-1 was completely consumed according to the TLC. The reaction solution was washed twice with a mixed solution of 0.4N HCl/10% NaCl (500 mL), and then washed once with a saturated salt solution. The organic phases were combined and dried with anhydrous $MgSO_4$, and the crude product was obtained after filtration and concentration. The crude product was separated and purified by silica gel column chromatography. The eluent of interest was collected and concentrated to obtain the small molecule intermediate of alcohol derivative S1-3 (79.02 g).

Step b: The above condensation product (S1-3, 50.02 g, 140.5 mmol) was dissolved in 500 mL DCM. After the temperature of the solution was cooled to 0° C., 2,2,6,6-tetramethylpiperidinooxy (Tempo, 11.00 mg) and a solution of KBr (20.06 g, 168.6 mmol) dissolved in 50 mL water were both added, and then a solution of NaClO (182.6 mmol) was slowly added dropwise, after which the reaction was continued until the materials were consumed completely according to the TLC. The reaction was quenched with a solution of sodium sulfite. The reaction solution was returned to room temperature, extracted twice with 500 mL DCM, the organic phases were combined, dried with anhydrous $MgSO_4$, filtrated and concentrated to obtain the crude product. The crude product was separated and purified by silica gel column chromatography. The eluent of interest was collected and concentrated to obtain the oxidation product S1-4 (23.12 g).

Step c: The above oxidation product (S1-4, 20.00 g, 56.5 mmol) was dissolved in a mixed solution of 200 mL THE and 20 mL methanol. After the temperature of said solution was cooled to 0° C., 2-(2-aminoethoxy)ethanol (S1-5, 2.82 g, 26.9 mmol) and glacial acetic acid (1.61 g, 26.9 mmol) were added, and then sodium triacetoxyborohydride ($NaBH(OAc)_3$, 17.49 g, 82.5 mmol) was added slowly in batches. After the feeding, the reaction was continued for 2 h until the materials were consumed completely according to the TLC.

A saturated solution of sodium bicarbonate was added to quench the reaction, then the temperature of the reaction solution was returned to room temperature, and then concentrated to remove THE and methanol. The residue was extracted twice with 200 mL DCM. The organic phases were combined, dried with anhydrous $MgSO_4$, filtrated and concentrated to obtain the crude product. The crude product was separated and purified by silica gel column chromatography.

The eluent of interest was collected and concentrated to obtain the cationic lipid E1-1 (12.09 g). The main data of $^1$H-NMR spectrum of E1-1 were as follows: $^1$H NMR (400 MHz, $CDCl_3$) δ: 4.07 (t, 4H), 3.70 (t, 2H), 3.63 (t, 4H), 2.65 (t, 2H), 2.49 (m, 4H), 2.32 (m, 2H), 1.71-1.22 (m, 64H), 0.87 (t, 12H). The molecular weight of E1-1 was determined to be 781.76 Da by MALDI-TOF.

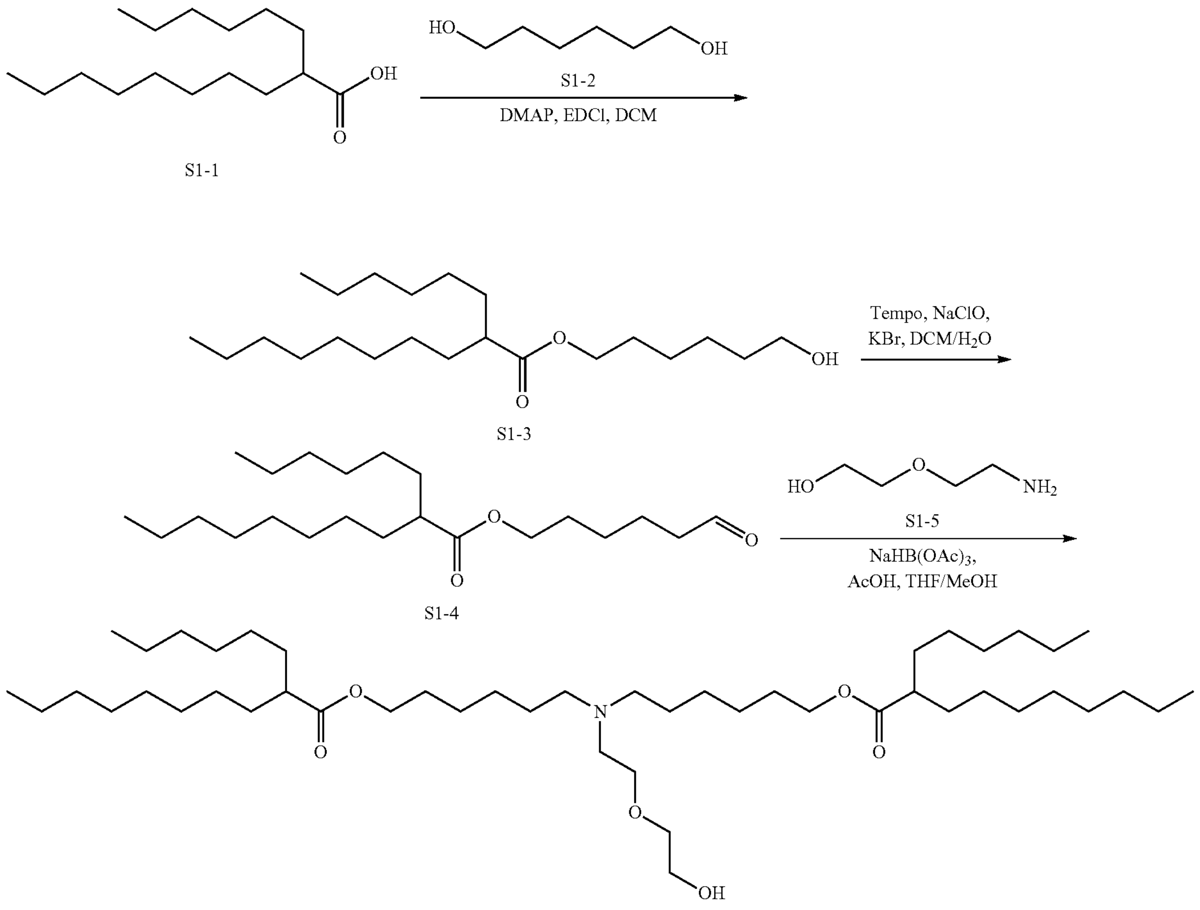

S1-1

S1-3

S1-4

E1-1

Example-2: Cationic Lipid (E2-1)

E2-1

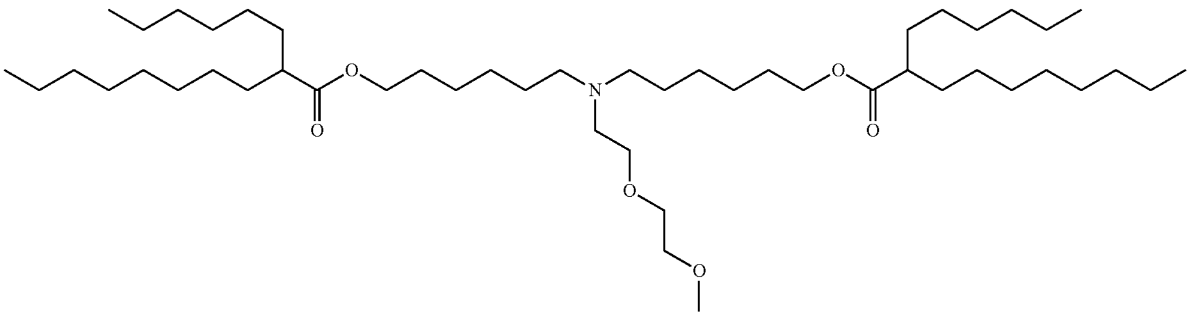

E2-1 corresponds to the general formula (1), wherein, $L_1$ and $L_2$ are both —C(═O)O—, $L_3$ is a linking bond, $B_1$ and $B_2$ are both hexylene groups, $R_1$ and $R_2$ are both

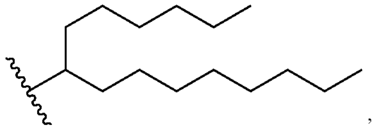

A is $—(CR_aR_b)_sO—$, $R_a$ and $R_b$ are both hydrogen atoms, s is 2, n is 2, and $R_3$ is $—CH_3$. The molecular weight is approximately 796 Da.

The preparation process is as follows:

The oxidation product (S1-4, 10.00 g, 28.2 mmol) prepared according to Example-1 was dissolved in a mixed solution of 100 mL THE and 10 mL methanol. After the temperature of the solution was cooled to 0° C., 1-(2-aminoethoxy)-2-methoxyethane (S2-1, 1.61 g, 13.5 mmol) and glacial acetic acid (0.81 g, 13.5 mmol) were added, and then sodium triacetoxyborohydride ($NaBH(OAc)_3$, 9.86 g, 47.1 mmol) was added slowly in batches. After the feeding, the reaction was continued for 2 h until the materials were consumed completely according to the TLC. A saturated solution of sodium bicarbonate was added to quench the reaction, and then the reaction solution was returned to room temperature, and then concentrated to remove THE and methanol. The residue was extracted twice with 100 mL DCM. The organic phases were combined, dried with anhydrous $MgSO_4$, filtrated and concentrated to obtain the crude product. The crude product was separated and purified by silica gel column chromatography. The eluent of interest was collected and concentrated to obtain the cationic lipid E2-1 (5.93 g). The main data of $^1$H-NMR spectrum of E2-1 were as follows: $^1$H NMR (400 MHz, $CDCl_3$) δ: 4.07 (t, 4H), 3.71 (t, 2H), 3.63 (t, 4H), 3.30 (s, 3H), 2.65 (t, 2H), 2.49 (m, 4H), 2.32 (m, 2H), 1.70-1.22 (m, 64H), 0.89 (t, 12H). The molecular weight of E2-1 was determined to be 795.71 Da by MALDI-TOF.

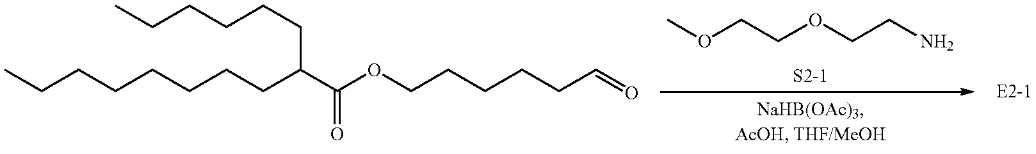

S1-4

Example-3: Cationic Lipid (E3-1)

E3-1

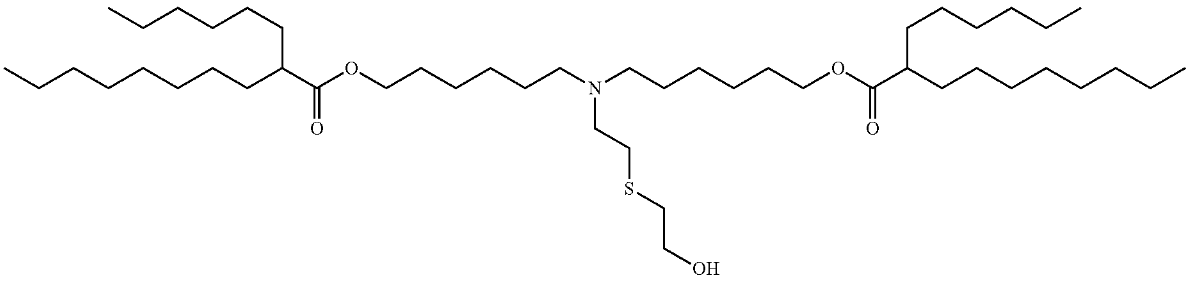

E3-1 corresponds to the general formula (1), wherein, $L_1$ and $L_2$ are both —C(═O)O—, $L_3$ is a linking bond, $B_1$ and $B_2$ are both hexylene groups, $R_1$ and $R_2$ are both

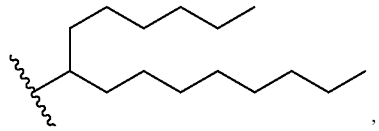

A is $—(CR_aR_b)_sS—$, $R_a$ and $R_b$ are both hydrogen atoms, s is 2, n is 1, and $R_3$ is $—CH_2CH_2OH$. The molecular weight is approximately 782 Da.

The preparation process is as follows:

The oxidation product (S1-4, 5.00 g, 14.1 mmol) prepared according to Example-1 was dissolved in a mixed solution of 50 mL THE and 5 mL methanol. After the temperature of the solution was cooled to 0° C., 2-(2-aminoethylmercapto) ethanol (S3-1, 0.81 g, 6.7 mmol) and glacial acetic acid (0.40 g, 6.7 mmol) were added, and then $NaBH(OAc)_3$ (5.00 g, 23.6 mmol) was added slowly in batches. After the feeding, the reaction was continued for 2 h until the materials were consumed completely according to the TLC. A saturated solution of sodium bicarbonate was added to quench the reaction. The reaction solution was returned to room temperature, and then concentrated to remove THE and methanol. The residue was extracted twice with 50 mL DCM, and the organic phases were combined and dried with anhydrous $MgSO_4$. The crude product was obtained after filtration and concentration, and then separated and purified by silica gel column chromatography. The eluent of interest was collected and concentrated to obtain the cationic lipid E3-1 (2.64 g). The main data of $^1H$-NMR spectrum of E3-1 were as follows: $^1H$ NMR (400 MHz, $CDCl_3$) δ: 4.06 (t, 4H), 3.70 (t, 2H), 2.75-2.45 (m, 10H), 2.32 (m, 2H), 1.70-1.22 (m, 64H), 0.87 (t, 12H). The molecular weight of E3-1 was determined to be 782.37 Da by MALDI-TOF.

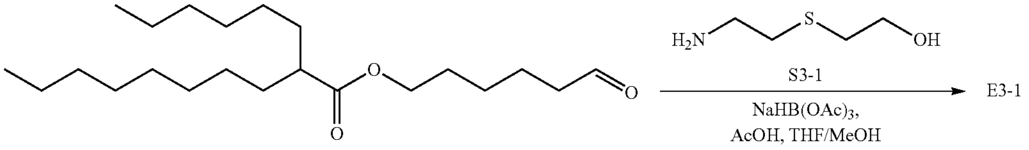

S1-4

Example-4: Cationic Lipid (E4-1)

E4-1

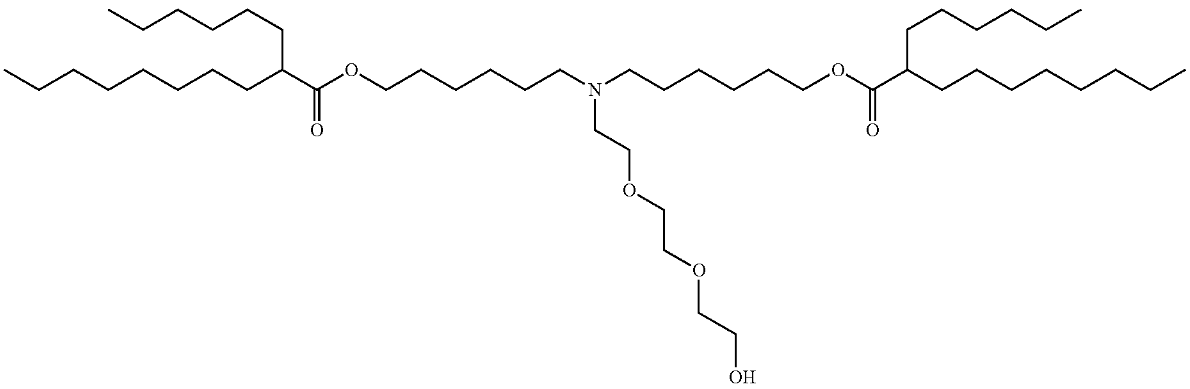

E4-1 corresponds to the general formula (1), wherein, $L_1$ and $L_2$ are both —C(═O)O—, $L_3$ is —$CH_2CH_2$—, $B_1$ and $B_2$ are both hexylene groups, $R_1$ and $R_2$ are both

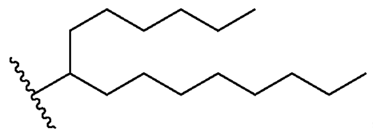

,

A is —$O(CR_aR_b)_s$—, $R_a$ and $R_b$ are both hydrogen atoms, s is 2, n is 2, and $R_3$ is —OH. The molecular weight is approximately 826 Da.

The preparation process is as follows:

The oxidation product (S1-4, 5.00 g, 14.1 mmol) prepared according to Example-1 was dissolved in a mixed solution of 50 mL THE and 5 mL methanol. After the temperature of the solution was cooled to 0° C., triethyleneglycolamine (S4-1, 1.00 g, 6.7 mmol) and glacial acetic acid (0.40 g, 6.7 mmol) were added, and then $NaBH(OAc)_3$ (5.00 g, 23.6 mmol) was added slowly in batches. After the feeding, the reaction was continued for 2 h until the materials were consumed completely according to the TLC. A saturated solution of sodium bicarbonate was added to quench the reaction, and then the reaction solution was returned to room temperature, and then concentrated to remove THE and methanol. The residue was extracted twice with 50 mL DCM, and the organic phases were combined and dried with anhydrous $MgSO_4$. The crude product was obtained after filtration and concentration, and then separated and purified by silica gel column chromatography. The eluent of interest was collected and concentrated to obtain the cationic lipid E4-1 (3.15 g). The main data of $^1$H-NMR spectrum of E4-1 were as follows: $^1$H NMR (400 MHz, $CDCl_3$) δ: 4.08 (t, 4H), 3.81-3.58 (m, 10H), 2.65 (t, 2H), 2.49 (m, 4H), 2.32 (m, 2H), 1.70-1.23 (m, 64H), 0.88 (t, 12H). The molecular weight of E4-1 was determined to be 825.73 Da by MALDI-TOF.

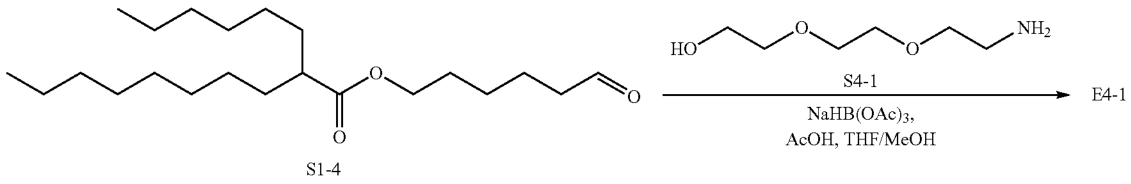

Example-5: Cationic Lipid (E5-1)

E5-1

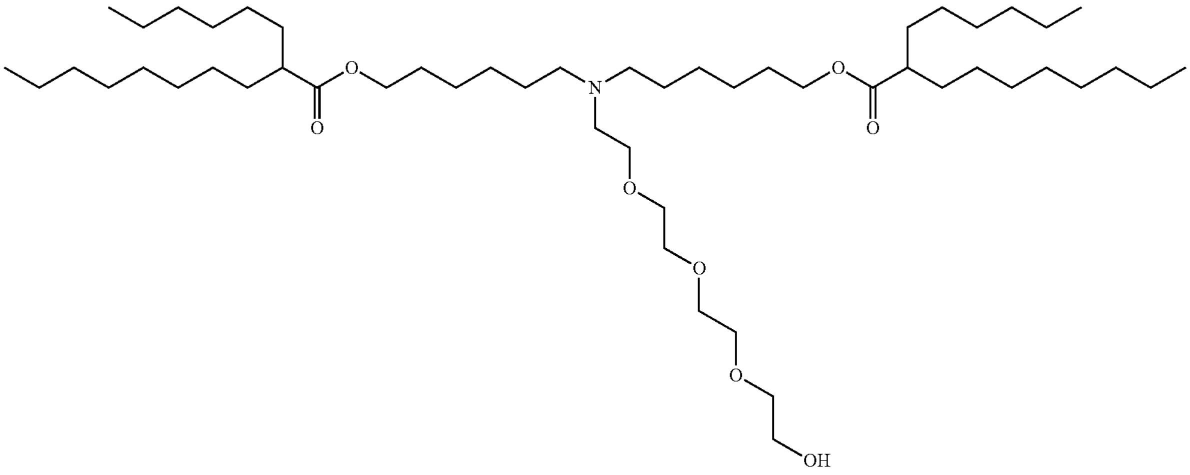

E5-1 corresponds to the general formula (1), wherein, $L_1$ and $L_2$ are both —C(=O)O—, $L_3$ is —$CH_2CH_2O$—, $B_1$ and $B_2$ are both hexylene groups, $R_1$ and $R_2$ are both

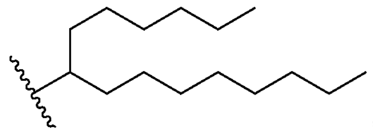

,

A is —$(CR_aR_b)_sO$—, $R_a$ and $R_b$ are both hydrogen atoms, s is 2, n is 2, and $R_3$ is —$CH_2CH_2OH$. The molecular weight is approximately 869 Da.

The preparation process is as follows:

Step a: The oxidation product (S1-4, 5.00 g, 14.1 mmol) prepared according to Example-1 was dissolved in a mixed solution of 50 mL THF and 5 mL methanol. After the temperature of the solution was cooled to 0° C., tetraethyleneglycolamine (S5-1, 1.29 g, 6.7 mmol) and glacial acetic acid (0.40 g, 6.7 mmol) were added, and then $NaBH(OAc)_3$ (5.00 g, 23.6 mmol) was added slowly in batches. After the feeding, the reaction was continued for 2 h until the materials were consumed completely according to the TLC. A saturated solution of sodium bicarbonate was added to quench the reaction, and then the reaction solution was returned to room temperature, and then concentrated to remove THE and methanol. The residue was extracted twice with 50 mL DCM, and the organic phases were combined and dried with anhydrous $MgSO_4$. The crude product was obtained after filtration and concentration, and then separated and purified by silica gel column chromatography. The eluent of interest was collected and concentrated to obtain the cationic lipid E5-1 (3.54 g). The main data of $^1$H-NMR spectrum of E5-1 were as follows: $^1$H NMR (400 MHz, $CDCl_3$) δ: 4.07 (t, 4H), 3.85-3.55 (m, 14H), 2.64 (t, 2H), 2.49 (m, 4H), 2.32 (m, 2H), 1.70-1.22 (m, 64H), 0.87 (t, 12H). The molecular weight of E5-1 was determined to be 869.37 Da by MALDI-TOF.

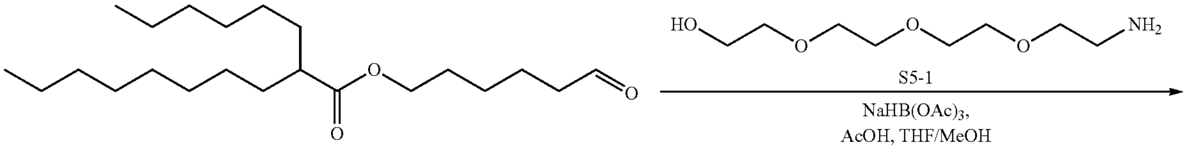

S1-4

E5-1

Example-6: Cationic Lipid (E6-1)

E6-1

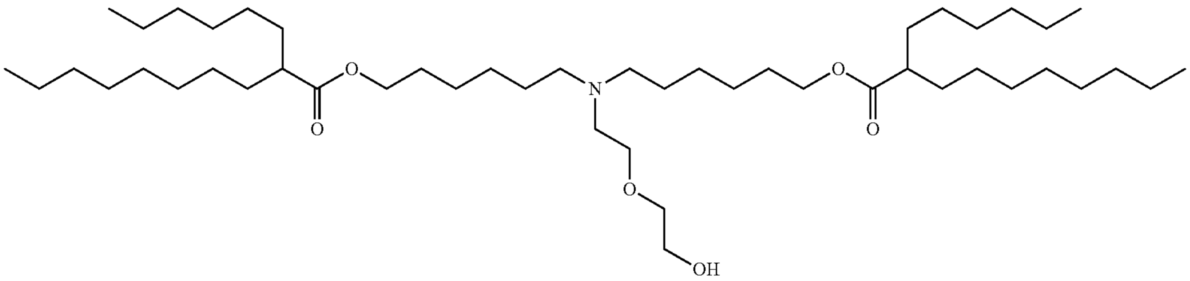

E6-1 corresponds to the general formula (1), wherein, $L_1$ and $L_2$ are both —O—, $L_3$ is a linking bond, $B_1$ and $B_2$ are both hexylene groups, $R_1$ and $R_2$ are both

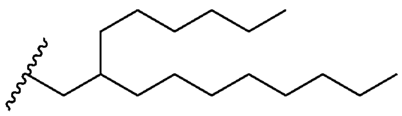

,

A is $—(CR_aR_b)_sO—$, $R_a$ and $R_b$ are both hydrogen atoms, s is 2, n is 2, and $R_3$ is a hydrogen atom. The molecular weight is approximately 754 Da.

The preparation process is as follows:

Step a: In a flask under nitrogen protection, 2-hexyl-1-decanol (compound S6-1, 24.20 g, 100.0 mmol) was dissolved in 250 mL THF. After the temperature of the solution was cooled to 0-10° C., sodium hydride (6.00 g, 150.0 mmol, 60%) was added carefully. After reaction for 0.5 h, (6-bromohexyloxy)-tert-butyldimethylsilane (S6-2, 26.46 g, 90.0 mmol) was added carefully, and then the reaction solution was returned to room temperature and continued for 12 h. When S6-1 was completely consumed according to the TLC, 100 mL water was added to quench the reaction and the reaction solution was concentrated to remove THF. The residue of concentration was extracted twice with 100 mL DCM, and the organic phases were combined and dried with anhydrous $MgSO_4$. The crude product was obtained after filtration and concentration, and then separated and purified by silica gel column chromatography. The eluent of interest was collected and concentrated to obtain the product S6-3 (25.25 g).

Step b: In a flask under nitrogen protection, the substitution product (S6-3, 25.00 g, 54.8 mmol) was dissolved in 250 mL THF, and a solution of tetrabutylammonium fluoride (TBAF, 110 mL, 1N in THF) was added therein. After reaction for 1 h, the materials were completely consumed according to the TLC, and 100 mL water was added to quench the reaction. The reaction solution was concentrated to remove THF, and the residue was extracted twice with 100 mL DCM. The organic phases were combined and dried with anhydrous $MgSO_4$. The crude product was obtained after filtration and concentration, and further separated and purified by silica gel column chromatography. The eluent of interest was collected and concentrated to obtain the oxidation product S6-4 (16.33 g).

Step c: The condensation product (S6-4, 16.28 g, 47.6 mmol) was dissolved in 200 mL DCM. After the temperature of the solution was cooled to 0° C., Tempo (4.00 mg) and a solution of KBr (0.29 g, 2.4 mmol) dissolved in 20 mL purified water were added to the former solution, followed by slowly adding a solution of NaClO (57.2 mmol). Then, the reaction was continued until the materials were consumed completely according to the TLC. Then, a solution of sodium sulfite was added to quench the reaction. The reaction solution was extracted twice with 200 mL DCM after returning to room temperature. The organic phases were combined and dried with anhydrous $MgSO_4$. The crude product was obtained after filtration and concentration, and further separated and purified by silica gel column chromatography. The eluent of interest was collected and concentrated to obtain the oxidation product S6-5 (12.94 g, 80%).

Step d: The oxidation product (S6-5, 12.92 g, 38.0 mmol) prepared according to Example-1 was dissolved in a mixed solution of 150 mL THE and 15 mL methanol. When the temperature of the solution was cooled to 0° C., S1-5 (1.90 g, 18.1 mmol) prepared according to the step a of Example-1, as well as glacial acetic acid (1.09 g, 18.1 mmol), were both added, and then $NaBH(OAc)_3$ (13.44 g, 63.4 mmol) was added slowly in batches. After the feeding, the reaction was continued for 2 h until the materials were consumed completely according to the TLC. Then, a saturated solution of sodium bicarbonate was added to quench the reaction.

The reaction solution was returned to room temperature, and then concentrated to remove THE and methanol. The residue was extracted twice with 200 mL DCM, and the organic phases were combined and dried with anhydrous MgSO4. The crude product was obtained after filtration and concentration, and further separated and purified by silica gel column chromatography. The eluent of interest was collected and concentrated to obtain the cationic lipid E6-1 (6.37 g). The main data of $^1$H-NMR spectrum of E6-1 were as follows: $^1$H NMR (400 MHz, $CDCl_3$) δ: 3.84-3.55 (m, 14H), 2.65 (t, 2H), 2.48 (m, 4H), 1.82-1.22 (m, 66H), 0.86 (t, 12H). The molecular weight of E6-1 was determined to be 753.96 Da by MALDI-TOF.

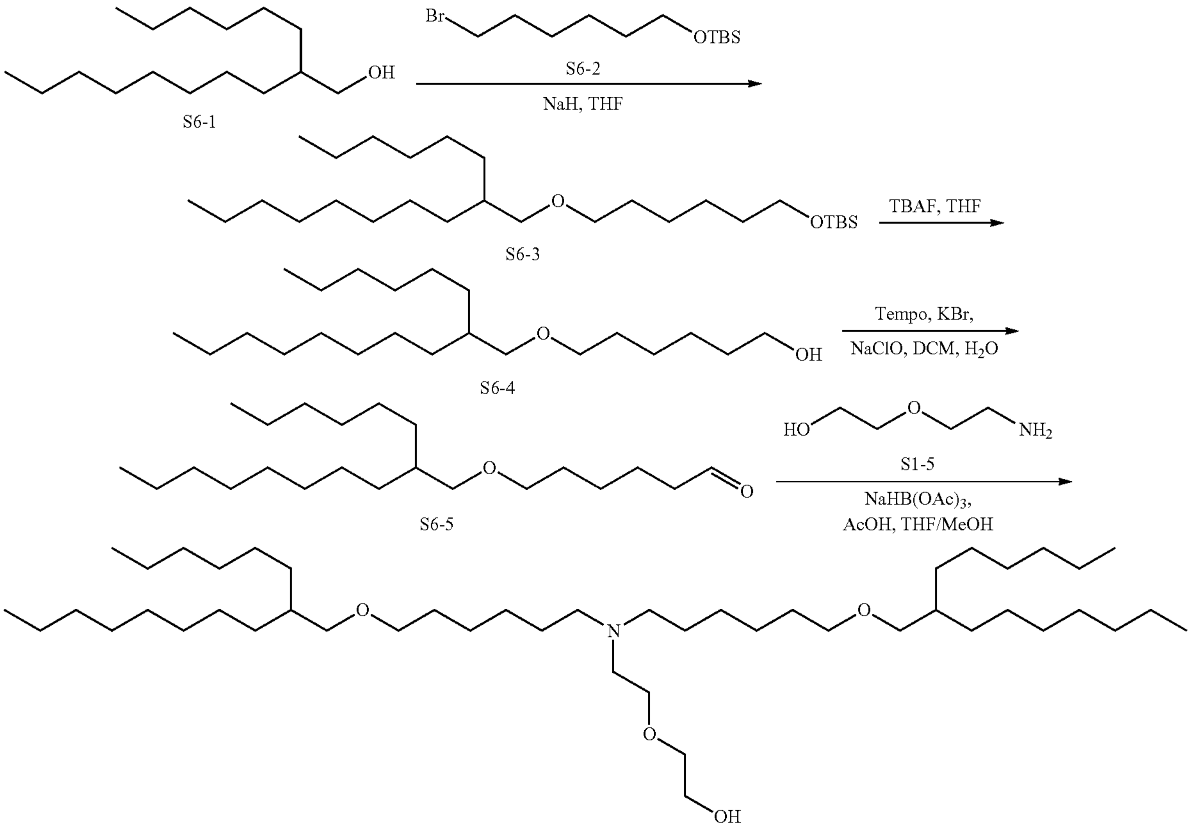

E6-1

Example-7: Cationic Lipid (E7-2)

E7-2

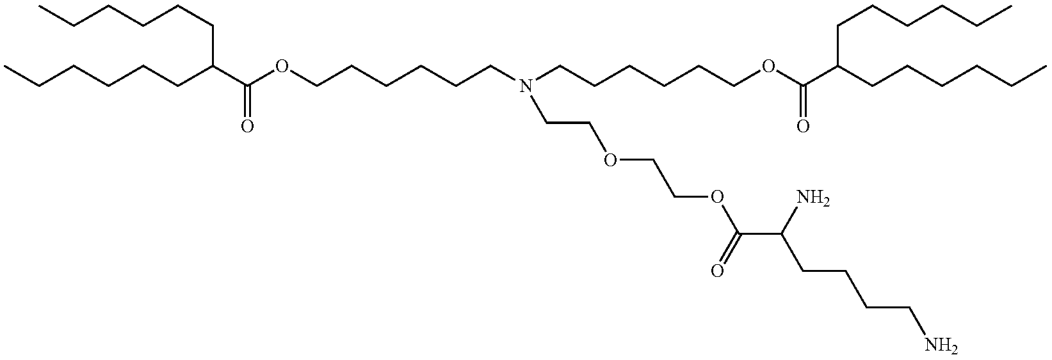

E7-2 corresponds to the general formula (1), wherein, $L_1$ and $L_2$ are both —C(═O)O—, $L_3$ is a linking bond, $B_1$ and $B_2$ are both hexylene groups, $R_1$ and $R_2$ are both

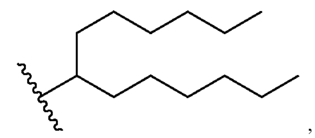

,

A is —$(CR_aR_b)_sO$—, $R_a$ and $R_b$ are both hydrogen atoms, s is 2, n is 2, and $R_3$ is

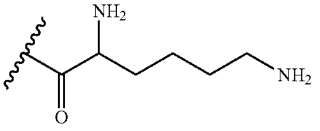

.

The molecular weight is approximately 854 Da.

The preparation process is as follows:

Step a: In a flask under nitrogen protection, 2-hexyloctanoic acid (S7-1, 100.00 g, 438.6 mmol) was dissolved in anhydrous DCM (1 L). When the temperature of the solution was cooled to 0-10° C., S1-2 (92.19 g, 781.3 mmol) prepared according to the step a of Example-1 and DMAP (57.18 g, 468.7 mmol) were added carefully, and then EDCI (82.56 g, 430.0 mmol) was added in batches. Then, the reaction solution was returned to room temperature, and the reaction was continued for 16 h. When S7-1 was completely consumed according to the TLC, the reaction solution was washed twice with a mixed solution of 0.4N HCl/10% NaCl (500 mL), and then washed once with a saturated salt solution. The organic phases were combined and dried with anhydrous $MgSO_4$. The crude product was obtained after filtration and concentration, and further separated and purified by silica gel column chromatography. The eluent of interest was collected and concentrated to obtain the product S7-2 (84.90 g).

Step b: The condensation product (S7-2, 50.00 g, 152.4 mmol) was dissolved in 500 mL DCM. After the temperature of the solution was cooled to 0° C., Tempo (11.00 mg) and a solution of KBr (20.06 g, 168.6 mmol) dissolved in 50 mL purified water were added to the former solution, and then a solution of NaClO (182.6 mmol) was added slowly. Then, the reaction was continued until the materials were consumed completely according to the TLC. Then, a solution of sodium sulfite was added to quench the reaction, after which the reaction solution was extracted twice with 500 mL DCM after returning to room temperature. The organic phases were combined and dried with anhydrous $MgSO_4$. The crude product was obtained after filtration and concentration, and further separated and purified by silica gel column chromatography. The eluent of interest was collected and concentrated to obtain the oxidation product S7-3 (23.05 g).

Step c: The oxidation product (S7-3, 20.00 g, 61.3 mmol) was dissolved in a mixed solution of 200 mL THE and 20 mL methanol. After the temperature of the solution was cooled to 0° C., S7-4 (21.73 g, 32.1 mmol, obtained by the coupling of bis-Fmoc-protected lysine with S1-5 prepared according to the step c of Example-1) and glacial acetic acid (1.61 g, 26.9 mmol) were added, and then $NaBH(OAc)_3$ (17.49 g, 82.5 mmol) was added slowly in batches. After the feeding, the reaction was continued for 2 h until the materials were consumed completely according to the TLC. Then, a saturated solution of sodium bicarbonate was added to quench the reaction. The reaction solution was then brought back to room temperature, and concentrated to remove THE and methanol. The residue of concentration was extracted twice with 200 mL DCM. The organic phases were combined and dried with anhydrous $MgSO_4$. The crude product was obtained after filtration and concentration, and further separated and purified by silica gel column chromatography. The eluent of interest was collected and concentrated to obtain the cationic lipid E7-1 containing two Fmoc-protected amino groups (24.00 g). The main data of $^1H$-NMR spectrum of E7-1 were as follows: $^1H$ NMR (400 MHz, $CDCl_3$) δ: 7.20-7.80 (m, 16H), 4.37-4.45 (d, 4H), 4.42 (m, 1H), 4.25 (t, 2H), 4.20 (m, 2H), 4.07 (t, 4H), 3.63 (t, 4H), 2.69 (m, 2H), 2.66 (t, 2H), 2.49 (m, 4H), 2.32 (m, 2H), 1.76-2.00 (m, 2H), 1.72-1.22 (m, 56H), 1.24-1.66 (m, 4H), 0.86 (t, 12H).

Step d: Removal of the Fmoc protecting group. E7-1 (10.00 g, 7.7 mmol) was treated with a solution of 20% piperidine in DMF. The solvent was removed by rotary evaporation, and then the residue was dissolved in dichloromethane, precipitated with anhydrous ether, filtered, and recrystallized with isopropanol to obtain the cationic lipid E7-2 containing two naked amino groups (6.45 g, 98.1%). The main data of $^1H$-NMR spectrum of E7-2 was as follows: 4.36 (t, 1H). The characteristic peaks of Fmoc were disappeared from the $^1H$-NMR spectrum. The molecular weight of E7-2 was determined to be 853.85 Da by MALDI-TOF.

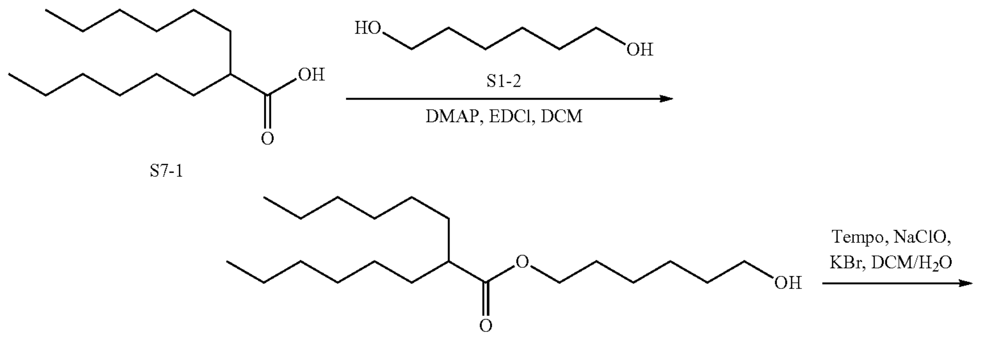

S7-2

-continued

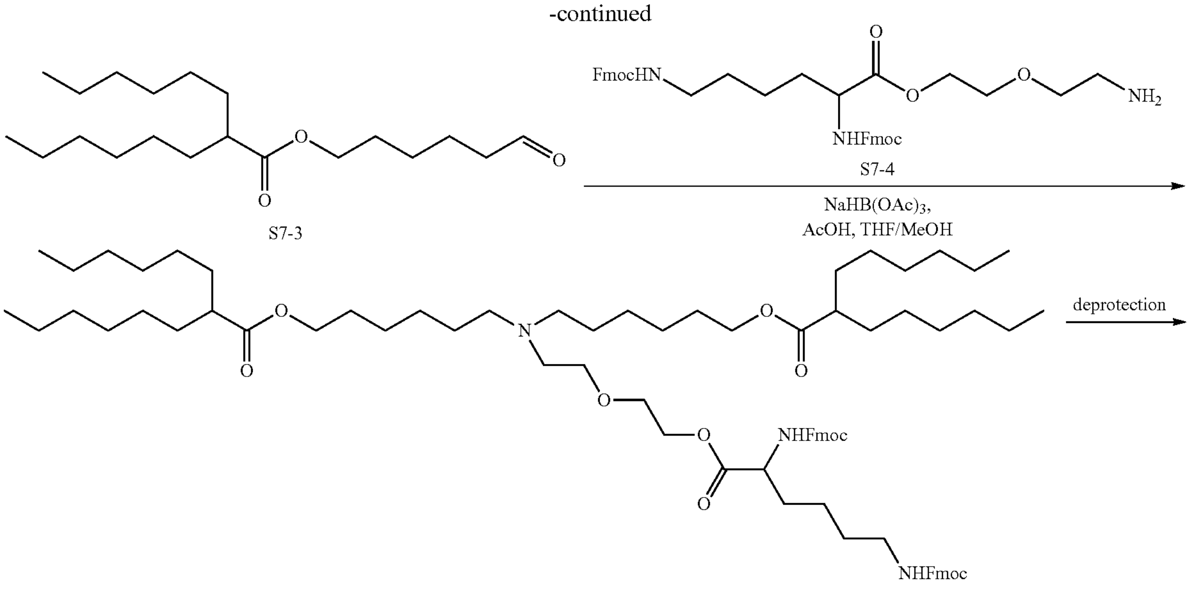

S7-3

S7-4

E7-1

E7-2

Example-8: Cationic Lipid (E8-1)

E8-1

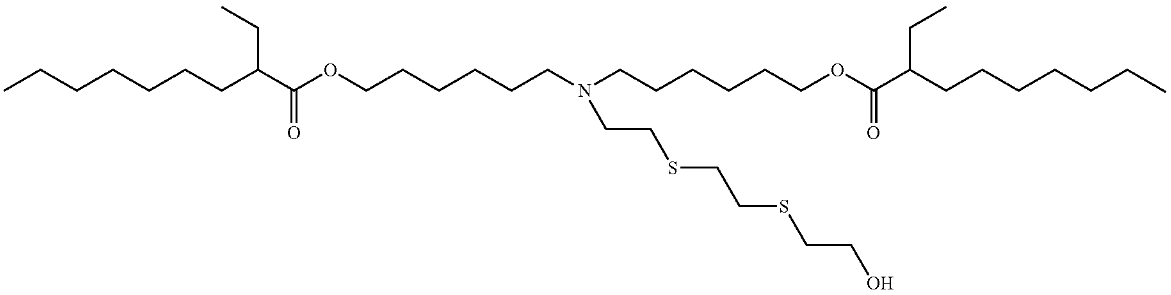

E8-1 corresponds to the general formula (1), wherein, $L_1$ and $L_2$ are both —C(═O)O—, $L_3$ is —$CH_2CH_2$—, $B_1$ and $B_2$ are both hexylene groups, $R_1$ and $R_2$ are both

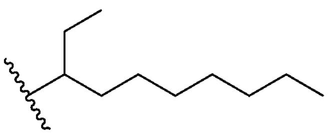

,

A is —$S(CR_aR_b)_s$—, $R_a$ and $R_b$ are both hydrogen atoms, s is 2, n is 2, and $R_3$ is —OH. The molecular weight is approximately 718 Da.

The preparation process is as follows:

Step a: In a flask under nitrogen protection, 2-hexylnonanoic acid (S8-1, 100.00 g, 537.6 mmol) was dissolved in anhydrous DCM (1 L). After the temperature of the solution was cooled to 0-10° C., S1-2 (92.19 g, 781.3 mmol) prepared according to the step a of Example-1 and DMAP (57.18 g, 468.7 mmol) were added carefully, and then EDCI (82.56 g, 430.0 mmol) was added in batches. The reaction solution was returned to room temperature and continued for 16 h. When S8-1 was completely consumed according to the TLC, the reaction solution was washed twice with a mixed solution of 0.4N HCl/10% NaCl (500 mL), and then washed once with a saturated salt solution. The organic phases were combined and dried with anhydrous $MgSO_4$. The crude product was obtained after filtration and concentration, and further separated and purified by silica gel column chromatography. The eluent of interest was collected and concentrated to obtain the product S8-2 (87.35 g).

Step b: The condensation product S8-2 (50.00 g, 174.8 mmol) was dissolved in 500 mL DCM. After the temperature of the solution was cooled to 0° C., Tempo (11.00 mg) and a solution of KBr (20.06 g, 168.6 mmol) dissolved in 50 mL purified water were added, and then a solution of NaClO (182.6 mmol) was added slowly. Then, the reaction was continued until the materials were consumed completely according to the TLC. Then, a solution of sodium sulfite was added to quench the reaction. The reaction solution was extracted twice with 500 mL DCM after being brought back to room temperature. The organic phases were combined and dried with anhydrous $MgSO_4$. The crude product was obtained after filtration and concentration, and further separated and purified by silica gel column chromatography. The eluent of interest was collected and concentrated to obtain the oxidation product S8-3 (24.78 g).

Step c: The oxidation product (S8-3, 20.00 g, 70.4 mmol) was dissolved in a mixed solution of 200 mL THE and 20 mL methanol. After the temperature of the solution was cooled to 0° C.,

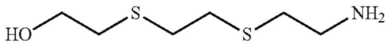

(S8-4, 6.41 g, 35.4 mmol) and glacial acetic acid (1.61 g, 26.9 mmol) were added, and then $NaBH(OAc)_3$ (17.49 g, 82.5 mmol) was added in batches slowly. After the feeding, the reaction was continued for 2 h until the materials were consumed completely according to the TLC. Then, a saturated solution of sodium bicarbonate was added to quench the reaction. The reaction solution was returned to room temperature and concentrated to remove THE and methanol. The residue was extracted twice with 200 mL DCM. The organic phases were combined and dried with anhydrous $MgSO_4$. The crude product was obtained after filtration and concentration, and further separated and purified by silica gel column chromatography. The eluent of interest was collected and concentrated to obtain the cationic lipid E8-1 (11.79 g). The main data of $^1$H-NMR spectrum of E8-1 were as follows: $^1$H NMR (400 MHz, $CDCl_3$) δ: 4.07 (t, 4H), 3.70 (t, 2H), 2.81 (m, 4H), 2.75-2.45 (m, 10H), 2.32 (m, 2H), 1.72-1.22 (m, 44H), 0.88 (t, 12H). The molecular weight of E8-1 was determined to be 717.50 Da by MALDI-TOF.

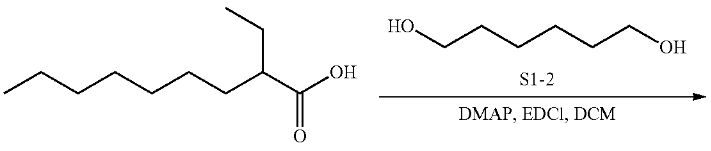

S8-1

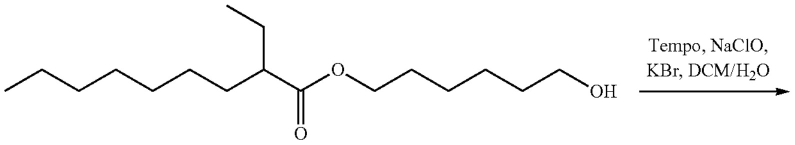

S8-2

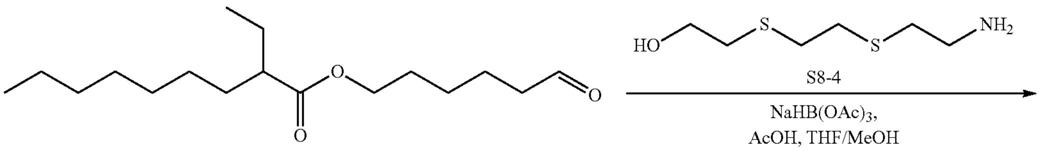

S8-3

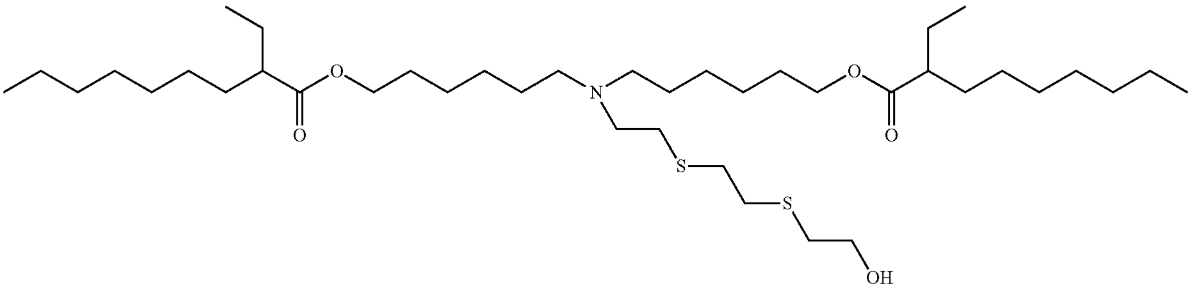

E8-1

Example-9: Cationic Lipid (E9-2)

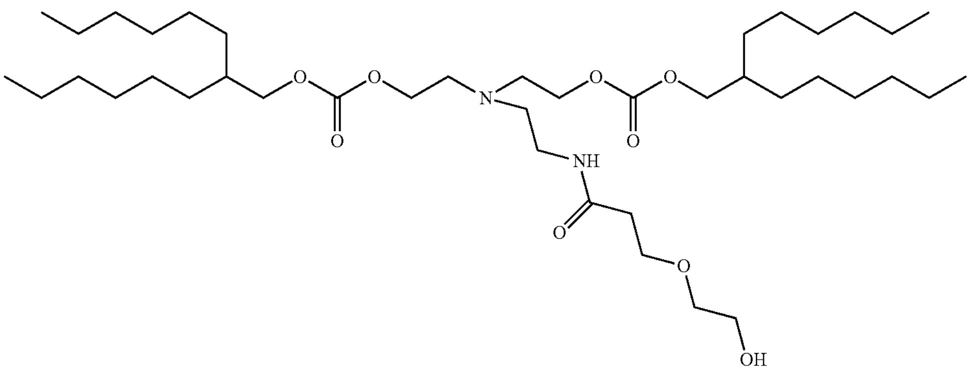

E9-2

E9-2 corresponds to the general formula (1), wherein, $L_1$ and $L_2$ are both —OC(═O)O—, $L_3$ is —$CH_2CH_2NHC$(═O)—, $B_1$ and $B_2$ are both —$CH_2CH_2$—, $R_1$ and $R_2$ are both

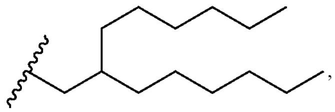

,

A is —$(CR_aR_b)_sO$—, $R_a$ and $R_b$ are both hydrogen atoms, s is 2, n is 2, and $R_3$ is a hydrogen atom. The molecular weight is approximately 744 Da.

The preparation process is as follows:

Step a: In a dry and clean 1000 mL round-bottom flask, N,N-diethyl-1,3-propanediamine succinimidyl carbonate with a Fmoc-protected amino group

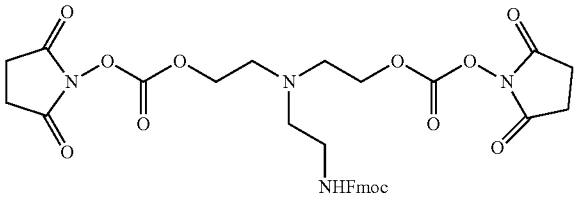

(S9-2, 96.54 g, 233.2 mmol) was dissolved in dichloromethane. DMAP (62.59 g, 513.0 mmol) was added and stirred well. Then, 2-hexyl-1-octanol S9-1 (100.0 g, 467.3 mmol) was added to the reaction solution which was stirred for another 16 h. When the reaction was completed, the reaction solution was dried by rotary evaporation, which was followed by recrystallization with isopropanol and purification by silica gel column. Then, an ethylamine derivative with an Fmoc-protected amino group (S9-3, 127.86 g, 93.9%) was obtained.

Step b: Deprotection of S9-3 containing a Fmoc-protected amino group. S9-3 (50.00 g, 85.6 mmol) was treated with the 20% piperidine/DMF solution, after which the solvent was removed by rotary evaporation and then the residue was dissolved in dichloromethane. After the crude reaction solution was cooled to 0-10° C.,

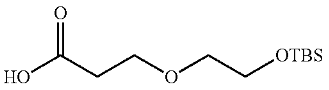 [SMILES: CC(C)(C)[Si](C)(C)OCCOCCC(=O)O]

(S9-4, 13.00 g, 52.4 mmol) and TEA (7.80 g, 77.1 mmol) were added under nitrogen protection. Then, the reaction solution was returned to room temperature, and the reaction was continued overnight. When the TLC indicated that the materials were consumed completely, 100 mL water was added to quench the reaction. The reaction solution was extracted twice with 100 mL DCM, and the organic phases were combined and dried with anhydrous $MgSO_4$. The crude product was obtained after filtration and concentration, and further separated and purified by silica gel column chromatography. The eluent of interest was collected and concentrated to obtain the cationic lipid E9-1 (27.54 g). The main data of $^1$H-NMR spectrum of E9-1 were as follows: $^1$H NMR (400 MHz, $CDCl_3$) δ: 4.22 (m, 8H), 3.75 (t, 2H), 3.65 (m, 2H), 3.59 (t, 2H), 3.14 (m, 2H), 2.65 (t, 2H), 2.60 (t, 2H), 2.51 (t, 4H), 2.32 (m, 2H), 1.82-1.22 (m, 40H), 0.98 (m, 9H), 0.88 (t, 12H), 0.21 (m, 6H).

Step c: In a flask under nitrogen protection, the substitution product (E9-1, 20.00 g, 23.2 mmol) was dissolved in 250 mL THF, and a solution of tetrabutylammonium fluoride (TBAF, 110 mL, 1N in THF) was added therein. After reaction for 1 h, the materials were consumed completely according to the TLC, and then 100 mL water was added to quench the reaction. The reaction solution was concentrated to remove THF, and the residue was extracted twice with 100 mL DCM. The organic phases were combined and dried with anhydrous $MgSO_4$. The crude product was obtained after filtration and concentration, and further separated and purified by silica gel column chromatography. The eluent of interest was collected and concentrated to obtain the cationic lipid E9-2 (15.14 g, 87.7%). The characteristic peak of TBS disappeared in the $^1$H-NMR spectrum. The molecular weight of E9-2 was determined to be 744.52 Da by MALDI-TOF.

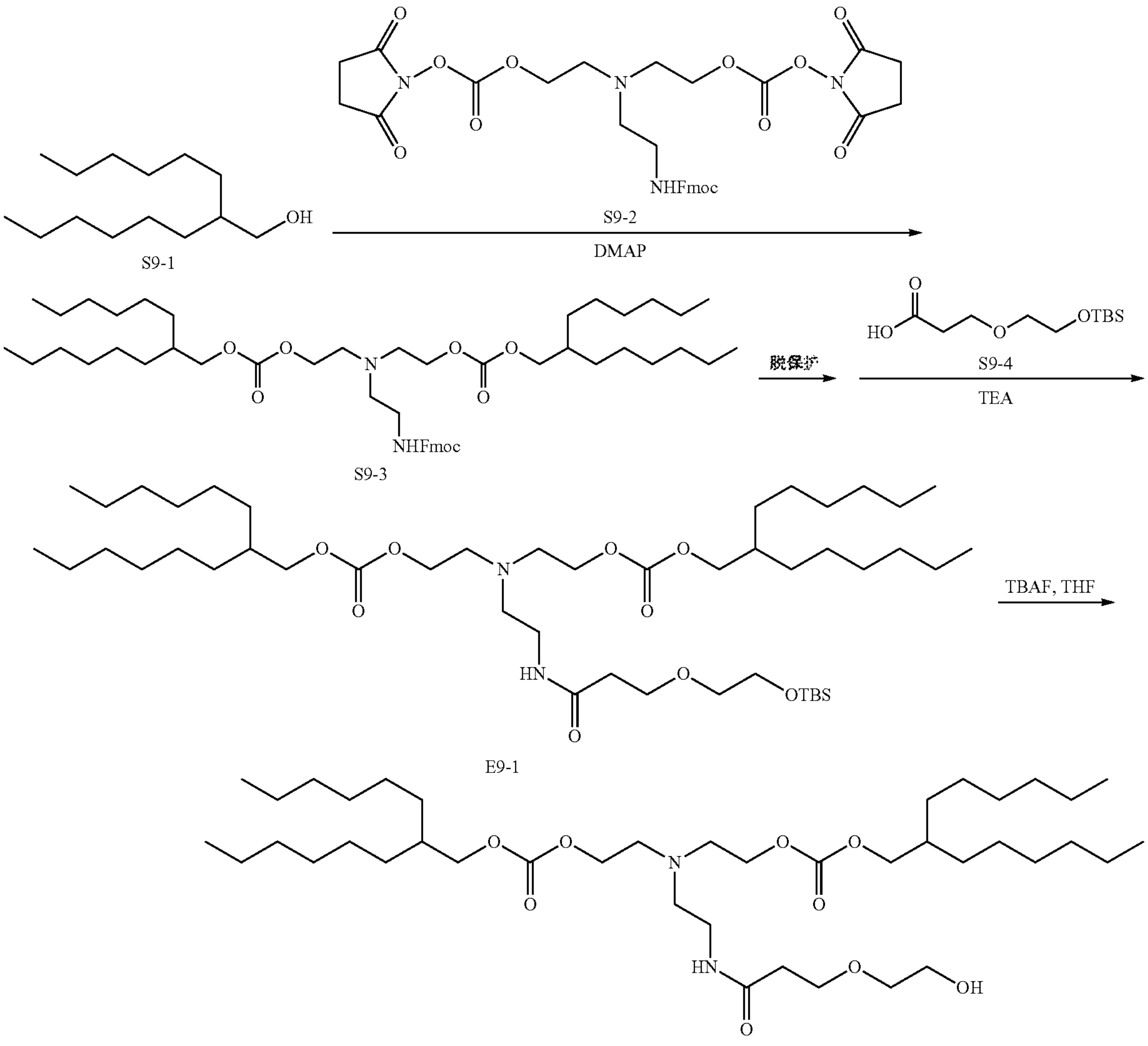
E9-2
Example-10: Cationic Lipid (E10-1)
E10-1
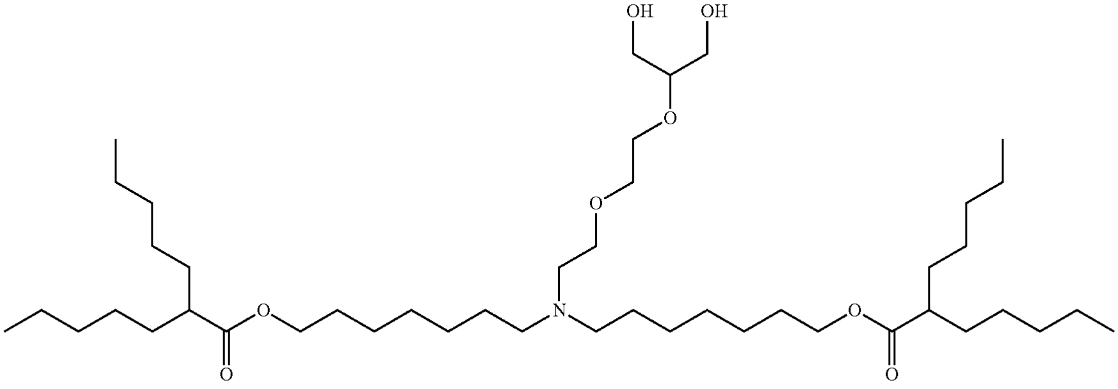

E10-1 corresponds to the general formula (1), wherein, $L_1$ and $L_2$ are both —C(═O)O— $L_3$ is a linking bond, $B_1$ and $B_2$ are both heptylene groups, $R_1$ and $R_2$ are both

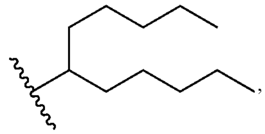

,

A is —$(CR_aR_b)_sO$—, $R_a$ and $R_b$ are both hydrogen atoms, s is 2, n is 2, and $R_3$ is

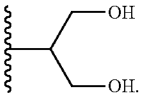

The molecular weight is approximately 772 Da.

The preparation process is as follows:

Step a: In a flask under nitrogen protection, 2-pentylheptanoic acid (S10-1, 100.00 g, 499.5 mmol) was dissolved in anhydrous DCM (1 L). After the temperature of the solution was cooled to 0-10° C., 1,7-heptanediol (S10-2, 132.00 g, 999.1 mmol) and DMAP (73.12 g, 599.4 mmol) were added carefully, and then EDCI (105.48 g, 549.4 mmol) was added in batches. The reaction solution was returned to room temperature, and the reaction was continued. After reaction for 16 h, S10-1 was completely consumed according to the TLC. The reaction solution was washed twice with a mixed solution of 0.4N HCl/10% NaCl (500 mL), and then washed once with a saturated salt solution. The organic phases were combined and dried with anhydrous $MgSO_4$. The crude product was obtained after filtration and concentration, and further separated and purified by silica gel column chromatography. The eluent of interest was collected and concentrated to obtain the product S10-3 (89.20 g).

Step b: The condensation product (S10-3, 50.00 g, 159.1 mmol) was dissolved in 500 mL DCM. After the temperature of the solution was cooled to 0° C., Tempo (12.40 mg) and a solution of KBr (22.72 g, 190.9 mmol) dissolved in 50 mL purified water were added to the former solution, and then a solution of NaClO (206.8 mmol) was added slowly. Then, the reaction was continued until the materials were consumed completely according to the TLC. Then, a solution of sodium sulfite was added to quench the reaction. The reaction solution was extracted twice with 500 mL DCM after being brought back to room temperature. The organic phases were combined and dried with anhydrous $MgSO_4$. The crude product was obtained after filtration and concentration, and further separated and purified by silica gel column chromatography. The eluent of interest was collected and concentrated to obtain the oxidation product S10-4 (25.90 g).

Step c: The oxidation product (S10-4, 20.00 g, 64.0 mmol) was dissolved in a mixed solution of 200 mL THE and 20 mL methanol. After the temperature of the solution was cooled to 0° C., S10-5 (5.50 g, 30.7 mmol, obtained by the reaction between S10-5 and

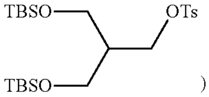

)

and glacial acetic acid (1.84 g, 30.7 mmol) were added, and then $NaBH(OAc)_3$ (19.80 g, 93.4 mmol) was added slowly in batches. After the feeding, the reaction was continued for 2 h until the materials were consumed completely according to the TLC. Then, a saturated solution of sodium bicarbonate was added to quench the reaction. The reaction solution was returned to room temperature and concentrated to remove THE and methanol. The residue was extracted twice with 200 mL DCM, and the organic phases were combined and dried with anhydrous $MgSO_4$. The crude product was obtained after filtration and concentration, and further separated and purified by silica gel column chromatography. The eluent of interest was collected and concentrated to obtain the cationic lipid E10-1 (13.30 g). The main data of $^1$H-NMR spectrum of E10-1 were as follows: $^1$H NMR (400 MHz, $CDCl_3$) δ: 4.13 (m, 4H), 3.65-3.77 (m, 6H), 3.48 (d, 4H), 3.30 (m, 1H), 3.01 (m, 4H), 2.51 (t, 2H), 2.13 (m, 2H), 1.60-1.26 (m, 52H), 0.87 (t, 12H). The molecular weight of E10-1 was determined to be 771.27 Da by MALDI-TOF.

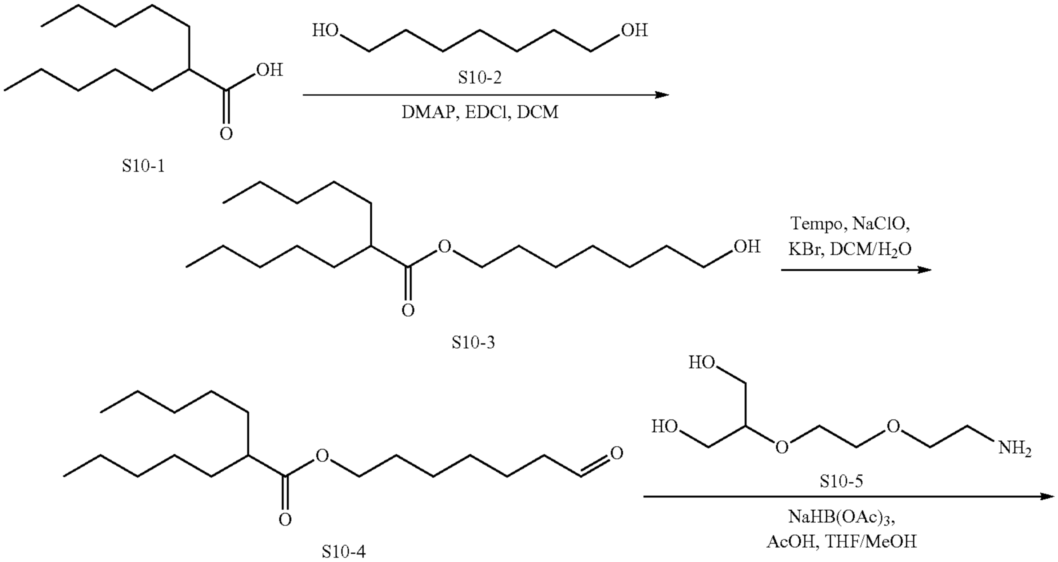

-continued

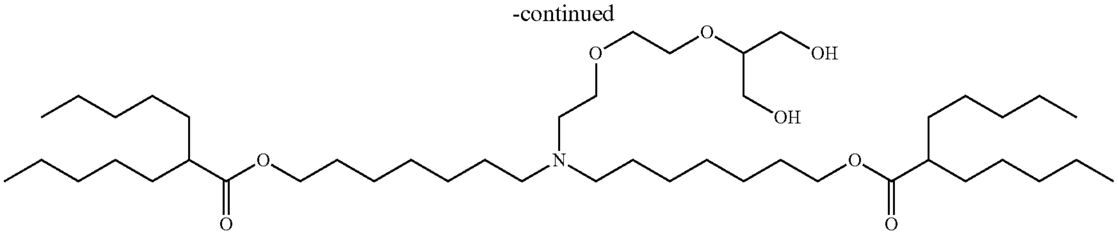

E10-1

Example-11: Cationic Lipid (E11-2)

E11-2

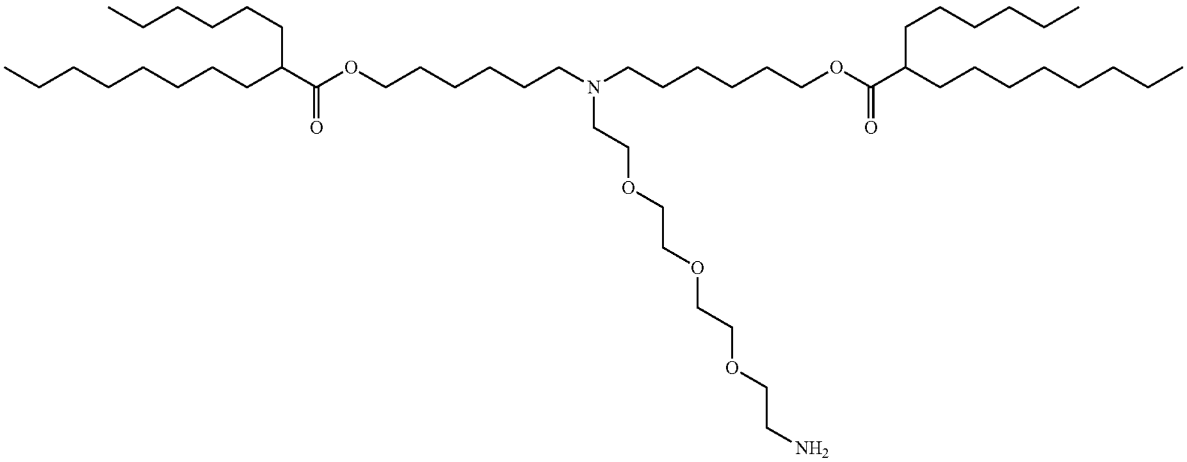

E11-2 corresponds to the general formula (1), wherein, $L_1$ and $L_2$ are both —C(═O)O— $L_3$ is —$CH_2CH_2O$—, $B_1$ and $B_2$ are both hexylene groups, $R_1$ and $R_2$ are both

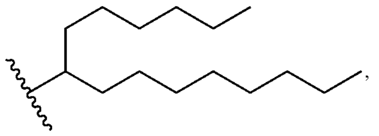

A is —$(CR_aR_b)_sO$—, $R_a$ and $R_b$ are both hydrogen atoms, s is 2, n is 2, and $R_3$ is

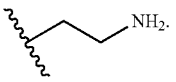

The molecular weight is approximately 869 Da.

The preparation process is as follows:

Step a: The oxidation product (S1-4, 10.00 g, 28.2 mmol) prepared according to Example-1 was dissolved in a mixed solution of 100 mL THE and 10 mL methanol. After the temperature of the solution was cooled to 0° C., S11-1 (3.11 g, 13.5 mmol) and glacial acetic acid (0.81 g, 13.5 mmol) were added, and then $NaBH(OAc)_3$ (10.00 g, 47.1 mmol) was added slowly in batches. After the feeding, the reaction was continued for 2 h until the materials were consumed completely according to the TLC. Then, a saturated solution of sodium bicarbonate was added to quench the reaction. The reaction solution was brought back to room temperature and concentrated to remove THE and methanol. The residue was extracted twice with 100 mL DCM. The organic phases were combined and dried with anhydrous $MgSO_4$. The crude product was obtained after filtration and concentration, and further separated and purified by silica gel column chromatography. The eluent of interest was collected and concentrated to obtain the cationic lipid E11-1 containing a Boc-protected amino group (6.31 g).

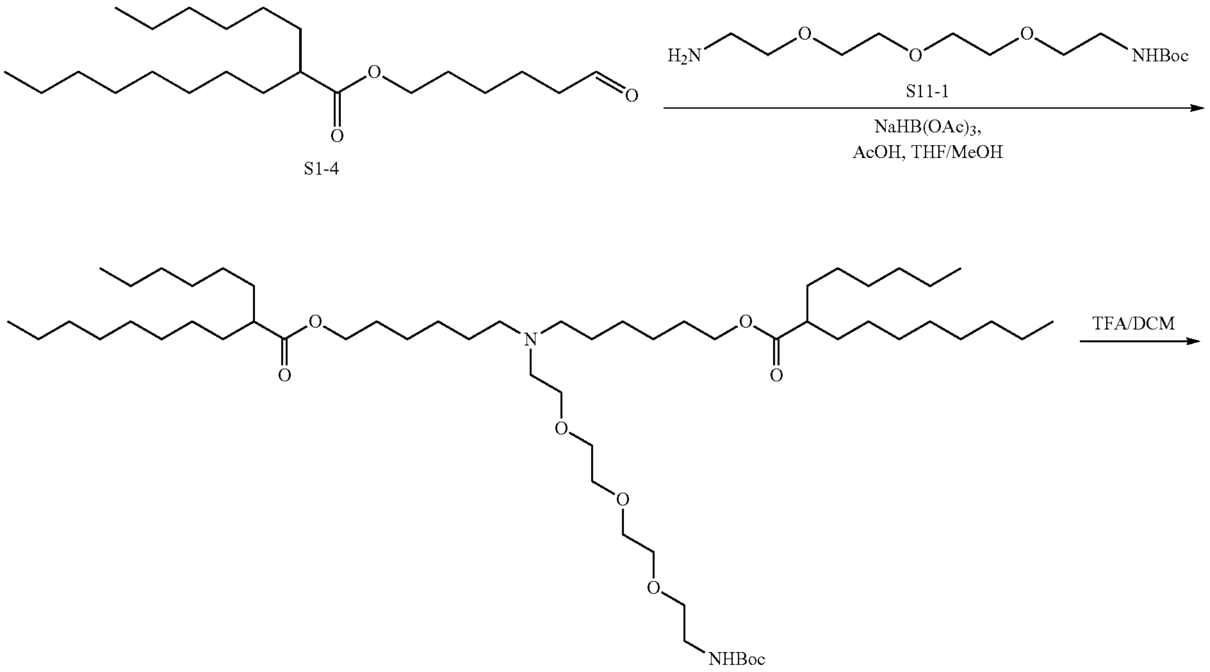

S1-4

S11-1

E11-1

E11-2

Step b: Removal of the Boc protecting group. In a dry and clean 500 mL round bottom flask, a solution of trifluoroacetic acid/dichloromethane (1:2, v/v) was prepared. The solution of E11-1 (5.00 g, 5.1 mmol) in dichloromethane was slowly added dropwise in an ice bath. The reaction was continued for 2 h at room temperature. The reaction solution was concentrated, which is followed by adding purified water, and then extracted with dichloromethane. The extract was dried with anhydrous $MgSO_4$, filtered, and concentrated. The cationic lipid containing a naked amino group (E11-2, 4.00 g, 90.3%) was obtained after recrystallization. The main data of $^1$H-NMR spectrum of E11-2 were as follows: $^1$H NMR (400 MHz, $CDCl_3$) δ: 4.05 (m, 4H), 3.71-3.57 (m, 10H), 3.49 (t, 2H), 3.01 (m, 4H), 2.85 (t, 2H), 2.51 (t, 2H), 2.13 (m, 2H), 1.60-1.25 (m, 64H), 0.88 (t, 12H). The molecular weight of E11-2 was determined to be 868.70 Da by MALDI-TOF.

Example-12: Cationic Lipid (E12-1)

E12-1

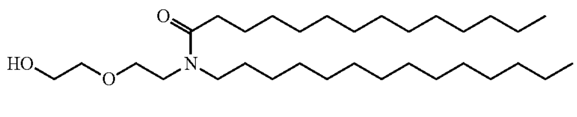

E12-1 corresponds to the general formula (1), wherein, $R_1$ is a tridecyl group, $R_2$ is a tetradecyl group, $B_1$ and $B_2$ are both linking bonds, $L_1$ is a carbonyl group (—C(═O)—), $L_2$ and $L_3$ are both linking bonds, A is —$CH_2CH_2O$—, n is 2, and $R_3$ is a hydrogen atom. The molecular weight is approximately 512 Da.

The preparation process is as follows:

Step a: Into a reaction flask under nitrogen protection, acetonitrile was added, and then S12-2 (2.66 g, 9.6 mmol), S12-1 (1.75 g, 8.0 mmol), and DIPEA (1.03 g, 8.0 mmol) were sequentially added with stirring slowly, and the reaction was stirred at room temperature for about 20 h. The reaction was completed when the material S12-1 was consumed completely according to the TLC. Then, the reaction solution was concentrated, dissolved in dichloromethane, and extracted with a mixed solution of 0.6M HCl/10% NaCl and a saturated solution of sodium bicarbonate in sequence. After ensuring that there was no product in the aqueous phase, the organic phases were combined and dried with anhydrous $MgSO_4$. The secondary amine derivative S12-3 (2.58 g) was obtained after filtration, concentration, and further purified by silica gel column chromatography.

Step b: S12-3 (2.15 g, 5.0 mmol), S12-4 (1.95 g, 6.0 mmol), and TEA (0.76 g, 7.5 mmol) were dissolved in dichloromethane (30 mL), and the reaction was stirred overnight. After completion of the reaction, the reaction solution was dissolved in 30 mL water and extracted twice with EtOAc (30 mL*2). The aqueous phase was retained and sodium chloride was added therein, which was followed by extraction twice with dichloromethane (30 mL*2). The organic phases were combined and concentrated to obtain the crude product. Under nitrogen protection, 15 mL tetrahydrofuran and 15 mL solution of TBAF in tetrahydrofuran (1M) were added to the crude product. After reacting overnight, the TBS protecting group was removed, and then the reaction solution was dried with anhydrous sodium sulfate. The crude product was obtained after filtration and concentration, and further separated and purified by silica gel column chromatography to obtain the cationic lipid E12-1 (1.64 g). The main data of $^1$H-NMR spectrum of E12-1 were as follows: $^1$H NMR (500 MHz, $CDCl_3$) δ: 3.83-3.45 (m, 6H), 3.35 (t, 2H), 3.16 (t, 2H), 2.23 (t, 2H), 1.56-1.46 (m, 4H), 1.26-1.19 (m, 42H), 0.86 (t, 6H). The molecular weight of E12-1 was determined to be 511.64 Da by MALDI-TOF.

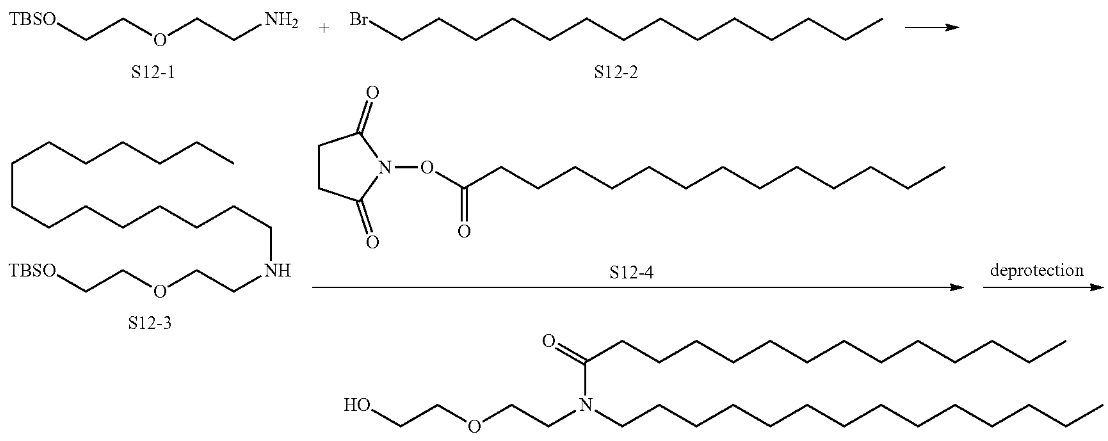

S12-1
S12-2
S12-3
S12-4
E12-1

Example-13: Cationic Lipid (E13-1)

E13-2

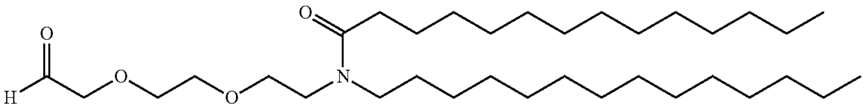

E13-2 corresponds to the general formula (1), wherein, $R_1$ is a tridecyl group, $R_2$ is a tetradecyl group, $B_1$ and $B_2$ are both linking bonds, $L_1$ is a carbonyl group, $L_2$ and $L_3$ are both linking bonds, A is $-(CR_aR_b)_sO-$, $R_a$ and $R_b$ are both hydrogen atoms, s is 2, n is 2, and $R_3$ is $-CH_2CHO$. The molecular weight is approximately 554 Da.

The preparation process is as follows:

Step a: S13-1 (6.67 g, 30.0 mmol) and toluene (120 mL) underwent azeotropic water removal at 140° C. After 40 mL of solvent was distilled off, and the reaction temperature was cooled to room temperature, TEA (6.07 g, 60.0 mmol) and MsCl (6.19 g, 54.0 mmol) were added, and the reaction was continued overnight at room temperature with stirring. After completion of the reaction, the reaction solution was poured into water (120 mL) and extracted twice with EtOAc (60 mL*2). The aqueous phase was retained and extracted twice with dichloromethane (60 mL*2). The organic phases were combined, dried, filtered, concentrated, and dissolved in isopropanol at 50° C. After recrystallization in an ice bath, and filtration, the compound S13-2 (8.11 g, 90%) was obtained.

Step b: The compound S13-2 (6.00 g, 20.0 mmol) was dissolved in 120 mL water with stirring at room temperature. Potassium carbonate (27.60 g, 200.0 mmol), compound S12-3 (21.3 g, 100.0 mmol), and tetrabutylammonium bromide (27.60 g, 200.0 mmol) were added, and the reaction was stirred at room temperature for 72 h. Upon completion of the reaction, the reaction solution was extracted twice with dichloromethane (120 mL*2). The organic phases were combined and backwashed with a saturated aqueous solution of sodium chloride (120 mL). The organic phase was retained, dried with anhydrous sodium sulfate, and filtered. The filtrate was concentrated to obtain the crude product which was further purified by silica gel column chromatography, concentrated, and dried with an oil pump to obtain the target compound S13-3 (5.60 g).

Step c: The compound S13-3 (5.01 g, 12.0 mmol), S12-4 (4.68 g, 14.4 mmol), and TEA (1.82 g, 18.0 mmol) were dissolved in dichloromethane (50 mL), and the reaction was stirred at room temperature overnight. The reaction solution was concentrated and dissolved in 50 mL water, and further extracted twice with dichloromethane (50 mL*2). The organic phases were combined, backwashed with a saturated aqueous solution of sodium chloride (50 mL), and dried with anhydrous $MgSO_4$. The crude product E13-1 was obtained after filtration and concentration, followed by deprotection of the acetal group. After purification by silica gel column chromatography, the cationic lipid E13-2 (5.26 g) was obtained. The main data of $^1H$-NMR spectrum of E13-2 were as follows: $^1H$ NMR (500 MHz, $CDCl_3$) δ: 9.87 (s, 1H), 4.17 (s, 2H), 3.83-3.45 (m, 6H), 3.35 (t, 2H), 3.16 (t, 2H), 2.23 (t, 2H), 1.56-1.46 (m, 4H), 1.26-1.19 (m, 42H), 0.86 (t, 6H). The molecular weight of E13-1 was determined to be 553.54 Da by MALDI-TOF.

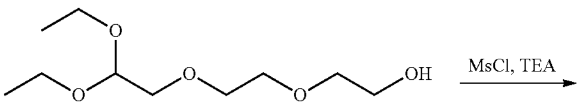

S13-1

-continued

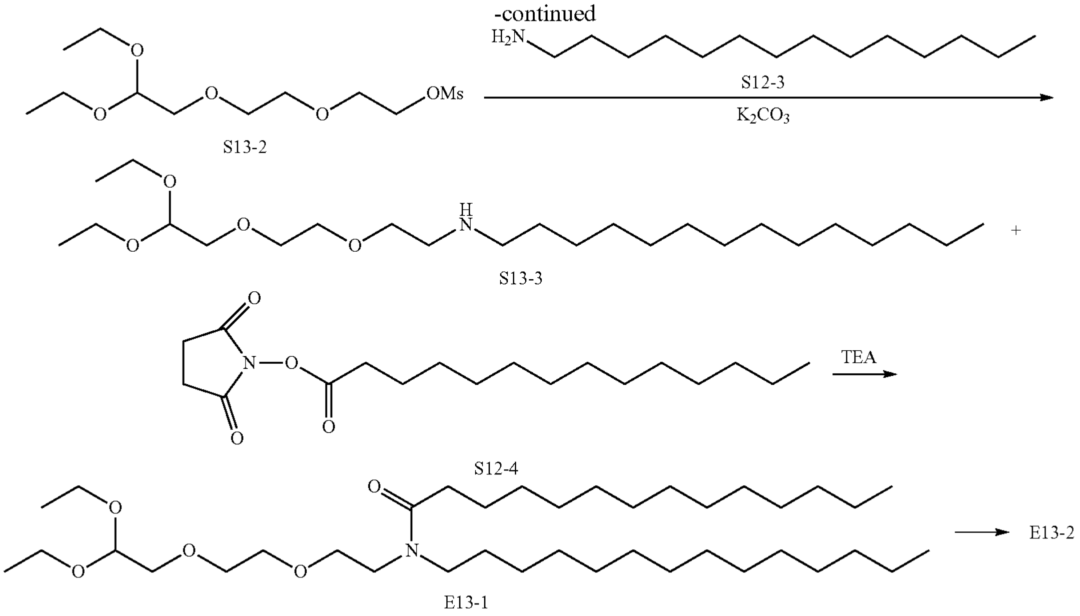

Example-14: Cationic Lipid (E14-1)

E14-1

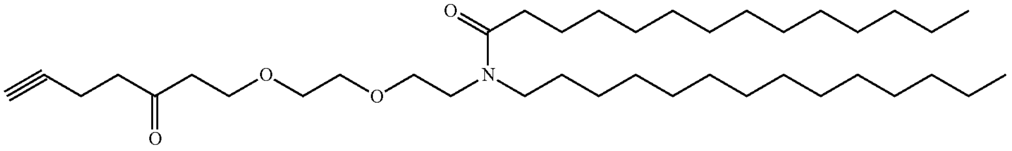

E14-1 corresponds to the general formula (1), wherein, $R_1$ is a tridecyl group, $R_2$ is a tetradecyl group, $B_1$ and $B_2$ are both linking bonds, $L_1$ is a carbonyl group, $L_2$ and $L_3$ are both linking bonds, A is —$(CR_aR_b)_sO$—, wherein $R_a$ and $R_b$ are both hydrogen atoms, s is 2, n is 2, and $R_3$ is

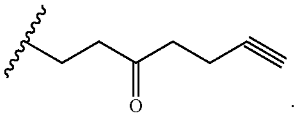

The molecular weight is approximately 620 Da.

The preparation process is as follows:

Step a: S14-1 (10.70 g, 50.0 mmol) and toluene (200 ml) underwent azeotropic water removal at 140° C. After 60 mL of solvent was distilled off, the reaction temperature was cooled to room temperature. TEA (10.12 g, 100.0 mmol) and MsCl (10.31 g, 90.0 mmol) were added, and the reaction was stirred at room temperature overnight. After completion of the reaction, the reaction solution was poured into water (200 mL) and extracted twice with EtOAc (100 mL*2). The aqueous phase was retained and extracted twice with dichloromethane (100 mL*2). The organic phases were combined, dried, filtered, concentrated, and dissolved in isopropanol at 50° C. After recrystallization in an ice bath, and filtration, the compound S14-2 (12.96 g, 88.8%) was obtained.

Step b: S14-2 (9.34 g, 32.0 mmol) was dissolved with 100 mL water with stirring at room temperature. Potassium carbonate (44.16 g, 320.0 mmol), S12-3 (34.08 g, 160.0 mmol), and tetrabutylammonium bromide (1.03 g, 3.2 mmol) were added. The reaction was stirred at room temperature for 72 h. Upon completion of the reaction, the reaction solution was extracted twice with dichloromethane (100 mL*2), and the organic phases were combined and backwashed with a saturated aqueous solution of sodium chloride (100 mL). The organic phase was retained, dried with anhydrous sodium sulfate, and filtered. The filtrate was concentrated to obtain the crude product which was further purified by silica gel column chromatography, concentrated, and dried with an oil pump to obtain the target compound S14-3 (8.39 g, 64.1%).

Step c: S14-3 (7.65 g, 18.7 mmol), S12-4 (7.29 g, 22.4 mmol), and TEA (2.84 g, 28.1 mmol) were dissolved in dichloromethane (100 mL), and the reaction was stirred at room temperature overnight. The reaction solution was concentrated and dissolved with 100 mL water, and further extracted twice with EtOAc (100 mL*2). The aqueous phase was retained and some sodium chloride was added, followed by extraction twice with dichloromethane (100 mL*2). The organic phases were combined and backwashed with a saturated aqueous solution of sodium chloride (100 mL). The organic phases were combined and dried with anhydrous $MgSO_4$. The crude product was obtained after filtration and concentration, and then purified by silica gel column chromatography, concentrated, and dried with an oil pump. The cationic lipid E14-1 (9.56 g, 82.6%) was thereby obtained. The main $^1H$-NMR spectrum data of E14-1 were as follows: $^1H$ NMR (500 MHz, $CDCl_3$) δ: 3.83-3.45 (m, 8H), 3.35 (t, 2H), 3.16 (t, 2H), 2.62-2.42 (m, 4H), 2.34 (t, 2H), 2.23 (t, 2H), 2.00 (s, 1H), 1.56-1.46 (m, 4H), 1.26-1.19 (m, 42H), 0.87 (t, 6H). The molecular weight of E14-1 was determined to be 619.15 Da by MALDI-TOF.

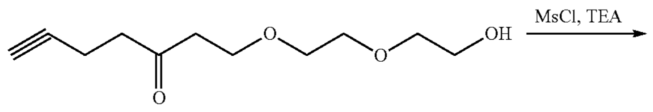

S14-1

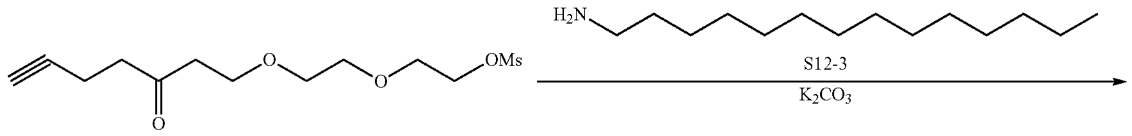

S14-2

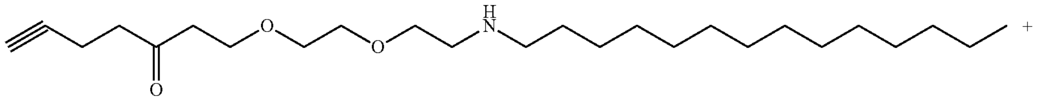

S14-3

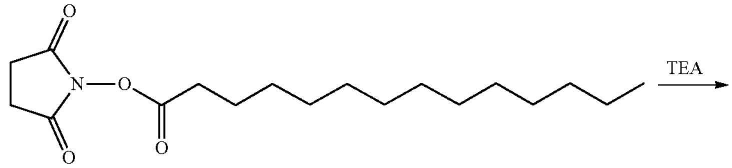

S12-4

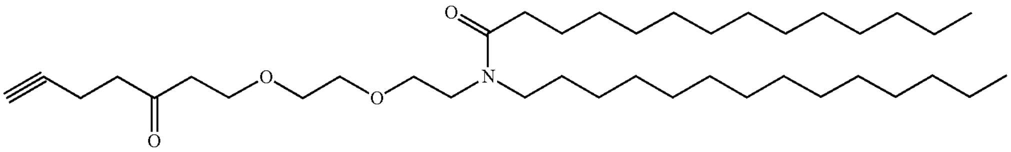

E14-1

Example-15: Cationic Lipid (E15-2)

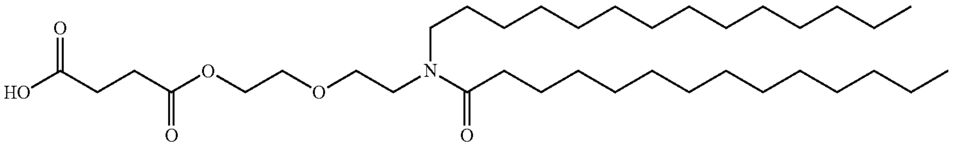

E15-2

E15-2 corresponds to the general formula (1), wherein, $R_1$ is a tetradecyl group, $R_2$ is a tridecyl group, $B_1$, $B_2$ are both linking bonds, $L_1$ is a linking bond, $L_2$ is a carbonyl group, $L_3$ is a linking bond, A is $-(CR_aR_b)_sO-$, wherein $R_a$ and $R_b$ are both hydrogen atoms, s is 2, n is 2, and $R_3$ is $-C(=O)CH_2CH_2COOH$. The molecular weight is approximately 612 Da.

The preparation process is as follows:

Step a: Compound S15-1 (13.11 g, 50.0 mmol) and toluene (250 ml) underwent azeotropic water removal at 140° C. After 80 mL of solvent was distilled off, the reaction temperature was cooled to room temperature. TEA (10.12 g, 100.0 mmol) and MsCl (10.31 g, 90.0 mmol) were added, and the reaction was stirred at room temperature overnight. After completion of the reaction, the reaction solution was poured into water (200 mL) and extracted twice with EtOAc (100 mL*2). The aqueous phase was retained and extracted twice with dichloromethane (150 mL*2). The organic phases were combined, dried, filtered, concentrated, and dissolved with isopropanol at 50° C. After recrystallization in an ice bath and filtration, the compound S15-2 (14.96 g, 87.9%) was obtained.

Step b: S15-2 (8.85 g, 26.0 mmol) was dissolved with 100 mL water with stirring at room temperature. Potassium carbonate (35.88 g, 260.0 mmol), compound S12-3 (27.69 g, 130.0 mmol) and tetrabutylammonium bromide (0.84 g, 2.6 mmol) were added, and the reaction was stirred at room temperature for 72 h. After completion of the reaction, the reaction solution was extracted twice with dichloromethane (200 mL*2). The organic phases were combined and back-washed with a saturated aqueous solution of sodium chloride (200 mL). The organic phase was retained, dried with anhydrous sodium sulfate, and filtered. The filtrate was concentrated to obtain crude product which was further purified by silica gel column chromatography, concentrated, and dried with an oil pump to obtain the target compound S15-3 (7.89 g).

Step c: S15-3 (7.32 g, 16.0 mmol), S13-4 (6.24 g, 19.2 mmol), and TEA (2.43 g, 24.0 mmol) were dissolved in dichloromethane (100 mL), and the reaction was stirred at room temperature overnight. The reaction solution was concentrated, dissolved with 100 mL water, and extracted twice with EtOAc (100 mL*2). The aqueous phase was retained and sodium chloride was added therein, followed by extraction twice with dichloromethane (100 mL*2). The organic phases were combined and backwashed with an aqueous saturated solution of sodium chloride (100 mL). The organic phases were combined and dried with anhydrous $MgSO_4$. The crude product was obtained after filtration and concentration, and further purified by silica gel column chromatography, concentrated, and dried with an oil pump to obtain the cationic lipid E15-1 (8.94 g, 83.6%).

Step d: Removal of tBu protecting group. In a dry and clean 500 mL round bottom flask, a solution of trifluoroacetic acid/dichloromethane (1:2, v/v) was prepared. A solution of E15-1 (8.95 g, 13.4 mmol) in dichloromethane was slowly added dropwise to the former solution in an ice bath, and the reaction was continued for 2 h at room temperature. Upon completion of the reaction, the reaction solution was concentrated, followed by addition of purified water and extraction with dichloromethane. The extract was dried with anhydrous $MgSO_4$, filtered, and then concentrated. The cationic lipid E15-2 (7.38 g, 92.1%) was obtained after recrystallization. The main $^1$H-NMR spectrum data of E15-2 were as follows: $^1$H NMR (500 MHz, $CDCl_3$) δ: 4.17 (t, 2H), 3.71-3.60 (m, 4H), 3.35 (t, 2H), 3.16 (t, 2H), 2.70-2.47 (m, 4H), 2.23 (t, 2H), 1.56-1.46 (m, 4H), 1.26-1.19 (m, 42H), 0.87 (t, 6H). The molecular weight of E15-2 was determined to be 611.51 Da by MALDI-TOF.

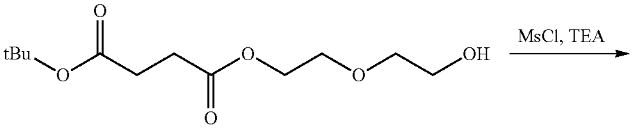

S15-1

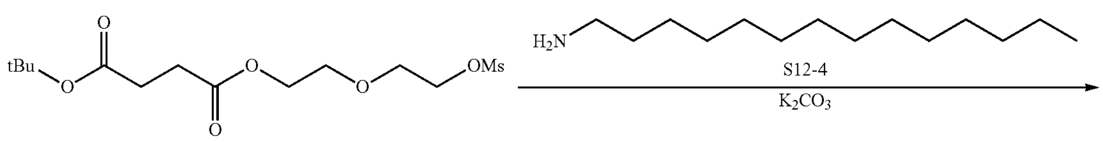

S15-2

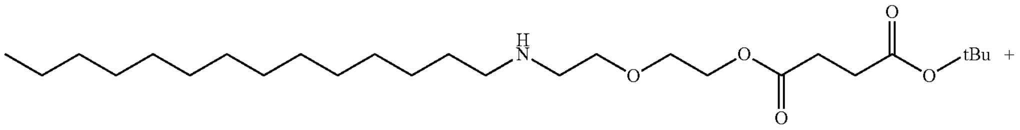

S15-3

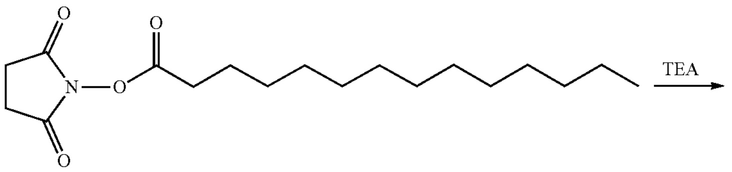

S13-4

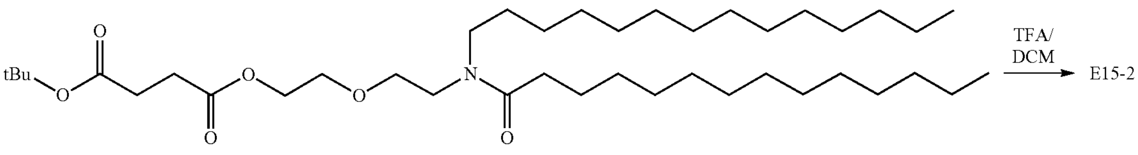

E15-1

Example-16: Cationic Lipid (E16-2, E16-4)

Example-16.1: Cationic Lipid (E16-2)

E16-2

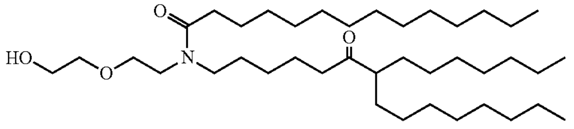

E16-2 corresponds to the general formula (1), wherein, $R_1$ is a tridecyl group, $R_2$ is

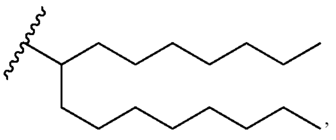

$B_1$ is a linking bond, $B_2$ is a hexylene group, $L_1$ is a carbonyl group, $L_2$ is —C(═O)O—, $L_3$ is a linking bond, A is —$(CR_aR_b)_sO$—, wherein $R_a$ and $R_b$ are both hydrogen atoms, s is 2, n is 2, and $R_3$ is a hydrogen atom. The molecular weight is approximately 668 Da.

The preparation process is as follows:

Step a: In a flask under nitrogen protection, 2-heptyldecanoic acid (S16-1, 10.00 g, 37.0 mmol) was dissolved in anhydrous DCM (100 mL). After the temperature of the solution was cooled to 0-10° C., 1,6-hexanediol (S1-2, 8.73 g, 74.0 mmol) and DMAP (78.14 g, 407.0 mmol) were added carefully, and then EDCI (78.14 g, 407.0 mmol) was added in batches. The reaction solution was brought back to room temperature and the reaction was continued. After 16 h of reaction, S16-1 was completely consumed according to the TLC. The reaction solution was washed twice with 500 mL 0.4N HCl/10% NaCl mixed solution, and then washed once with a saturated salt solution. The organic phases were combined and dried with anhydrous $MgSO_4$. The crude product was obtained after filtration and concentration, and further separated and purified by silica gel column chromatography. The eluent of interest was collected and concentrated to obtain the product S16-2 (8.10 g).

Step b: The condensation product (S16-2, 8.00 g, 21.6 mmol) was dissolved in 80 mL DCM. After the temperature of the solution was cooled to 0° C., Tempo (1.20 mg) and a solution of KBr solution (3.08 g, 25.9 mmol) dissolved in 50 mL purified water were added, and then a solution of NaClO (17.5 mmol) was added slowly. Then, the reaction was continued until the materials were consumed completely according to the TLC. Then, a solution of sodium sulfite was added to quench the reaction. The reaction solution was extracted twice with 50 mL DCM after being brought back to room temperature. The organic phases were combined and dried with anhydrous $MgSO_4$. The crude product was obtained after filtration and concentration, and further separated and purified by silica gel column chromatography. The eluent of interest was collected and concentrated to obtain the oxidation product S16-3 (3.98 g).

Step c: The oxidation product S16-3 (3.98 g, 10.8 mmol) was dissolved in a mixed solution of 50 mL THE and 5 mL methanol. After the temperature of the solution was cooled to 0° C., the amine derivative S12-1 (2.58 g, 9.8 mmol) and glacial acetic acid (0.58 g, 9.8 mmol) were added, and then $NaBH(OAc)_3$ (6.23 g, 29.4 mmol) was added slowly in batches. After the feeding, the reaction was continued for 2 h until the materials were consumed completely according to the TLC. After completion of the reaction, a saturated solution of sodium bicarbonate was added to quench the reaction. The reaction solution was brought back to room temperature, and concentrated to remove THE and methanol. The residue was extracted twice with 200 mL DCM, and the organic phases were combined and dried with anhydrous $MgSO_4$. The crude product was obtained after filtration and concentration, and further separated and purified by silica gel column chromatography. The eluent of interest was collected and concentrated to obtain the product S16-4 (3.45 g).

Step d: S16-4 (3.45 g, 5.6 mmol), S16-5 (1.66 g, 6.7 mmol), and TEA (0.85 g, 8.4 mmol) were dissolved in dichloromethane (100 mL), and the reaction was stirred at room temperature overnight. The reaction solution was concentrated, dissolved with 100 mL water, and extracted twice with EtOAc (100 mL*2). The aqueous phase was retained and some sodium chloride was added, followed by extraction twice with dichloromethane (100 mL*2). The organic phases were combined, backwashed with a solution of NaCl (100 mL), and dried with anhydrous $MgSO_4$. The crude product was obtained after filtration and concentration, and further purified by silica gel column chromatography, concentrated, and dried with an oil pump to obtain the cationic lipid E16-1 containing a TBS-protected hydroxyl group (3.91 g, 84.5%).

Step e: In a flask under nitrogen protection, E16-1 (3.91 g, 4.7 mmol) was dissolved in 50 mL THF, followed by adding a solution of tetrabutylammonium fluoride (TBAF, 50 mL, 1N in THF). The reaction was continued overnight to remove the TBS protecting group. Then, the reaction solution was extracted, concentrated, and dried with anhydrous $MgSO_4$. The cationic lipid E16-2 (2.92 g, 87.5%) was obtained after filtration, concentration, and recrystallization. The main $^1$H-NMR spectrum data of E16-2 were as follows: $^1$H NMR (500 MHz, $CDCl_3$) δ: 4.08 (t, 2H), 3.75-3.43 (m, 6H), 3.35 (t, 2H), 3.15 (t, 2H), 2.26-2.25 (m, 3H), 1.60-1.46 (m, 10H), 1.32-1.25 (m, 46H), 0.88 (t, 9H). The molecular weight of E16-2 was determined to be 667.64 Da by MALDI-TOF.

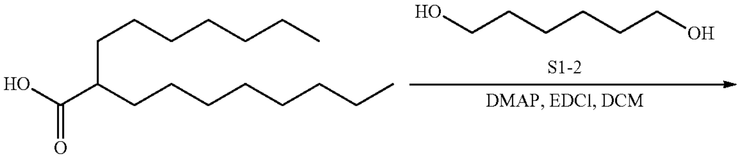

S16-1

-continued

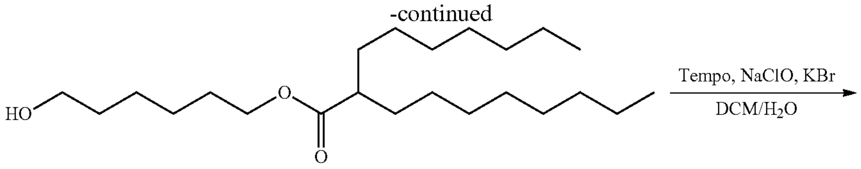

S16-2

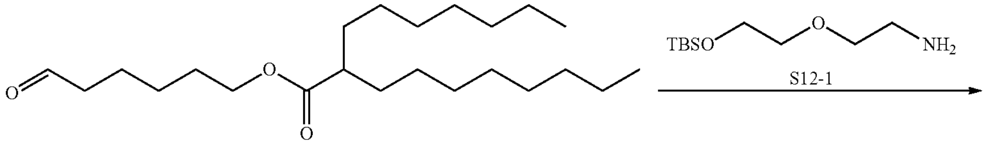

S16-3

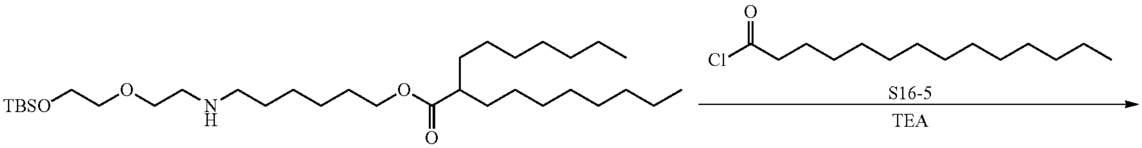

S16-4

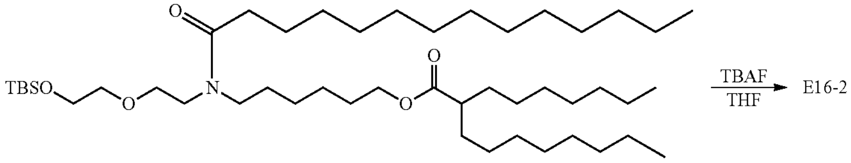

S16-1

Example-16.2: Cationic Lipid (E16-4)

E16-4

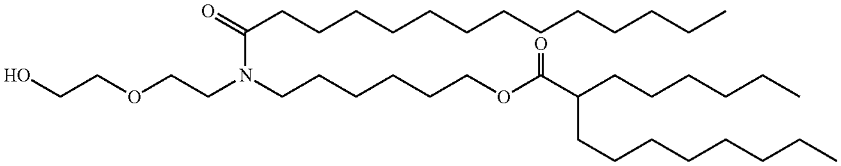

E16-4 corresponds to the general formula (1), wherein, $R_1$ is a tridecyl group, $R_2$ is

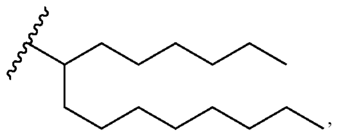

$B_1$ is a linking bond, $B_2$ is a hexylene group, $L_1$ is a carbonyl group, $L_2$ is —C(═O)O—, $L_3$ is a linking bond, A is —$(CR_aR_b)_sO$—, wherein $R_a$ and $R_b$ are both hydrogen atoms, s is 2, n is 2, and $R_3$ is a hydrogen atom. The molecular weight is approximately 654 Da.

The material S16-3 used in Example-16.1 was replaced with S1-4

( 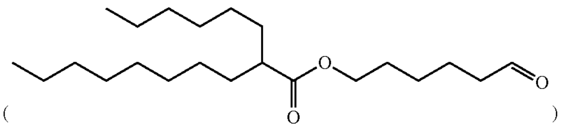 [SMILES: CCCCCCCCC(CCCCCC)C(=O)OCCCCCC=O] )

and the same preparation process of E16-2 was performed to obtain the cationic lipid E16-4. The main $^1H$-NMR spectrum data of E16-4 were as follows: H NMR (500 MHz, $CDCl_3$) δ: 4.08 (t, 2H), 3.75-3.43 (m, 6H), 3.35 (t, 2H), 3.15 (t, 2H), 2.26-2.25 (m, 3H), 1.60-1.46 (m, 10H), 1.32-1.25 (m, 44H), 0.88 (t, 9H). The molecular weight of E16-4 was determined to be 653.72 Da by MALDI-TOF.

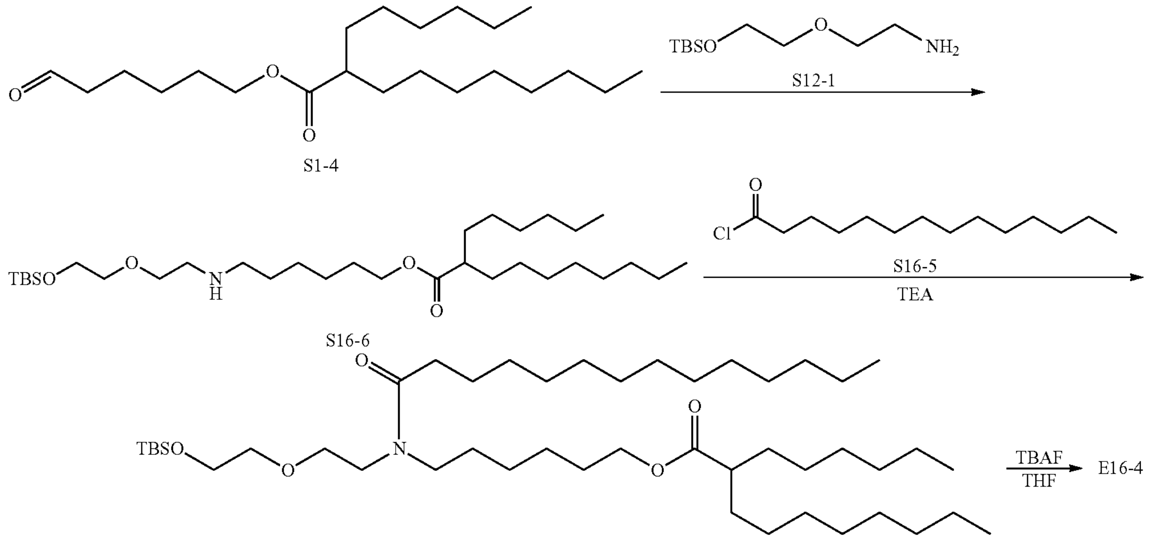

S16-3

Example-17: Cationic Lipid (E17-2, E17-4)

Example-17.1: Cationic Lipid (E17-2)

E17-2

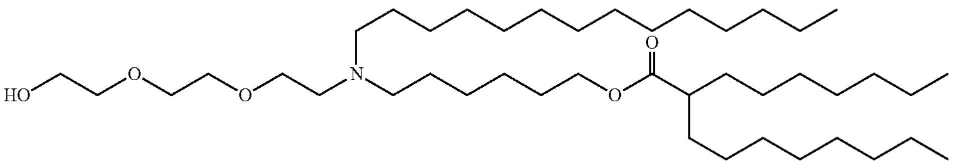

E17-2 corresponds to the general formula (1), wherein, $R_1$ is a tetradecyl group, $R_2$ is

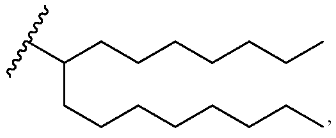

$B_1$ is a linking bond, $B_2$ is a hexylene group, $L_1$ is a linking bond, $L_2$ is —C(═O)O—, $L_3$ is $—CH_2CH_2—$, A is $—O(CR_aR_b)_s—$, wherein $R_a$ and $R_b$ are both hydrogen atoms, s is 2, n is 2, and $R_3$ is a hydroxyl group. The molecular weight is approximately 698 Da.

The preparation process is as follows:

Step a: S16-5 (3.45 g, 5.6 mmol) was dissolved in anhydrous THE (120 mL). NaH (60%, 2.24 g, 56.0 mmol) was added slowly to the solution in an ice bath, and the reaction was carried out for 1 h in an ice bath. Then, compound S12-5 (1.85 g, 6.7 mmol) was added to continue the reaction with stirring in an ice bath for another 1 h. Then, the reaction was brought back to room temperature and continued overnight. After completion of the reaction, the reaction solution was placed in an ice bath, and methanol was added slowly to quench the reaction. After stirring for 30 minutes, water (300 mL) was added and mixed with the solution. The mixture was extracted twice with EtOAc (150 mL*2), and the aqueous phase was retained and extracted twice with dichloromethane (100 mL*2). The organic phases were combined, backwashed with a saturated aqueous solution of sodium chloride (100 mL), dried with anhydrous sodium sulfate, filtered, and concentrated to obtain the crude product which was further purified by silica gel column chromatography, concentrated, and dried with an oil pump to obtain the target compound E17-1 (3.44 g, 75.8%).

Step b: In a flask under nitrogen protection, E17-1 (3.44 g, 4.2 mmol) was dissolved in 50 mL THF, followed by adding a solution of tetrabutylammonium fluoride (TBAF, 50 mL, 1N in THF). The reaction was carried out overnight to remove the TBS protecting group. After completion of the reaction, the reaction solution was extracted, concentrated, and dried with anhydrous $MgSO_4$. The cationic lipid E17-2 (2.57 g, 87.0%) was obtained after filtration, concentration, and recrystallization. The main $^1$H-NMR spectrum data of E17-2 were as follows: $^1$H NMR (500 MHz, $CDCl_3$) δ: 4.09 (t, 2H), 3.73-3.48 (m, 10H), 2.51 (t, 4H), 2.26-2.25 (m, 3H), 1.56-1.46 (m, 10H), 1.32-1.25 (m, 48H), 0.87 (t, 9H). The molecular weight of E17-2 was determined to be 697.51 Da by MALDI-TOF.

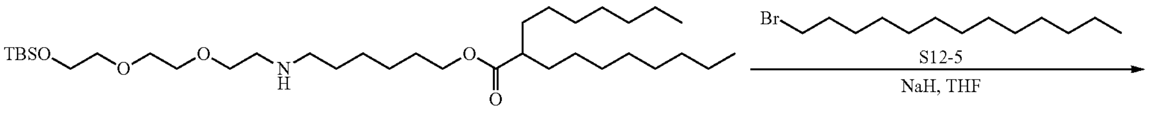

S16-5

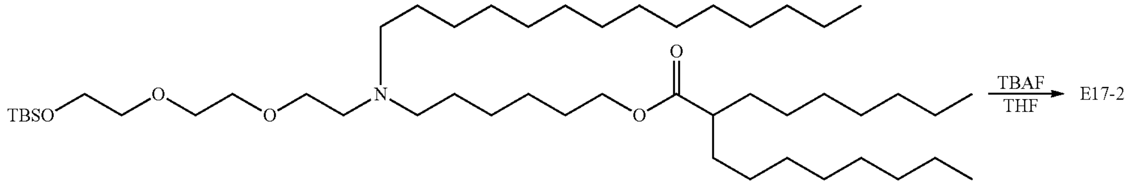

E17-1

Example-17.2: Cationic Lipid (E17-4)

E17-4

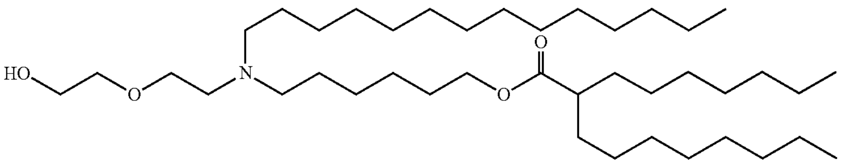

E17-4 corresponds to the general formula (1), wherein, $R_1$ is a tetradecyl group, $R_2$ is

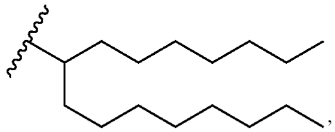

$B_1$ is a linking bond, $B_2$ is a hexylene group, $L_1$ is a linking bond, $L_2$ is —C(═O)O—, $L_3$ is a linking bond, A is —$(CR_aR_b)_sO$—, wherein $R_a$ and $R_b$ are both hydrogen atoms, s is 2, n is 2, and $R_3$ is a hydrogen atom. The molecular weight is approximately 654 Da.

The material S16-5 used in Example-17.1 was replaced with S16-6 (Example-16.2) and the same preparation process of E17-2 was performed to obtain the cationic lipid E17-4.

Example-18: Cationic Lipid (E18-1)

E18-1

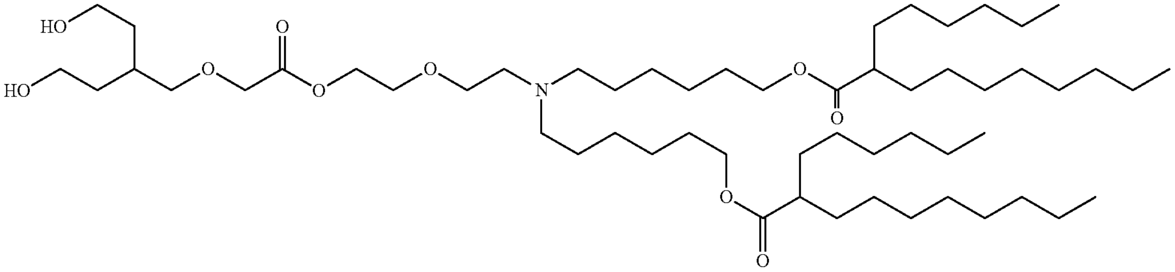

E18-1 corresponds to the general formula (1), wherein, $L_1$ and $L_2$ are both —C(═O)O—, $L_3$ is a linking bond, $B_1$ and $B_2$ are both hexylene groups, $R_1$ and $R_2$ are both

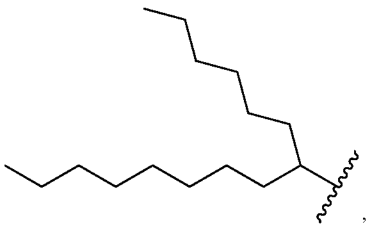

A is —$(CR_aR_b)_sO$—, wherein $R_a$ and $R_b$ are both hydrogen atoms, s is 2, n is 2, and $R_3$ is

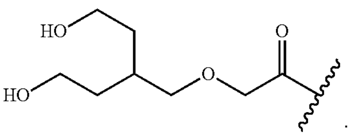 [SMILES: *C(=O)COCC(CCO)CCO]

The molecular weight is approximately 956 Da.

The preparation process is as follows:

Step a: The oxidation product S1-4 (8.85 g, 25.0 mmol) prepared according to Example-1 was dissolved in a mixed solution of 100 mL THF and 10 mL methanol. After the temperature of the solution was cooled to 0° C., S18-1 (3.35 g, 12.0 mmol) and glacial acetic acid (0.72 g, 12.0 mmol) were added therein, and then $NaBH(Oac)_3$ (8.90 g, 42.0 mmol) was added slowly in batches. After the feeding, the reaction was continued for 2 h until the materials were consumed completely according to the TLC. After completion of the reaction, a saturated solution of sodium bicarbonate was added to quench the reaction, the reaction solution was brought back to room temperature and concentrated to remove THF and methanol. The residue was extracted twice with DCM (100 mL*2), and the organic phases were combined and dried with anhydrous $MgSO_4$. The crude product was obtained after filtration and concentration, and further separated and purified by silica gel column chromatography. The eluent of interest was collected and concentrated to obtain the cationic lipid E18-1 (6.02 g). The main data of $^1$H-NMR spectrum of E18-1 were as follows: $^1$H NMR (500 MHz, $CDCl_3$) δ: 4.26 (s, 2H), 4.21 (t, 2H), 4.07 (t, 4H), 3.67 (t, 2H), 3.52 (t, 2H), 3.48 (t, 4H), 3.30 (d, 2H), 2.63 (t, 2H), 2.53 (t, 4H), 2.24 (m, 2H), 1.66-1.50 (m, 13H), 1.43-1.17 (m, 56H), 0.87 (t, 12H). The molecular weight of E18-1 was determined to be 955.61 Da by MALDI-TOF.

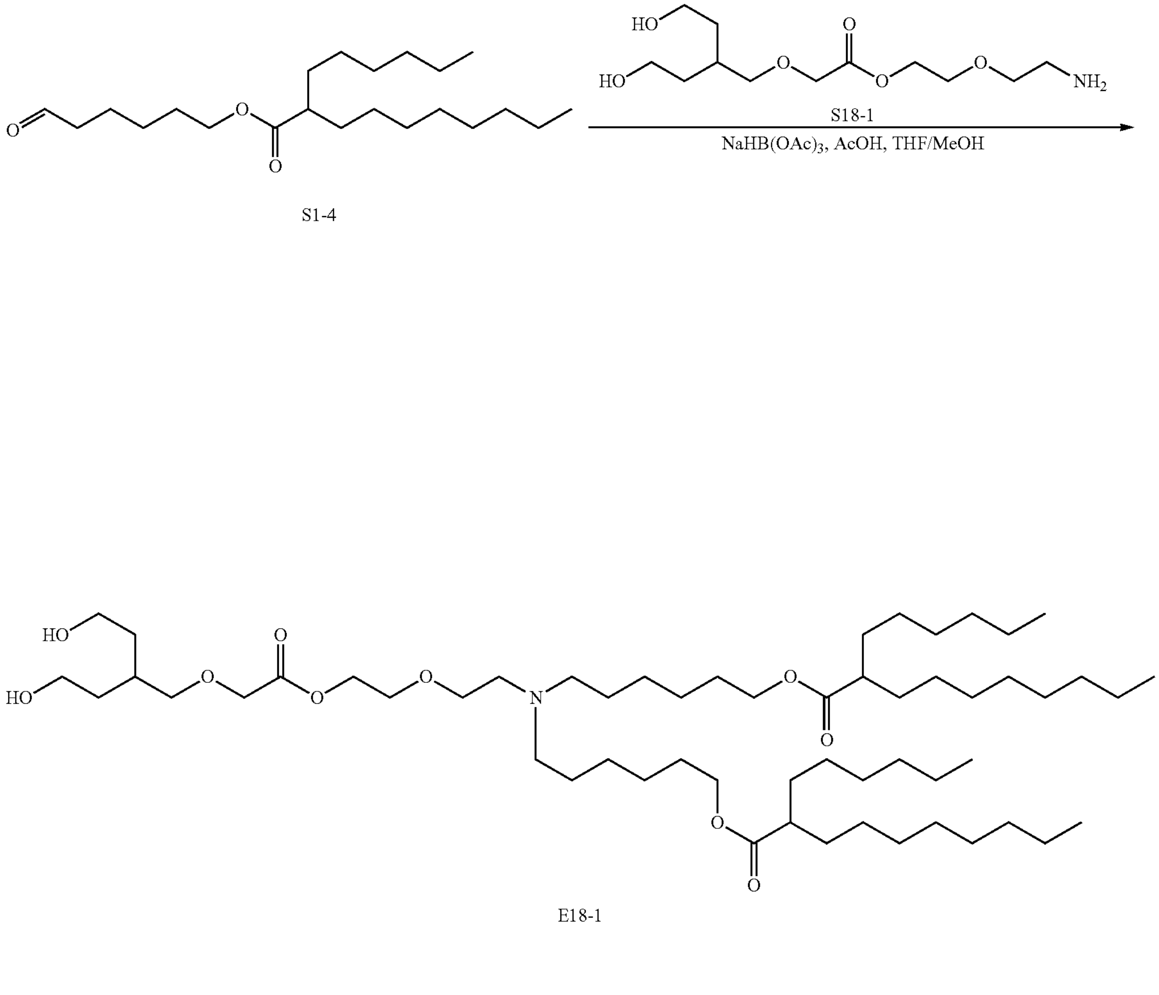

S1-4

E18-1

Example-19: Cationic Lipid (E19-2)

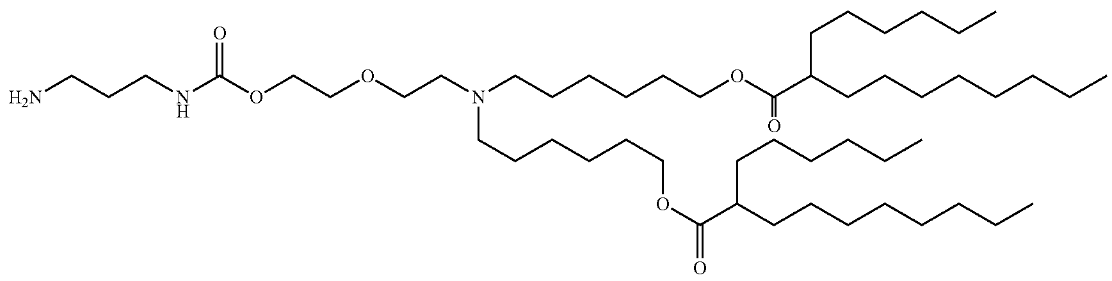

E19-2

E19-1 corresponds to the general formula (1), wherein, $L_1$ and $L_2$ are both —C(═O)O—, $L_3$ is a linking bond, $B_1$ and $B_2$ are both hexylene groups, $R_1$ and $R_2$ are both

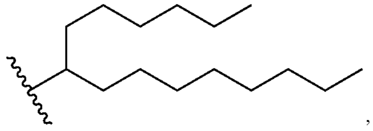

,

A is —$(CR_aR_b)_sO$— wherein $R_a$ and $R_b$ are both hydrogen atoms, s is 2, n is 2, and $R_3$ is

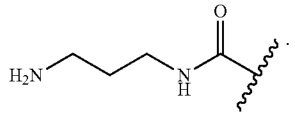 [SMILES: *C(=O)NCCCN]

.

The molecular weight is approximately 882 Da.

The preparation process is as follows:

Step a: The oxidation product (S1-4, 8.85 g, 25.0 mmol) prepared according to Example-1 was dissolved in a mixed solution of 100 mL THF and 10 mL methanol. After the temperature of the solution was cooled to 0° C., S19-1 (2.46 g, 12.0 mmol) and glacial acetic acid (0.72 g, 12.0 mmol) were added, and then $NaBH(Oac)_3$ (8.90 g, 42.0 mmol) was added slowly in batches. After the feeding, the reaction was continued for 2 h until the materials were consumed completely according to the TLC. After completion of the reaction, a saturated solution of sodium bicarbonate was added to quench the reaction. The reaction solution was brought back to room temperature, and then concentrated to remove THE and methanol. The residue was extracted twice with DCM (100 mL*2), and the organic phases were combined and dried with anhydrous $MgSO_4$. The crude product was obtained after filtration and concentration, and further separated and purified by silica gel column chromatography. The eluent of interest was collected and concentrated to obtain the cationic lipid E19-1 (5.48 g).

Step b: removal of Boc protecting group. In a dry and clean 500 mL round bottom flask, a solution of trifluoroacetic acid/dichloromethane (1:2, v/v) was prepared, and a solution of E19-1 (5.00 g, 5.1 mmol) in dichloromethane was slowly added dropwise in an ice bath. The reaction was carried our for 2 h at room temperature, after which the reaction solution was concentrated, added with some purified water, and extracted with dichloromethane. The organic phase was dried with anhydrous $MgSO_4$, filtered, and concentrated. The cationic lipid E19-2 (4.13 g, 91.8%) was obtained after recrystallization. The main data of $^1$H-NMR spectrum of E19-2 were as follows: $^1$H NMR (500 MHz, $CDCl_3$) δ: 4.21 (t, 2H), 4.07 (t, 4H), 3.64 (t, 2H), 3.52 (t, 2H), 3.20 (t, 2H), 3.06 (t, 2H), 2.63 (t, 2H), 2.52 (t, 4H), 2.24 (m, 2H), 1.87 (m, 2H), 1.66-1.50 (m, 12H), 1.45-1.17 (m, 52H), 0.88 (t, 12H). The molecular weight of E19-2 was determined to be 881.78 Da by MALDI-TOF.

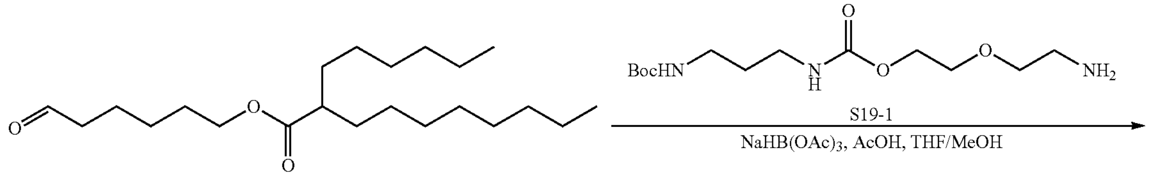

S1-4

-continued

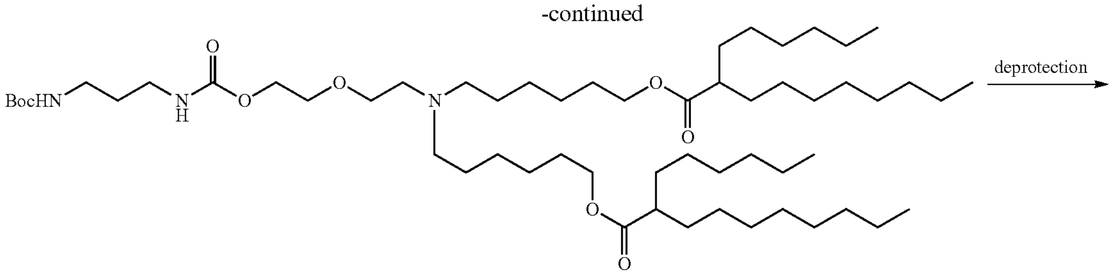

E19-2

E19-1

Example-20: Cationic Lipid (E20-1

E20-1

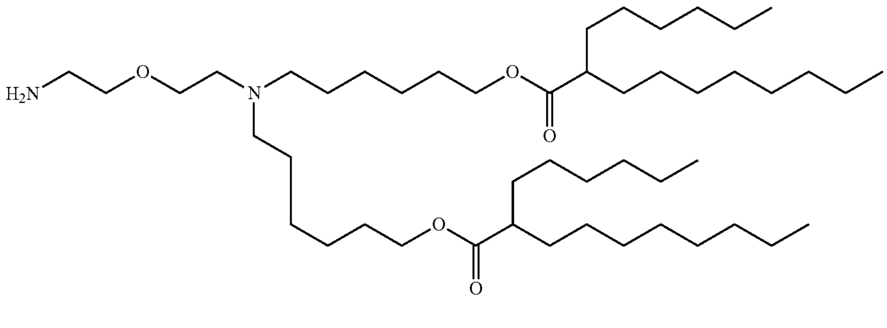

E20-1 corresponds to the general formula (1), wherein, $L_1$ and $L_2$ are both —C(═O)O—, $L_3$ is a linking bond, $B_1$ and $B_2$ are both hexylene groups, $R_1$ and $R_2$ are both

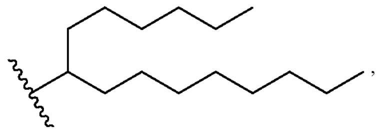

A is —$(CR_aR_b)_sO(CR_aR_b)_sNR_c$—, wherein $R_a$, $R_b$, and $R_c$ are all hydrogen atoms, s is 2, n is 1, and $R_3$ is a hydrogen atom. The molecular weight is approximately 781.21 Da.

The preparation process is as follows:

Step a: The oxidation product (S1-4, 8.85 g, 25.0 mmol) prepared according to Example-1 was dissolved in a mixed solution of 100 mL THF and 10 mL methanol. After the temperature of the solution was cooled to 0° C., S20-1 (2.45 g, 12.0 mmol) and glacial acetic acid (0.72 g, 12.0 mmol) were added, and then $NaBH(OAc)_3$ (8.90 g, 42.0 mmol) was added slowly in batches. After the feeding, the reaction was continued for 2 h until the materials were consumed completely according to the TLC. After completion of the reaction, a saturated solution of sodium bicarbonate was added to quench the reaction. The reaction solution was brought back to room temperature, and then concentrated to remove THE and methanol. The residue was extracted twice with DCM (100 mL*2), and the organic phases were combined and dried with anhydrous $MgSO_4$. The crude product was obtained after filtration and concentration, and further separated and purified by silica gel column chromatography. The eluent of interest was collected and concentrated to obtain the product E20-1 (5.82 g).

Step b: removal of Boc protecting group. A solution of trifluoroacetic acid/dichloromethane (1:2, v/v) was prepared, and slowly added dropwise with a solution of E20-1 (5.29 g, 6.0 mmol) in dichloromethane in an ice bath. The reaction was carried out for 2 h at room temperature. Then, the reaction solution was concentrated, added with some purified water, and extracted with dichloromethane. The extract was dried with anhydrous $MgSO_4$, filtered, and concentrated. The cationic lipid E20-2 (4.45 g) containing a naked amino group was obtained after recrystallization. The main data of $^1$H-NMR spectrum of E20-2 were as follows: $^1$H NMR (400 MHz, $CDCl_3$) δ: 4.05 (m, 4H), 3.71-3.49 (m, 4H), 3.01 (m, 4H), 2.85 (t, 2H), 2.51 (t, 2H), 2.13 (m, 2H), 1.60-1.25 (m, 64H), 0.88 (t, 12H). The molecular weight of E20-2 was determined to be 780.66 Da by MALDI-TOF.

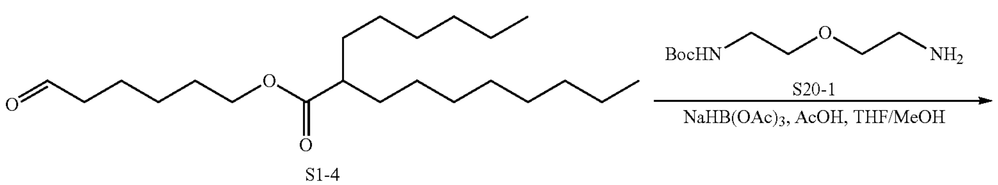

S1-4

-continued

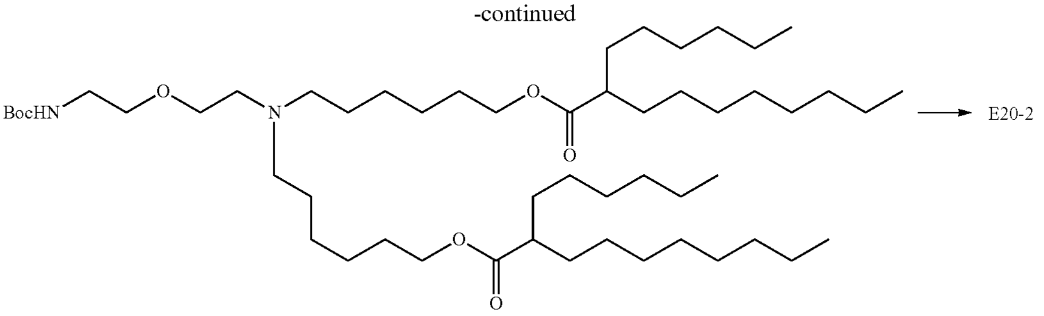

E20-1

Example-21: Cationic Lipid (E21-1)

E21-1

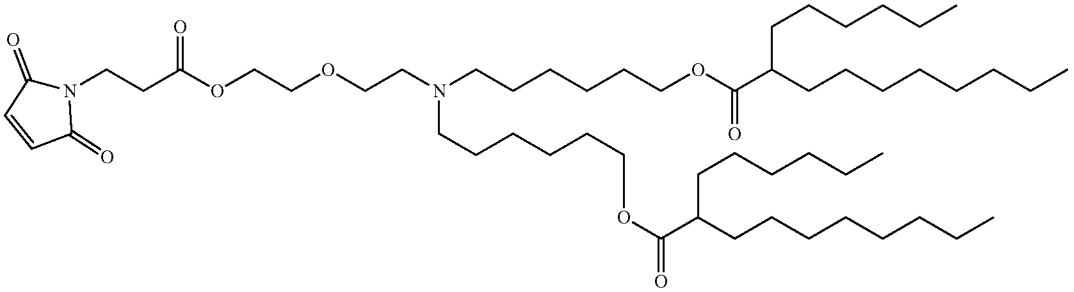

E21-1 corresponds to the general formula (1), wherein, $L_1$ and $L_2$ are both —C(═O)O—, $L_3$ is a linking bond, $B_1$ and $B_2$ are both hexylene groups, $R_1$ and $R_2$ are both

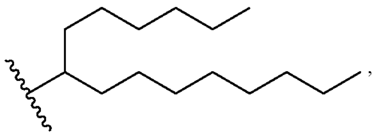

A is —$(CR_aR_b)_sO$—, wherein $R_a$ and $R_b$ are both hydrogen atoms, s is 2, n is 2, and $R_3$ is

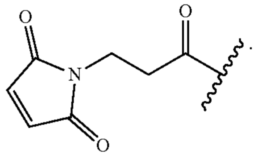 [SMILES: *C(=O)CCN1C(=O)C=CC1=O]

The molecular weight is approximately 933 Da.

The preparation process is as follows:

Step a: The oxidation product (S1-4, 8.85 g, 25.0 mmol) prepared according to Example-1 was dissolved in a mixed solution of 100 mL THF and 10 mL methanol. After the temperature of the solution was cooled to 0° C., S21-1 (3.06 g, 12.0 mmol) and glacial acetic acid (0.72 g, 12.0 mmol) were added, and then $NaBH(OAc)_3$ (8.90 g, 42.0 mmol) was added slowly in batches. After the feeding, the reaction was continued for 2 h until the materials were consumed completely according to the TLC. After completion of the reaction, a saturated solution of sodium bicarbonate was added to quench the reaction. The reaction solution was brought back to room temperature, and then concentrated to remove THE and methanol. The residue was extracted twice with DCM (100 mL*2), and the organic phases were combined and dried with anhydrous $MgSO_4$. The crude product was obtained after filtration and concentration, and further separated and purified by silica gel column chromatography. The eluent of interest was collected and concentrated to obtain the product E21-1 (5.65 g). The main $^1$H-NMR spectrum data: $^1$H NMR (500 MHz, $CDCl_3$) δ: 6.49 (s, 2H), 4.25-4.10 (m, 6H), 3.62 (t, 2H), 3.52 (t, 2H), 3.15 (t, 1H), 2.63 (t, 2H), 2.50 (t, 4H), 2.32 (t, 2H), 2.24 (m, 2H), 1.89 (m, 2H), 1.66-1.50 (m, 12H), 1.45-1.17 (m, 52H), 0.88 (t, 12H). The molecular weight of E21-1 was determined to be 932.79 Da by MALDI-TOF.

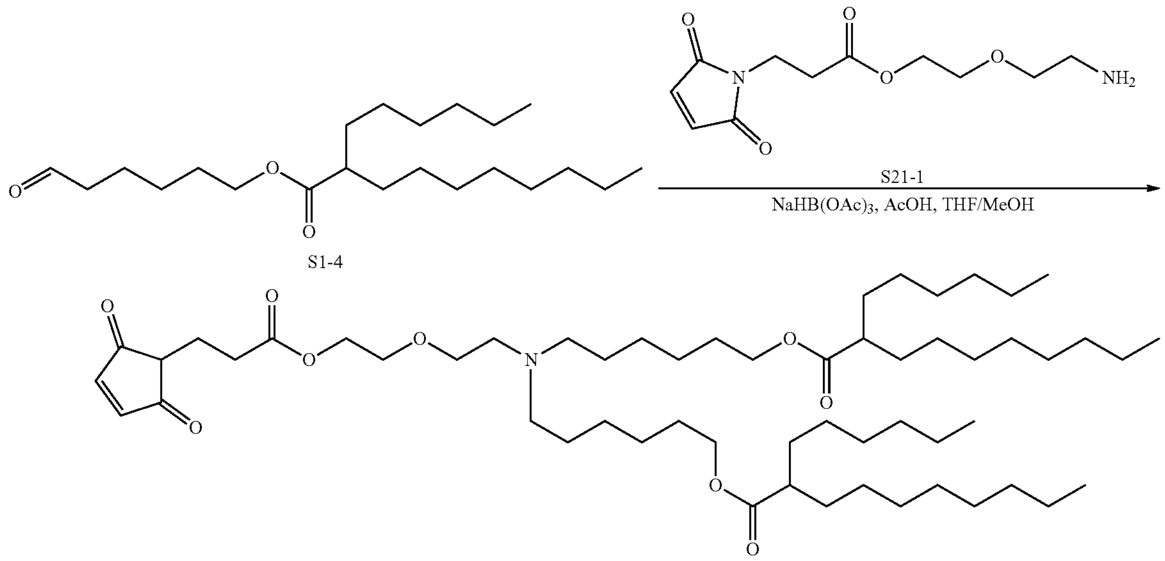

S1-4

E21-1

Example-22: Cationic Lipid (E22-1)

E22-1

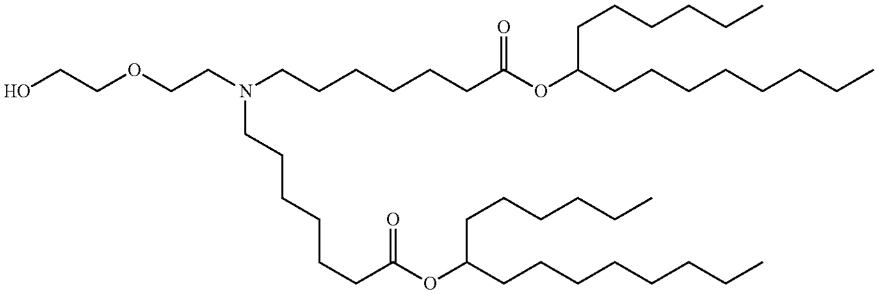

E22-1 corresponds to the general formula (1), wherein, $L_1$ and $L_2$ are both —OC(═O)—, $L_3$ is a linking bond, $B_1$ and $B_2$ are both hexylene groups, $R_1$ and $R_2$ are both

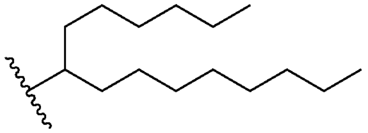

A is $—(CR_aR_b)_sO—$, $R_a$ and $R_b$ are both hydrogen atoms, s is 2, n is 2, and $R_3$ is a hydrogen atom. The molecular weight is approximately 781 Da.

The preparation process is as follows:

Step a: In a flask under nitrogen protection, 7-hydroxyheptanoic acid (S22-1, 14.60 g, 100.0 mmol) was dissolved in anhydrous DCM (200 mL). After the temperature of the solution was cooled to 0-10° C., 7-pentadecanol (S22-2, 45.60 g, 200.0 mmol) and DMAP (14.64 g, 120.0 mmol) were added carefully, and then EDCI (21.12 g, 110.0 mmol) was added in batches. The reaction solution was brought back to room temperature, and the reaction was continued. After 16 h of reaction, S22-1 was completely consumed according to the TLC. The reaction solution was washed twice with 100 mL 0.4N HCl/10% NaCl mixed solution, and then washed once with a saturated salt solution. The organic phases were combined and dried with anhydrous $MgSO_4$. The crude product was obtained after filtration and concentration, and further separated and purified by silica gel column chromatography. The eluent of interest was collected and concentrated to obtain the small-molecule alcohol-derivative intermediate S22-3 (20.79 g).

Step b: The condensation product (S22-3, 20.00 g, 56.2 mmol) was dissolved in 200 mL DCM. After the temperature of the solution was cooled to 0° C., Tempo (3.00 mg) and a solution of KBr (8.02 g, 67.4 mmol) dissolved in 50 mL purified water were added to the former solution, and then a solution of NaClO (73.1 mmol) was added slowly. Then, the reaction was continued until the materials were consumed completely according to the TLC, and a solution of sodium sulfite was added to quench the reaction. The reaction solution was extracted twice with 200 mL DCM after being brought back to room temperature. The organic phases were combined and dried with anhydrous $MgSO_4$. The crude product was obtained after filtration and concentration, and further separated and purified by silica gel column chromatography. The eluent of interest was collected and concentrated to obtain the oxidation product S22-4 (9.59 g).

Step c: The oxidation product (S22-4, 8.00 g, 22.6 mmol) was dissolved in a mixed solution of 100 mL THE and 10 mL methanol. After the temperature of the solution was cooled to 0° C., S1-5 (1.19 g, 11.3 mmol) and glacial acetic acid (0.68 g, 11.3 mmol) were added, and then $NaBH(OAc)_3$ (7.19 g, 33.9 mmol) was added slowly in batches. After the feeding, the reaction was continued for 2 h until the materials were consumed completely according to the TLC. After completion of the reaction, a saturated solution of sodium bicarbonate was added to quench the reaction. The reaction solution was brought back to room temperature, and then concentrated to remove THE and methanol. The residue was extracted twice with 100 mL DCM, and the organic phases were combined and dried with anhydrous $MgSO_4$. The crude product was obtained after filtration and concentration, and further separated and purified by silica gel column chromatography. The eluent of interest was collected and concentrated to obtain the cationic lipid E22-1 (4.76 g). The main data of $^1$H-NMR spectrum of E22-1 were as follows: $^1$H NMR (400 MHz, $CDCl_3$) δ: 4.87 (m, 2H), 3.70 (t, 2H), 3.63 (t, 4H), 2.65 (t, 2H), 2.49 (m, 4H), 2.30 (t, 4H), 1.71-1.22 (m, 64H), 0.87 (t, 12H). The molecular weight of E22-1 was determined to be 781.42 Da by MALDI-TOF.

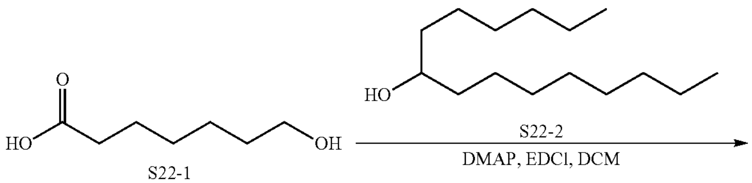

S22-1

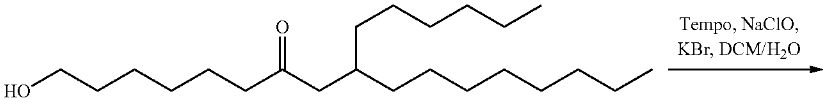

S22-3

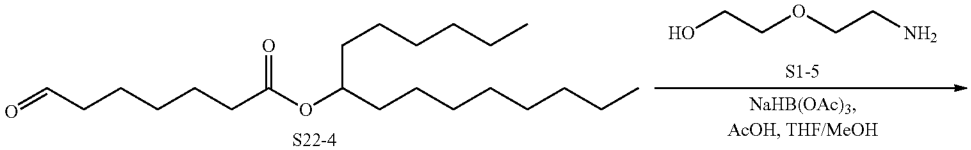

S22-4

E22-1

Example-23: Cationic Lipid (E23-1)

E23-1

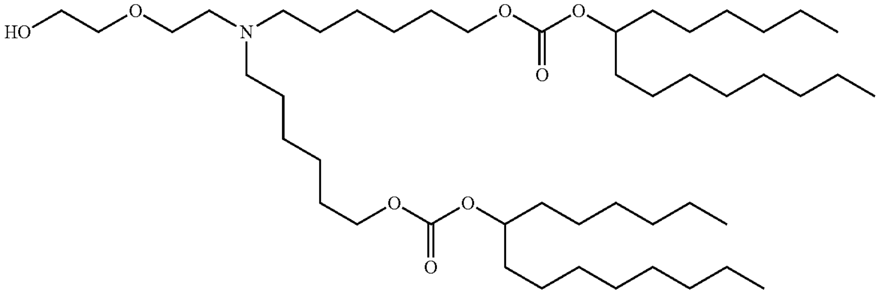

E23-1 corresponds to the general formula (1), wherein, $L_1$ and $L_2$ are both —OC(=O)O—, $L_3$ is a linking bond, $B_1$ and $B_2$ are both hexylene groups, $R_1$ and $R_2$ are both

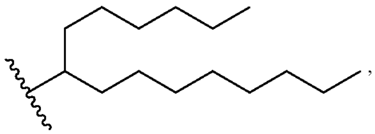

A is —$(CR_aR_b)_sO$—, $R_a$ and $R_b$ are both hydrogen atoms, s is 2, n is 2, and $R_3$ is a hydrogen atom. The molecular weight is approximately 814 Da.

The preparation process is as follows:

Step a: Under nitrogen protection, 6-bromohexyl-4-nitrophenyl carbonate (S23-1, 4.48 g, 13.0 mmol, prepared via the reaction between 4-nitrophenyl chloroformate and 6-bromo-1-hexanol) was dissolved in DCM (100 mL), and S22-2 (11.86 g, 52.0 mmol) was added dropwise with stirring at room temperature, which was followed by slowly adding dropwise pyridine (1.28 mL, 16.25 mmol) in over 10 min, and then DMAP (0.32 g, 2.6 mmol) was added in one batch. The reaction was stirred at room temperature for 16 h. After completion of the reaction, the reaction solution was extracted with purified water and DCM respectively. The organic phases were combined, washed with brine, and dried with anhydrous $MgSO_4$. The crude product was obtained after filtration and concentration, and further separated and purified by silica gel column chromatography. The eluent of interest was collected and concentrated to obtain the product S23-2 (5.86 g).

Step b: Under nitrogen protection, 100 mL acetonitrile was added, S23-2 (5.56 g, 12.8 mmol), S1-5 (0.60 g, 5.8 mmol), and N,N-diisopropylethylamine (DIPEA, 1.50 g, 11.6 mmol) were successively added with stirring slowly. The reaction was stirred at room temperature for about 20 h. The reaction was continued until the material S1-5 was consumed completely according to the TLC. After completion of the reaction, the reaction solution was concentrated, dissolved with dichloromethane, and then extracted with a solution of 0.6M HCl/10% NaCl and a saturated solution of sodium bicarbonate in sequence. After ensuring that there was no product in the aqueous phase, the organic phases were combined and dried with anhydrous $MgSO_4$. The cationic lipid E23-1 (3.67 g) was obtained after filtration, concentration, and purification by silica gel column chromatography. The main data of $^1H$-NMR spectrum of E23-1 were as follows: $^1H$ NMR (400 MHz, $CDCl_3$) δ: 4.21 (t, 4H), 4.12 (m, 2H), 3.70 (t, 2H), 3.63 (t, 4H), 2.65 (t, 2H), 2.51 (m, 4H), 1.72-1.25 (m, 64H), 0.90 (t, 12H). The molecular weight of E23-1 was determined to be 813.84 Da by MALDI-TOF.

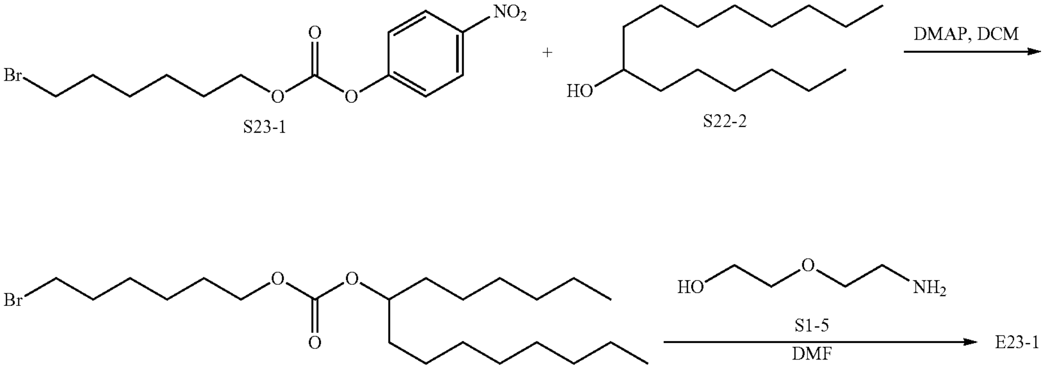

S23-1 S22-2 S23-2 E23-1

Example-24: Cationic Lipid (E24-1)

E24-1

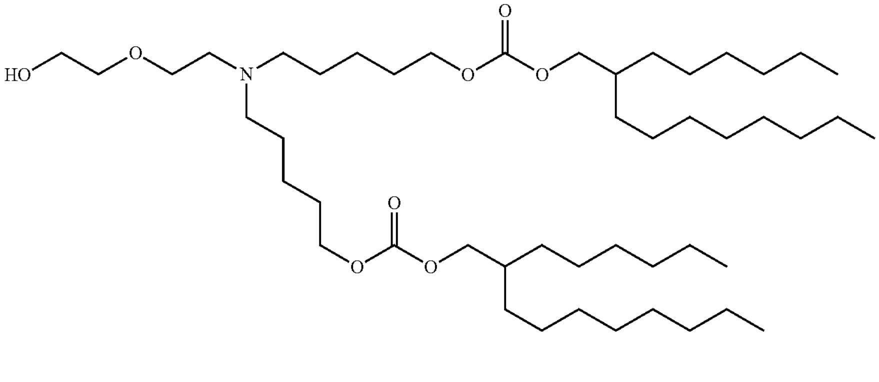

E24-1 corresponds the general formula (1), wherein, $L_1$ and $L_2$ are both —OC(=O)O—, $L_3$ is a linking bond, $B_1$ and $B_2$ are both

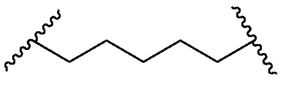

, $R_1$ and $R_2$ are both

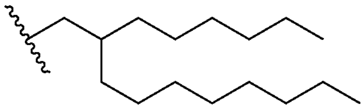

,

A is —$(CR_aR_b)_sO$—, $R_a$ and $R_b$ are both hydrogen atoms, s is 2, n is 2, and $R_3$ is a hydrogen atom. The molecular weight is approximately 814 Da.

The preparation process is as follows:

Step a: Under nitrogen protection, 5-bromopentyl-4-nitrophenyl carbonate (S24-1, 4.30 g, 13.0 mmol, prepared via the reaction between 4-nitrophenyl chloroformate and 5-bromopentyl-1-hexanol) was dissolved in DCM (100 mL), 2-hexyl-1-decanol (S24-2, 12.58 g, 52.0 mmol) was added dropwise with stirring at room temperature, pyridine (1.28 mL, 16.25 mmol) was slowly added dropwise in over 10 min, and then DMAP (0.32 g, 2.6 mmol) was added in one batch. The reaction was stirred at room temperature for 16 h. After completion of the reaction, the reaction solution was extracted twice with DCM. The organic phases were combined, washed with brine, and dried with anhydrous $MgSO_4$. The crude product was obtained after filtration and concentration, and further separated and purified by silica gel column chromatography. The eluent of interest was collected and concentrated to obtain the product S24-3 (6.14 g).

Step b: Under nitrogen protection, 100 mL acetonitrile was added, S24-3 (5.56 g, 12.8 mmol), S1-5 (0.60 g, 5.8 mmol), and N,N-diisopropylethylamine (DIPEA, 1.50 g, 11.6 mmol) were successively added with stirring slowly. The reaction was stirred at room temperature for about 20 h. The reaction was continued until the material S1-5 was consumed completely according to the TLC. After completion of the reaction, the reaction solution was concentrated, dissolved with dichloromethane, and then extracted with a solution of 0.6M HCl/10% NaCl and a saturated solution of sodium bicarbonate successively. After ensuring that there was no product in the aqueous phase, the organic phases were combined and dried with anhydrous $MgSO_4$. The cationic lipid E24-1 (3.58 g) was obtained after filtration, concentration, and purification by silica gel column chromatography. The main data of $^1H$-NMR spectrum of E24-1 were as follows: $^1H$ NMR (400 MHz, $CDCl_3$) δ: 4.26 (d, 4H), 4.20 (t, 4H), 3.71 (t, 2H), 3.64 (t, 4H), 2.65 (t, 2H), 2.50 (m, 4H), 2.08 (m, 2H), 1.72-1.18 (m, 60H), 0.89 (t, 12H). The molecular weight of E24-1 was determined to be 813.67 Da by MALDI-TOF.

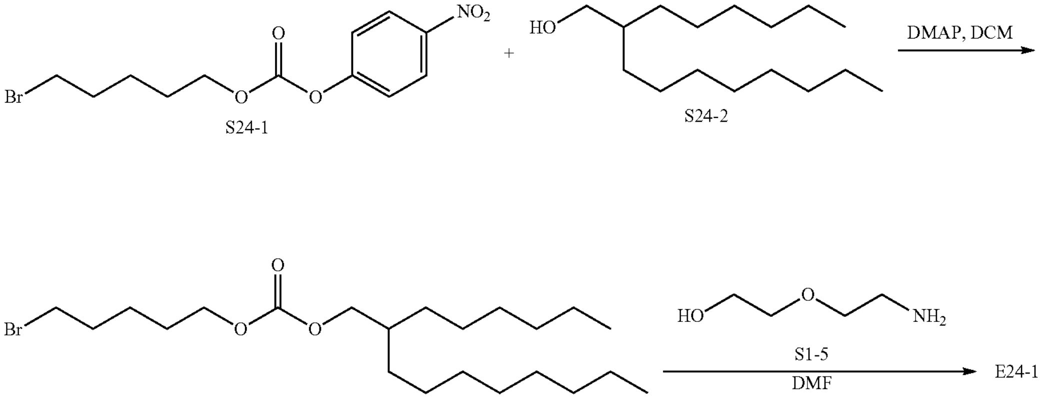

Example-25: Cationic Lipid (E25-1)

E25-1

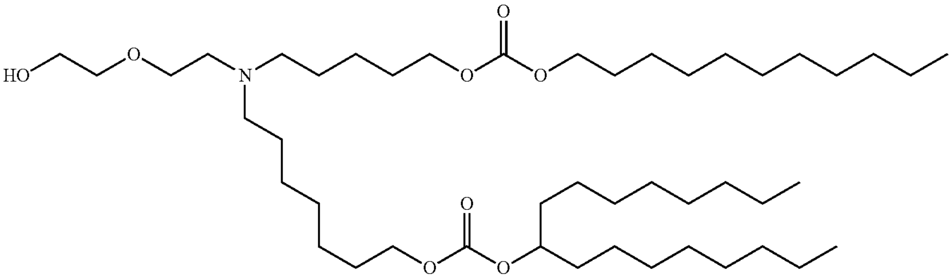

E25-1 corresponds to the general formula (1), wherein, $L_1$ and $L_2$ are both —OC(═O)O—, $L_3$ is a linking bond, $B_1$ is a pentylene group, $B_2$ is a heptylene group, $R_1$ is an undecyl group, $R_2$ is

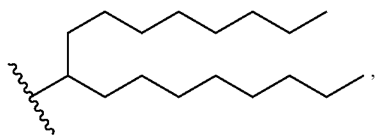

A is —$(CR_aR_b)_sO$—, $R_a$ and $R_b$ are both hydrogen atoms, s is 2, n is 2, and $R_3$ is a hydrogen atom. The molecular weight is approximately 786 Da.

The preparation process is as follows:

Step a: Under nitrogen protection, S24-2 (10.59 g, 32.0 mmol) was dissolved in DCM (30 mL), 1-undecanol (S25-1, 22.02 g, 128.0 mmol) was added dropwise with stirring at room temperature, pyridine (3.2 mL, 40.0 mmol) was slowly added dropwise in over 25 min, and then DMAP (0.78 g, 6.4 mmol) was added in one batch. The reaction was stirred at room temperature for 16 h. After completion of the reaction, the reaction solution was extracted twice with DCM. The organic phases were combined, washed with brine, and dried with anhydrous $MgSO_4$. The crude product was obtained after filtration and concentration, and further separated and purified by silica gel column chromatography. The eluent of interest was collected and concentrated to obtain the 5-bromopentylundecyl carbonate (S25-2, 3.03 g).

Step b: Under nitrogen protection, 70 mL acetonitrile was added, S25-2 (3.51 g, 9.6 mmol), S1-5 (0.84 g, 8.0 mmol), and N,N-diisopropylethylamine (DIPEA, 1.03 g, 8.0 mmol) were successively added with stirring slowly. The reaction was stirred at room temperature for about 20 h. The reaction was continued until the material S1-5 was consumed completely according to the TLC. After completion of the reaction, the reaction solution was concentrated, dissolved with dichloromethane, and then extracted with a solution of 0.6M HCl/10% NaCl and a saturated solution of sodium bicarbonate in sequence. After ensuring that there was no product in the aqueous phase, the organic phases were combined and dried with anhydrous $MgSO_4$. The secondary amine derivative S25-3 (2.33 g) was obtained after filtration, concentration, and purification by silica gel column chromatography.

Step c: S25-3 (2.33 g, 6.0 mmol) was dissolved in anhydrous THE (60 mL), NaH (60%, 2.40 g, 60.0 mmol) was added slowly in an ice bath, and the reaction was continued for 1 h in the ice bath. S25-4 (3.43 g, 7.2 mmol, prepared via the reaction between 7-bromoheptyl-4-nitrophenyl carbonate and 9-heptadecanol, the process of which can refer to Example-22) was added, and the reaction was brought back to room temperature after stirring in an ice bath for 1 h, and then was continued overnight. Then, the reaction solution was placed in an ice bath, and 2 mL methanol was added slowly to quench the reaction. After 30 minutes of stirring, 100 mL water was added and mixed with the solution while stirring. The mixture was extracted twice with EtOAc (100 mL*2). The aqueous phase was retained and extracted twice with dichloromethane (100 mL*2). The organic phases were combined, backwashed with an aqueous saturated solution of sodium chloride (100 mL), dried with anhydrous sodium sulfate, filtered, and concentrated to obtain the crude product which was further purified by silica gel column chromatography, concentrated, and dried with an oil pump to obtain the target compound E25-1 (3.56 g). The main data of $^1$H-NMR spectrum of E25-1 were as follows: $^1$H NMR (400 MHz, $CDCl_3$) δ: 4.22 (t, 2H), 4.16 (t, 4H), 4.13 (m, 1H), 3.70 (t, 2H), 3.62 (t, 4H), 2.65 (t, 2H), 2.48 (m, 4H), 1.72-1.25 (m, 62H), 0.90 (t, 9H). The molecular weight of E25-1 was determined to be 785.66 Da by MALDI-TOF.

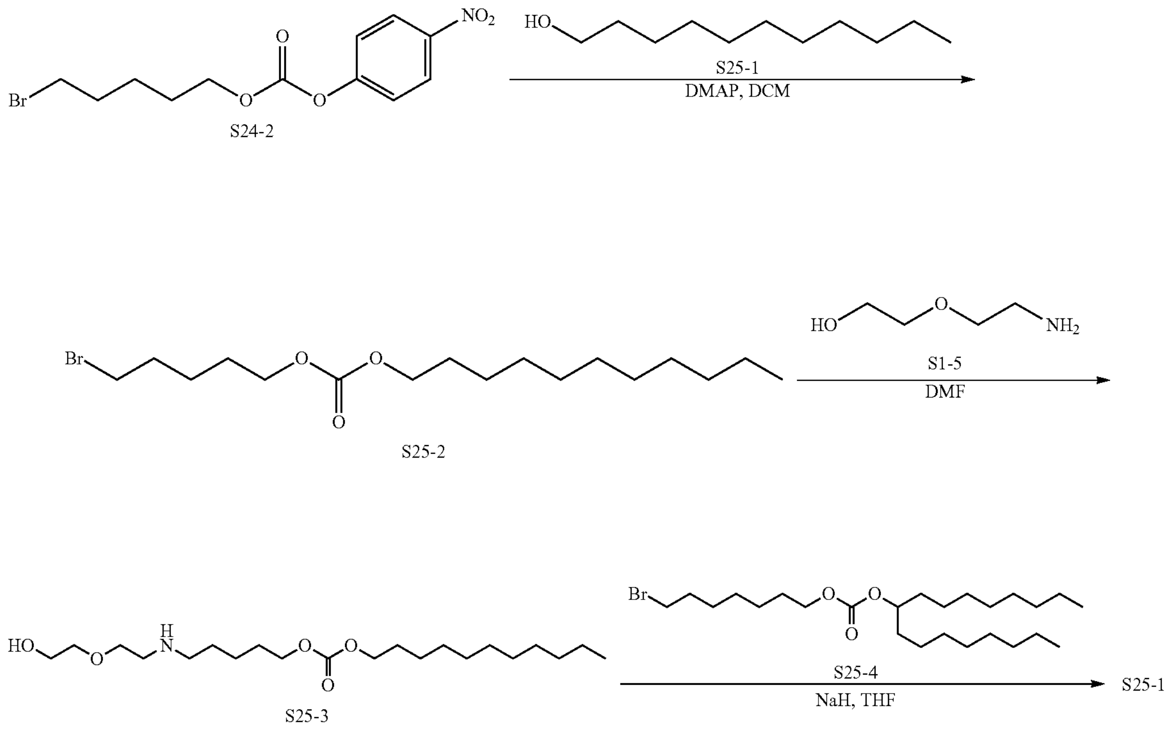

Example-26: Cationic Lipid (E26-1)

E26-1

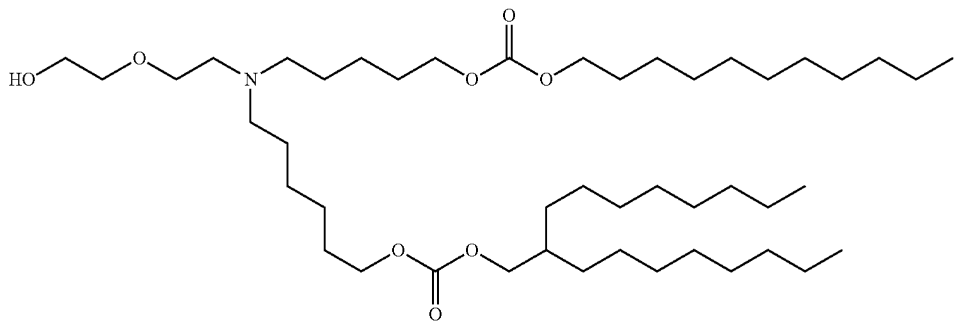

E26-1 corresponds to the general formula (1), wherein, $L_1$ and $L_2$ are both —OC(=O)O—, $L_3$ is a linking bond, $B_1$ is a pentylene, $B_2$ is a hexylene group, $R_1$ is an undecyl group, $R_2$ is

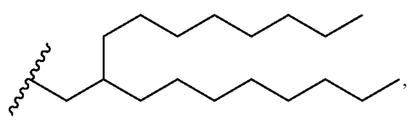

A is $-(CR_aR_b)_sO-$, $R_a$ and $R_b$ are both hydrogen atoms, s is 2, n is 2, and $R_3$ is a hydrogen atom. The molecular weight is approximately 786 Da.

The preparation process is as follows:

Step a: Under nitrogen protection, S23-1 (11.04 g, 32.0 mmol) prepared according to Example-23 was dissolved in DCM (200 mL), S26-1 (34.56 g, 128.0 mmol) was added dropwise with stirring at room temperature, pyridine (3.2 mL, 16.3 mmol) was slowly added dropwise in over 25 min, and then DMAP (0.78 g, 6.4 mmol) was added in one batch. The reaction was stirred at room temperature for 16 h. After completion of the reaction, the reaction solution was extracted twice with DCM. The organic phases were combined, washed with brine, and dried with anhydrous $MgSO_4$. The crude product was obtained after filtration and concentration, and further separated and purified by silica gel column chromatography. The eluent of interest was collected and concentrated to obtain the product S26-2 (3.66 g).

Step b: S25-3 (2.33 g, 6.0 mmol) prepared according to Example-25 was dissolved in anhydrous THE (60 mL), NaH (60%, 2.40 g, 60.0 mmol) was added slowly in an ice bath, and the reaction was continued for 1 h in the ice bath. S26-2 (3.43 g, 7.2 mmol) was added and the reaction was stirred in an ice bath for 1 h. After being brought back to room temperature, the reaction was continued overnight. Then, the reaction solution was placed in an ice bath, 2 mL methanol was added slowly to quench the reaction. After 30 minutes of stirring, 100 mL water was added and mixed with the solution while stirring. The mixture was extracted twice with EtOAc (150 mL*2). The aqueous phase was retained and extracted twice with dichloromethane (100 mL*2). The organic phases were combined, backwashed with an aqueous saturated solution of sodium chloride (100 mL), dried with anhydrous sodium sulfate, filtered, and concentrated to obtain the crude product which was further purified by silica gel column chromatography, concentrated, and dried with an oil pump to obtain the target compound E26-1 (3.57 g). The main data of $^1$H-NMR spectrum of E26-1 were as follows: $^1$H NMR (400 MHz, $CDCl_3$) δ: 4.26 (d, 2H), 4.21 (t, 2H), 4.16 (t, 4H), 3.70 (t, 2H), 3.63 (t, 4H), 2.65 (t, 2H), 2.49 (m, 4H), 2.07 (m, 1H), 1.72-1.18 (m, 60H), 0.90 (t, 9H). The molecular weight of E26-1 was determined to be 785.67 Da by MALDI-TOF.

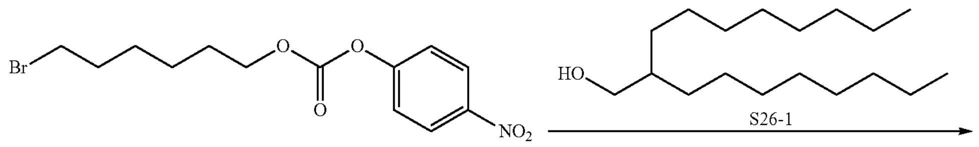

S23-1

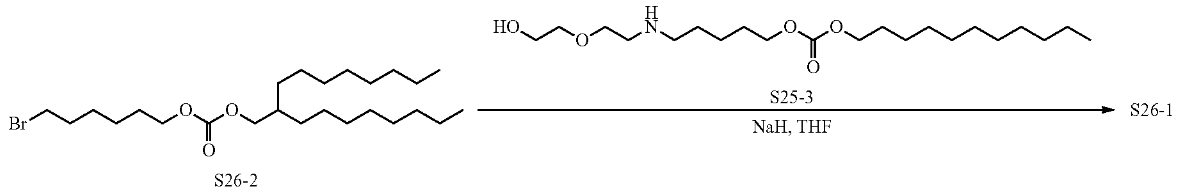

S26-2

Example-27: Cationic Lipid (E27-1)

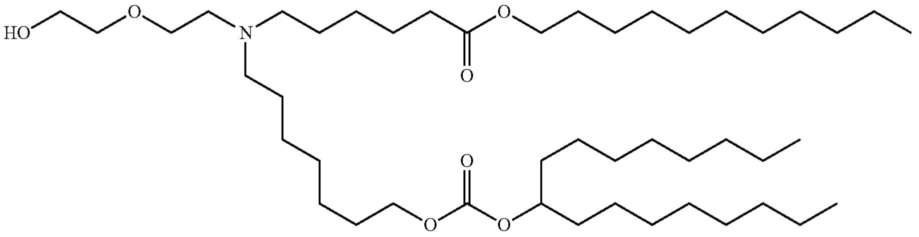

E27-1

E27-1 corresponds to the general formula (1), wherein, $L_1$ is —OC(═O)—, $L_2$ is —OC(═O)O—, $L_3$ is a linking bond, $B_1$ is a pentylene group, $B_2$ is a heptylene group, $R_1$ is an undecyl group, $R_2$ is

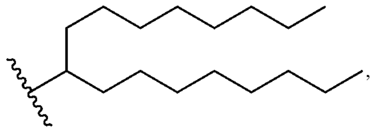

A is $—(CR_aR_b)_sO—$, $R_a$ and $R_b$ are both hydrogen atoms, s is 2, n is 2, and $R_3$ is a hydrogen atom. The molecular weight is approximately 770 Da.

The preparation process is as follows:

Step a: Under nitrogen protection, 100 mL acetonitrile was added, 25-4 (10.45 g, 21.88 mmol), S1-5 (1.84 g, 17.5 mmol), and DIPEA (2.20 g, 17.0 mmol) were added in sequence with stirring slowly, followed by stirring at room temperature for about 20 h. The reaction was continued until the material S1-5 was consumed completely according to the TLC. After completion of the reaction, the reaction solution was concentrated and dissolved in dichloromethane, and then extracted with a solution of 0.6M HCl/10% NaCl and a saturated solution of sodium bicarbonate in sequence. After ensuring that there was no product in the aqueous phase, the organic phases were combined and dried with anhydrous $MgSO_4$. The secondary amine derivative S27-1 (7.54 g) was obtained after filtration, concentration, and purification by silica gel column chromatography.

Step b: S27-1 (5.68 g, 12.0 mmol) was dissolved in anhydrous THE (60 mL), NaH (60%, 4.80 g, 120.0 mmol) was added slowly in an ice bath, and the reaction was continued for 1 h in the ice bath. S27-2 (5.01 g, 14.4 mmol, prepared via the reaction between 8-bromooctanoicacid and 1-nonanol, the process of which can refer to Example-16) was added, and the reaction was stirred in an ice bath for 1 h. Then, the reaction was brought back to room temperature before continuing overnight. After completion of the reaction, the reaction solution was placed in an ice bath, and 2 mL methanol was added slowly to quench the reaction. After 30 minutes of stirring, 200 mL water was added to mixing with the solution while stirring. The mixture was extracted twice with EtOAc (200 mL*2). The aqueous phase was retained and extracted twice with dichloromethane (200 mL*2). The organic phases were combined, backwashed with a saturated aqueous solution of sodium chloride (200 mL), dried with anhydrous sodium sulfate, filtered, and concentrated to obtain the crude product which was further purified by silica gel column chromatography, concentrated, and dried with an oil pump to obtain the target compound E27-1 (6.93 g). The main data of $^1H$-NMR spectrum of E27-1 were as follows: $^1H$ NMR (400 MHz, $CDCl_3$) δ: 4.21 (t, 2H), 4.12 (m, 1H), 4.07 (t, 2H), 3.70 (t, 2H), 3.63 (t, 4H), 2.65 (t, 2H), 2.51 (m, 4H), 2.37 (t, 2H), 1.72-1.25 (m, 62H), 0.90 (t, 9H). The molecular weight of E27-1 was determined to be 769.69 Da by MALDI-TOF.

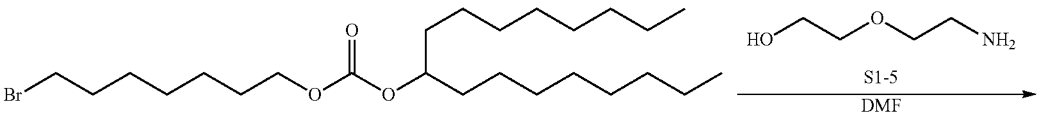

S25-4

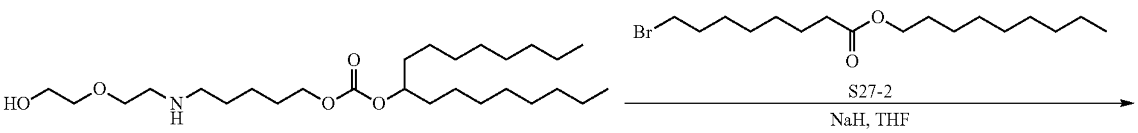

S27-1

-continued

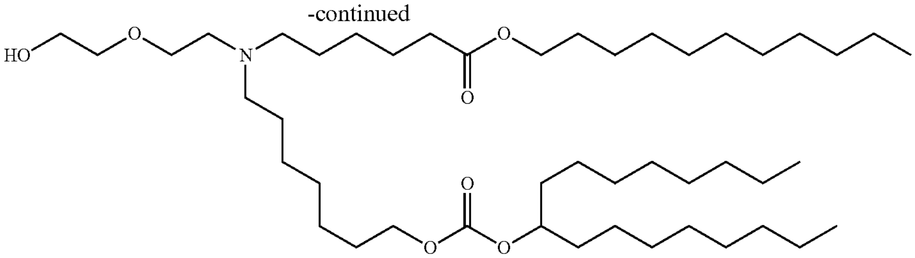

S27-1

Example-28: Cationic Lipid (E28-1)

E28-1

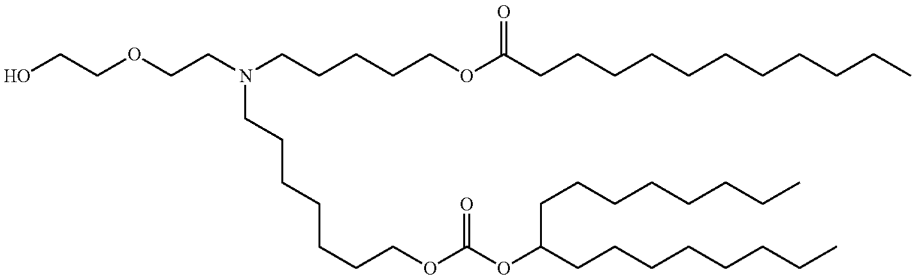

E28-1 corresponds to the general formula (1), wherein, $L_1$ is —C(═O)O—, $L_2$ is —OC(═O)O—, $L_3$ is a linking bond, $B_1$ is a pentylene group, $B_2$ is a heptylene group, $R_1$ is an undecyl group, $R_2$ is

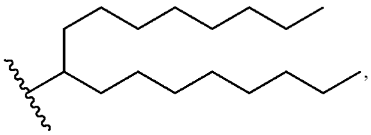

A is —$(CR_aR_b)_sO$—, $R_a$ and $R_b$ are both hydrogen atoms, s is 2, n is 2, and $R_3$ is a hydrogen atom. The molecular weight is approximately 770 Da.

The preparation process is as follows:

Step a: S27-1 (5.68 g, 12.0 mmol) was dissolved in anhydrous THE (60 mL). In an ice bath, NaH (60%, 4.80 g, 120.0 mmol) was added slowly to the solution, after which the reaction was continued for 1 h. Then, S28-1 (5.01 g, 14.4 mmol, prepared via the reaction between lauric acid and 5-bromo-1-pentanol, the process of which can refer to Example-16) was added and the reaction was continued for another 1 h with stirring in the ice bath. After being brought back to room temperature, the reaction was continued overnight. After completion of the reaction, the reaction solution was placed in an ice bath, and 2 mL methanol was added slowly to quench the reaction. After stirring for 30 minutes, 200 mL water was added and mixed with stirring. The mixture was extracted twice with EtOAc (200 mL*2), and the aqueous phase was retained and extracted twice with dichloromethane (200 mL*2). The organic phases were combined, backwashed with an aqueous saturated solution of sodium chloride (200 mL), dried with anhydrous sodium sulfate, filtered, and concentrated to obtain the crude product which was further purified by silica gel column chromatography, concentrated, and dried with an oil pump to obtain the target compound E28-1 (6.87 g). The main data of $^1$H-NMR spectrum of E28-1 were as follows: $^1$H NMR (400 MHz, $CDCl_3$) δ: 4.20 (t, 2H), 4.12 (m, 1H), 4.08 (t, 2H), 3.70 (t, 2H), 3.63 (t, 4H), 2.64 (t, 2H), 2.50 (m, 4H), 2.37 (t, 2H), 1.72-1.25 (m, 62H), 0.88 (t, 9H). The molecular weight of E28-1 was determined to be 769.58 Da by MALDI-TOF.

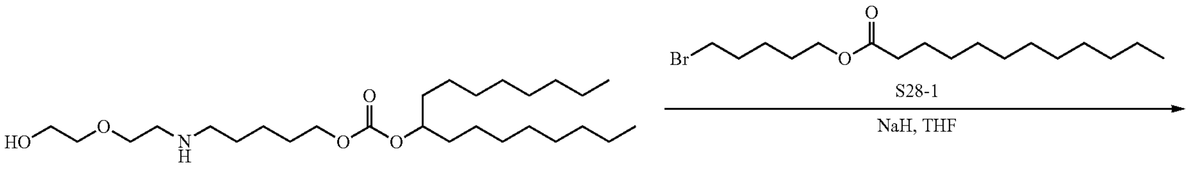

S27-1

E28-1

Example-29: Cationic Lipid (E29-1)

E29-1

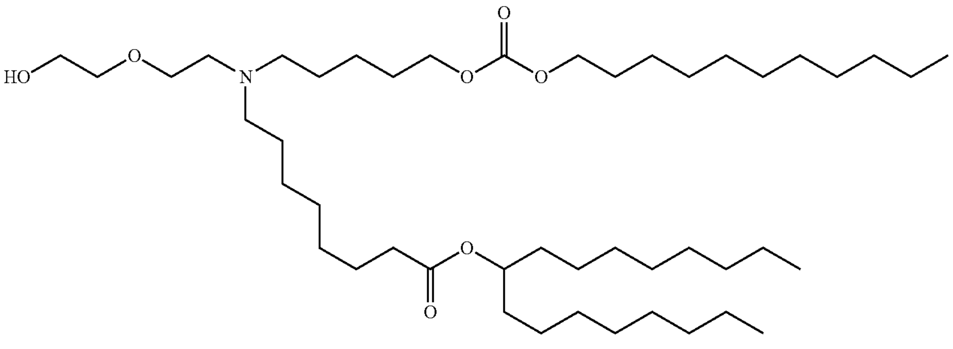

E29-1 corresponds to the general formula (1), wherein, $L_1$ is —OC(=O)O—, $L_2$ is —OC(=O)—, $L_3$ is a linking bond, $B_1$ is a pentylene group, $B_2$ is a heptylene group, $R_1$ is an undecyl group, $R_2$ is

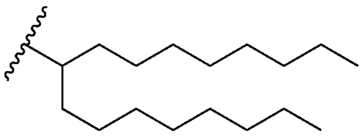
,

A is $—(CR_aR_b)_sO—$, $R_a$ and $R_b$ are both hydrogen atoms, s is 2, n is 2, and $R_3$ is a hydrogen atom. The molecular weight is approximately 770 Da.

The preparation process is as follows:

S25-3 (4.67 g, 12.0 mmol) was dissolved in anhydrous THE (60 mL). Under ice bath, NaH (60%, 4.80 g, 120.0 mmol) was added slowly and the reaction was carried out for 1 h. Then, S29-1 (6.62 g, 14.4 mmol, prepared via the reaction between 8-bromooctanoicacid and 9-heptadecanol, the process of which can refer to Example-16) was added and the reaction was stirred under ice bath for another 1 h before being brought back to room temperature and the reaction was continued overnight. Then, the reaction solution was placed in an ice bath, and 2 mL methanol was added slowly to quench the reaction. After 30 minutes of stirring, 100 mL water was added to mixing with the solution while stirring. The mixture was extracted twice with EtOAc (100 mL*2), and the aqueous phase was retained and extracted twice with dichloromethane (100 mL*2). The organic phases were combined, backwashed with an aqueous saturated solution of sodium chloride (100 mL), dried with anhydrous sodium sulfate, filtered, and concentrated to obtain the crude product which was further purified by silica gel column chromatography, concentrated, and dried with an oil pump to obtain the target compound E29-1 (6.52 g). The main data of $^1$H-NMR spectrum of E29-1 were as follows: $^1$H NMR (400 MHz, $CDCl_3$) δ: 4.86 (m, 1H), 4.16 (t, 4H), 3.70 (t, 2H), 3.62 (t, 4H), 2.65 (t, 2H), 2.48 (m, 4H), 2.30 (t, 2H), 1.72-1.25 (m, 62H), 0.88 (t, 9H). The molecular weight of E29-1 was determined to be 769.47 Da by MALDI-TOF.

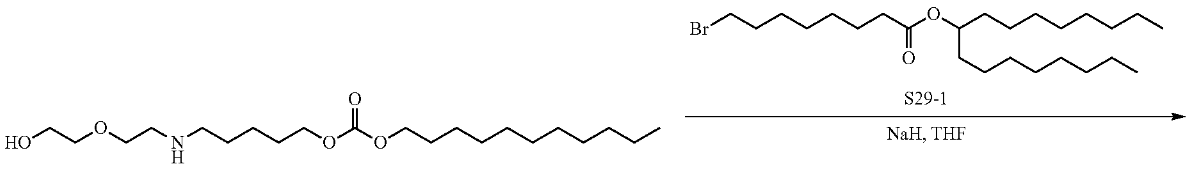

S25-3

E29-1

Example-30: Cationic Lipid (E30-1)

E30-1

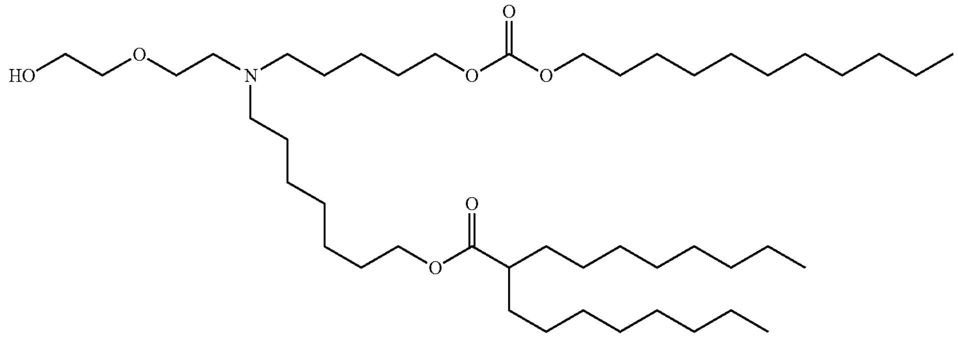

E30-1 corresponds to the general formula (1), wherein, $L_1$ is —OC(═O)O—, $L_2$ is —C(═O)O—, $L_3$ is a linking bond, $B_1$ is a pentylene group, $B_2$ is a heptylene group, $R_1$ is an undecyl group, $R_2$ is

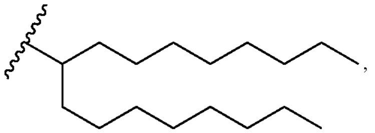

A is $-(CR_aR_b)_sO-$, $R_a$ and $R_b$ are both hydrogen atoms, s is 2, n is 2, and $R_3$ is a hydrogen atom. The molecular weight is approximately 770 Da.

The preparation process is as follows:

Step a: S25-3 (4.67 g, 12.0 mmol) was dissolved in anhydrous THF (60 mL). Under ice bath, NaH (60%, 4.80 g, 120.0 mmol) was added slowly and the reaction was carried out for 1 h. Then, S30-1 (6.62 g, 14.4 mmol, prepared via the reaction between 2-octyldecanoic acid and 7-bromo-1-heptanol, the process of which can refer to Example-16) was added and the reaction was stirred under ice bath for another 1 h before being brought back to room temperature and continued overnight. Then, the reaction solution was placed in an ice bath again, and 2 mL methanol was added slowly to quench the reaction. After 30 minutes of stirring, 100 mL water was added to mixing with the solution while stirring. The mixture was extracted twice with EtOAc (100 mL*2), and the aqueous phase was retained and extracted twice with dichloromethane (100 mL*2). The organic phases were combined, backwashed with a saturated aqueous solution of sodium chloride (100 mL), dried with anhydrous sodium sulfate, filtered, and concentrated to obtain the crude product which was further purified by silica gel column chromatography, concentrated, and dried with an oil pump to obtain the cationic lipid E30-1 (6.79 g). The main data of $^1$H-NMR spectrum of E30-1 were as follows: H NMR (400 MHz, $CDCl_3$) δ: 4.16 (t, 4H), 4.08 (t, 2H), 3.70 (t, 2H), 3.62 (t, 4H), 2.65 (t, 2H), 2.48 (m, 4H), 2.25 (m, 1H), 1.72-1.25 (m, 62H), 0.88 (t, 9H). The molecular weight of E30-1 was determined to be 769.38 Da by MALDI-TOF.

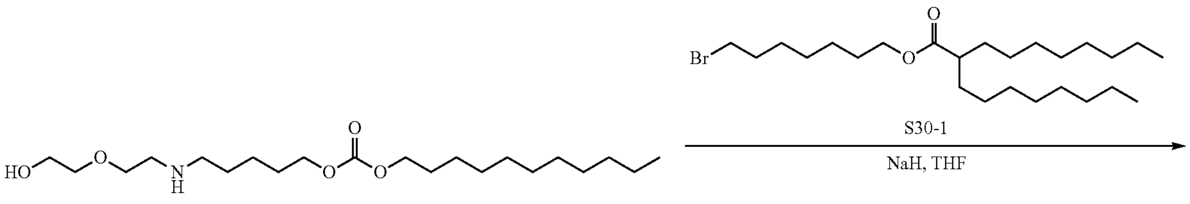

S30-1

S25-3

E30-1

Example-31: Cationic Lipid E31-1)

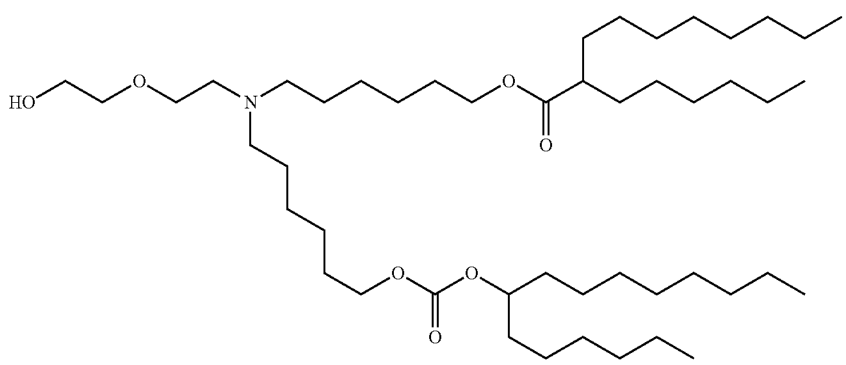

E31-1

E31-1 corresponds to the general formula (1), wherein, $L_1$ is —C(═O)O—, $L_2$ is —OC(═O)O—, $L_3$ is a linking bond, $B_1$ and $B_2$ are both hexylene groups, $R_1$ and $R_2$ are both

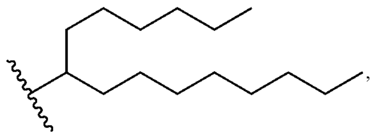

A is —$(CR_aR_b)_sO$—, $R_a$ and $R_b$ are both hydrogen atoms, s is 2, n is 2, and $R_3$ is a hydrogen atom. The molecular weight is approximately 798 Da.

The preparation process is as follows:

Step a: Under nitrogen protection, 50 mL acetonitrile was added, S23-2 (3.65 g, 8.38 mmol), S1-5 (0.70 g, 6.7 mmol), and DIPEA (0.87 g, 6.7 mmol) were added in sequence with stirring slowly, and reacted at room temperature for about 20 h with stirring. The reaction was continued until the material S1-5 was consumed completely according to the TLC. After completion of the reaction, the reaction solution was concentrated and dissolved in dichloromethane, and then extracted with a solution of 0.6M HCl/10% NaCl and a saturated solution of sodium bicarbonate in sequence. After ensuring that there was no product in the aqueous phase, the organic phases were combined and dried with anhydrous $MgSO_4$. The secondary amine derivative S31-1 (2.70 g) was obtained after filtration, concentration, and purification by silica gel column chromatography.

Step b: S31-1 (2.75 g, 6.0 mmol) was dissolved in anhydrous THF (60 mL). Under ice bath, NaH (60%, 2.40 g, 60.0 mmol) was added slowly and the reaction was carried out for 1 h. Then, S31-2 (3.01 g, 7.2 mmol, prepared via the reaction between 6-bromo-1-hexanol and 2-hexyldecanoic acid, the process of which can refer to Example-16) was added and the reaction was stirred for another 1 h before being brought back to room temperature and the reaction was continued overnight. After completion of the reaction, the reaction solution was placed in an ice bath, and 2 mL methanol was added slowly to quench the reaction. After 30 minutes of stirring, 100 mL water was added to mixing with the solution while stirring. The mixture was extracted twice with EtOAc (100 mL*2), and the aqueous phase was retained and extracted twice with dichloromethane (100 mL*2). The organic phases were combined, backwashed with an aqueous saturated solution of sodium chloride (100 mL), dried with anhydrous sodium sulfate, filtered, and concentrated to obtain the crude product which was further purified by silica gel column chromatography, concentrated, and dried with an oil pump to obtain the target compound E31-1 (3.52 g). The main data of $^1H$-NMR spectrum of E31-1 were as follows: $^1H$ NMR (400 MHz, $CDCl_3$) δ: 4.21 (t, 2H), 4.12 (m, 1H), 4.08 (t, 2H), 3.70 (t, 2H), 3.63 (t, 4H), 2.65 (t, 2H), 2.51 (m, 4H), 2.25 (m, 1H), 1.72-1.25 (m, 64H), 0.90 (t, 12H). The molecular weight of E31-1 was determined to be 797.72 Da by MALDI-TOF.

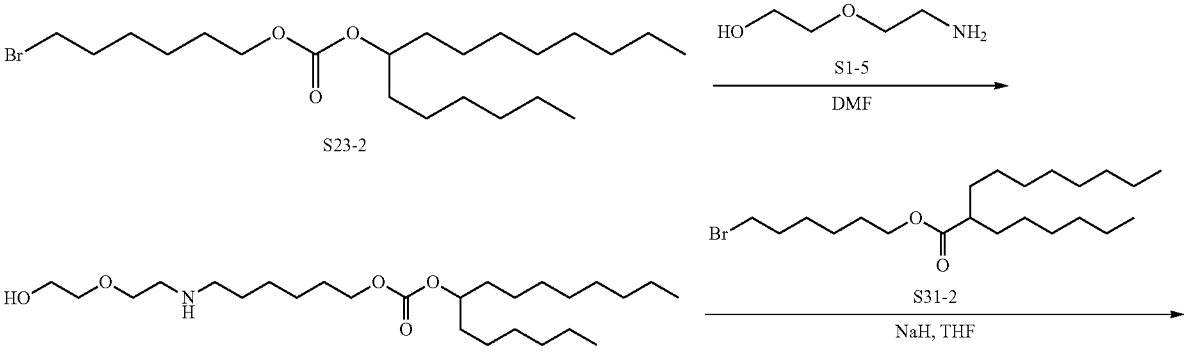

S23-2

S31-1

E31-1

Example-32: Cationic Lipid (E32-1)

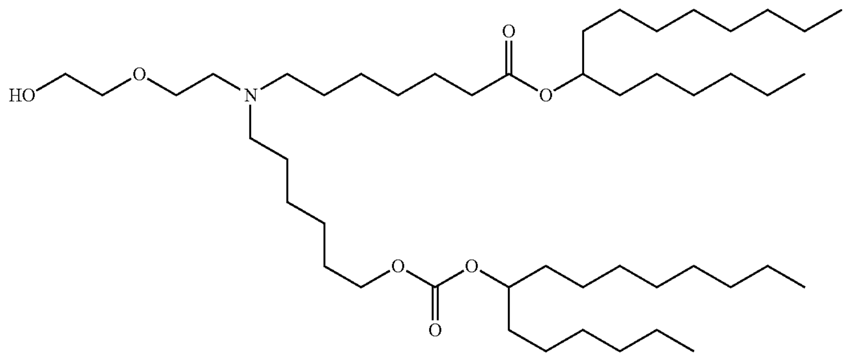

E32-1

E32-1 corresponds to the general formula (1), wherein, $L_1$ is —OC(═O)—, $L_2$ is —OC(O)O—, $L_3$ is a linking bond, $B_1$ and $B_2$ are both hexylene groups, $R_1$ and $R_2$ are

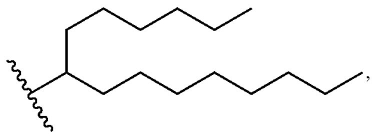

A is $-(CR_aR_b)_sO-$, $R_a$ and $R_b$ are both hydrogen atoms, s is 2, n is 2, and $R_3$ is a hydrogen atom. The molecular weight is approximately 798 Da.

The preparation process is as follows:

Compound S31-1 (2.75 g, 6.0 mmol) prepared according to Example-31 was dissolved in anhydrous THE (60 mL). Under ice bath, NaH (60%, 2.40 g, 60.0 mmol) was added slowly and the reaction was carried out for 1 h. Then, S31-2 (3.01 g, 7.2 mmol, prepared via the reaction between 7-bromoheptanoic acid and 7-pentadecanol, the process of which can refer to Example-16) was added and the reaction was stirred for another 1 h before being brought back to room temperature and continued overnight. After completion of the reaction, the reaction solution was placed in an ice bath again, and 2 mL methanol was added slowly to quench the reaction. After 30 minutes of stirring, 100 mL water was added to mixing with the solution while stirring. The mixture was extracted twice with EtOAc (100 mL*2), and the aqueous phase was retained and extracted twice with dichloromethane (100 mL*2). The organic phases were combined, backwashed with a saturated aqueous solution of sodium chloride (100 mL), dried with anhydrous sodium sulfate, filtered, and concentrated to obtain the crude product which was further purified by silica gel column chromatography, concentrated, and dried with an oil pump to obtain the target compound E32-1 (3.63 g). The main data of $^1$H-NMR spectrum of E32-1 were as follows: $^1$H NMR (400 MHz, $CDCl_3$) δ: 4.87 (m, 1H), 4.21 (t, 2H), 4.13 (m, 1H), 3.70 (t, 2H), 3.63 (t, 4H), 2.65 (t, 2H), 2.51 (m, 4H), 2.30 (t, 2H), 1.72-1.25 (m, 64H), 0.88 (t, 12H). The molecular weight of E32-1 was determined to be 797.72 Da by MALDI-TOF.

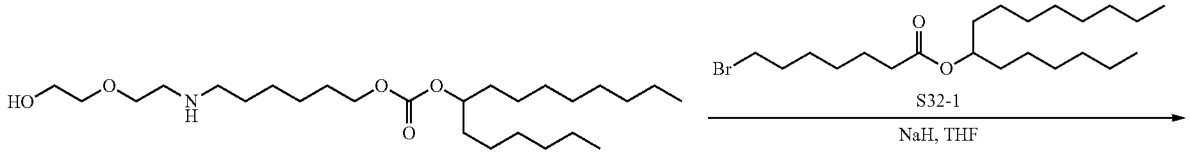

S31-1

E32-1

Example-33: Cationic Lipid (E32-1)

E33-1

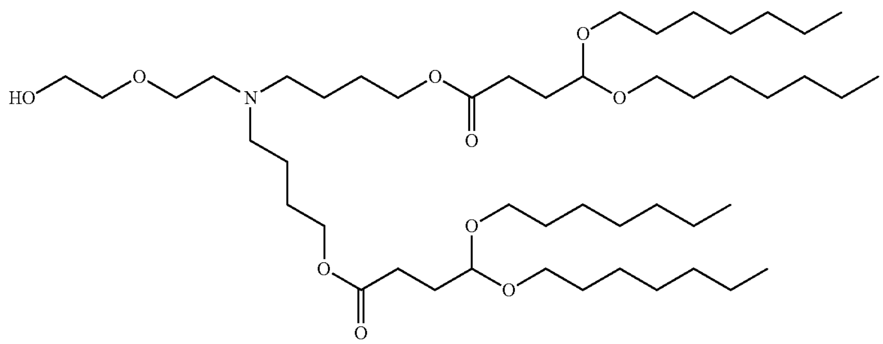

E33-1 corresponds to the general formula (1), wherein, $L_1$ and $L_2$ are both —C(═O)O—, $L_3$ is a linking bond, $B_1$ and $B_2$ are both butylene groups, $R_1$ and $R_2$ are both

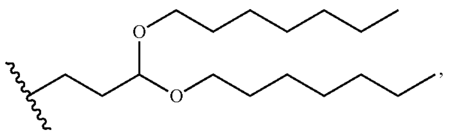

A is $—(CR_aR_b)_sO—$, $R_a$ and $R_b$ are both hydrogen atoms, s is 2, n is 2, and $R_3$ is a hydrogen atom. The molecular weight is approximately 846 Da.

The preparation process is as follows:

Step a: 1,3-propanediol (S33-1, 9.50 g, 50 mmol) containing a TBS protected hydroxy group was dissolved in 200 mL dichloromethane. Pyridinium chlorochromate (PCC, 16.13 g, 75.0 mmol) was added and the reaction was conducted for at least 2 h at 15° C. After completion of the reaction, the reaction solution was filtered, concentrated under reduced pressure, and purified by silica gel column chromatography to obtain S33-2 (6.02 g).

Step b: Compound S33-2 (5.64 g, 30.0 mmol) and 1-octanol (S33-3, 9.75 g, 75.0 mmol) were dissolved in 200 mL dichloromethane, followed by adding p-toluenesulfonic acid monohydrate ($TsOH·H_2O$, 1.14 g, 6.0 mmol) and anhydrous sodium sulfate (10.65 g, 75.0 mmol). The reaction was conducted for at least 24 h at 15° C., and the solution was filtered and concentrated under reduced pressure. 15 mL tetrahydrofuran and 15 mL solution of TBAF in tetrahydrofuran (1M) were added, then the reaction was conducted overnight to remove the TBS protecting group. Then, the reaction solution was dried with anhydrous sodium sulfate, filtered, concentrated, and purified by silica gel column chromatography to obtain S33-4 (2.84 g).

Step c: Under argon atmosphere and into a round bottom flask containing dichloromethane with dissolved S33-4 (2.53 g, 8.0 mmol), 6-bromohexanoic acid (S33-5, 1.71 g, 8.8 mmol), and DMAP (0.27 g, 2.2 mmol), DCC (2.72 g, 13.2 mmol) was added and the reaction was conducted for 16 h at room temperature. After completion of the reaction, the precipitate was removed by filtering, and the filtrate was concentrated and purified by silica gel column chromatography to obtain S33-6 (3.38 g).

Step d: Under nitrogen protection, 50 mL acetonitrile was added, S33-6 (2.47 g, 5.0 mmol), S1-5 (0.21 g, 2.0 mmol), and DIPEA (0.26 g, 2.0 mmol) were added in sequence with stirring slowly, the reaction was conducted at room temperature for about 20 h with stirring. The reaction was continued until the material S1-5 was consumed completely according to the TLC. After completion of the reaction, the reaction solution was concentrated and dissolved in dichloromethane, and then extracted with a solution of 0.6M HCl/10% NaCl and a saturated solution of sodium bicarbonate in sequence. After ensuring that there was no product in the aqueous phase, the organic phases were combined and dried with anhydrous $MgSO_4$. The cationic lipid E33-1 (1.40 g) was obtained after filtration, concentration, and purification by silica gel column chromatography. The main data of $^1H$-NMR spectrum of E33-1 were as follows: $^1H$ NMR (400 MHz, $CDCl_3$) δ: 4.64 (m, 2H), 4.20 (t, 4H), 3.70 (t, 2H), 3.63 (t, 4H), 3.52-3.36 (m, 8H), 2.65 (t, 2H), 2.49 (m, 4H), 2.30 (t, 4H), 1.98 (m, 4H), 1.72-1.21 (m, 48H), 0.87 (t, 12H). The molecular weight of E33-1 was determined to be 845.86 Da by MALDI-TOF.

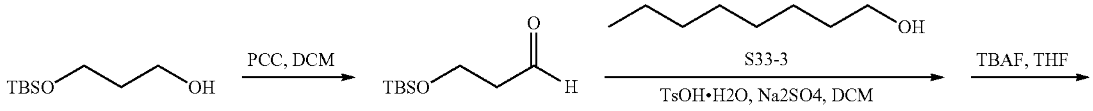

S33-1 S33-2

-continued

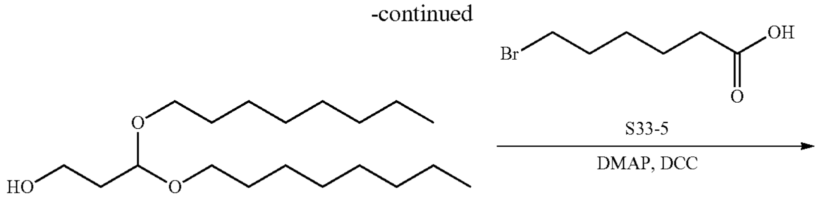

S33-4

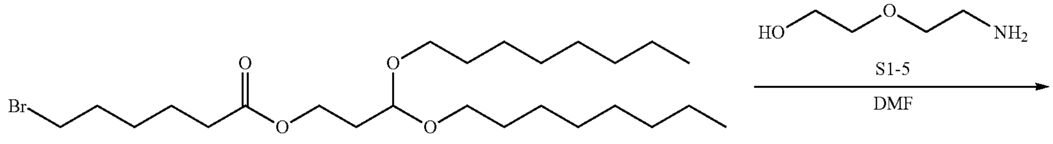

E33-1

S33-6

Example-34: Cationic Lipid (E34-1, E34-2)

E34-1

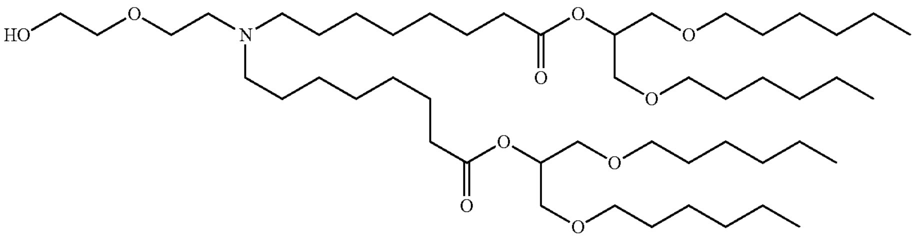

E34-1 corresponds to the general formula (1), wherein, $L_1$ and $L_2$ are both —OC(═O)—, $L_3$ is a linking bond, $B_1$ and $B_2$ are both heptylene groups, $R_1$ and $R_2$ are both

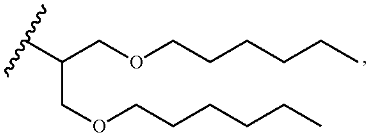

A is $—(CR_aR_b)_sO—$, $R_a$ and $R_b$ are both hydrogen atoms, s is 2, n is 2, and $R_3$ is a hydrogen atom. The molecular weight is approximately 874 Da.

The preparation process is as follows:

Step a: Under argon atmosphere, glycerol (S34-1, 3.09 g, 15.0 mmol) containing a TBS-protected hydroxy group, $K_2CO_3$ (6.21 g, 45.0 mmol), and 1-bromohexane (S34-2, 2.71 g, 16.5 mmol) were dissolved in 60 mL DMF. The mixture was stirred for 16 h at 110° C. After the completion of the reaction was confirmed by thin-layer chromatography, precipitation was performed by pouring the reaction solution into water (200 mL). The precipitate was filtered and dissolved in 100 mL THF, followed by adding 100 mL solution of TBAF in tetrahydrofuran (1M), and then the reaction was conducted overnight to remove the TBS protecting group. After the deprotection, the reaction solution was dried with anhydrous sodium sulfate, filtered, concentrated, and purified by silica gel column chromatography to obtain S34-3 (2.32 g).

Step b: Under argon atmosphere and into a round bottom flask containing S34-3 (1.72 g, 6.6 mmol), 8-bromooctanoicacid (S34-4, 1.33 g, 6.0 mmol), and DMAP (0.18 g, 1.5 mmol) dissolved in dichloromethane (30 mL), DCC (1.85 g, 9.0 mmol) was added and the reaction was conducted for 16 h at room temperature. After completion of the reaction, the precipitate was removed by filtering, and the filtrate was concentrated and purified by silica gel column chromatography to obtain S34-5 (2.33 g).

Step c: Under nitrogen protection, 50 mL acetonitrile was added, S34-5 (2.33 g, 5.0 mmol), S1-5 (0.21 g, 2.0 mmol), and DIPEA (0.26 g, 2.0 mmol) were added in sequence with stirring slowly, and reacted at room temperature for about 20 h with stirring. The reaction was continued until the material S1-5 was consumed completely according to the TLC. After completion of the reaction, the reaction solution was concentrated and dissolved in dichloromethane, and then extracted with a solution of 0.6M HCl/10% NaCl and a saturated solution of sodium bicarbonate in sequence. After ensuring that there was no product in the aqueous phase, the organic phases were combined and dried with anhydrous $MgSO_4$. The cationic lipid E34-1 (1.45 g) was obtained after filtration, concentration, and purification by silica gel column chromatography. The main data of $^1$H-NMR spectrum of E34-1 were as follows: $^1$H NMR (400 MHz, $CDCl_3$) δ: 4.97 (m, 2H), 3.70 (t, 2H), 3.63 (t, 4H), 3.59-3.40 (m, 16H), 2.65 (t, 2H), 2.49 (m, 4H), 2.30 (t, 4H), 1.71-1.21 (m, 52H), 0.87 (t, 12H). The molecular weight of E34-1 was determined to be 873.81 Da by MALDI-TOF.

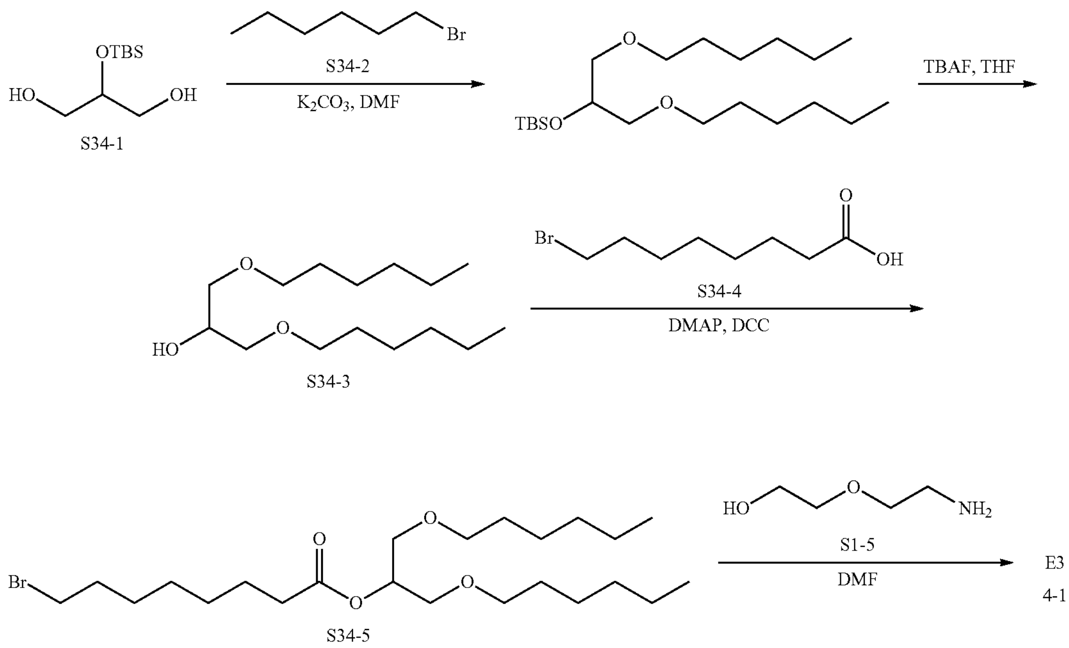

Following the preparation process of E34-1, the cationic lipid E34-2 (1.58 g) was obtained while adopting the same molar amounts of materials including S34-1, heptyl bromide (S34-6), S34-4, and S1-5. The structure is provided below:

E34-2

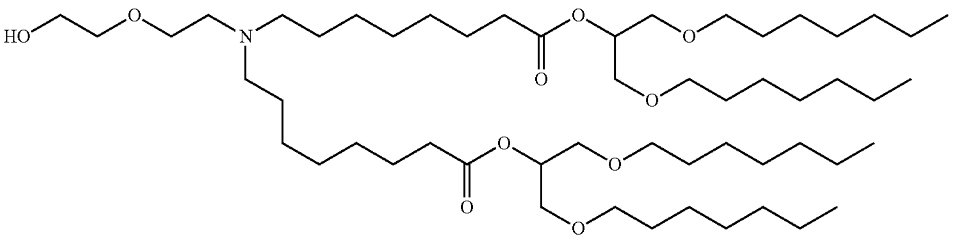

E34-2 corresponds to the general formula (1), wherein, $L_1$ and $L_2$ are both —OC(═O)—, $L_3$ is a linking bond, $B_1$ and $B_2$ are both heptylene groups, $R_1$ and $R_2$ are both

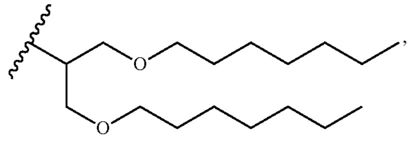

A is —$(CR_aR_b)_sO$—, $R_a$ and $R_b$ are both hydrogen atoms, s is 2, n is 2, and $R_3$ is a hydrogen atom. The molecular weight is approximately 930 Da.

The main data of $^1$H-NMR spectrum of E34-2 were as follows: $^1$H NMR (400 MHz, $CDCl_3$) δ: 4.97 (m, 2H), 3.70 (t, 2H), 3.63 (t, 4H), 3.59-3.40 (m, 16H), 2.65 (t, 2H), 2.49 (m, 4H), 2.30 (t, 4H), 1.72-1.21 (m, 60H), 0.87 (t, 12H). The molecular weight of E34-2 was determined to be 929.84 Da by MALDI-TOF.

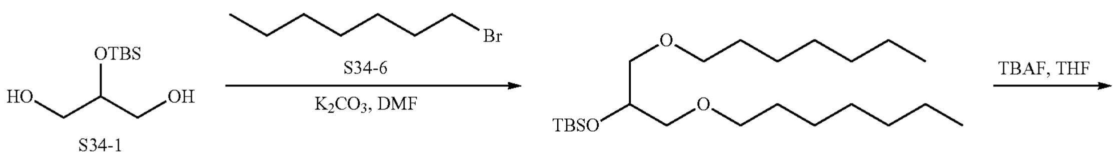

-continued

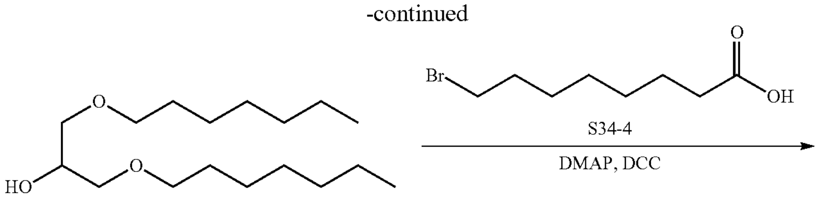

S34-7

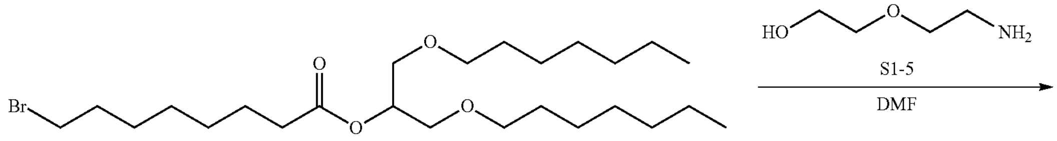

E34-2

S34-8

Example-35: Cationic Lipid (E35-1, E35-2)

E35-1

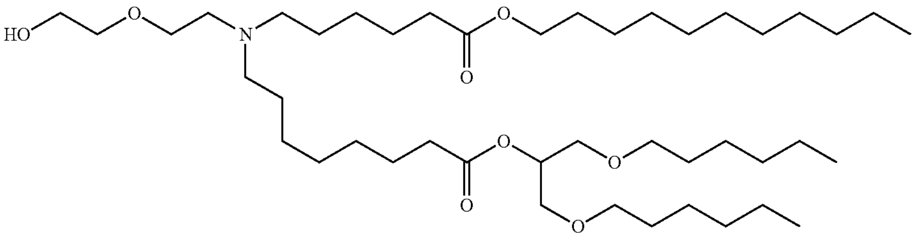

E35-1 corresponds to the general formula (1), wherein, $L_1$ and $L_2$ are both —OC(═O)—, $L_3$ is a linking bond, $B_1$ is a pentylene group, $B_2$ is a heptylene group, $R_1$ is an undecyl group, $R_2$ is

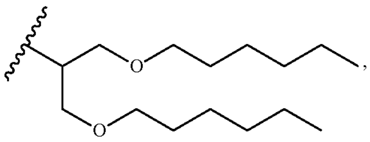

A is $—(CR_aR_b)_sO—$, $R_a$ and $R_b$ are both hydrogen atoms, s is 2, n is 2, and $R_3$ is a hydrogen atom. The molecular weight is approximately 758 Da.

The preparation process is as follows:

Compound S27-1 (2.84 g, 6.0 mmol) was dissolved in anhydrous THE (60 mL). Under ice bath, NaH (60%, 2.40 g, 60.0 mmol) was added slowly and the reaction was conducted for 1 h. Then, compound S34-5 (3.34 g, 7.2 mmol) was added, and the reaction was stirred for another 1 h before being brought back to room temperature and continued overnight. After completion of the reaction, the reaction solution was placed in an ice bath again, and 2 mL methanol was added slowly to quench the reaction. After 30 minutes of stirring, water (100 mL) was added to mixing with the solution while stirring. The mixture was extracted twice with EtOAc (100 mL*2). The aqueous phase was retained and extracted twice with dichloromethane (100 mL*2).

The organic phases were combined, backwashed with an aqueous saturated solution of sodium chloride (100 mL), dried with anhydrous sodium sulfate, filtered, and concentrated to obtain the crude product which was further purified by silica gel column chromatography, concentrated, and dried with an oil pump to obtain the cationic lipid E35-1 (3.37 g). The main data of $^1$H-NMR spectrum of E35-1 were as follows: $^1$H NMR (400 MHz, $CDCl_3$) δ: 4.97 (m, 1H), 4.07 (t, 2H), 3.70 (t, 2H), 3.63 (t, 4H), 3.59-3.40 (m, 8H), 2.65 (t, 2H), 2.49 (m, 4H), 2.30 (t, 4H), 1.71-1.21 (m, 50H), 0.88 (t, 9H). The molecular weight of E35-1 was determined to be 757.69 Da by MALDI-TOF.

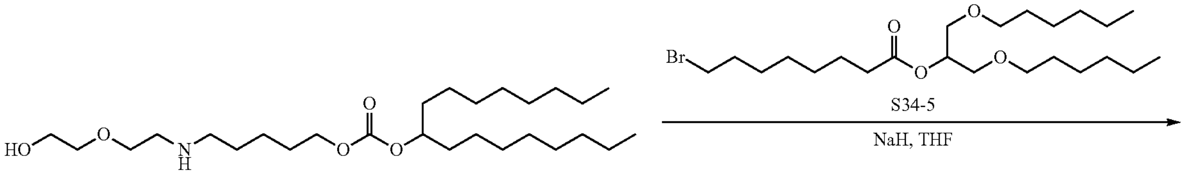

S27-1

E35-1

Following the preparation process of E35-1, the cationic lipid E35-2 (3.35 g) was obtained while adopting the same molar amounts of materials including S27-1 and S34-8. The structure is provided below:

E35-2

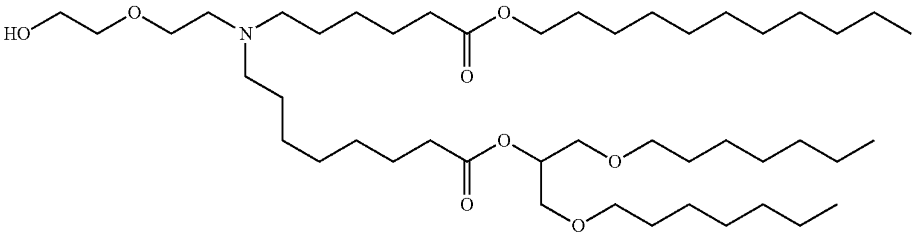

E35-2 corresponds to the general formula (1), wherein, $L_1$ and $L_2$ are both —OC(=O)—, $L_3$ is a linking bond, $B_1$ is a pentylene group, $B_2$ is a heptylene group, $R_1$ is an undecyl group, $R_2$ is

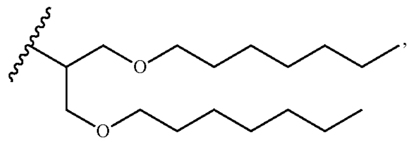

A is —$(CR_aR_b)_sO$—, $R_a$ and $R_b$ are both hydrogen atoms, s is 2, n is 2, and $R_3$ is a hydrogen atom. The molecular weight is approximately 786 Da.

The main data of $^1$H-NMR spectrum of E35-2 were as follows: $^1$H NMR (400 MHz, $CDCl_3$) δ: 4.97 (m, 1H), 4.07 (t, 2H), 3.70 (t, 2H), 3.63 (t, 4H), 3.59-3.40 (m, 8H), 2.65 (t, 2H), 2.49 (m, 4H), 2.30 (t, 4H), 1.70-1.22 (m, 54H), 0.88 (t, 9H). The molecular weight of E35-2 was determined to be 785.71 Da by MALDI-TOF.

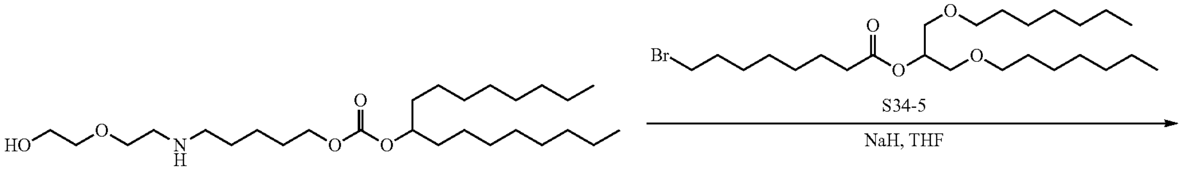

S27-1

E35-2

Example-36: Cationic Lipid (E36-1)

E36-1

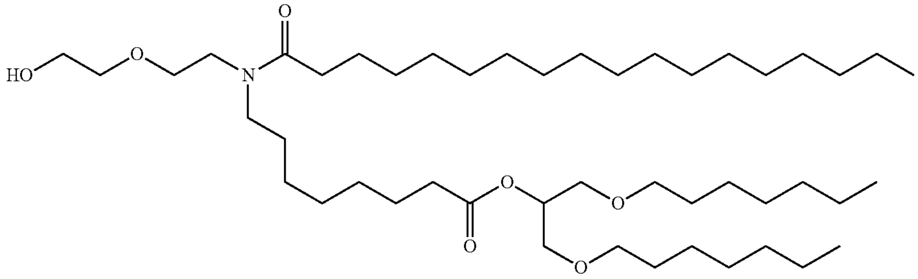

E36-1 corresponds to the general formula (1), wherein, $L_1$ is —C(═O)—, $L_2$ is —OC(═O)—, $L_3$ is a linking bond, $B_1$ is a linking bond, $B_2$ is a heptylene group, $R_1$ is an heptadecyl group, $R_2$ is

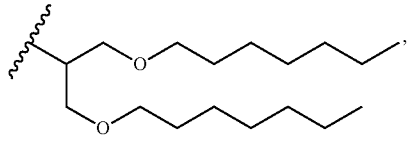

A is $-(CR_aR_b)_sO-$, $R_a$ and $R_b$ are both hydrogen atoms, s is 2, n is 2, and $R_3$ is a hydrogen atom. The molecular weight is approximately 874 Da.

The preparation process is as follows:

Step a: Under argon atmosphere and into a round bottom flask containing S34-7 (2.53 g, 8.8 mmol), 8-aminocaprylic acid with a Boc protecting group (S36-1, 2.07 g, 8.0 mmol), and DMAP (0.24 g, 2.0 mmol) dissolved in dichloromethane (100 mL), DCC (2.47 g, 12.0 mmol) was added, and then the reaction was conducted for 16 h at room temperature. After completion of the reaction, the precipitate was removed by filtering. Trifluoroacetic acid (TFA) was added until its concentration reached 0.1M. After 4 hours of reaction, the pH was adjusted to neutral. The reaction solution was concentrated, purified water was added, and the reaction solution was extracted with dichloromethane. The extract was concentrated, precipitated, filtered, dried, and purified by silica gel column chromatography in sequence to obtain the intermediate with a naked amino group S36-2 (2.82 g).

Step b: Diethylene glycol (S36-3, 0.36 g, 1.2 mmol) with one terminal hydroxyl group protected by TBS and the other terminal hydroxyl group protected by OMs was added into 50 mL water, and dissolved at room temperature with stirring. $K_2CO_3$ (1.66 g, 12.0 mmol), S36-2 (2.58 g, 6.0 mmol), and tetrabutylammonium bromide (0.04 g, 0.12 mmol) were added, and the reaction solution was stirred for 72 h at room temperature. After completion of the reaction, the reaction solution was extracted twice with dichloromethane (50 mL*2). The organic phases were combined and backwashed with a saturated aqueous solution of sodium chloride (50 mL). The organic phase was retained, dried with anhydrous sodium sulfate, filtered, concentrated, and purified by silica gel column chromatography to obtain the S36-4 (2.54 g).

Step c: Compound S36-4 (1.90 g, 3.0 mmol), stearic acid-N-hydroxysuccinimide ester (S36-5, 1.48 g, 3.6 mmol), and TEA (0.45 g, 4.5 mmol) were dissolved in dichloromethane (50 mL), and reacted overnight at room temperature with stirring. The reaction solution was concentrated and dissolved in 50 mL water, and then extracted twice with EtOAc (50 mL*2). The aqueous phase was retained and some sodium chloride was added before being extracted twice with dichloromethane (50 mL*2). The organic phases were combined, backwashed with a saturated aqueous solution of sodium chloride (50 mL), and concentrated under reduced pressure. THE (30 mL) and a solution of TBAF in tetrahydrofuran (1M, 30 mL) were added to the residue of concentration, the reaction was conducted overnight to remove the TBS protecting group. Then, the reaction solution was dried with anhydrous sodium sulfate, filtered, concentrated, and purified by silica gel column chromatography to obtain cationic lipid E36-1 (1.98 g). The main $^1$H-NMR spectrum data were as follows: $^1$H NMR (500 MHz, $CDCl_3$) δ: 4.97 (m, 1H), 3.70 (t, 2H), 3.63-3.42 (m, 12H), 3.35 (t, 2H), 3.16 (t, 2H), 2.30 (t, 2H), 2.23 (t, 2H), 1.72-1.25 (m, 60H), 0.89 (t, 9H). The molecular weight of E36-1 was determined to be 783.78 Da by MALDI-TOF.

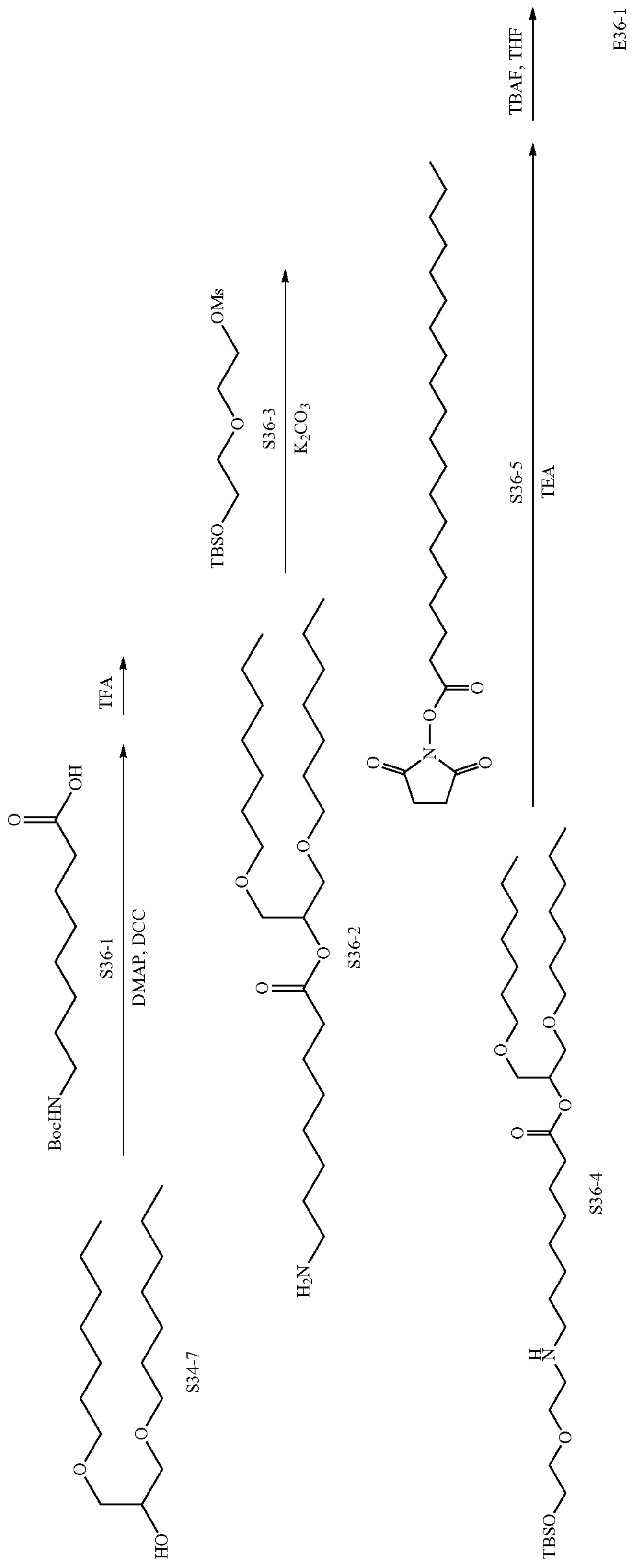
S34-7
S36-1
DMAP, DCC
TFA
S36-2
S36-3
$K_2CO_3$
S36-4
S36-5
TEA
TBAF, THF
E36-1

Example-37: Cationic Lipid (E37-1)

E37-1

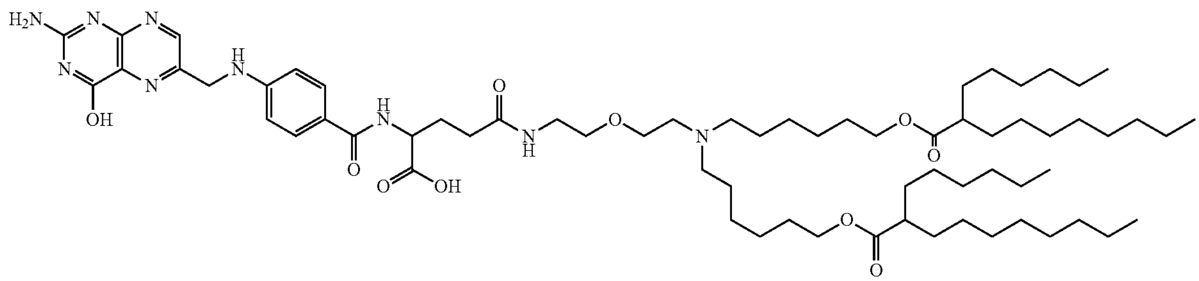

E37-1 corresponds to the general formula (1), wherein, $L_1$ and $L_2$ are both —C(=O)O—, $L_3$ is a linking bond, $B_1$ and $B_2$ are both hexylene groups, $R_1$ and $R_2$ are both

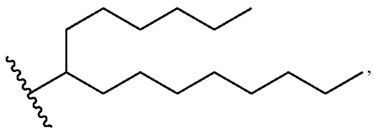

,

A is $-(CR_aR_b)_sO(CR_aR_b)_sNR_c-$, $R_a$, $R_b$, and $R_c$ are all hydrogen atoms, s is 2, n is 1, and $R_3$ is

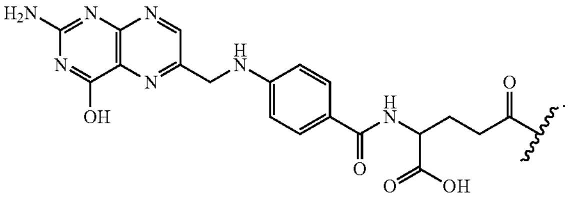 [SMILES: *C(=O)CCC(NC(=O)c1ccc(NCc2cnc3nc(N)nc(O)c3n2)cc1)C(=O)O]

.

The molecular weight is approximately 1204 Da.

The preparation process is as follows:

Into a dry and clean 250 mL round bottom flask, folic acid (S37-2, 3.75 g, 8.5 mmol), E20-2 (3.90 g, 5.0 mmol), pyridine (40 mL), and DCC (4.64 g, 22.5 mmol) dissolved in DMSO were added, and reacted at room temperature for 4 h with stirring. After completion of the reaction, the reaction solution was concentrated under reduced pressure by rotary evaporation to remove pyridine, and the residue was extracted twice with 100 mL DCM. The organic phases were combined, dried with anhydrous sodium sulfate, filtered, and concentrated to obtain the crude product. The crude product was purified by silica gel column chromatography and the eluent of interest was collected and concentrated to obtain the cationic lipid E37-1 (5.59 g, 92.8%). The main $^1$H-NMR spectrum data were as follows: $^1$H NMR (500 MHz, $CDCl_3$) δ: 8.68 (s, 1H), 7.68 (d, 1H), 6.67 (d, 1H), 4.51 (d, 2H), 4.36 (m, 1H), 4.06 (m, 4H), 3.83-3.45 (m, 6H), 2.63 (t, 2H), 2.53 (t, 4H), 2.34 (t, 2H), 2.18 (m, 2H), 2.08-1.94 (m, 2H), 1.56-1.46 (m, 8H), 1.36-1.19 (m, 56H), 0.88 (t, 12H). The molecular weight of E37-1 was determined to be 1203.87 Da by MALDI-TOF.

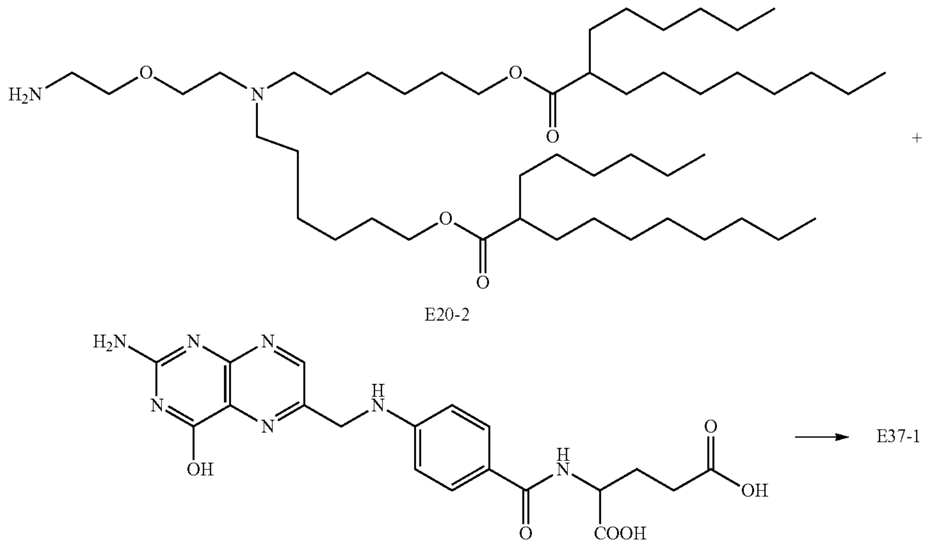

E20-2

S37-2

Example-38: Cationic Lipid (E38-1)

E38-1

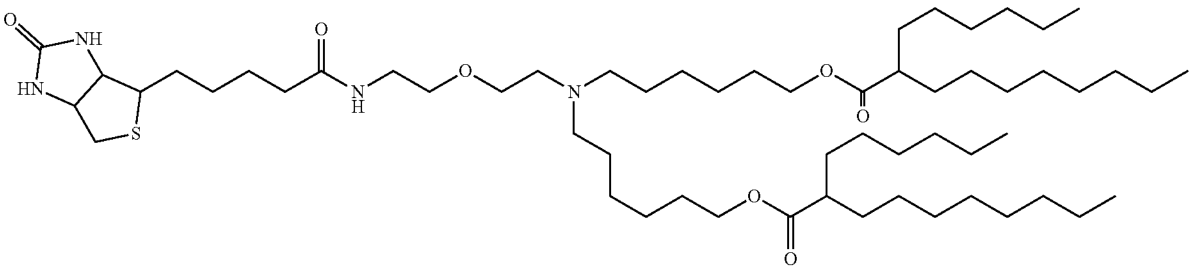

E38-1 corresponds to the general formula (1), wherein, $L_1$ and $L_2$ are both —C(=O)O—, $L_3$ is a linking bond, $B_1$ and $B_2$ are both hexylene groups, $R_1$ and $R_2$ are both,

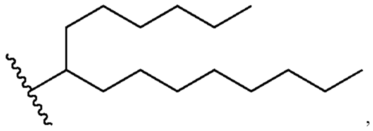

A is $-(CR_aR_b)_sO(CR_aR_b)_sNR_c-$, $R_a$, $R_b$, and $R_c$ are all hydrogen atoms, s is 2, n is 1, and $R_3$ is

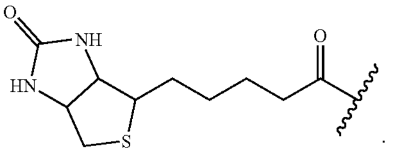 [SMILES: *C(=O)CCCCC1SCC2NC(=O)NC21]

The molecular weight is approximately 1006 Da.

The preparation process is as follows:

Into a dry and clean 250 mL round bottom flask, biotin succinimide ester (S38-1, 1.88 g, 5.5 mmol) dissolved in DMF and S37-1 (3.90 g, 5.0 mmol) dissolved in DCM were added. After being adequately mixed by stirring, triethylamine (2.3 mL, 16.5 mmol) was also added. The reaction was conducted at room temperature until completed, which was monitored by TLC. Then, the reaction solution was filtered, concentrated, and purified by silica gel column chromatography. The eluent of interest was collected, concentrated, and freeze-dried to obtain the cationic lipid E38-1 (3.65 g, 72.5%). The main $^1$H-NMR spectrum data were as follows: $^1$H NMR (500 MHz, $CDCl_3$) δ: 4.18 (s, 2H), 4.06 (m, 4H), 3.84-3.55 (m, 6H), 3.27 (m, 1H), 2.83 (d, 2H), 2.63 (t, 2H), 2.52 (t, 4H), 2.22-2.18 (m, 4H), 1.70-1.40 (m, 12H), 1.36-1.19 (m, 58H), 0.87 (t, 12H). The molecular weight of E38-1 was determined to be 1006.62 Da by MALDI-TOF.

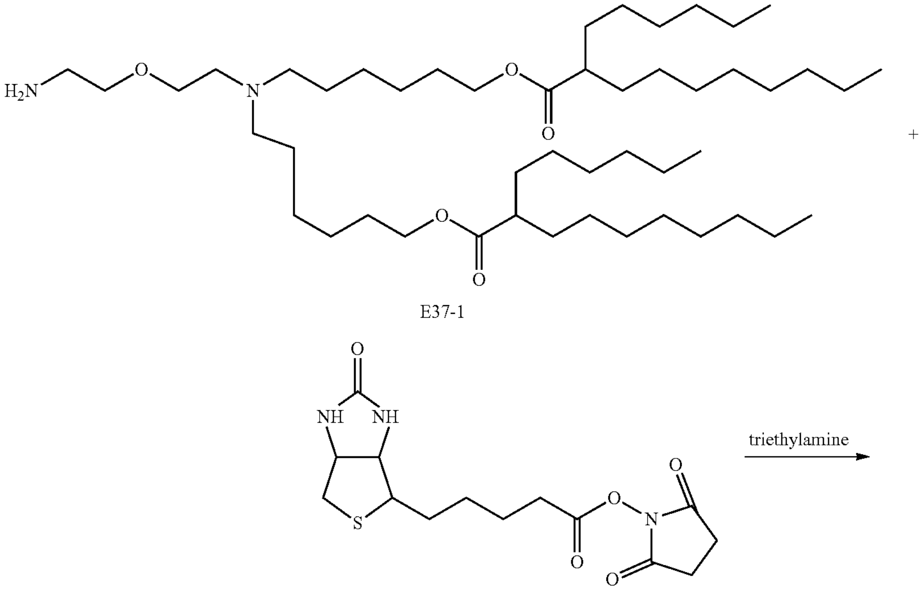

E37-1

S38-1

-continued

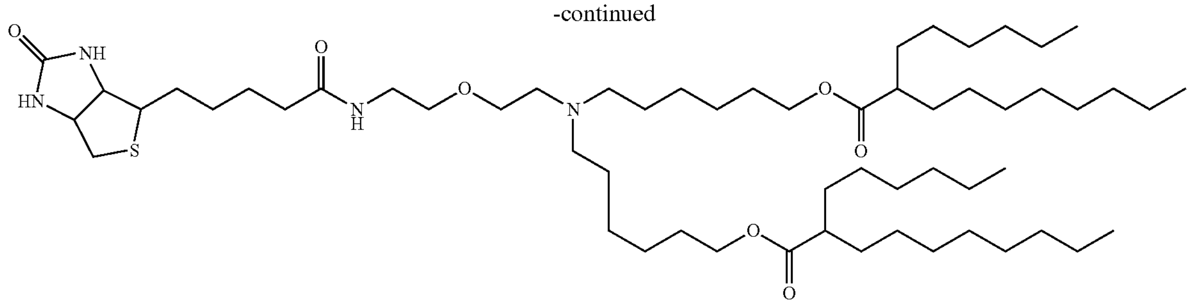

E38-1

Example-39: Preparation of PEGylated Lipid E39-1

Example-39.1: Preparation of PEGylated Lipid E39-1

E39-1

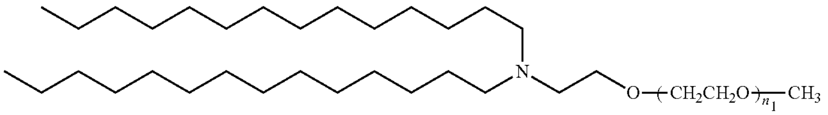

E39-1 corresponds to the general formula (2), wherein, $R_1$ and $R_2$ are both tetradecyl groups, $B_3$ and $B_4$ are both linking bonds, $L_7$ and $L_8$ are both linking bonds, $L_3$ is $—CH_2CH_2O—$ or $—CH_2CH_2—$, A is $—CH_2CH_2O—$ or $—OCH_2CH_2—$, $n_1 \approx 45$, and R is a methyl group or a methoxy group. The molecular weight is approximately 2450 Da.

The preparation process is as follows:

Step a: Compound S39-1 (20.00 g, 10.0 mmol, mPEG-OH, $M_w \approx 2000$, $n_1 \approx 45$, PDI=1.03) and toluene (200 mL) underwent azeotropic water removal at 140° C. After 60 mL of solvent was distilled off, the reaction temperature was reduced to room temperature. TEA (2.02 g, 20.0 mmol) and MsCl (2.05 g, 18.0 mmol) were added and the reaction was stirred at room temperature overnight. After completion of the reaction, the reaction solution was poured into water (200 mL) and extracted twice with EtOAc (100 mL*2). The aqueous phase was retained and extracted twice with dichloromethane (100 mL*2). The organic phases were combined, dried, filtered, concentrated, dissolved with isopropanol at 50° C., and then recrystallized in an ice bath. After filtration, compound S39-2 (18.00 g, 90%) was obtained.

Step b: Compound S39-2 (18.00 g, 9.0 mmol) was dissolved with 80 mL water with stirring at room temperature. Potassium carbonate (12.42 g, 90.0 mmol), compound S39-3 (9.58 g, 45.0 mmol), and tetrabutylammonium bromide (0.29 g, 0.9 mmol) were added, and reacted at room temperature for 72 h with stirring. After completion of the reaction, the reaction solution was extracted twice with dichloromethane (100 mL*2), and the organic phases were combined and backwashed with a saturated aqueous solution of sodium chloride (100 mL). The organic phase was retained, dried with anhydrous sodium sulfate, filtered, and concentrated to obtain crude product which was further purified by silica gel column chromatography, concentrated, and dried with an oil pump to obtain the target compound S39-4 (12.00 g).

Step c: Compound S39-4 (12.00 g, 6.0 mmol) was dissolved in anhydrous THE (120 mL). Under ice bath, NaH (60%, 2.40 g, 60.0 mmol) was added slowly and the reaction was conducted for 1 h. Then, compound S39-5 (8.28 g, 30.0 mmol) was added and the reaction was stirred for another 1 h before being brought back to room temperature and continued overnight. After completion of the reaction, the reaction solution was placed in an ice bath, and 2 mL methanol was added slowly to quench the reaction. After 30 minutes of stirring, 300 mL water was added to mixing with the solution while stirring. The mixture was extracted twice with EtOAc (150 mL*2). The aqueous phase was retained and extracted twice with dichloromethane (100 mL*2). The organic phases were combined and backwashed with a saturated aqueous solution of sodium chloride (100 mL), dried with anhydrous sodium sulfate, filtered, and concentrated to obtain the crude product which was further purified by silica gel column chromatography, concentrated, and dried with an oil pump to obtain the PEGylated lipid E39-1 (9.00 g, 75%). The main data of $^1$H-NMR spectrum of E39-1 were as follows: $^1$H NMR (500 MHz, $CDCl_3$) δ: 3.85-3.45 (m, 182H), 3.37 (s, 3H), 3.15 (t, 2H), 2.94 (t, 2H), 2.62 (t, 2H), 1.58-1.48 (m, 4H), 1.36-1.19 (m, 44H), 0.86 (t, 6H). The molecular weight of E39-1 was determined to be 2447 Da by MALDI-TOF, PDI=1.03.

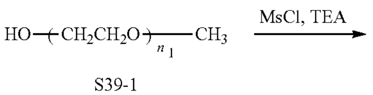

S39-1

-continued

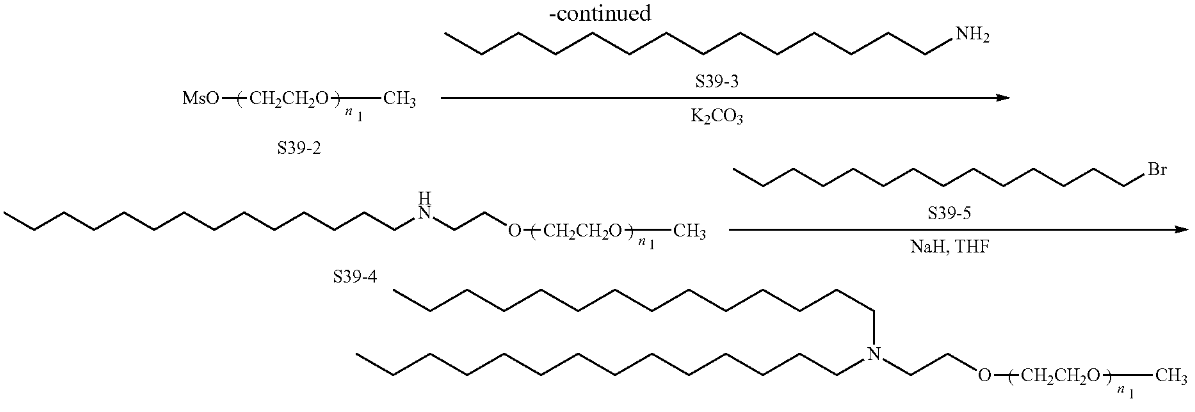

S39-1

Example-39.2: Preparation of PEGylated Lipid E39-2

E39-2

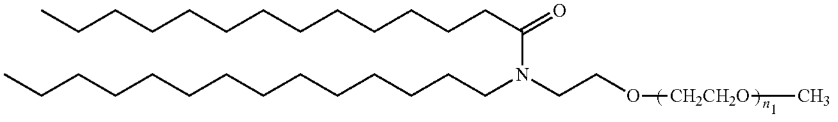

E39-2 corresponds to the general formula (2), wherein, $R_1$ is a tridecyl group, $R_2$ is a tetradecyl groups, $B_3$ and $B_4$ are both linking bonds, $L_7$ is a carbonyl group, $L_8$ is a linking bond, $L_3$ is $—CH_2CH_2—$, A is $—OCH_2CH_2—$, $n_1≈45$, and R is a methoxy group. The molecular weight is approximately 2460 Da.

The preparation process is as follows:

Compound S39-4 (11.26 g, 5.0 mmol), S39-5 (1.95 g, 6.0 mmol), and triethylamine (TEA, 0.76 g, 7.5 mmol) were dissolved in dichloromethane (100 mL), and reacted at room temperature overnight with stirring. Then, the reaction solution was concentrated, dissolved with 100 mL water, and extracted twice with EtOAc (100 mL*2). The aqueous phase was retained and added with some sodium chloride before being extracted twice with dichloromethane (100 mL*2). The organic phases were combined and backwashed with a solution of NaCl (100 mL). The organic phases were dried with anhydrous $MgSO_4$. The crude product was obtained after filtration and concentration, and further purified by silica gel column chromatography (DCM:MeOH=10:1), concentrated, and dried with an oil pump to obtain the target compound E39-2 (10.1 g, 84.8%). The main data of $^1$H-NMR spectrum of E39-2 were as follows: $^1$H NMR (500 MHz, $CDCl_3$) δ: 3.84-3.45 (m, 182H), 3.37 (s, 3H), 3.35 (t, 2H), 3.18 (t, 2H), 2.27 (t, 2H), 1.56-1.40 (m, 4H), 1.36-1.18 (m, 46H), 0.87 (t, 6H). The molecular weight of E39-2 was determined to be 2461 Da by MALDI-TOF, PDI=1.03.

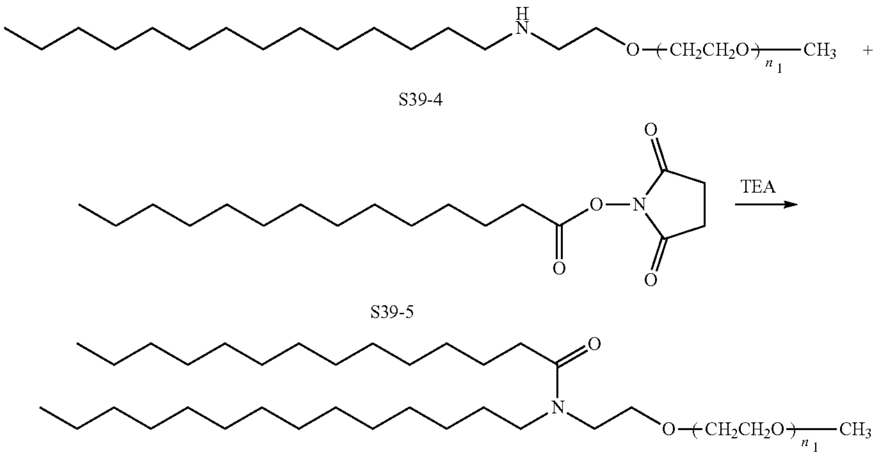

S39-2

Example-40: Preparation of Cationic Liposomes

In this embodiment, multiple groups of cationic liposomes were prepared for comparison. In the composition of each group of cationic liposomes, the neutral lipid was DSPC and the sterol lipid was cholesterol, while the difference lied in the cationic lipids and the PEGylated lipids; wherein, for the control group, the cationic lipid was DLin-MC3-DMA (MC3 for short) and the PEGylated lipid was PEG2k-DMG (DMG for short); for experimental groups L-1 to L-18, and L-29, the cationic lipids were the those prepared in the foregoing examples, and the PEGylated lipids were PEG-DMG; for experimental groups L-19 to L-28, the cationic lipids were the those prepared in the foregoing examples, and the PEGylated lipids were the PEGylated lipid E39-1 or E39-2; specific details are shown in Table 1.

The preparation process for cationic liposomes is as follows:

Step a: The cationic lipid CL (15.0 μmol), distearoylphosphatidylcholine (DSPC, 3.0 μmol), cholesterol (12.0 μmol), and the PEGylated lipid PL (0.45 μmol) at a molar ratio of 50:10:40:1.5 were weighed for each group from L-0 to L-28 listed in Table 1, and added into a 100 mL round-bottom flask. Then, 30 mL chloroform was added to dissolve the solids and shaked well;

Step b: The solvent (chloroform) was removed by rotary evaporator at 140 rpm and 55° C. to generate a thin oil film which was dried with a vacuum pump for 12 h to ensure the chloroform was removed completely;

Step c: Into a flask, 30 mL phosphate buffer (PBS, pH=7.4) containing 10% lactose was added. The reaction solution was sonicated by an ultrasonic cleaner at 90% frequency for 30 min to generate a translucent emulsion;

Step d: The emulsion was added into a high-pressure homogenizer, and overpressurized for 5 times under the pressure of 100 MPa; then, the emulsion was added into the liposome extruder and extruded for 10 times under the pressure of 150 MPa to prepare cationic liposome powders of groups L-0 to L-28.

Following the above steps and conditions but with cationic lipid, DSPC, cholesterol, and PEGylated lipid at another molar ratio of 48:9:42:1.5, the cationic lipid CL (16.0 μmol), distearoylphosphatidylcholine (DSPC, 3.0 μmol), cholesterol (14.0 μmol), and the PEGylated lipid PL (0.5 μmol) were weighed and used to prepare the cationic liposome powder of L-29.

Example-41: Preparation of Cationic Liposome-Nucleic Acid Pharmaceutical Compositions and Formulations Thereof Step a: 0.03 mL physiological saline was used as the working solution for the formulations of nucleic acid pharmaceutical compositions;

Step b: 0.1 mg cationic liposome (from L-0 to L-29) prepared according to Example-40 was weighed, dissolved in physiological saline, and equilibrated for 30 min. The N/P ratio was 10/1, according to which, 1.00 μg siRNA was weighed, dissolved in 10 μL physiological saline, and complexed with cationic liposomes dissolved in physiological saline for 30 min to prepare a control group (L-0/siRNA) and formulations of cationic liposome-nucleic acid pharmaceutical compositions ("LNP/siRNA formulations" for short, including L-1/siRNA~L-29/siRNA) of the present invention.

Example-42: Biological Activity Assays for the Formulations of Cationic Liposome-Nucleic Acid Pharmaceutical Compositions (1) Determination of Nanoparticle Size and Gene Complexation Ability Gel electrophoresis experiment was used to evaluate the gene complexation ability of the LNP/siRNA of each group. 0.8 g agarose was weighed and dissolved in 40 mL TAE solution. The solution was heated in a microwave until the granules of agarose were completely dissolved, and then cooled. 5 μL nucleic acid dye (GelGreen) was added in the cooled agarose gel, and then the agarose gel was added into the gel slot and dried with natural air. LNP/siRNA mixed with 2 μL loading buffer was added into the agarose gel well, and the electrophoresis voltage was set to 90 V. The electrophoresis was carried out at room temperature for 10 min. The results showed that free siRNA was essentially absent in both the experimental groups (L-1/siRNM~L-29/siRNA) and the control group (L-1/siRNA), indicating that the formulations of cationic liposome-nucleic acid pharmaceutical compositions prepared with the cationic lipids of the present invention had high gene complexation ability and the ionizable cationic lipids could adequately combine with negatively charged nucleic acids because of their partial positive charges.

TABLE 1

Summary of the liposome formulations and the particle size and encapsulation efficiency of LNP/siRNA prepared with the liposomes

| Liposome | L-0 | L-1 | L-2 | L-3 | L-4 | L-5 |
|---|---|---|---|---|---|---|
| Cationic lipid CL | MC3 | E1-1 | E2-1 | E4-1 | E7-2 | E10-1 |
| PEGylated lipid PL | | | DMG | | | |
| Particle size/nm | 91.25 | 96.01 | 106.32 | 102.37 | 123.15 | 117.63 |
| Encapsulation efficiency/% | 93.1 | 93.7 | 85.2 | 92.1 | 75.4 | 83.6 |
| Liposome | L-6 | L-7 | L-8 | L-9 | L-10 | L-11 |
| Cationic lipid CL | E16-4 | E17-4 | E20-1 | E22-1 | E23-1 | E24-1 |
| PEGylated lipid PL | | | DMG | | | |
| Particle size/nm | 105.37 | 92.07 | 116.43 | 95.39 | 100.19 | 101.21 |
| Encapsulation efficiency/% | 90.5 | 88.3 | 83.2 | 87.8 | 85.2 | 86.7 |

TABLE 1-continued

Summary of the liposome formulations and the particle size and encapsulation efficiency of LNP/siRNA prepared with the liposomes

| Liposome | L-12 | L-13 | L-14 | L-15 | L-16 | L-17 |
|---|---|---|---|---|---|---|
| Cationic lipid CL | E25-1 | E33-1 | E34-1 | E34-2 | E35-1 | E35-2 |
| PEGylated lipid PL | DMG | | | | | |
| Particle size/nm | 103.83 | 102.62 | 98.25 | 105.12 | 98.41 | 99.83 |
| Encapsulation efficiency/% | 83.8 | 91.6 | 94.5 | 95.1 | 93.2 | 92.8 |
| **Liposome** | **L-18** | **L-19** | **L-20** | **L-21** | **L-22** | **L-23** |
| Cationic lipid CL | E36-1 | E1-1 | E1-1 | E16-4 | E16-4 | E33-1 |
| PEGylated lipid PL | DMG | E39-1 | E39-2 | E39-1 | E39-2 | E39-1 |
| Particle size/nm | 102.79 | 103.51 | 106.07 | 97.55 | 95.10 | 103.82 |
| Encapsulation efficiency/% | 90.4 | 90.3 | 92.7 | 89.5 | 90.2 | 88.9 |
| **Liposome** | **L-24** | **L-25** | **L-26** | **L-27** | **L-28** | **L-29** |
| Cationic lipid CL | E33-1 | E34-1 | E34-1 | E35-1 | E35-1 | E1-1 |
| PEGylated lipid PL | E39-2 | E39-1 | E39-2 | E39-1 | E39-2 | DMG |
| Particle size/nm | 105.18 | 104.23 | 107.20 | 96.72 | 98.29 | 93.95 |
| Encapsulation efficiency/% | 93.7 | 89.6 | 92.8 | 91.4 | 93.6 | 94.1 |

Determination of encapsulation efficiency: The LNP/siRNA was ultracentrifuged (4° C., 60000 rpm, 1 h) with an ultracentrifuge. The concentration of unencapsulated siRNA in the supernatant was determined by a nucleic acid quantifier. The encapsulation efficiency of the liposomes for siRNA was calculated. The results are summarized in Table 1, which indicate that the cationic liposomes of the present invention (L-1~L-29) had higher encapsulation efficiency for nucleic acid drugs. MC3 is a well-established cationic liposome commercially available. With the same PEGylated lipid DMG, the encapsulation efficiency of L-1 containing the cationic lipid E1-1, L-3 containing the cationic lipid E4-1, L-14 containing the cationic lipid E34-1, L-15 containing the cationic lipid E34-2, and L-16 containing the cationic lipid E35-1 of the present invention for siRNA were all higher than that of MC3; L-19-L-28 containing the PEGylated lipids prepared in the present invention also showed higher encapsulation efficiency; the cationic liposome L-29 which was prepared with a different ratio of lipids showed higher encapsulation efficiency for nucleic acid as well.

Determination of particle size: In this embodiment, the particle size of LNP/siRNA was determined by dynamic light scattering (DLS). The measured size of LNP/siRNA had a relatively high uniformity, and the PDI values were all smaller than 0.3. The particle sizes of LNP/siRNA prepared with the cationic liposomes of the present invention were in the range of 90-120 nm.

(2) Assays for Cytotoxicity (Biocompatibility)

The cytotoxicity of the formulations of cationic liposome-nucleic acid pharmaceutical compositions in the present invention was examined by MTT assay. The formulations of cationic liposome-nucleic acid pharmaceutical compositions were dissolved in the culture medium and prepared to the required concentration, and an appropriate amount of solubilizer could be added when necessary. Using the HeLa cell model at a density of $1\times10^4$ cells/well, the cell suspension was inoculated into a 96-well plate (100 μL/well). After inoculation, the cells were incubated in a cell incubator at 37° C., 4% $CO_2$ for 24 h. After 24 hours of incubation, the culture medium was discarded. Then, 100 μL culture medium containing 3.3 μg/mL LNP/siRNA (formulation of cationic liposome-nucleic acid pharmaceutical composition prepared according to Example-41) was added into each well of the experimental group; 100 L fresh culture medium was added into each well of the blank control group; each group at each concentration used 6 wells. The Hela cells were incubated with the formulations of cationic liposome-nucleic acid pharmaceutical compositions for 24 h, followed by adding 20 L PBS solution containing 5 mg/mL MTT into each well. After incubation with MTT for 4 h, the mixture of cell medium and MTT-containing buffer was discarded, followed by adding 150 L DMSO per well to dissolve the purple formazan crystals formed in living cells. After shaking sufficiently, the absorbance was determined using a microplate reader. According to the results calculated from the measured absorbance, the cell survival of the formulations of cationic liposome-nucleic acid pharmaceutical compositions prepared in the present invention were all over 95% in contrast to the blank control group, indicating that the formulations modified with the PEGylated lipids of the present invention offered great biocompatibility.

(3) Assays for the Transport Efficiency of Nucleic Acids

In order to examine the efficiency of nucleic-acid transport using the formulations of cationic liposome-nucleic acid pharmaceutical compositions prepared with the cationic lipids of the present invention, the Luc-Hela cells which could stably express luciferase were used as the model to evaluate the nucleic-acid transport efficiency for said formulations (according to Example-41) at the N/P ratio of 10/1. When the cell density reached 80% in the 96-well plate, said formulations were each respectively added to the culture medium. The cells were incubated in a cell incubator at 37° C., 4% $CO_2$ for 24 h. Then, the culture medium was discarded and replaced by one containing 3.3 μg/mL LNP/siRNA for further incubation for 24 h. After incubation, the cells were treated with lysis buffer, and the fluorescent intensity was measured using a luciferase assay kit and a chemiluminescence detector. Another group (the siRNA group) was set up with naked siRNA added to the cultured cells at the same dose. Considering that the transfected siRNAs could inhibit the expression of the luciferase gene (or Fluc mRNA), the untreated cells were used as the negative control group (i.e., the blank cell group). The expression (fluorescent intensity) of the target gene in the blank cell group was designated as 100%. The results were shown in FIG. 1. The fluorescent intensity of the siRNA group was approximately 78%, that of the L-0/siRNA group was approximately 43%, that of the L-1/siRNA group was approximately 33%, that of the L-3/siRNA group was approximately 35%, that of the L-9/siRNA group was approximately 48%, that of the L-14/siRNA group was approximately 34%, and that of the L-26/siRNA group was approximately 36%. Compared with the blank cell group and the siRNA group, the positive control group (i.e., the control group L-0/siRNA) and the experimental groups (L-1/siRNA~L-29/siRNA) showed good inhibitory effect on the luciferase gene, indicating that cationic liposomes could improve the transport efficiency of nucleic acid drugs. Moreover, all the experimental groups except L-9/siRNA had better inhibitory effect on the luciferase gene than the control group L-0/siRNA, indicating that the cationic liposomes prepared with the cationic lipids of the present invention could improve the nucleic acid transport efficiency to a greater extent.

Those described above are only embodiments of the present invention, and are not for the purpose of limitation. Any modification of equivalent structures or equivalent routes according to the present invention, which may be applied in other related art in a direct or an indirect way, should be included into the scope of the present invention.

For those skilled in the art, without departing from the spirit and scope of the present invention, and without unnecessary experimentation, the present invention can be implemented in a wider range under equivalent parameters, concentrations, and conditions. While the present invention has given particular examples, it should be understood that the present invention can be further modified. In conclusion, in accordance with the principles of the present invention, the present application is intended to cover any alterations, uses, or improvements of the present invention, including changes departing from the scope disclosed in this application but made using conventional techniques known in the art.

What is claimed is:

1. A cationic lipid, wherein, the structure is represented by the general formula (1):

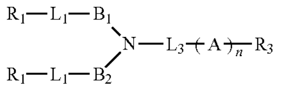

(1)

wherein N is the nitrogen-atom branching center;

wherein one of $L_1$ and $L_2$ is —OC(═O)—, —C(═O)O—, or —OC(═O)O—, the other is —C(═O)O—, —OC(═O)O—, or —C(═O)—; wherein; $L_3$ is selected from the group consisting of a linking bond, -$L_4$-, —Z-$L_4$-, -$L_4$-Z—, —Z-$L_4$-Z—, -$L_4$-Z-$L_5$-, —Z-$L_4$-Z-$L_5$-, and -$L_4$-Z-$L_5$-Z—;

wherein, said $L_4$ and $L_5$ are carbon-chain linking groups, each independently represented by $—(CR_aR_b)_t—(CR_aR_b)_o—(CR_aR_b)_p—$; wherein t, o, and p are each independently an integer from 0 to 12, not being 0 simultaneously; wherein $R_a$ and $R_b$ are, at each occurrence, independently a hydrogen atom or a $C_{1-6}$ alkyl group; wherein said Z is, at each occurrence, independently selected from the group consisting of —C(═O)—, —OC(═O)—, —C(═O)O—, —OC(═O)O—, —O—, —S—, —C(═O)S—, —SC(═O)—, $—NR_cC(═O)—$, $—C(═O)NR_c—$, $—NR_cC(═O)NR_c—$, $—OC(═O)NR_c—$, $—NR_cC(═O)O—$, $—SC(═O)NR_c—$, $—NR_cC(═O)S—$, and

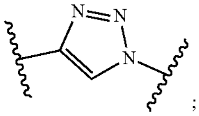 [SMILES: *c1cn(*)nn1]

;

and wherein $R_c$ is, at each occurrence, independently a hydrogen atom or a $C_{1-12}$ alkyl group;

wherein $B_1$ and $B_2$ are each independently a linking bond or a $C_{1-30}$ alkylene group;

wherein $R_1$ and $R_2$ are each independently a $C_{5-30}$ aliphatic group or

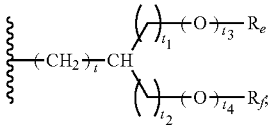

;

wherein t is an integer from 0 to 12; wherein $t_1$ and $t_2$ are each independently an integer from 0 to 5; wherein; $t_3$ and $t_4$ are each 1; and wherein $R_e$ and $R_f$ are each independently selected from the group consisting of a $C_{1-15}$ alkyl group, a $C_{2-15}$ alkenyl group, and a $C_{2-15}$ alkynyl group;

wherein $R_3$ comprises H, $—(CH_2)_tOH$, $—(CH)_tSH$, $—OCH_3$, $—OCH_2CH_3$, $—(CH_2)_tNH_2$, $—(CH_2)_tC(═O)OH$, $—C(═O)(CH_2)_tC(═O)OH$, $—C(═O)CH_3$, $—(CH_2)_tN_3$, $—C(═O)CH_2CH_3$, $—C(═O)OCH_3$, $—OC(═O)OCH_3$, $—C(═O)OCH_2CH_3$, $—OC(═O)OCH_2CH_3$, $—(CH_2)_tN(CH_3)_2$, $—(CH_2)_tCHO$,

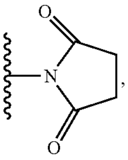

,

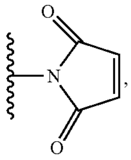

,

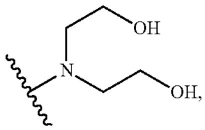

,

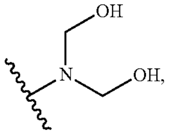

,

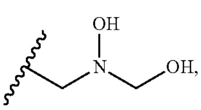

, or

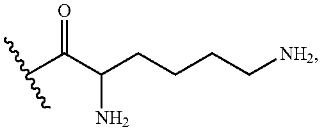

, wherein t is an integer from 0 to 12;

wherein A is $—CH_2CH_2O—$ or $—OCH_2CH_2—$, and n is an integer from 2 to 6; and wherein said alkyl group, alkylene group, alkoxy group, and aliphatic hydrocarbon group are each independently substituted or unsubstituted.

2. The cationic lipid according to claim 1, wherein said $B_1$ and $B_2$ are each independently a linking bond or a $C_{1-20}$ alkylene group.

3. The cationic lipid according to claim 1, wherein said $L_3$ is selected from the group consisting of a linking bond, $—(CH_2)_t—$, $—(CH_2)_tZ—$, $—Z(CH_2)_t—$, $—(CH_2)_tZ(CH_2)_t—$, and $—Z(CH_2)_tZ—$; wherein t is an integer from 1 to 12.

4. The cationic lipid according to claim 1, wherein said $R_3$ comprises a hydrogen atom, an alcoholic hydroxyl group, a thiol group, a carboxyl group, an amino group, an aldehyde group, an ester group, a succinimidyl group, a maleimido group, a dimethylamino group, or an azido group.

5. The cationic lipid according to claim 1, wherein said $L_1$ and $L_2$ are selected from one of the following Groups:

Group (1): $L_1$ and $L_2$ are both —C(=O)O—, or both —OC(=O)O—;

Group (2): one of $L_1$ and $L_2$ is selected from the group consisting of —OC(=O)—, —C(=O)O—, and —OC(=O)O—, and the other is —C(=O)—.

6. The cationic lipid according to claim 1, wherein; the $C_{5-30}$ aliphatic group of said $R_1$ and $R_2$ is each independently a linear alkyl group, a branched alkyl group, a linear alkenyl group, a branched alkenyl group, a linear alkynyl group, or a branched alkynyl group.

7. The cationic lipid according to claim 1, wherein the $C_{5-30}$ aliphatic group of said $R_1$ and $R_2$ is each independently represented as

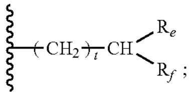;

wherein $R_e$ and $R_f$ are each independently selected from the group consisting of a $C_{1-15}$ alkyl group, a $C_{2-15}$ alkenyl group, and a $C_{2-15}$ alkynyl group.

8. The cationic lipid according to claim 7, wherein; $R_1$ and $R_2$ are each independently selected from the group consisting of the following structures:

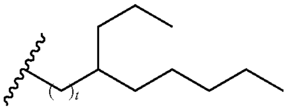,

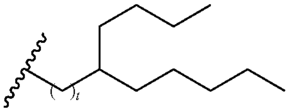,

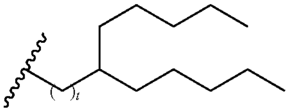,

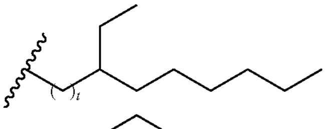,

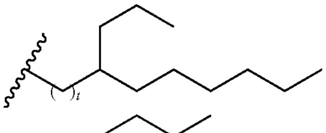,

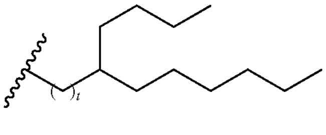,

-continued

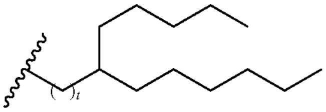,

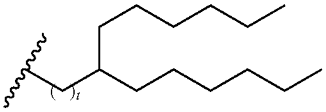,

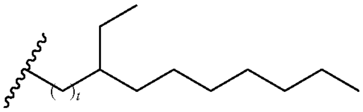,

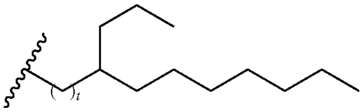,

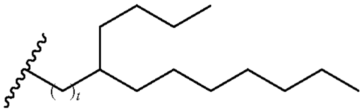,

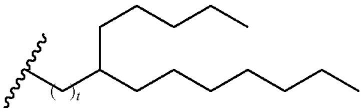,

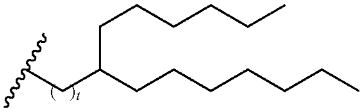,

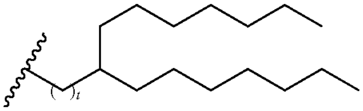,

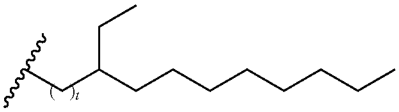,

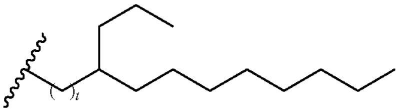,

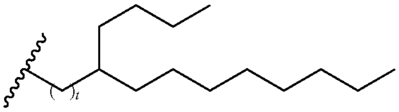,

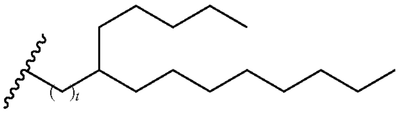,

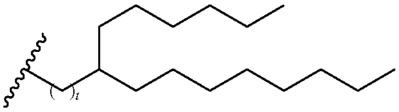,

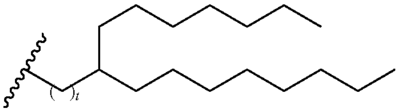,

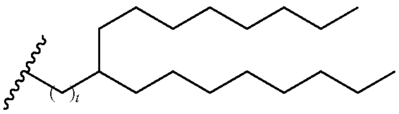,

-continued
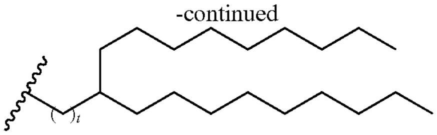
,
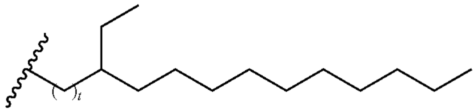
,
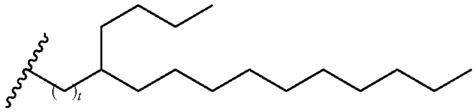
,
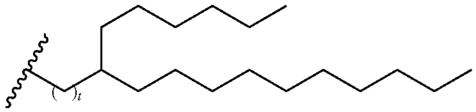
,
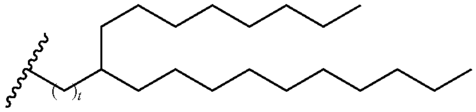
,
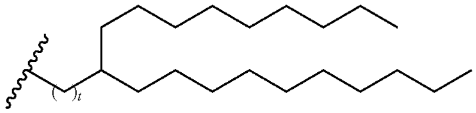
,
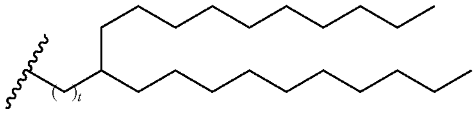
,
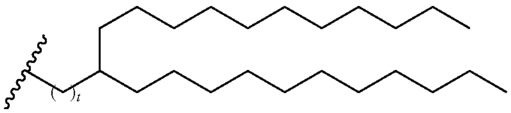
,
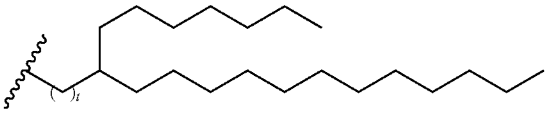
,
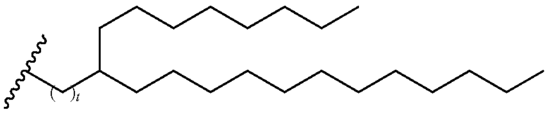
,
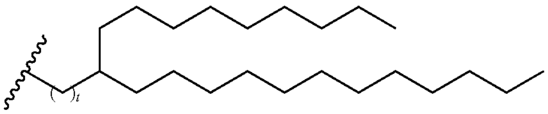
,
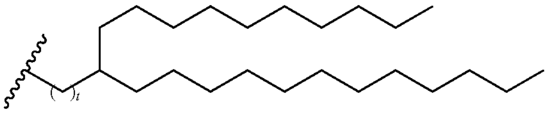
,
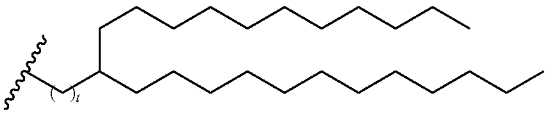
,
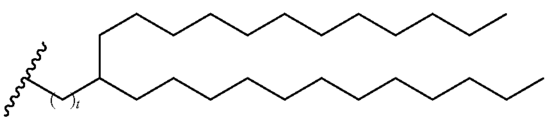
,
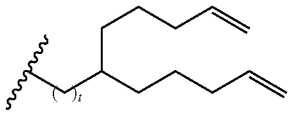
,
-continued
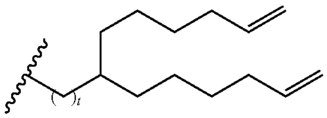
,
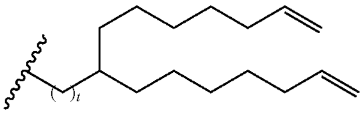
,
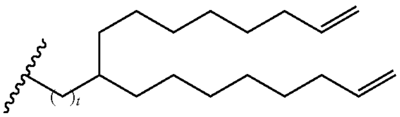
,
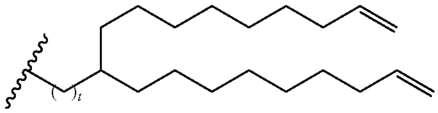
,
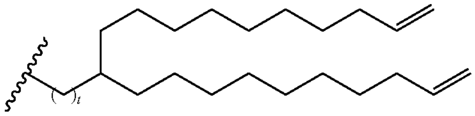
,
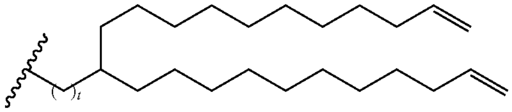
,
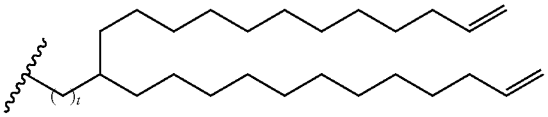
,
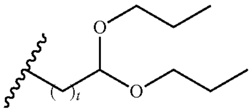
,
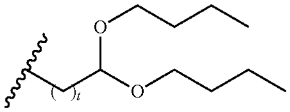
,
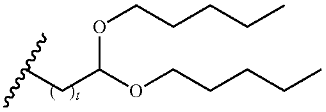
,
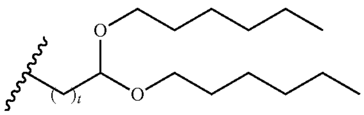
,
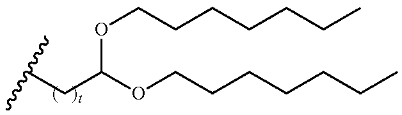
,
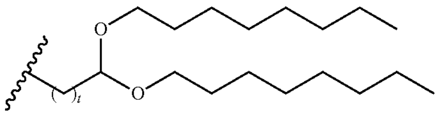
,
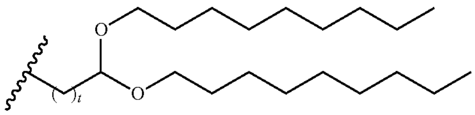
,
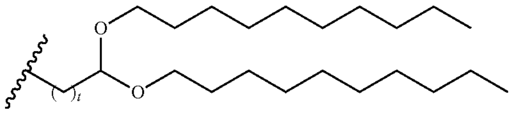
, -continued

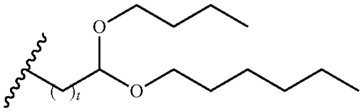

,

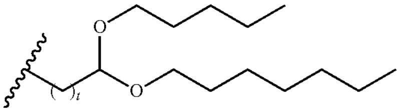

,

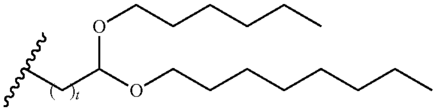

,

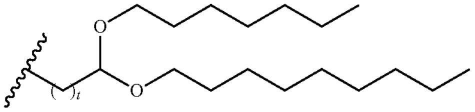

,

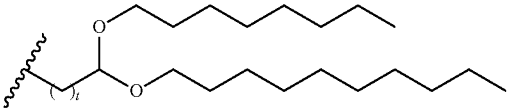

,

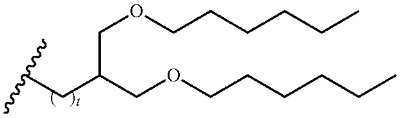

,

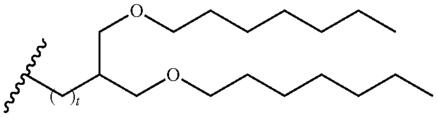

, and

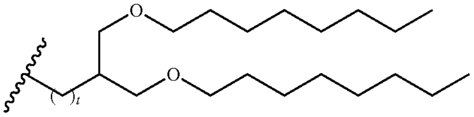

.

9. The cationic lipid according to claim 1, wherein, the structure of said cationic lipid is selected from the group consisting of the following formulas:

(1-1)

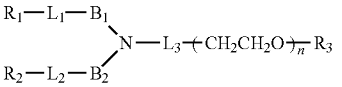

and (1-4)

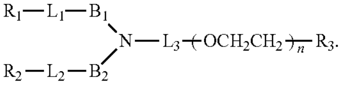

.

10. The cationic lipid according to claim 1, wherein; the structure of said cationic lipid is selected from the group consisting of the following formulas:

(2-3)

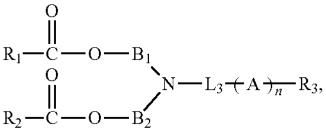

(2-4)

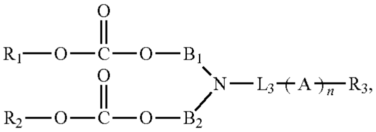

(2-12)

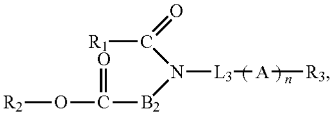

(2-13)

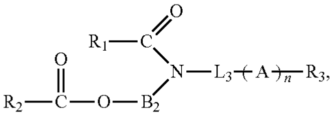

(2-14)

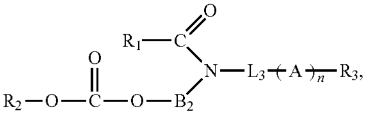

(2-23)

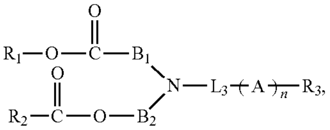

(2-24)

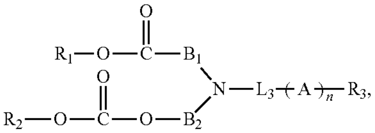

and (2-41)

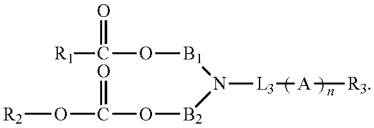

11. The cationic lipid according to claim 1, wherein; the structure of said cationic lipid is one of the following structures:

P-1

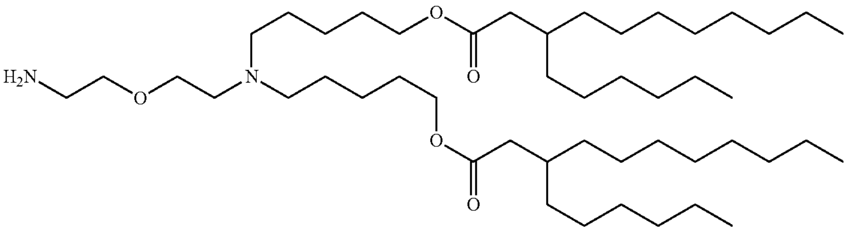

,

-continued
P-3
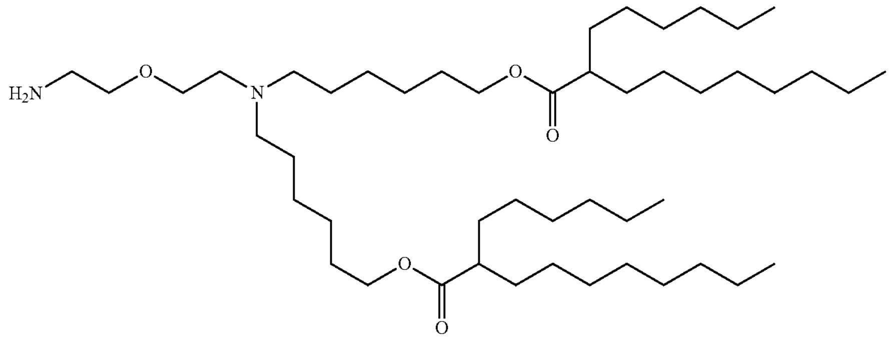
,
P-4
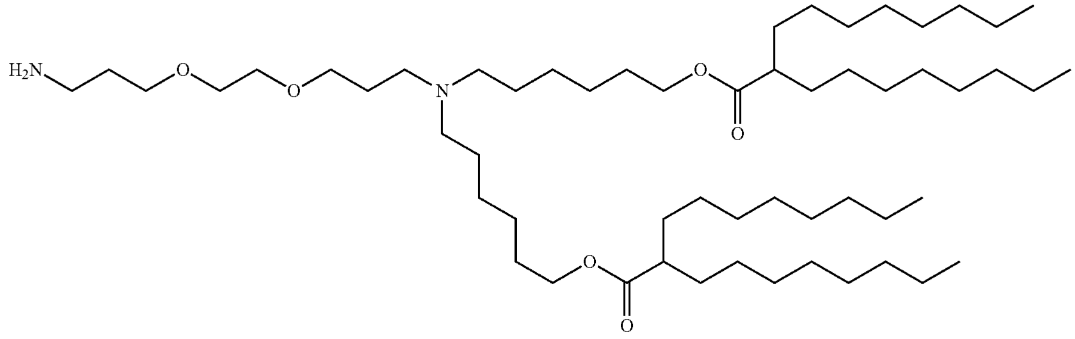
,
P-7
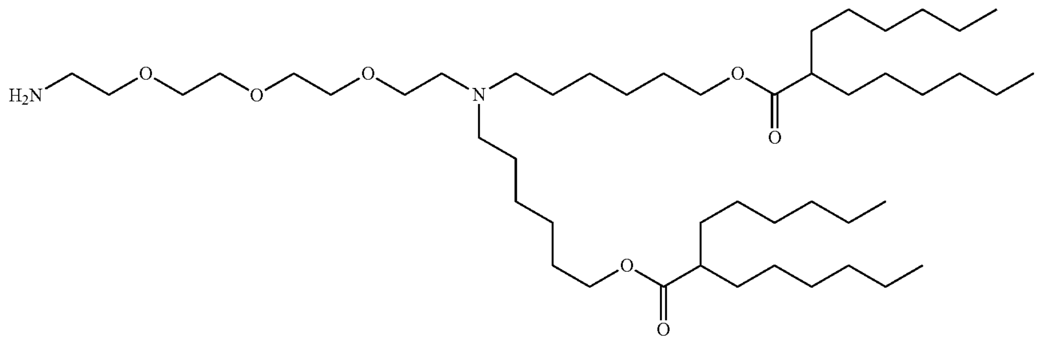
,
P-9
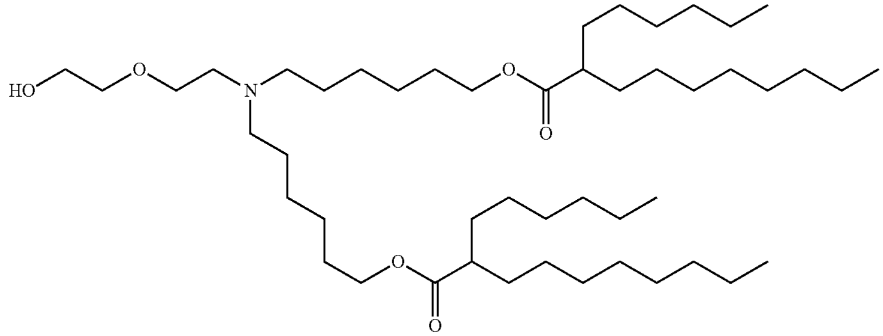
, -continued
P-10
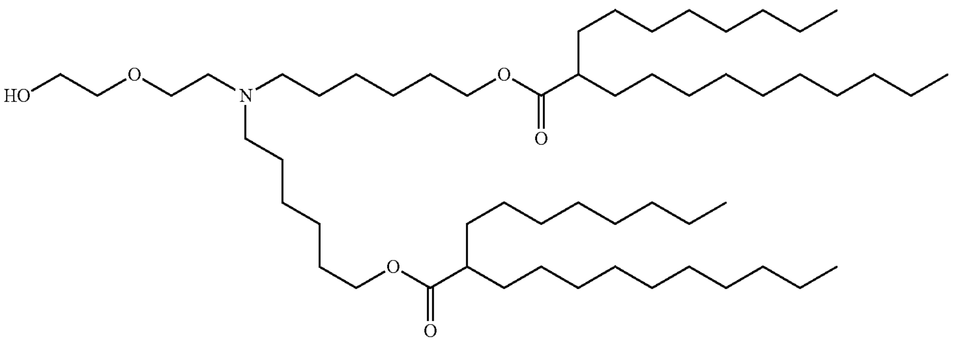
,
P-15
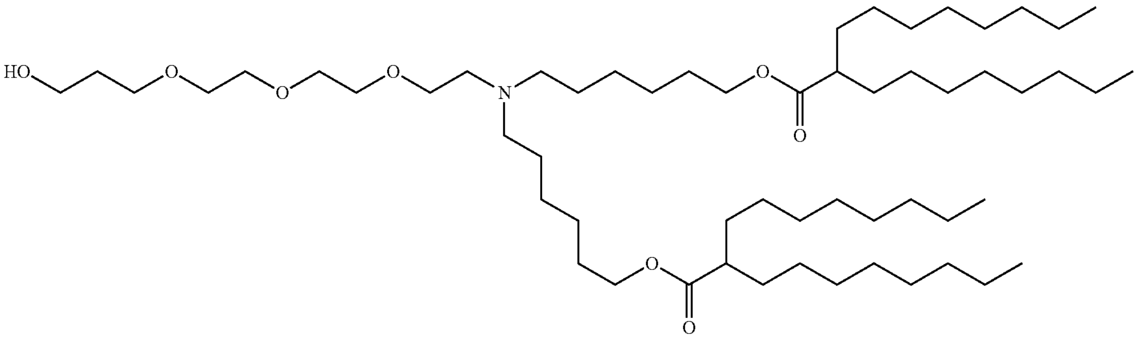
,
P-18
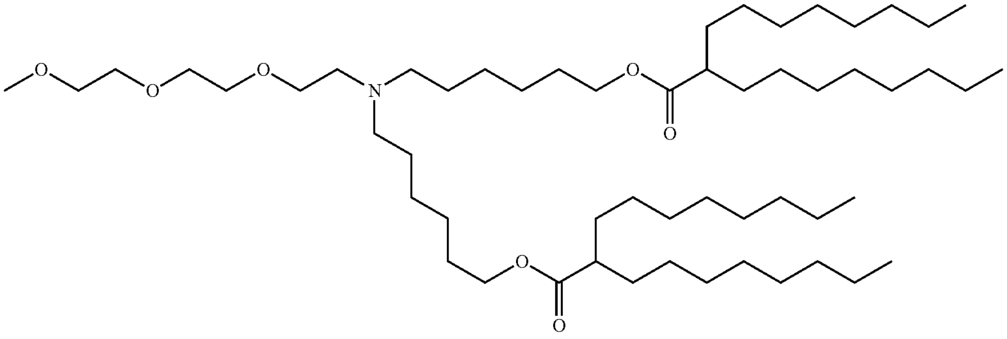
,
P-23
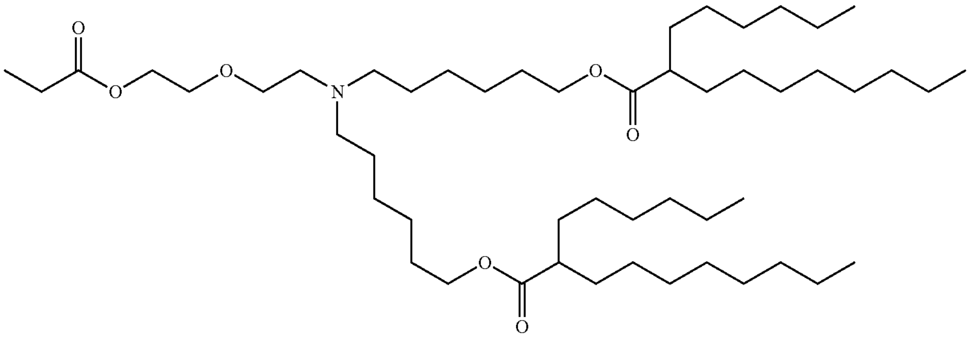
, -continued
P-24
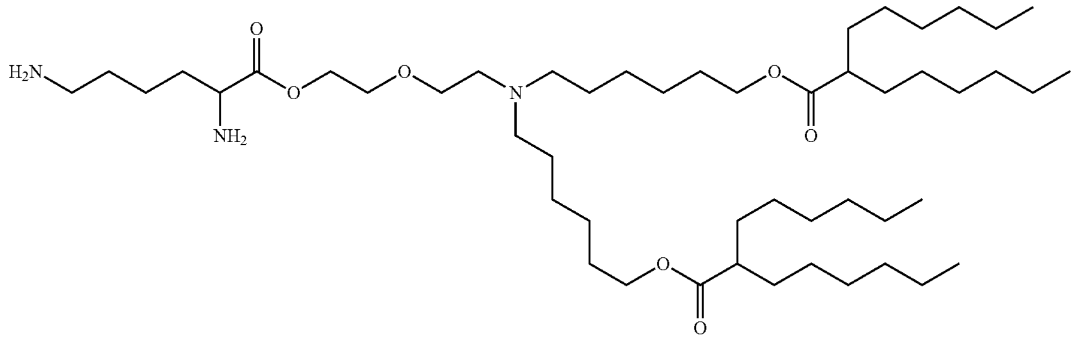
,
P-25
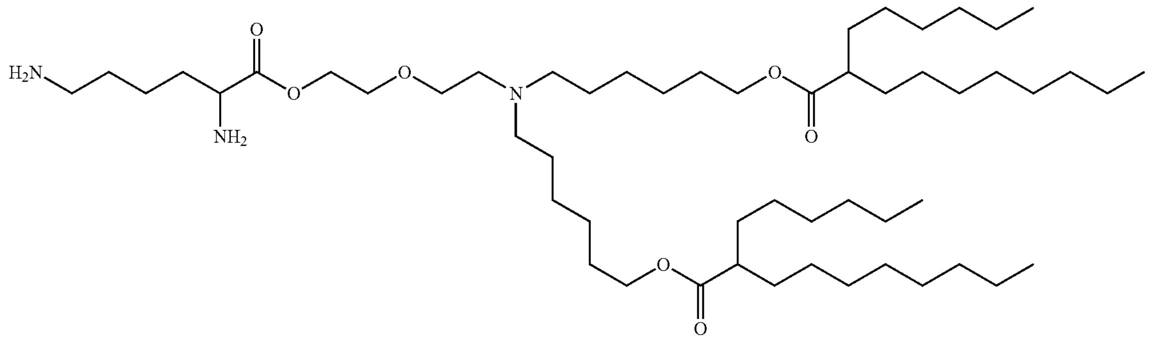
,
P-29
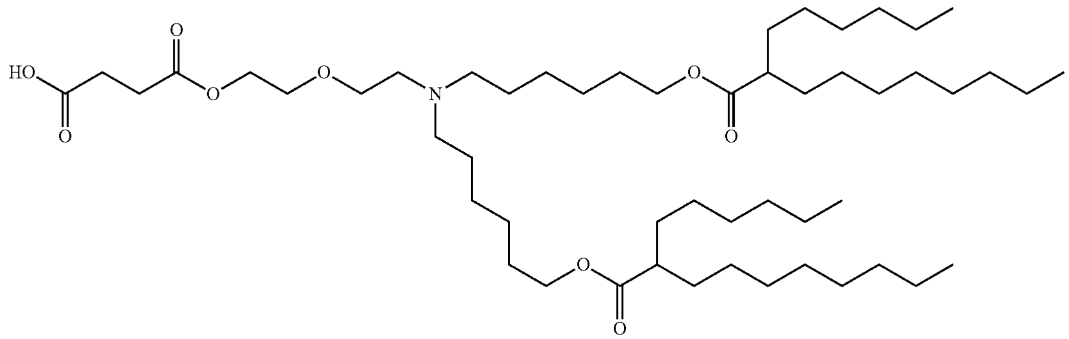
,
P-35
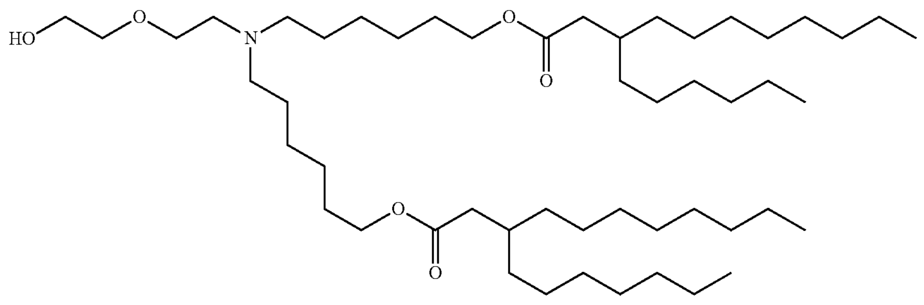
,
P-40
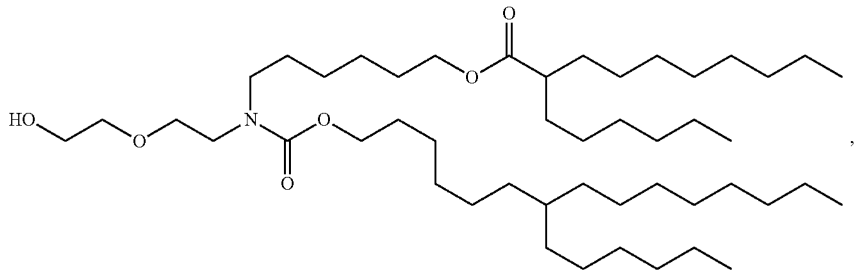
, -continued
P-41
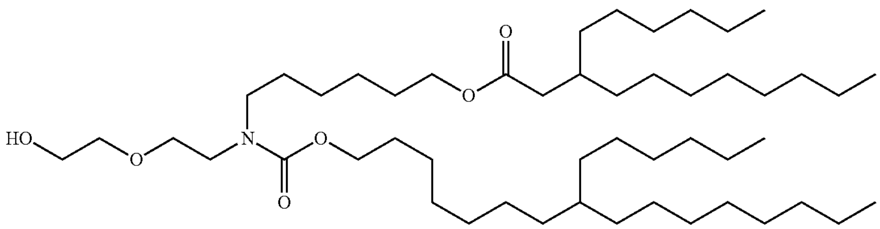
,
P-42
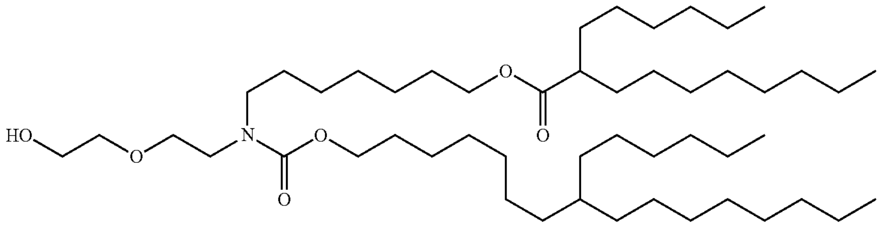
,
P-43
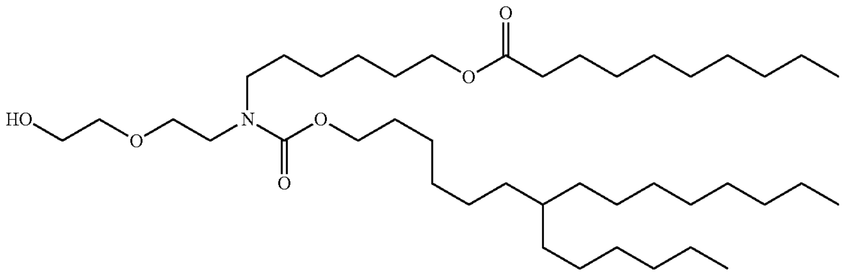
,
P-48
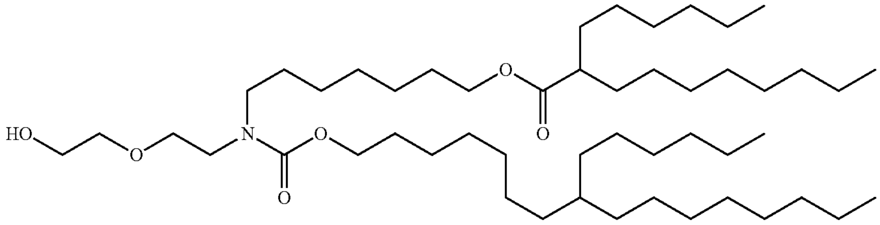
,
P-49
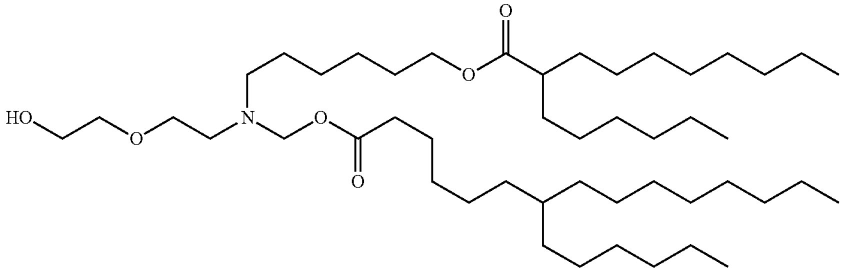
,
P-50
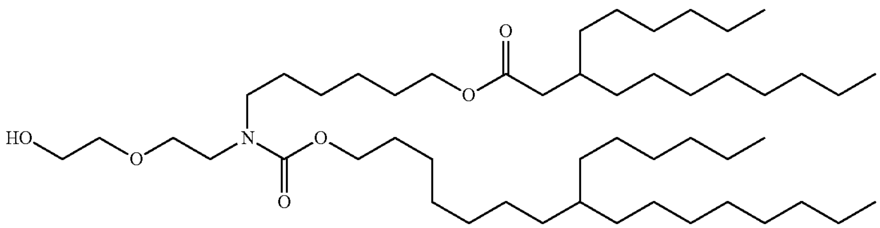
, -continued
P-51
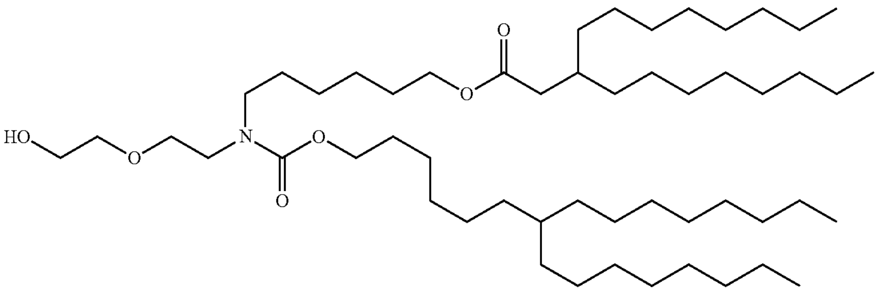
,
P-52
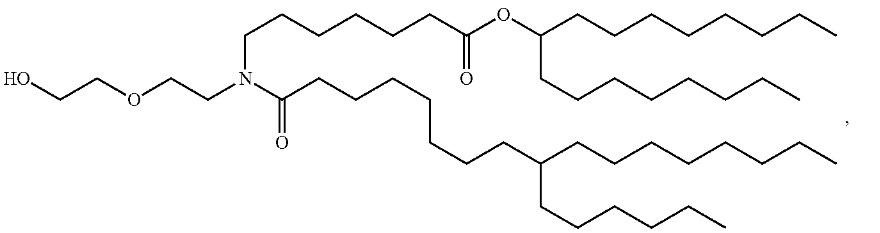
,
P-53
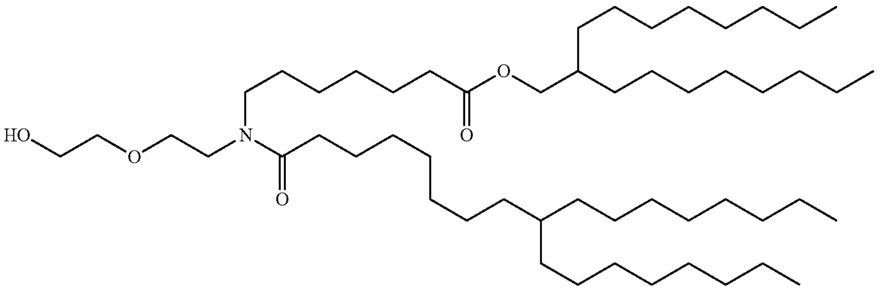
,
P-54
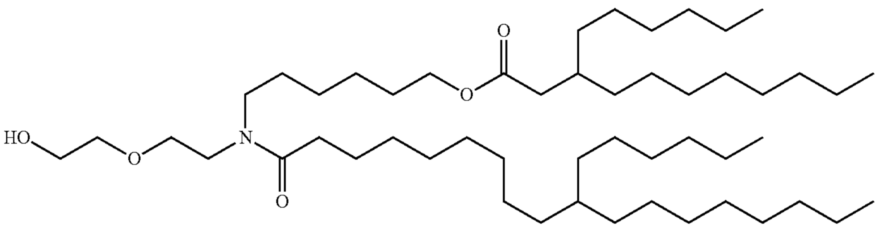
,
P-55
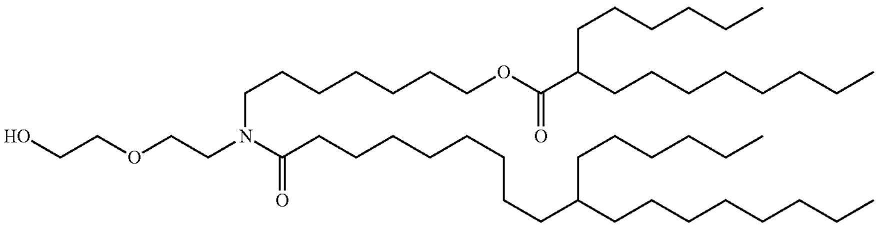
, -continued
P-56
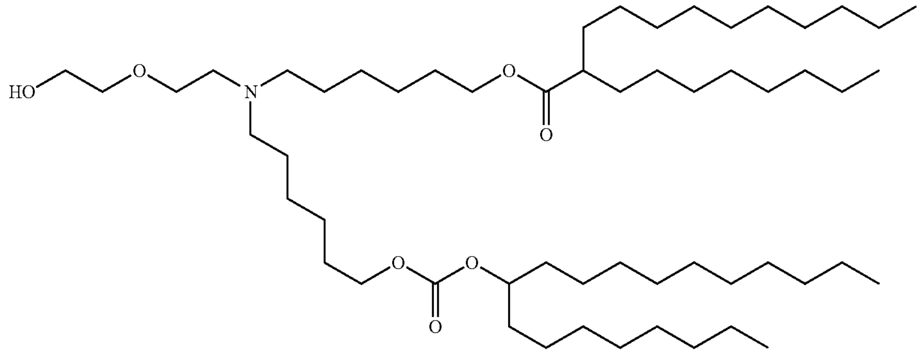
,
P-57
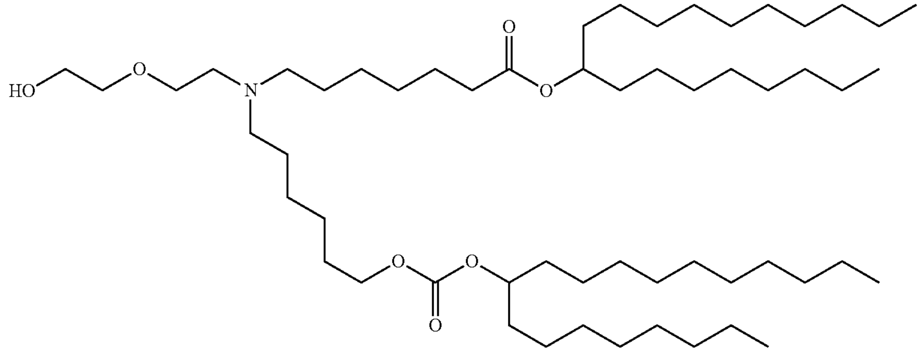
,
P-58
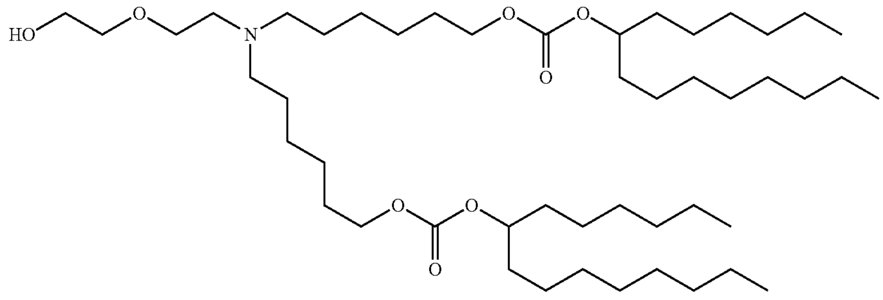
,
P-59
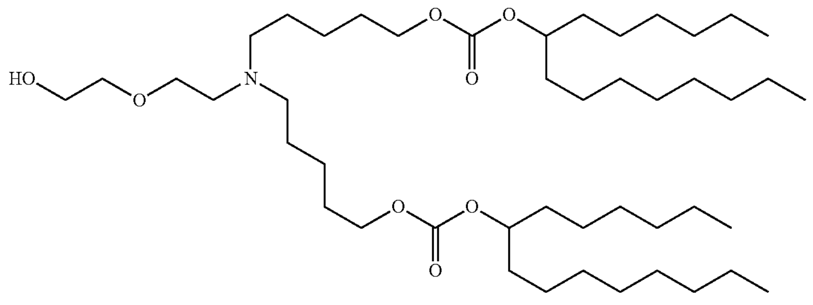
,
P-60
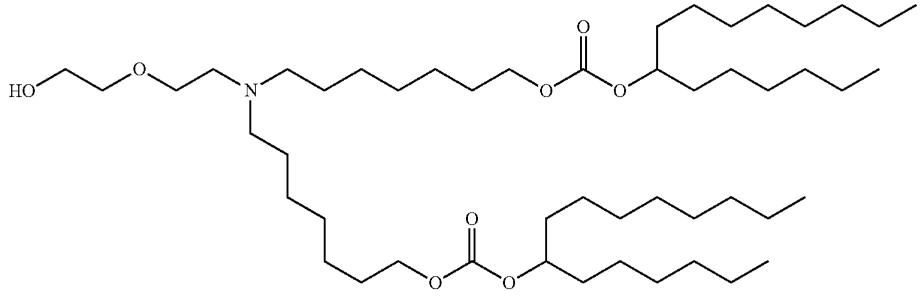
, -continued
P-61
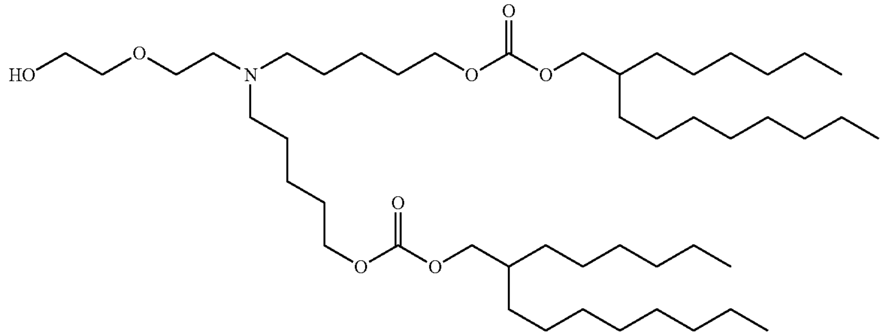
,
P-62
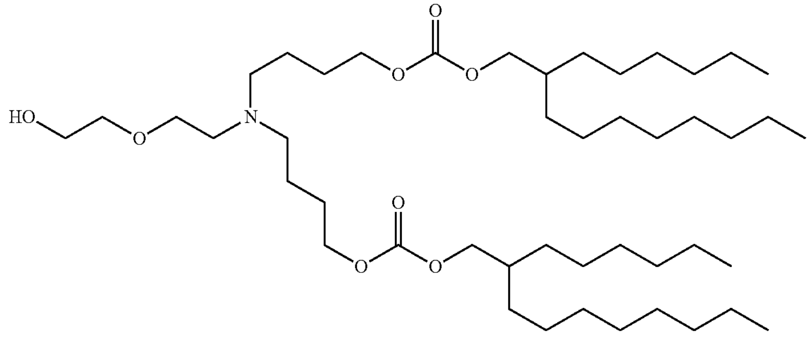
,
P-63
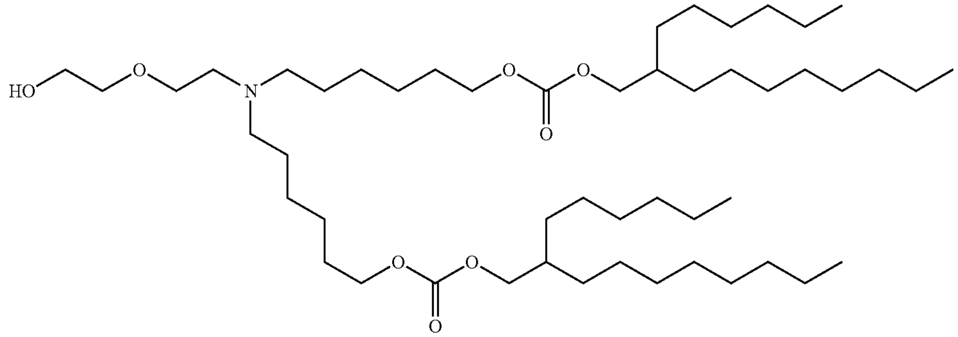
,
P-65
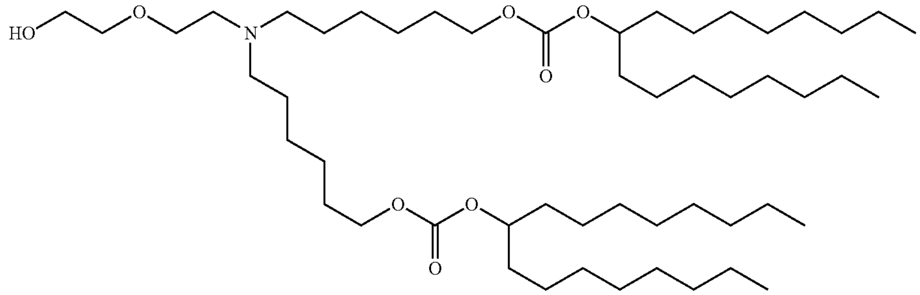
,
P-66
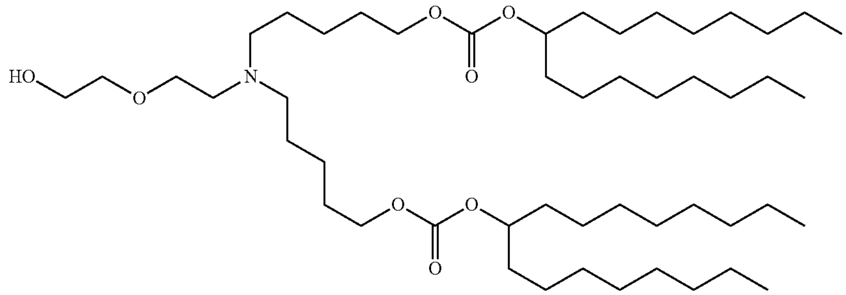
, -continued
P-67
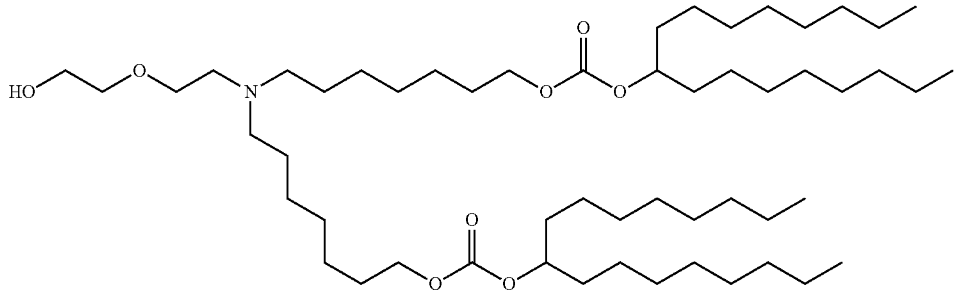
,
P-68
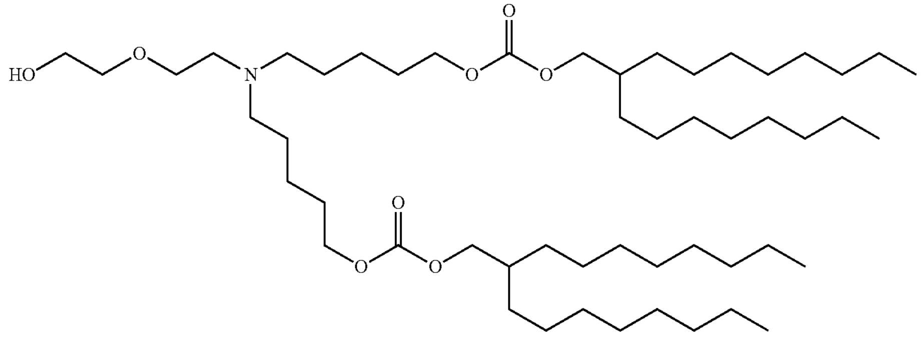
,
P-69
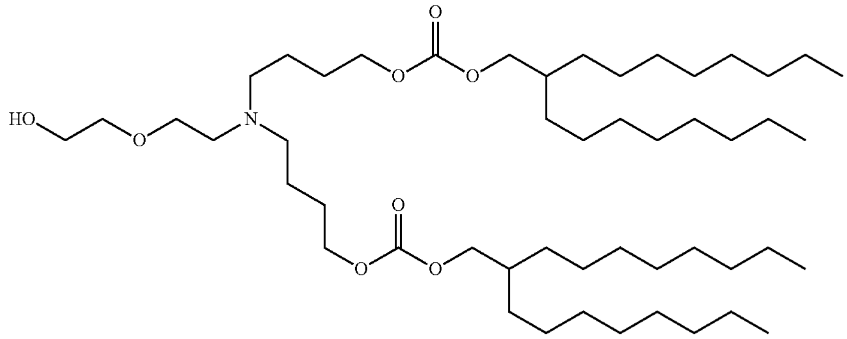
,
P-70
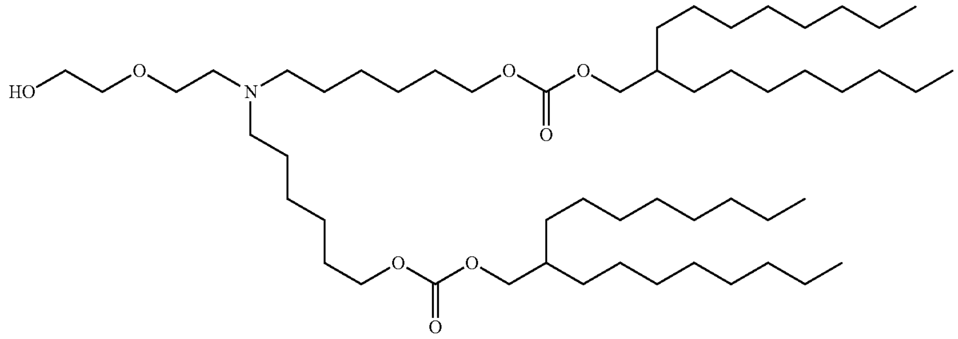
, -continued
P-83
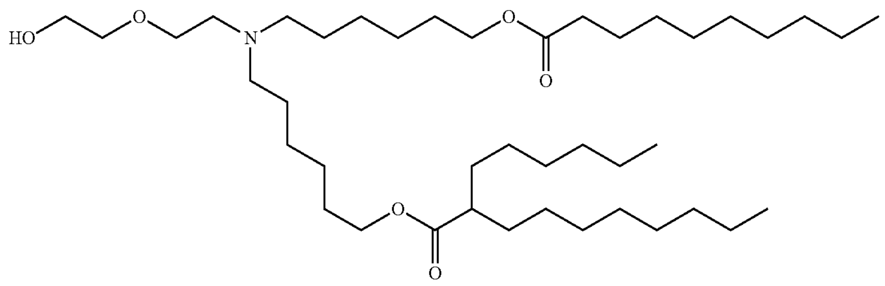
,
P-85
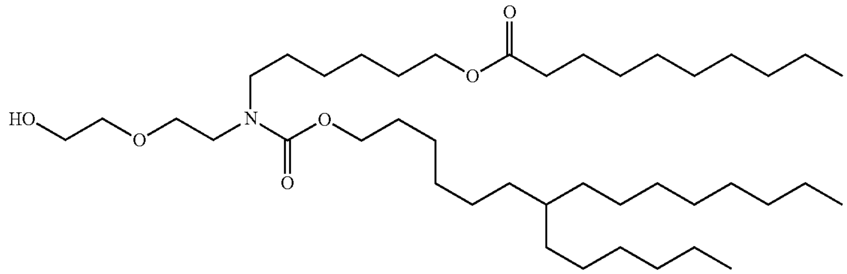
,
P-86
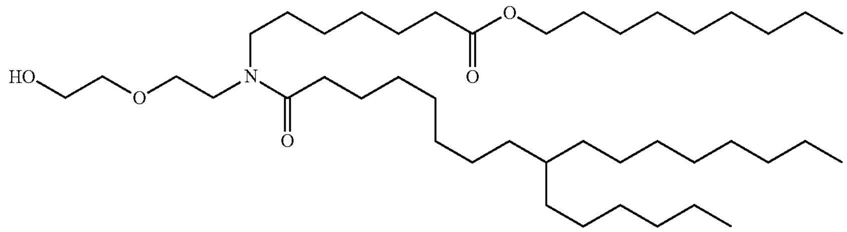
,
P-87
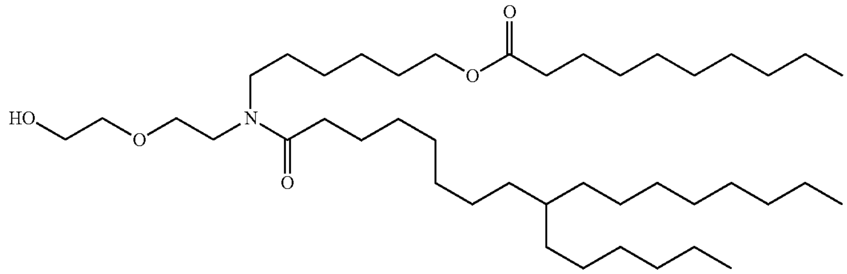
,
P-88
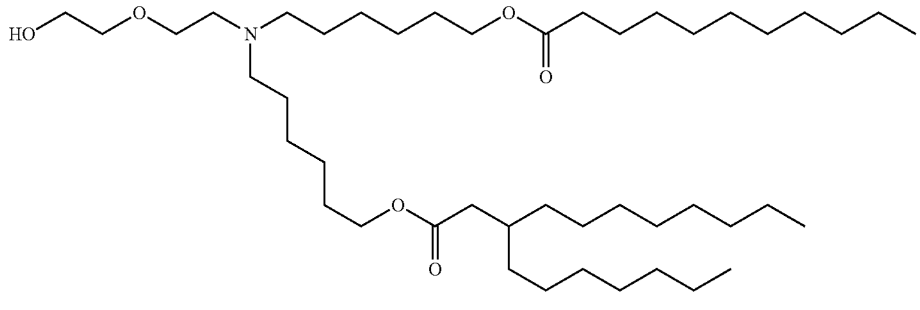
, -continued
P-90
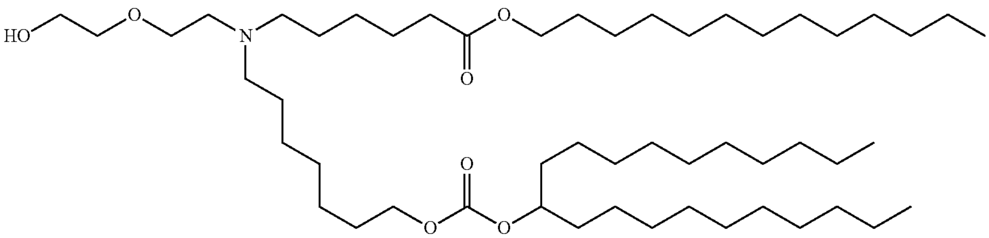
,
P-91
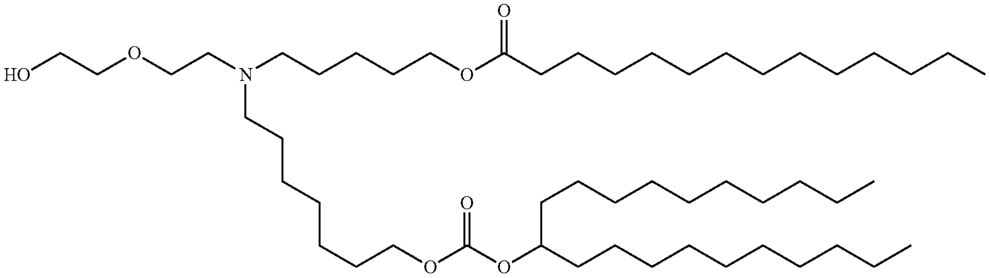
,
P-92
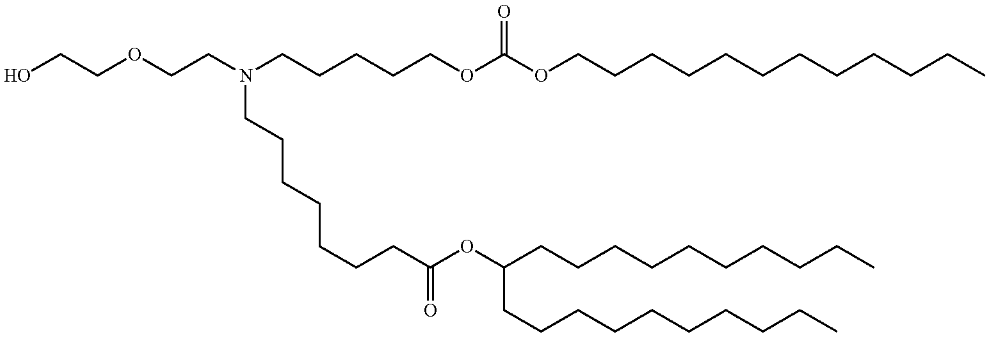
,
P-93
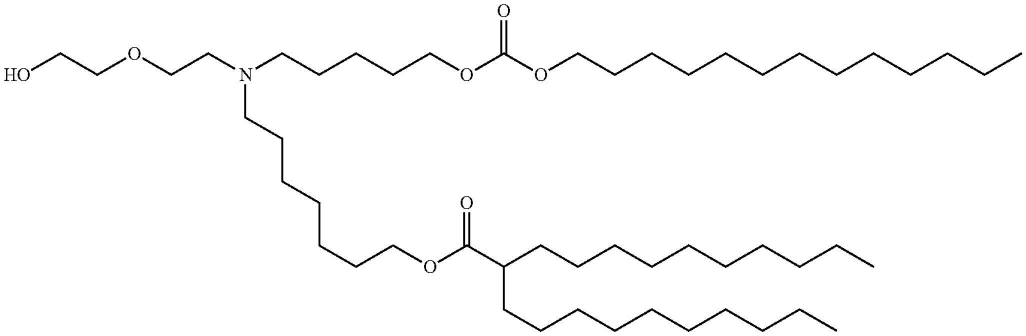
,
P-94
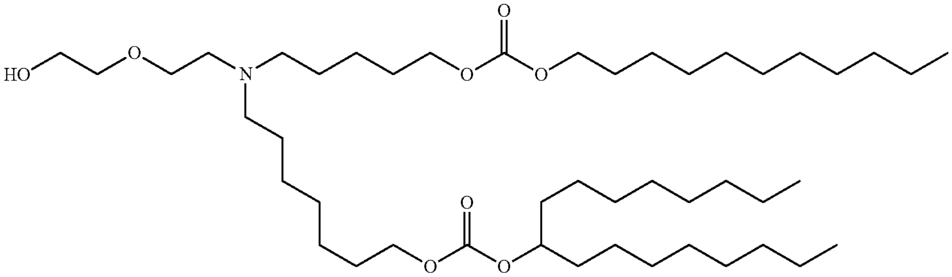
, -continued
P-95
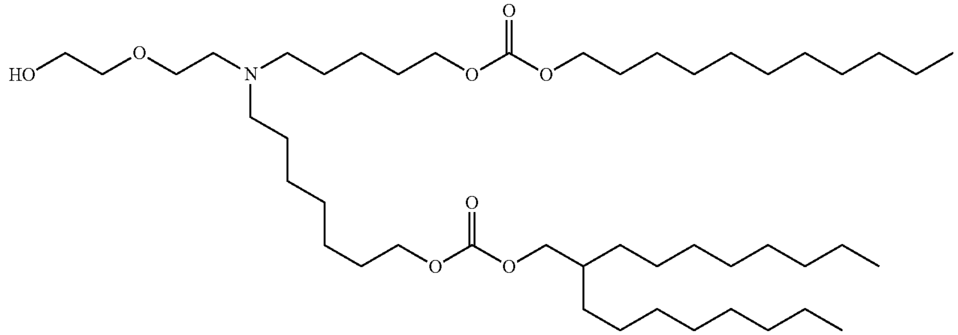
,
P-102
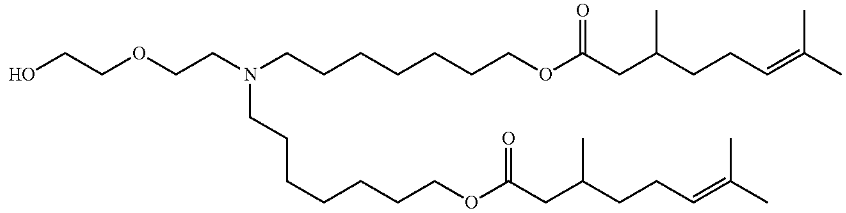
,
P-105
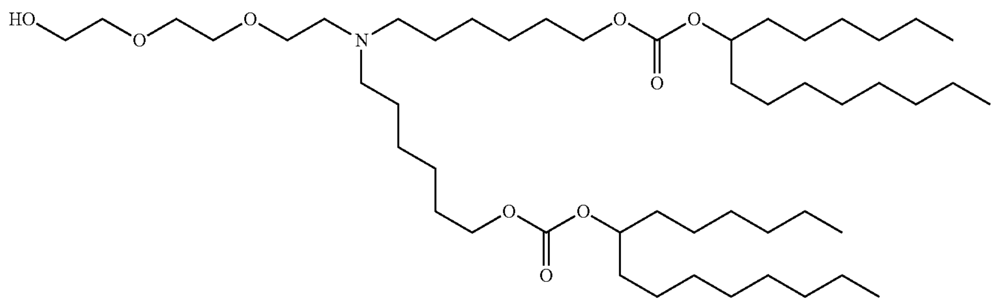
,
P-106
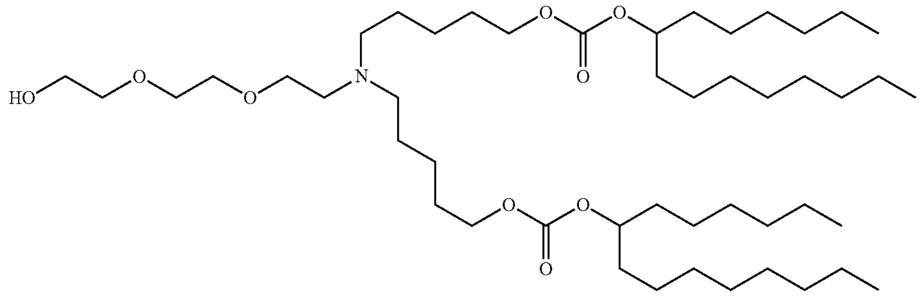
,
P-107
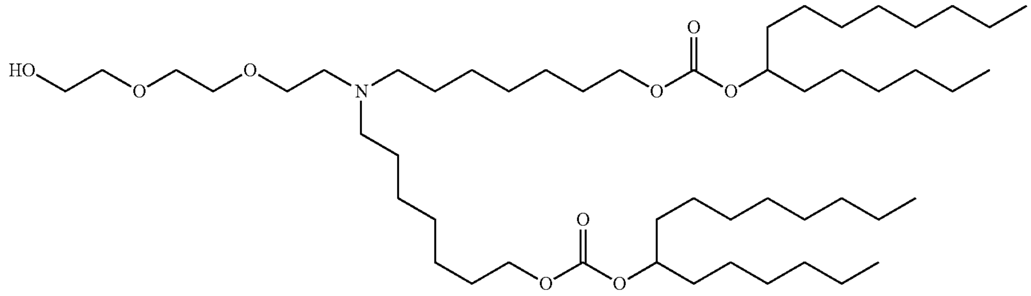
, -continued
P-108
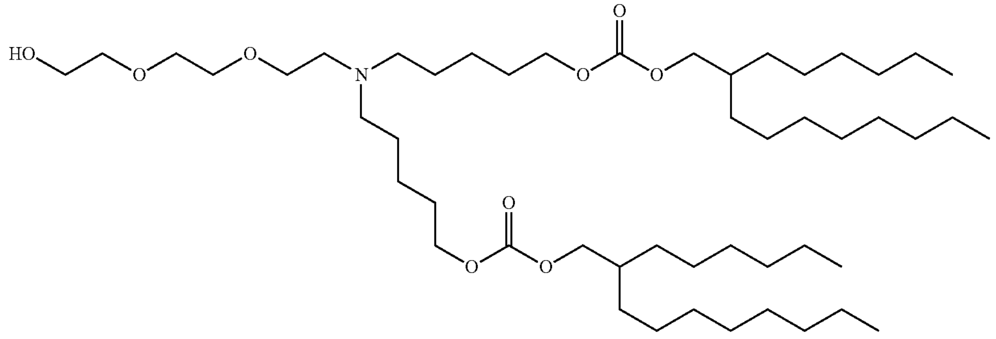
,
P-109
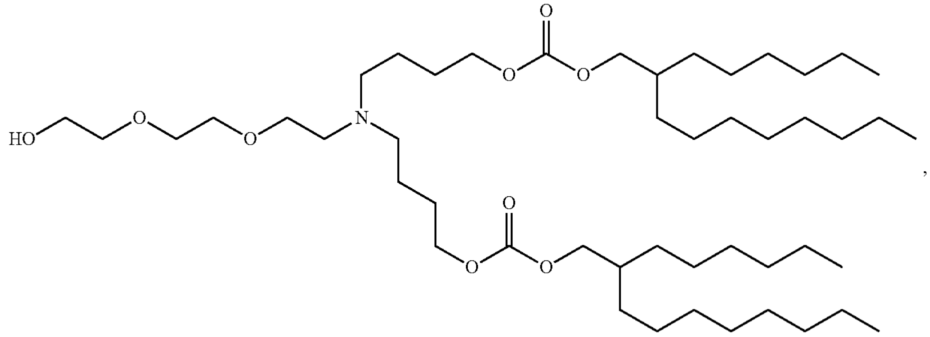
,
P-110
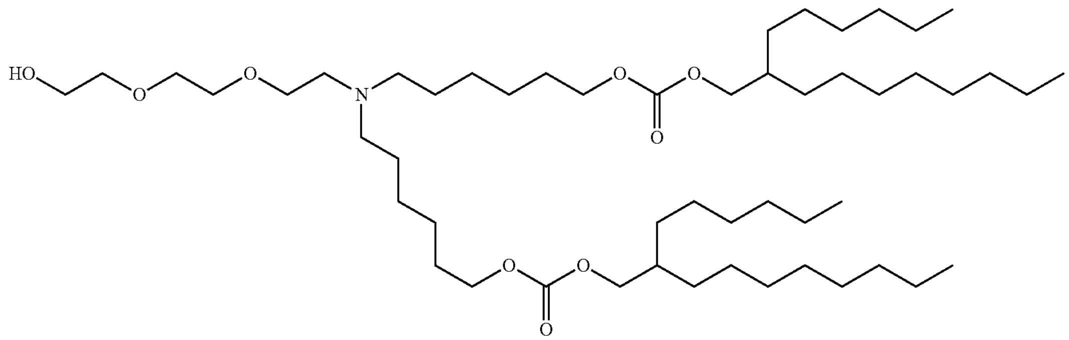
,
P-111
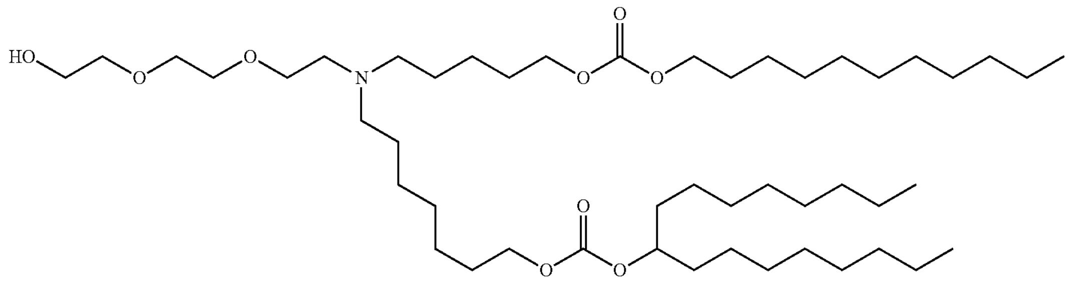
, -continued
P-112
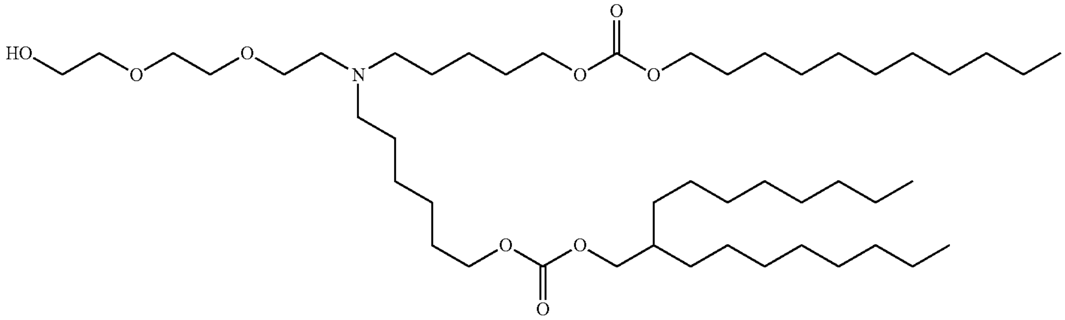
,
P-113
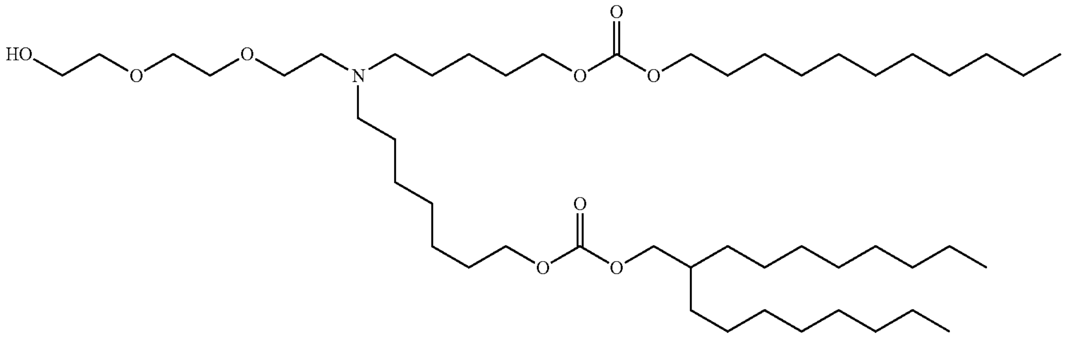
,
P-114
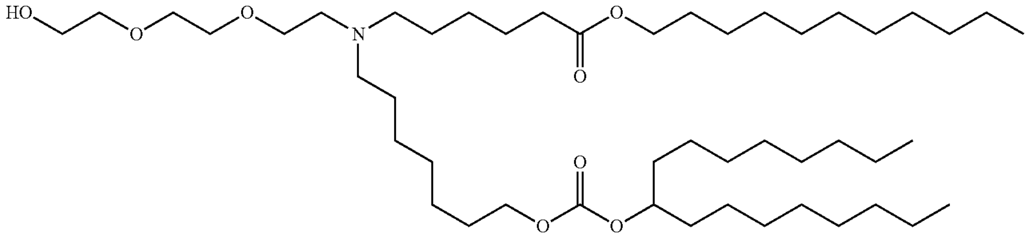
,
P-115
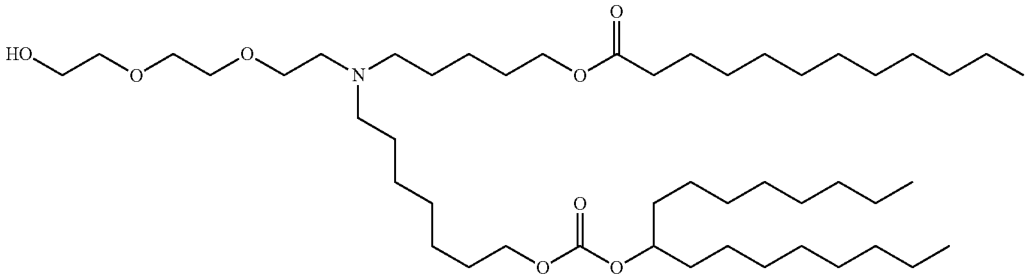
,
P-116
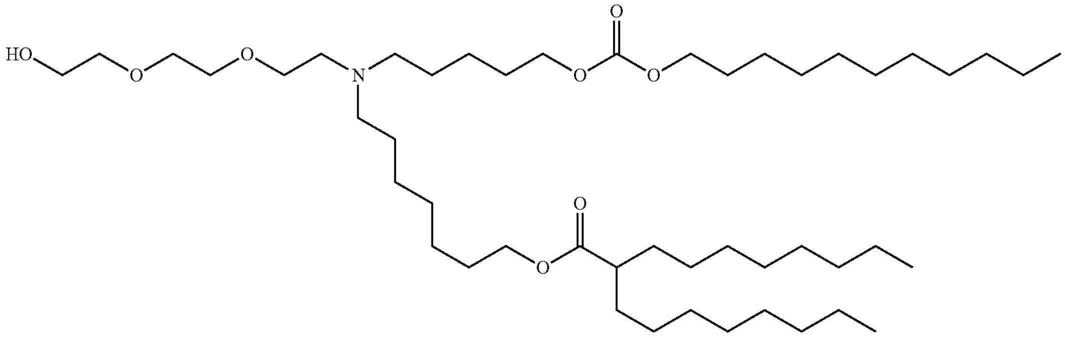
, -continued
P-117
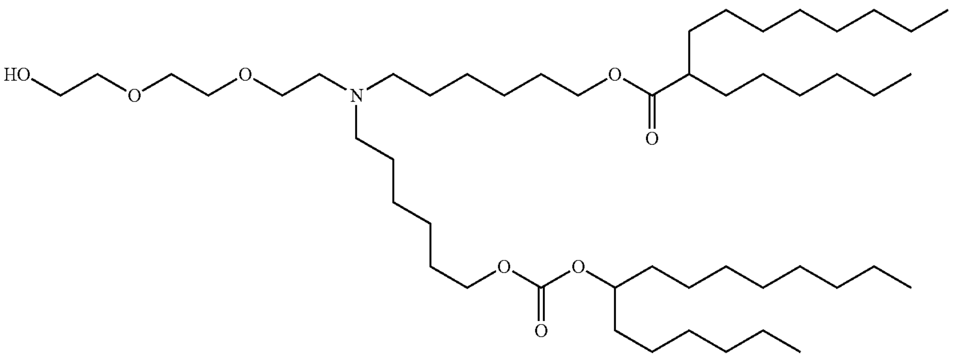
,
P-118
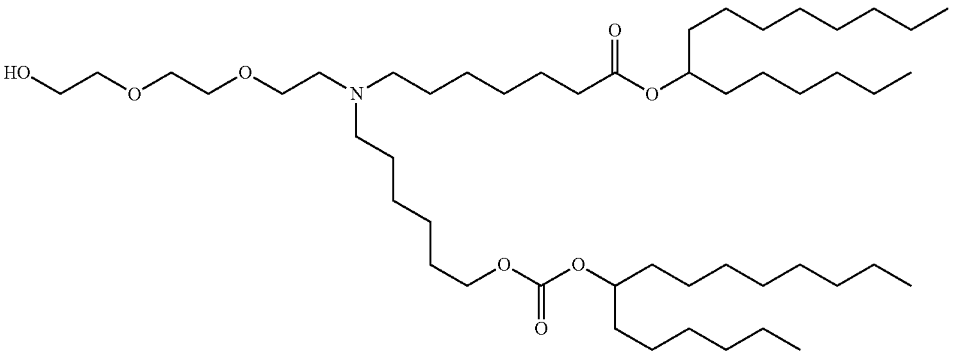
,
P-119
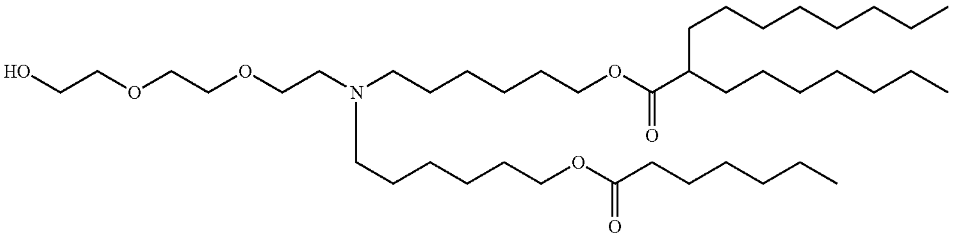
,
P-126
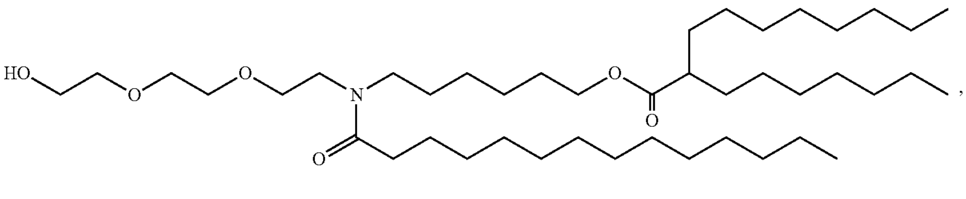
,
P-130
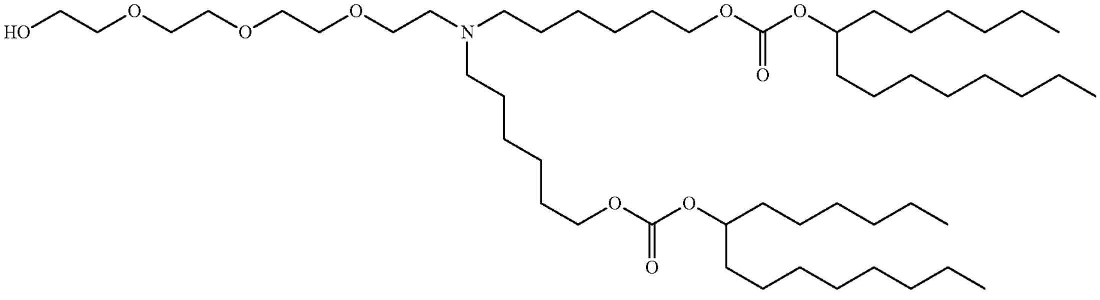
, -continued
P-131
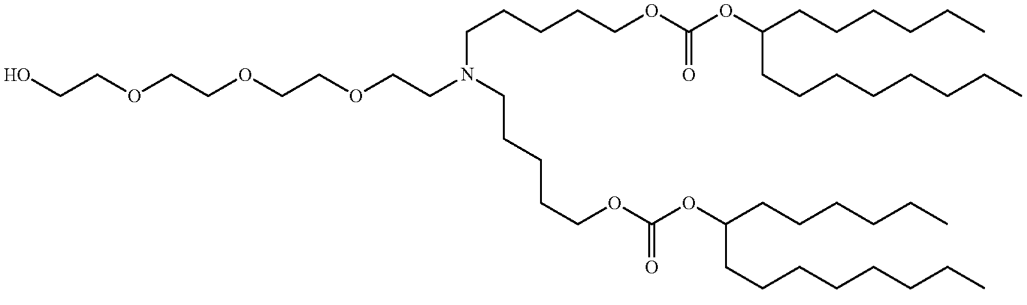
,
P-132
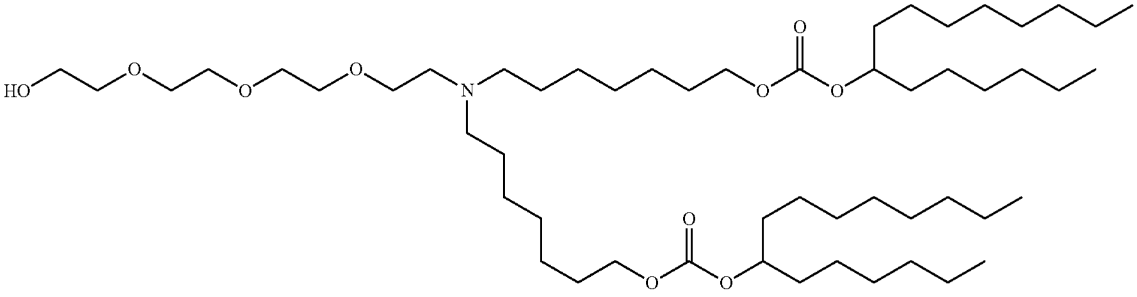
,
P-133
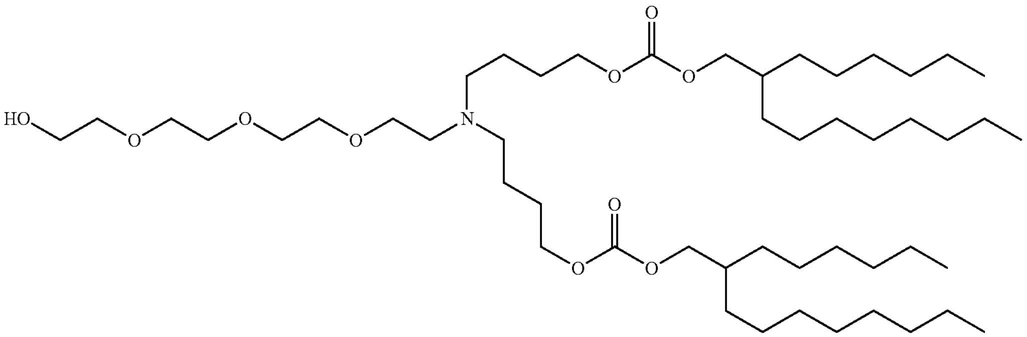
,
P-134
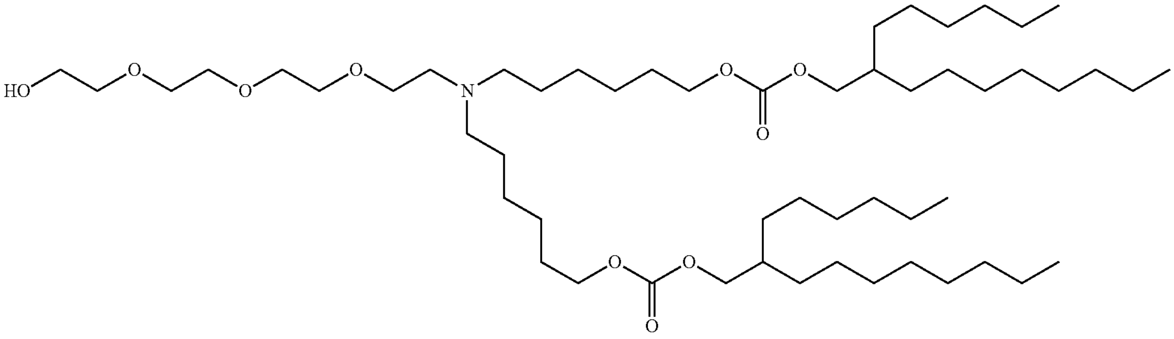
,
P-135
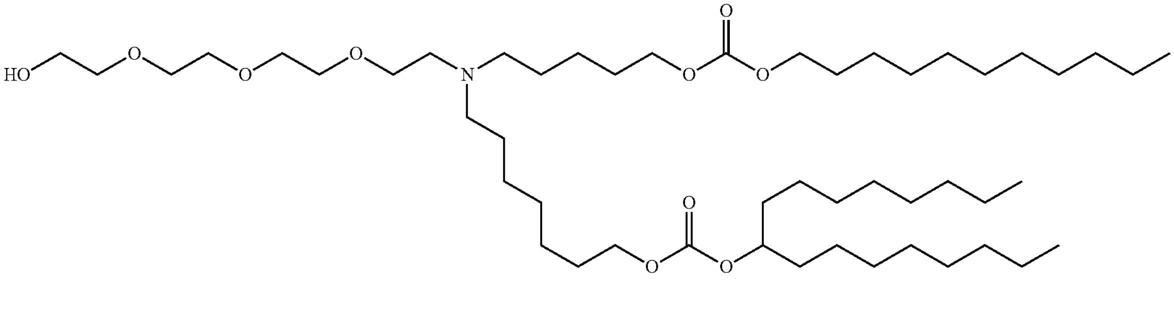
, -continued
P-136
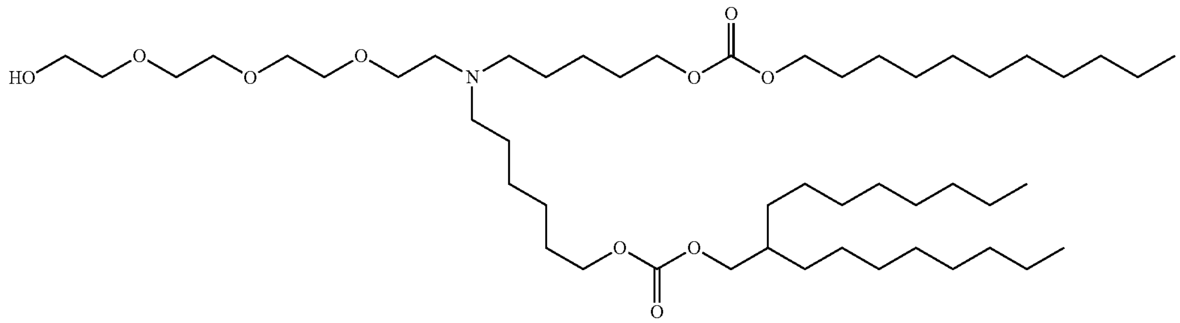
,
P-137
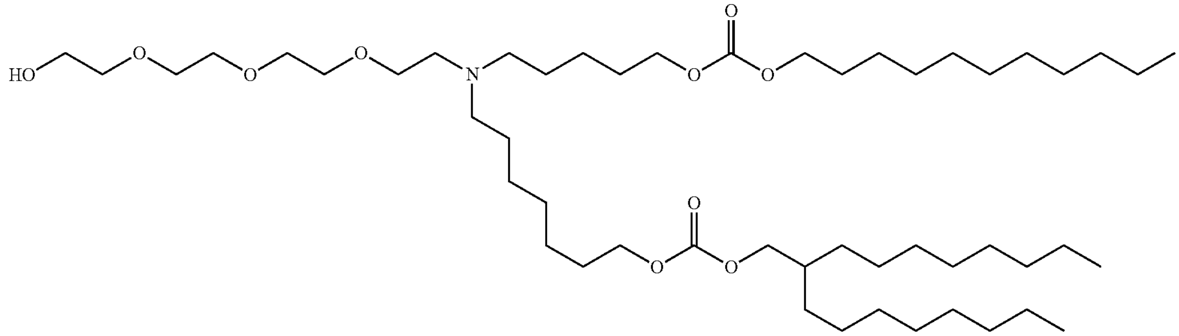
,
P-138
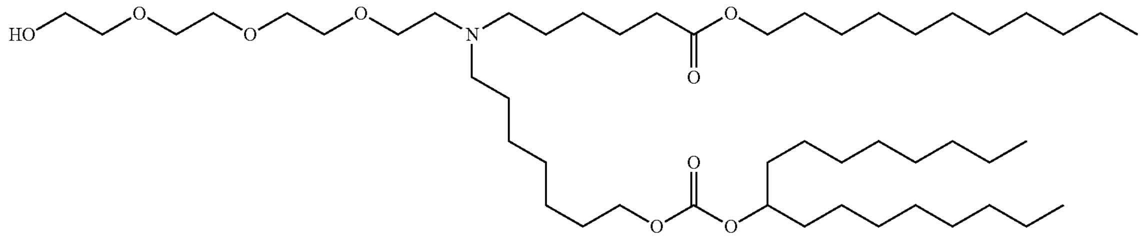
,
P-139
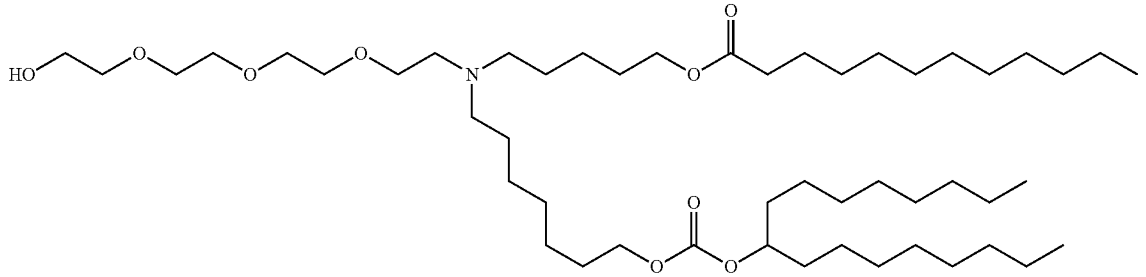
,
P-140
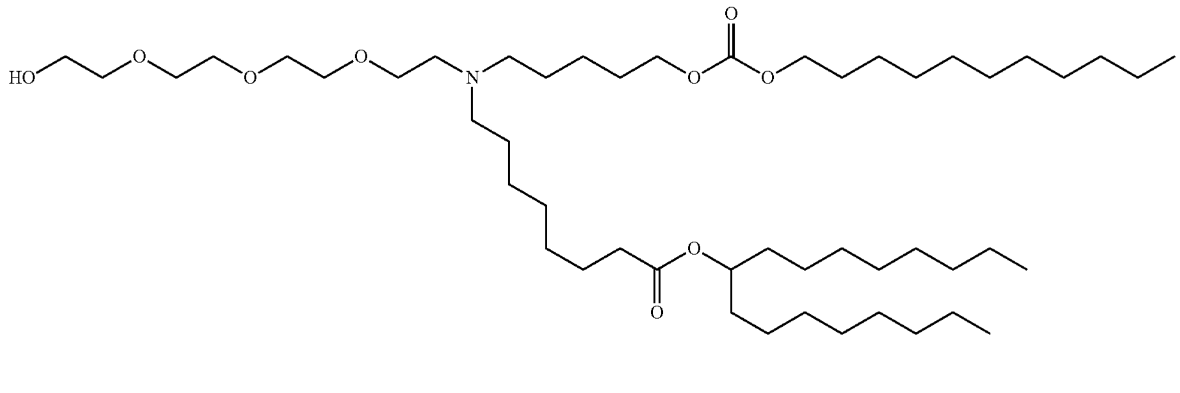
, -continued
P-141
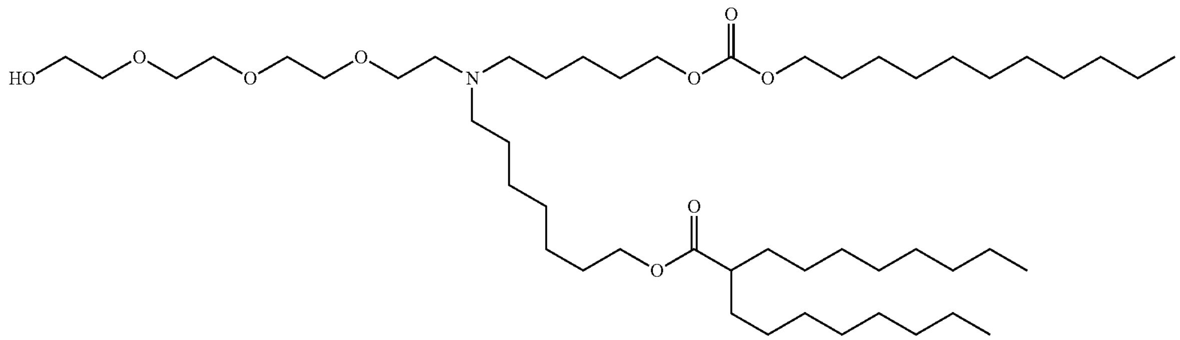
,
P-142
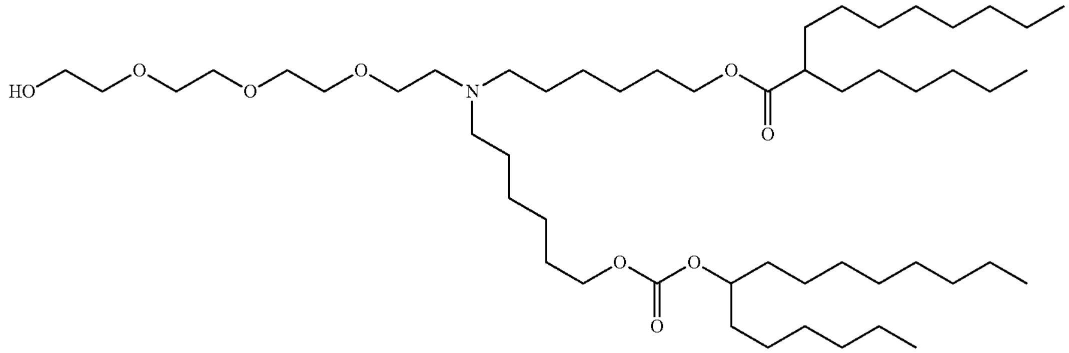
,
P-143
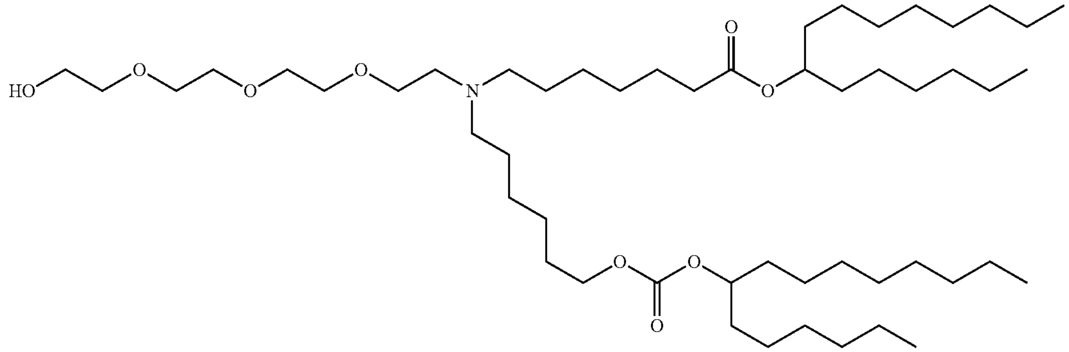
,
P-152
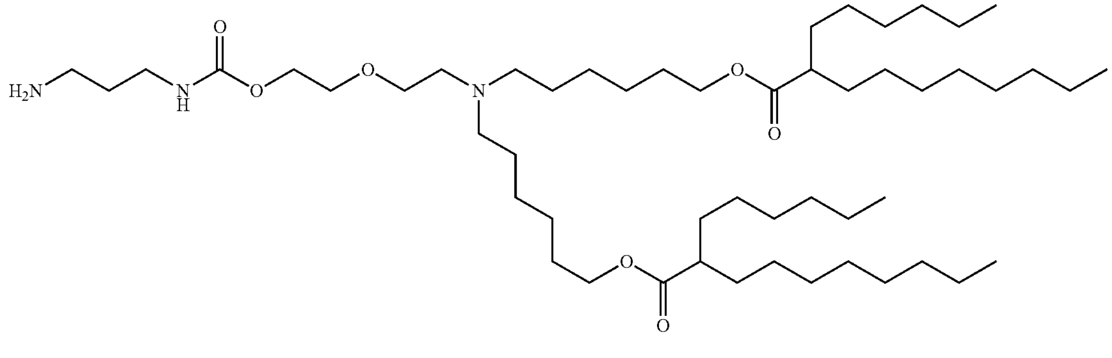
,
P-155
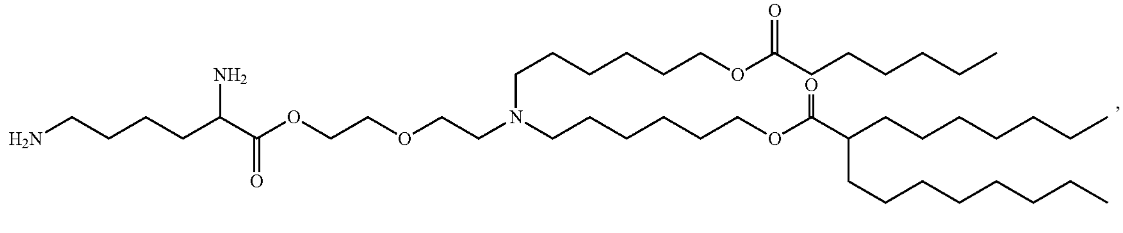
, -continued
P-162
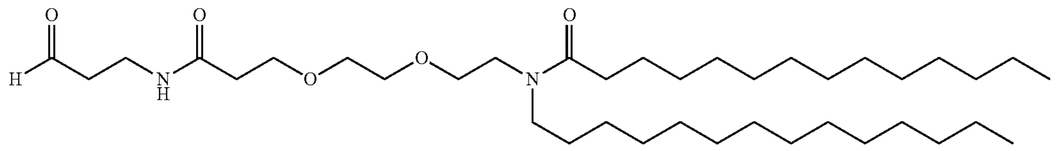
,
P-163
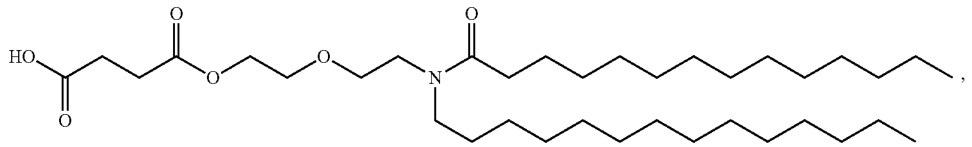
,
P-166
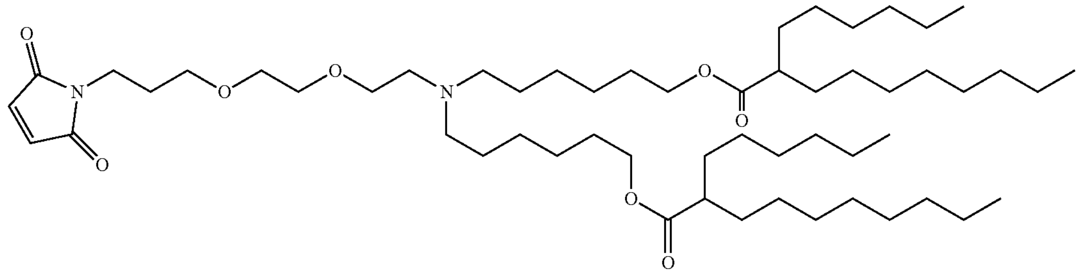
,
P-168
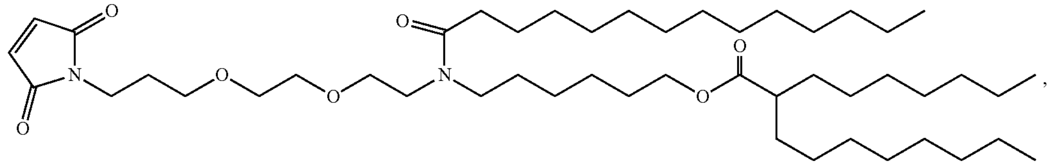
,
P-169
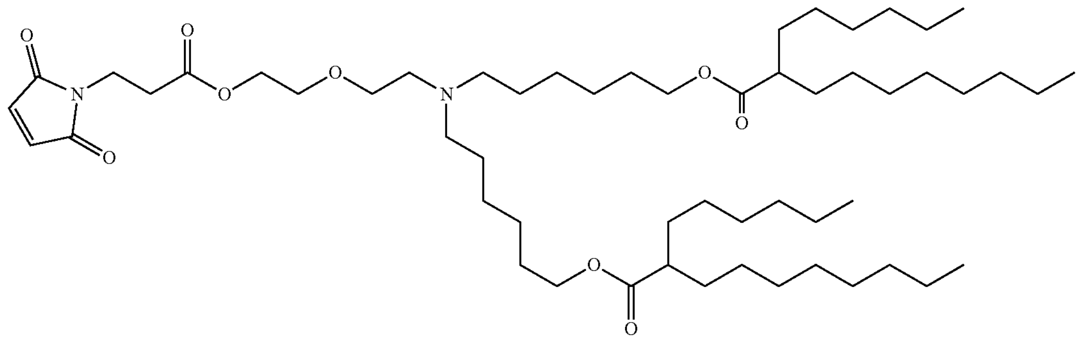
,
P-172
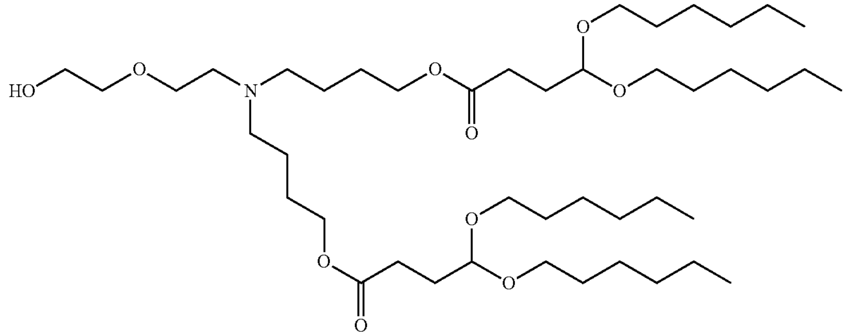
, -continued

P-173

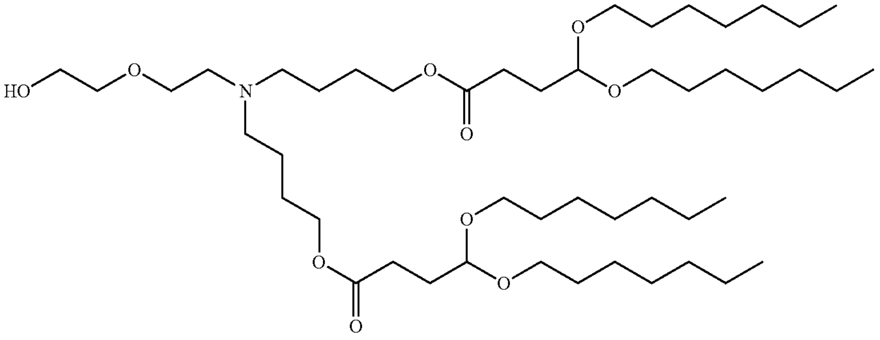

,

P-174

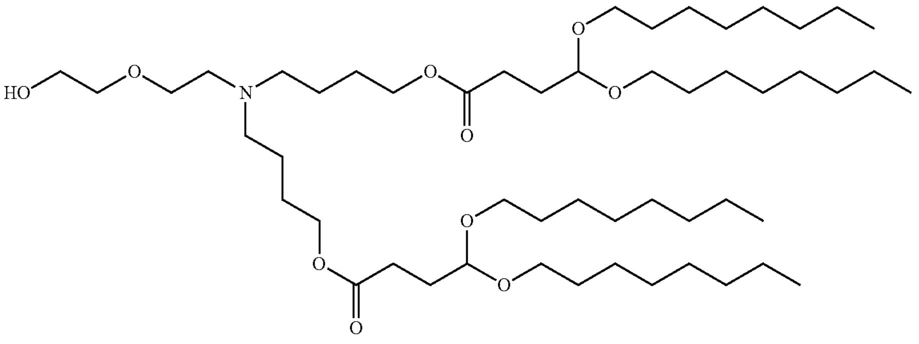

, and

P-178

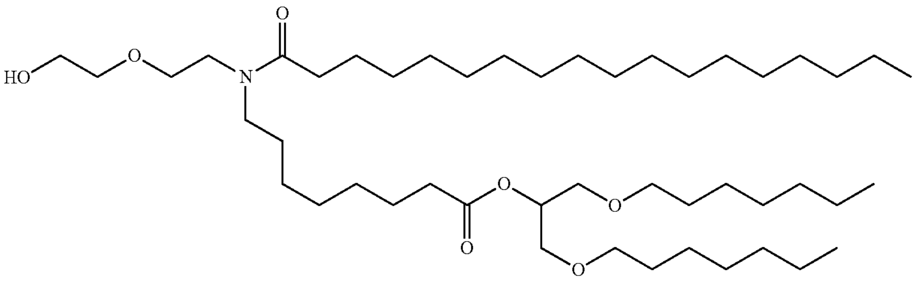

.

12. A cationic liposome, wherein the cationic liposome comprises the cationic lipid of claim 1.

13. The cationic liposome according to claim 12, wherein the cationic liposome comprises one or more lipids selected from the group consisting of neutral lipids, steroid lipids, and PEGylated lipids; wherein said neutral lipid is phospholipid.

14. The cationic liposome according to claim 13, wherein the cationic liposome comprises neutral lipids, steroid lipids, and PEGylated lipids simultaneously.

15. The cationic liposome according to claim 13, wherein said neutral lipid is selected from the group consisting of 1,2-dilinoleoyl-sn-glycero-3-phosphocholines, 1,2-dimyristoleoyl-sn-glycero-3-phosphocholines, 1,2-dioleoyl-sn-glycero-3-phosphocholines, 1,2-dipalmitoyl-sn-glycero-3-phosphocholines, 1,2-distearoyl-sn-glycero-3-phosphatidylcholines, 1,2-diundecanoyl-sn-glycero-3-phosphatidylcholines, 1-plamitoyl-2-oleoyl-sn-glycero-3-phosphocholines, 1,2-di-O-octadecenyl-sn-glycero-3-phosphatidylcholines, 1-oleoyl-2-cholesterylhemisuccinyl-sn-glycero-3-phosphocholines, 1-O-hexadecyl-sn-glycero-3-phosphatidylcholines, 1,2-dilinolenoyl-sn-glycero-3-phosphatidylcholines, 1,2-diarachidonoyl-sn-glycero-3-phosphatidylcholines, 1,2-didecosahexaenoyl-sn-glycero-3-phosphocholines, 1,2-dioleoyl-sn-glycero-3-phosphoethanolamines, 1,2-diphytanyl-sn-glycero-3-phosphoethanolamines, 1,2-distearoyl-sn-glycero-3-phosphoethanolamines, 1,2-dilinoleoyl-sn-glycero-3-phosphoethanolamines, 1,2-dilinolenoyl-sn-glycero-3-phosphoethanolamines, 1,2-diarachidonoyl-sn-glycero-3-phosphoethanolamines, 1,2-didecosahexaenoyl-sn-glycero-3-phosphoethanolamines, 1,2-dioleoyl-sn-glycero-3-phospho-rac-(1-glycerol) sodium salts, dioleoyl phosphatidylserines, dipalmitoylphosphatidylglycerols, palmitoyloleoyl phosphatidylethanolamines, distearoyl phosphatidylethanolamines, dipalmitoyl phosphatidylethanolamines, dimyristoleoyl phosphoethanolamines, 1-stearoyl-2-oleoyl-stearoylethanolamines, 1-stearoyl-2-oleoyl-phosphatidylcholines, sphingomyelins, phosphatidylcholines, phosphatidylethnolamines, phosphatidylserines, phosphatidylinositols, phosphatidic acids, palmitoyloleoyl phosphatidylcholines, lysophosphatidylcholines, lysophosphatidylethanolamines, and combinations thereof.

16. The cationic liposome according to claim 13, wherein said steroid lipid is selected from the group consisting of cholesterols, coprostanols, sitosterols, ergosterols, campesterols, stigmasterols, brassicasterol tomatidines, ursolic acids, α-tocopherols, and any mixture thereof.

17. The cationic liposome according to claim 13, wherein said PEGylated lipid is selected from the group consisting of 1,2-dimyristoyl-sn-glycerol methoxypolyethylene glycol, 1,2-distearoyl-sn-glycero-3-phosphoethanolamine-N-[amino(polyethylene glycol)], PEG-cholesterol, PEG-diacylglycamide, and PEG-dialkyloxypropyl.

18. The cationic liposome according to claim 13, wherein the structure of said PEGylated lipid is represented by the general formula (2):

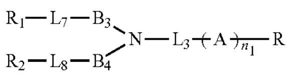

(2)

or pharmaceutically acceptable salts, tautomers, and stereoisomers thereof;

wherein $L_7$ and $L_8$ are each independently a linking bond or a divalent linking group, said divalent linking group is selected from the group consisting of —OC(═O)—, —C(═O)O—, —OC(═O)O—, —C(═O)—, —O—, —S—, —C(═O)S—, —SC(═O)—, —$NR_c$C(═O)—, —C(═O)$NR_c$—, —$NR_c$C(═O)$NR_c$—, —OC(═O)$NR_c$—, —$NR_c$C(═O)O—, —SC(═O)$NR_c$—, and —$NR_c$C(═O)S—; and wherein $R_c$ is, at each occurrence, independently a hydrogen atom or a $C_{1-12}$ alkyl group;

wherein $L_3$ is selected from the group consisting of a linking bond, -$L_4$-, —Z-$L_4$-Z—, -$L_4$-Z-$L_5$-, —Z-$L_4$-Z-$L_5$-, and -$L_4$-Z-$L_5$-Z—; said $L_4$ and $L_5$ are carbon-chain linking groups, which are each independently represented by —$(CR_aR_b)_t$—$(CR_aR_b)_o$—$(CR_aR_b)_p$—; wherein; t, o, and p are each independently an integer from 0 to 12, not being 0 simultaneously; wherein $R_a$ and $R_b$ are, at each occurrence, independently a hydrogen atom or an alkyl group; and wherein said Z is, at each occurrence, independently selected from the group consisting of —C(═O)—, —OC(═O)—, —C(═O)O—, —OC(═O)O—, —O—, —S—, —C(═O)S—, —SC(═O)—, —$NR_c$C(═O)—, —C(═O)$NR_c$—, —$NR_c$C(═O)$NR_c$—, —OC(═O)$NR_c$—, —$NR_c$C(═O)O—, —SC(═O)$NR_c$—, —$NR_c$C(═O)S—, and

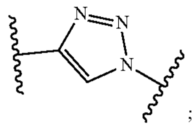 [SMILES: *c1cn(*)nn1]

;

wherein $R_c$ is, at each occurrence, independently a hydrogen atom or a $C_{1-12}$ alkyl group;

wherein $B_3$ and $B_4$ are each independently a linking bond or a $C_{1-12}$ alkylene group;

wherein $R_1$ and $R_2$ are each independently a $C_{1-30}$ aliphatic group;

wherein R is selected from the group consisting of a hydrogen atom, an alkyl group, an alkoxy group, —C(═O)$R_d$, —C(═O)O$R_d$, —OC(═O)$R_d$, and —OC(═O)O$R_d$; wherein $R_d$ is a $C_{1-12}$ alkyl group;

wherein A is —$(CR_aR_b)_s$O— or —O$(CR_aR_b)_s$—; wherein s is 2, 3 or 4; and wherein; $R_a$ and $R_b$ are each independently a hydrogen atom or a $C_{1-12}$ alkyl group;

wherein $n_1$ is an integer from 20 to 250; and wherein said alkyl group, alkylene group, alkoxy group, and aliphatic group are each independently substituted or unsubstituted.

19. The cationic liposome according to claim 18, wherein the structure of said PEGylated lipid is selected from the following structures:

PL-1

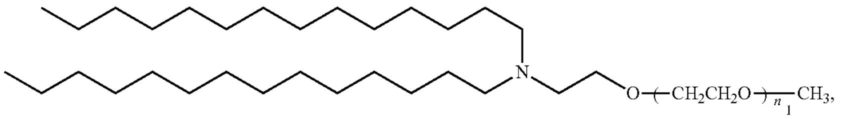

PL-2

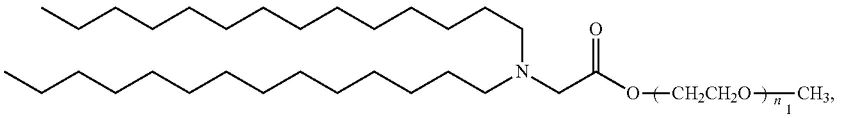

PL-3

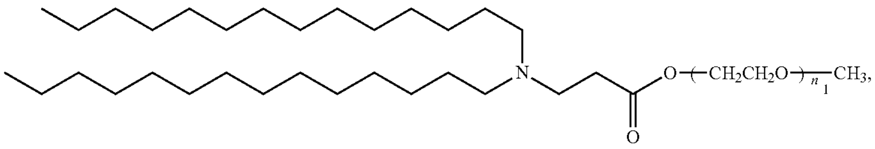

PL-4

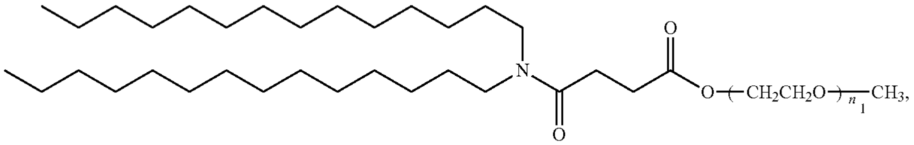

-continued
PL-5
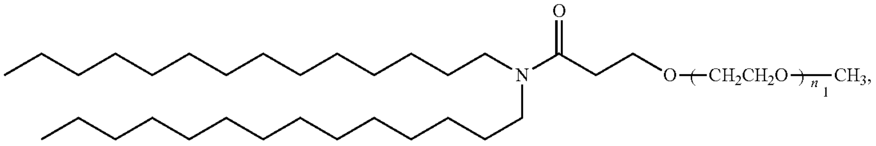
PL-6
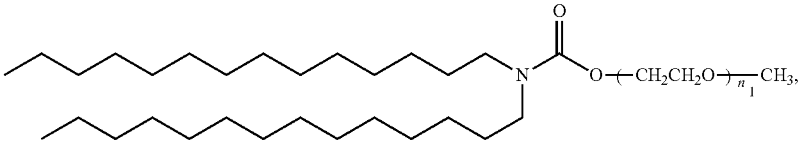
PL-7
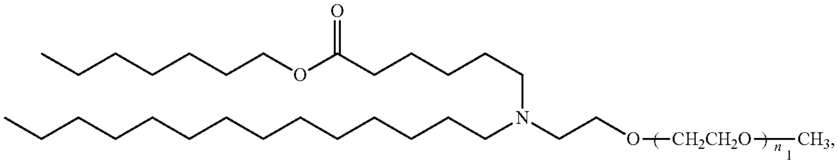
PL-8
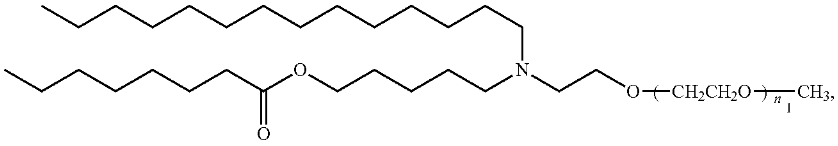
PL-9
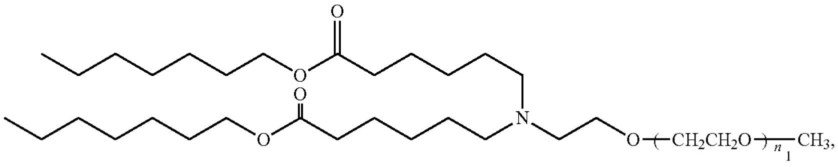
PL-10
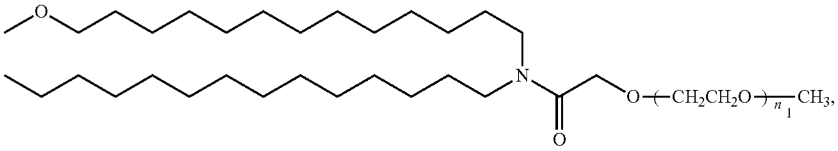
PL-11
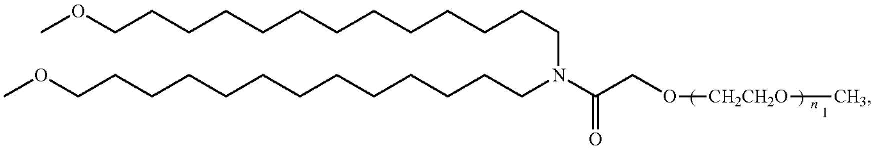
PL-12
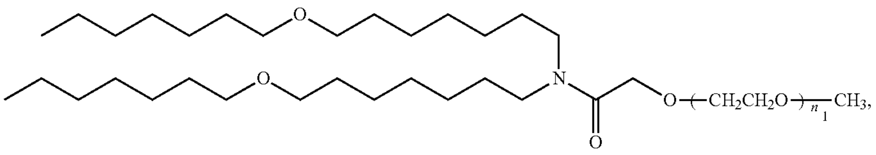
PL-13
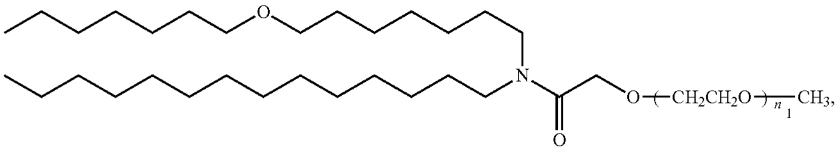

-continued
PL-14
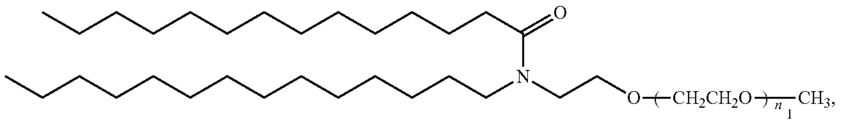
PL-15
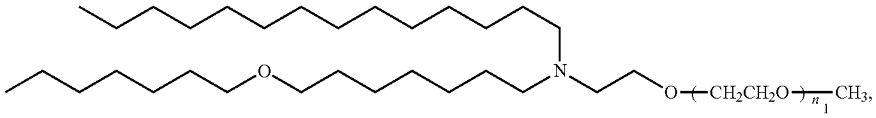
PL-16
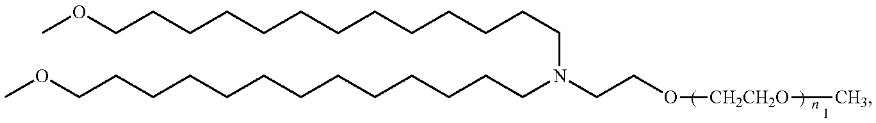
PL-17
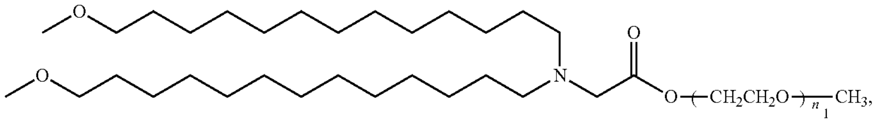
PL-18
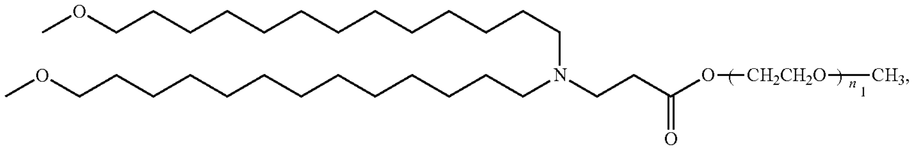
PL-19
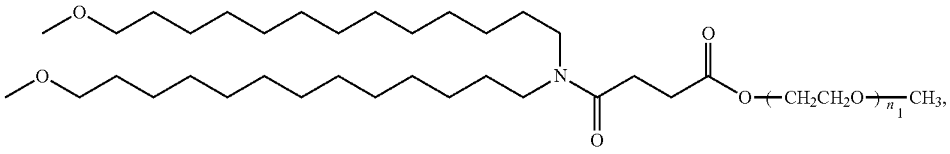
PL-20
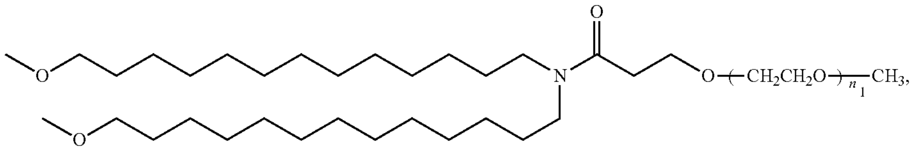
PL-21
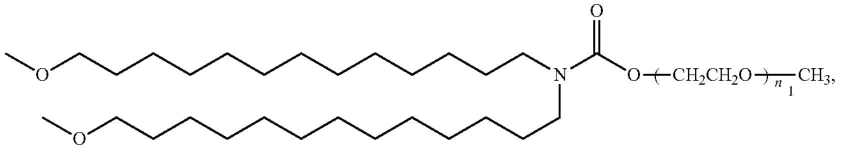
PL-22
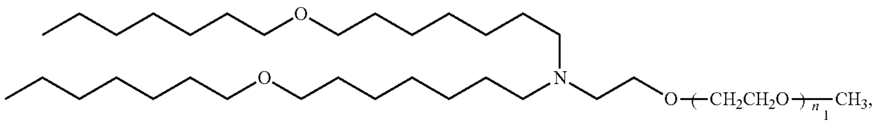
PL-23
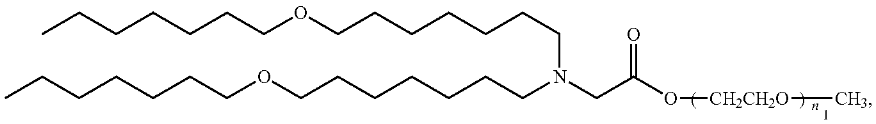

-continued

PL-24

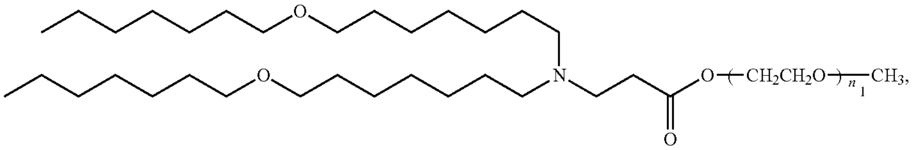

PL-25

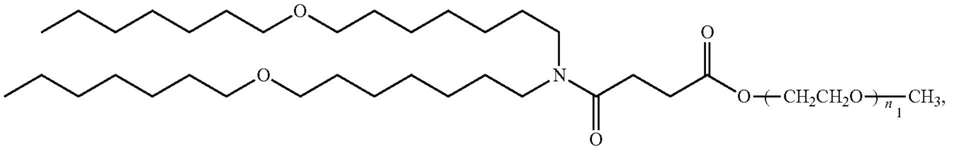

and

PL-26

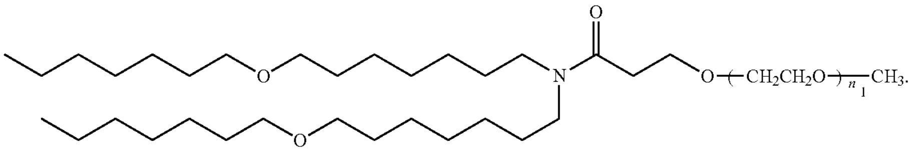

20. The cationic liposome according to claim 13, wherein cationic liposome comprises 20-80% cationic lipids, 5-15% neutral lipids, 25-55% steroid lipids, and 0.5-10% PEGylated lipids represented by the general formula (2), said percentage being the molar percentage of each type of lipid relative to the total lipids in a solution comprising a solvent.

21. The cationic liposome according to claim 13, wherein the molar percentage of cationic lipids relative to the total lipids in a solution comprising a solvent is 30% to 65%.

22. The cationic liposome according to claim 13, wherein the molar percentage of neutral lipids relative to the total lipids in a solution comprising a solvent is 7.5% to 13%.

23. The cationic liposome according to claim 13, wherein the molar percentage of steroid lipids relative to the total lipids in a solution comprising a solvent is 35% to 50%.

24. The cationic liposome according to claim 13, wherein the molar percentage of PEGylated lipids relative to the total lipids in a solution comprising a solvent is 0.5% to 5%.

25. A cationic liposome-nucleic acid pharmaceutical composition, wherein, the cationic liposome-nucleic acid pharmaceutical composition comprises the cationic liposome of claim 13 and nucleic acid drug.

26. The cationic liposome-nucleic acid pharmaceutical composition according to claim 25, wherein said nucleic acid drug is selected from the group consisting of DNA, antisense nucleic acid, plasmid, mRNA, interfering nucleic acid, aptamer, antagomir, miRNA, ribozyme, and siRNA.

27. The cationic liposome-nucleic acid pharmaceutical composition according to claim 26, wherein said pharmaceutical composition is used as a drug selected from the group consisting of drugs for treating any disease from cancer and malignant tumor, anti-infectious agents, antiviral agents, antifungal agents, and vaccines.

28. A cationic lipid, wherein the structure is represented by the general formula (1):

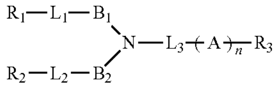

(1)

wherein N is the nitrogen-atom branching center;

wherein both $L_1$ and $L_2$ are —OC(=O)—; wherein $L_3$ is selected from the group consisting of a linking bond, -$L_4$-, —Z-$L_4$-, -$L_4$-Z—, —Z-$L_4$-Z—, -$L_4$-Z-$L_5$-, —Z-$L_4$-Z-$L_5$-, and -$L_4$-Z-$L_5$-Z—; wherein said $L_4$ and $L_5$ are carbon-chain linking groups, each independently represented by $—(CR_aR_b)_t—(CR_aR_b)_o—(CR_aR_b)_p—$; wherein t, o, and p are each independently an integer from 0 to 12, not being 0 simultaneously; wherein $R_a$ and $R_b$ are, at each occurrence, independently a hydrogen atom or a $C_{1-6}$ alkyl group; wherein said Z is, at each occurrence, independently selected from the group consisting of —C(=O)—, —OC(=O)—, —C(=O)O—, —OC(=O)O—, —O—, —S—, —C(=O)S—, —SC(=O)—, —$NR_c$C(=O)—, —C(=O)$NR_c$—, —$NR_c$C(=O)$NR_c$—, —OC(=O)$NR_c$—, —$NR_c$C(=O)O—, —SC(=O)$NR_c$—, —$NR_c$C(=O)S—, and

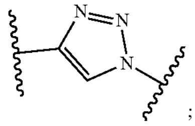 [SMILES: *c1cn(*)nn1]

;

and wherein $R_c$ is, at each occurrence, independently a hydrogen atom or a $C_{1-12}$ alkyl group;

wherein $B_1$ and $B_2$ are each independently a linking bond or a $C_{1-30}$ alkylene group;

wherein $R_1$ is a $C_{5-30}$ aliphatic group or

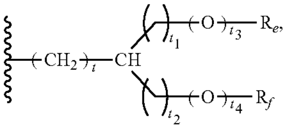

and $R_2$ is

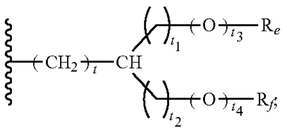

wherein t is an integer from 0 to 12; wherein $t_1$ and $t_2$ are each independently an integer from 0 to 5; wherein $t_3$ and $t_4$ are 1; and wherein $R_e$ and $R_f$ are each independently selected from the group consisting of a $C_{1-15}$ alkyl group, a $C_{2-15}$ alkenyl group, and a $C_{2-15}$ alkynyl group;

wherein $R_3$ comprises H, $-(CH_2)_tOH$, $-(CH_2)_tSH$, $-OCH_3$, $-OCH_2CH_3$, $-(CH_2)_tNH_2$, $-(CH_2)_tC(=O)OH$, $-C(=O)(CH_2)_tC(=O)OH$, $-C(=O)CH_3$, $-(CH_2)_tN_3$, $-C(=O)CH_2CH_3$, $-C(=O)OCH_3$, $-OC(=O)OCH_3$, $-C(=O)OCH_2CH_3$, $-OC(=O)OCH_2CH_3$, $-(CH_2)_tN(CH_3)_2$, $(CH_2)_tCHO$,

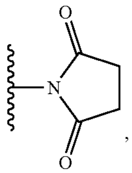
,
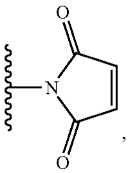
,
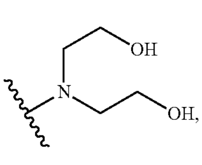

-continued

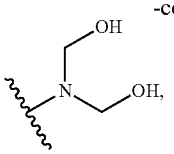
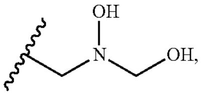
or

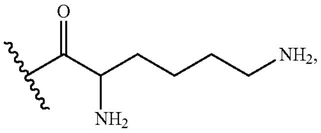

wherein t is an integer from 0 to 12;

wherein A is $-CH_2CH_2O-$ or $-OCH_2CH_2-$, and n is an integer from 2 to 6; and wherein said alkyl group, alkylene group, alkoxy group, and aliphatic hydrocarbon group are each independently substituted or unsubstituted.

29. The cationic lipid according to claim 28, wherein the structure of said cationic lipid is one of the following structures:

P-175

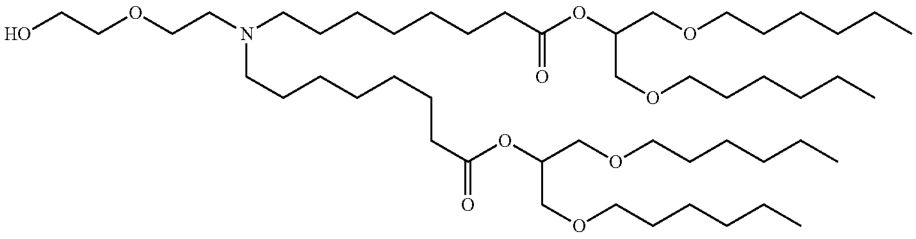
,

P-176

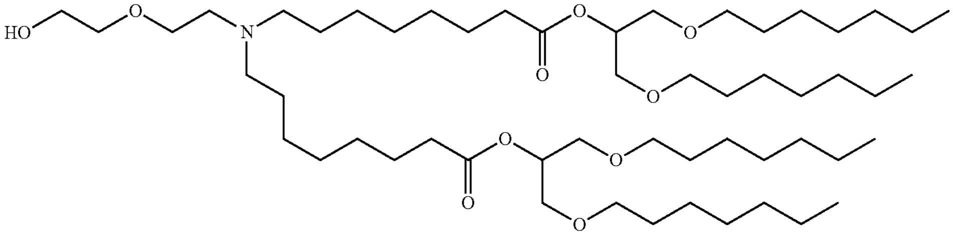
, and

P-177

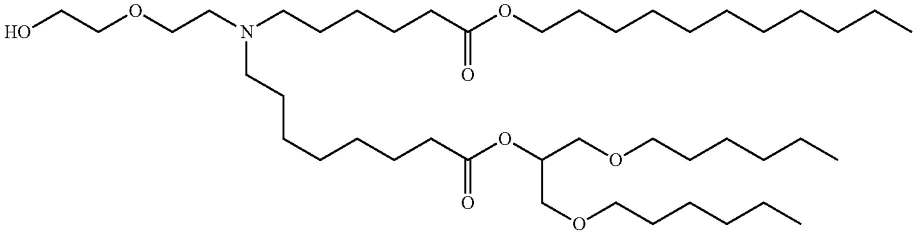
.

30. A cationic liposome, wherein the cationic liposome comprises the cationic lipid of claim 28.

31. The cationic lipid according to claim 2, wherein said $B_1$ and $B_2$ are selected from one of the following Groups:

Group (1): one of $B_1$ and $B_2$ is a linking bond, and the other is a $C_{1-20}$ alkylene group;

Group (2): $B_1$ and $B_2$ are each independently selected from the group consisting of a methylene group, an ethylene group, a propylene group, a butylene group, a pentylene group a hexylene group, a heptylene group, an octylene group, a nonylene group, a decylene group, an undecylene group, a dodecylene group, a tridecylene group, a tetradecylene group, a pentadecylene group, a hexadecylene group, a heptadecylene group, an octadecylene group, nonadecylene group, and an eicosylene group.

32. The cationic lipid according to claim 3, wherein said $L_3$ is selected from the group consisting of a linking bond, $-(CH_2)_t-$, $-(CH_2)_tO-$, $-(CH_2)_tC(=O)-$, $-(CH_2)_tC(=O)O-$, $-(CH_2)_tOC(=O)-$, $-(CH_2)_tC(=O)NH-$, $-(CH_2)_tNHC(=O)-$, $-(CH_2)_tOC(=O)O-$, $(CH_2)_tNHC(=O)O-$, $-(CH_2)_tOC(=O)NH-$, $-(CH_2)_tNHC(=O)NH-$, $-O(CH_2)_t-$, $-C(=O)(CH_2)_t-$, $-C(=O)O(CH_2)_t-$, $-OC(=O)(CH_2)_t-$, $-C(=O)NH(CH_2)_t-$, $-NHC(=O)(CH_2)_t-$, $-OC(=O)O(CH_2)_t-$, $NHC(=O)O(CH_2)_t-$, $-OC(=O)NH(CH_2)_t-$, $-NHC(=O)NH(CH_2)_t-$, $-(CH_2)_tO(CH_2)_t-$, $-(CH_2)_tC(=O)(CH_2)_t-$, $-(CH_2)_tC(=O)O(CH_2)_t-$, $-(CH_2)_tOC(=O)(CH_2)-$, $-(CH_2)_tC(=O)NH(CH_2)_t-$, $-(CH_2)_tNHC(=O)(CH_2)_t-$, $-(CH_2)_tOC(=O)O(CH_2)_t-$, $-(CH_2)_tNHC(=O)O(CH_2)_t-$, $-(CH_2)_tOC(=O)NH(CH_2)_t-$, $-(CH_2)_tNHC(=O)NH(CH_2)_t-$, $-O(CH_2)_tO-$, $-C(=O)(CH_2)_tC(=O)-$, $-C(=O)O(CH_2)_tC(=O)O-$, $-OC(=O)(CH_2)_tOC(=O)-$, $-C(=O)O(CH_2)_tOC(=O)-$, $-OC(=O)(CH_2)_tC(=O)O-$, $-OC(=O)O(CH_2)_tOC(=O)O-$, $-C(=O)NH(CH_2)_tC(=O)NH-$, $-NHC(=O)(CH_2)_tNHC(=O)-$, $-NHC(=O)(CH_2)_tC(=O)NH-$, $-C(=O)NH(CH_2)NHC(=O)-$, $-NHC(=O)O(CH_2)_tNHC(=O)O-$, $-OC(=O)NH(CH_2)_tOC(=O)NH-$, $-NHC(=O)O(CH_2)_tOC(=O)NH-$, $-OC(=O)NH(CH_2)_tNHC(=O)O-$, $-NHC(=O)NH(CH_2)_tNHC(=O)NH-$, $-C(=O)(CH_2)_tO-$, $-C(=O)(CH_2)_tC(=O)O-$, $-C(=O)(CH_2)_tOC(=O)-$, $-C(=O)(CH_2)_tOC(=O)O-$, $-C(=O)(CH_2)_tNHC(=O)O-$, $-C(=O)(CH_2)_tOC(=O)NH-$, and $-C(=O)(CH_2)_tNHC(=O)NH-$.

33. The cationic lipid according to claim 6, wherein said $R_1$ and $R_2$ are each independently a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a heneicosyl group, a docosyl group, a tricosyl group, a lignoceroylv group, a (Z)-tridec-8-enyl group, a (Z)-tetradec-9-enyl group, a (Z)-pentadec-8-enyl group, a (Z)-hexadec-9-enyl group, a (Z)-heptadec-5-enyl group, a (Z)-heptadec-8-enyl group, an (E)-heptadec-8-enyl group, a (Z)-heptadec-10-enyl group, an (8Z,11Z)-heptadec-8,11-dienyl group, a (Z)-octodec-6-enyl group, a (Z)-octodec-9-enyl group, an (E)-octodec-9-enyl group, a (Z)-octodec-11-enyl group, a (9Z,12Z)-octodec-9,12-dienyl group, a (9Z,12Z, 15Z)-octodec-9,12,15-trienyl group, an (8Z,11Z, 14Z)-octodec-8,11,14-trienyl group, a (Z)-eicos-11-enyl group, an (11Z,14Z)-eicos-11,14-dienyl group, a (Z)-nonadec-10-enyl group, a (10Z,13Z)-nonadec-10,13-dienyl group, a 2,6,10-trimethylundec-1,5,9-trienyl group, a 3,7,11-trimethyldodec-2,6,10-trienyl group, or a 3,7,11,15-tetramethylhexadec-2-enyltridecyl group when $R_1$ and $R_2$ are each independently a linear alkyl group.

34. The cationic lipid according to claim 7, wherein $R_e$ and $R_f$ are each independently selected from the group consisting of a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a vinyl group, a propenyl group, an allyl group, a butenyl group, an allyl carbinyl group, a pentenyl group, a neopentyl group, a hexenyl group, a neohexenyl group, a heptenyl group, a neoheptenyl group, an octenyl group, a neooctenyl group, a nonenyl group, a neononenyl group, a decenoyl group, a neodecenoyl group, an ethynyl group, a propynyl group, a propargyl group, a butynyl group, a butynediyl group, a pentynyl group, a neopentyl group, a hexynyl group, a neohexyl group, a heptynyl group, a neoheptyl group, an octynyl group, a neooctyl group, a nonynyl group, a neononyl group, a decynylgroup, and a neodecyl group.

35. The cationic liposome according to claim 17, wherein said PEGylated lipid is selected from the group consisting of PEG500-dipalmitoylphosphatidylcholine, PEG2000-dipalmitoylphosphatidylcholine, PEG500-stearylphosphatidylethanolamine, PEG2000-distearylphosphatidylethanolamine, PEG500-1,2-dioleoylphosphatidylethanolamine, PEG2000-1,2-dioleoylphosphatidylethanolamine, and PEG2000-2,3-distearoylglycerol.

* * * * *